(12) United States Patent
Aspostolou et al.

(10) Patent No.: US 12,018,284 B2
(45) Date of Patent: Jun. 25, 2024

(54) PHYSIOLOGY AND PATHOPHYSIOLOGY OF HUMAN GUT: INTESTINE-ON-CHIP

(71) Applicant: EMULATE, INC., Boston, MA (US)

(72) Inventors: Athanasia Apostolou, Brookline, MA (US); Antonio Varone, West Roxbury, MA (US); Magdalena Kasendra, Boston, MA (US); Raymond Luc, Quincy, MA (US)

(73) Assignee: EMULATE, INC., Boston, MA (US)

( * ) Notice: Subject to any disclaimer, the term of this patent is extended or adjusted under 35 U.S.C. 154(b) by 0 days.

(21) Appl. No.: 17/984,023

(22) Filed: Nov. 9, 2022

(65) Prior Publication Data

US 2023/0151333 A1 May 18, 2023

Related U.S. Application Data

(63) Continuation of application No. 16/825,213, filed on Mar. 20, 2020, now Pat. No. 11,566,231, which is a
(Continued)

(51) Int. Cl.
*C12N 5/071* (2010.01)
*B01L 3/00* (2006.01)
(Continued)

(52) U.S. Cl.
CPC ...... *C12N 5/0679* (2013.01); *B01L 3/502715* (2013.01); *B01L 3/502761* (2013.01);
(Continued)

(58) Field of Classification Search
CPC ..... C12N 5/0679; C12M 23/16; C12M 25/02; G01N 1/30
See application file for complete search history.

(56) References Cited

U.S. PATENT DOCUMENTS

| 8,647,861 B2 | 2/2014 | Ingber et al. ............ 435/289.1 |
| 2008/0167226 A1 | 7/2008 | Flink et al. .................... 514/2 |

(Continued)

FOREIGN PATENT DOCUMENTS

| WO | WO/2016/123474 | 8/2016 |
| WO | WO/2017/096297 | 6/2017 |

(Continued)

OTHER PUBLICATIONS

U.S. Appl. No. 15/248,690 (2017-0058248), Mar. 2, 2017, Hinojosa, et al., filed Aug. 26, 2016.
(Continued)

*Primary Examiner* — Jennifer Wecker
*Assistant Examiner* — Kathryn Elizabeth Limbaugh
(74) *Attorney, Agent, or Firm* — Medlen & Carroll, LLP

(57) ABSTRACT

An in vitro microfluidic intestine on-chip is described herein that mimics the structure and at least one function of specific areas of the gastrointestinal system in vivo. In particular, a multicellular, layered, microfluidic intestinal cell culture, which is some embodiments is derived from patient's enteroids-derived cells, is described comprising L cells, allowing for interactions between L cells and gastrointestinal epithelial cells, endothelial cells and immune cells. This in vitro microfluidic system can be used for modeling inflammatory gastrointestinal autoimmune tissue, e.g., diabetes, obesity, intestinal insufficiency and other inflammatory gastrointestinal disorders. These multicellular-layered microfluidic intestine on-chips further allow for comparisons between types of gastrointestinal tissues, e.g., small intestinal duodenum, small intestinal jejunum, small intestinal ileum, large intestinal colon, etc., and between disease states of gastrointestinal tissue, i.e. healthy, pre-disease and diseased areas. Additionally, these microfluidic gut-on-chips allow identification of cells and cellular derived factors
(Continued)

driving disease states and drug testing for reducing inflammation.

5 Claims, 96 Drawing Sheets

Related U.S. Application Data continuation of application No. PCT/US2018/052233, filed on Sep. 21, 2018.

(60) Provisional application No. 62/561,513, filed on Sep. 21, 2017.

(51) Int. Cl.
| | | |
|---|---|---|
| *C12M 1/00* | (2006.01) | |
| *C12M 1/12* | (2006.01) | |
| *C12M 3/06* | (2006.01) | |
| *G01N 1/30* | (2006.01) | |
| *G01N 33/50* | (2006.01) | |

(52) U.S. Cl.
CPC ............ *C12M 23/16* (2013.01); *C12M 23/26* (2013.01); *C12M 25/02* (2013.01); *C12N 5/069* (2013.01); *G01N 1/30* (2013.01); *G01N 33/5047* (2013.01); *G01N 33/5064* (2013.01); *B01L 2200/16* (2013.01); *B01L 2300/123* (2013.01); *B01L 2300/16* (2013.01); *C12N 2500/00* (2013.01); *C12N 2501/052* (2013.01); *C12N 2501/2301* (2013.01); *C12N 2501/2306* (2013.01); *C12N 2501/25* (2013.01)

(56) References Cited

U.S. PATENT DOCUMENTS

| | | | |
|---|---|---|---|
| 2009/0263468 A1 | 10/2009 | McAnulty et al. | 424/78.06 |
| 2010/0240132 A1 | 9/2010 | Lanza et al. | 435/377 |
| 2012/0196312 A1* | 8/2012 | Sato | C12N 5/0677 |
| | | | 435/405 |
| 2017/0058248 A1 | 3/2017 | Hinojosa et al. | 435/325 |
| 2017/0101628 A1* | 4/2017 | Ingber | C12M 41/12 |
| 2019/0076842 A1* | 3/2019 | Vulto | C12N 5/0697 |
| 2020/0231938 A1 | 7/2020 | Ingber et al. | 435/1.1 |
| 2022/0204941 A1* | 6/2022 | Retting | A61K 35/38 |

FOREIGN PATENT DOCUMENTS

| | | | |
|---|---|---|---|
| WO | WO/2017/136462 | 8/2017 | |
| WO | WO-2017179021 A1 * | 10/2017 | ............ C12M 23/16 |

OTHER PUBLICATIONS

Karam, S. M. "Lineage commitment and maturation of epithelial cells in the gut," *Frontiers in Bioscience* 4, D286-298. (1999).

Lund, M. L. et al. "Enterochromaffin 5-HT cells—A major target for GLP-1 and gut microbial metabolites," *Molecular Metabolism* 11, 70-83. (2018).

Meunier, V. et al. "The human intestinal epithelial cell line Caco-2; pharmacological and pharmacokinetic applications," *Cell Biology and Toxicology* 11(3-4), 187-194. (1995).

Pageot, L. P. et al. "Human cell models to study small intestinal functions: Recapitulation of the crypt-villus axis," *Microscopy Research and Technique* 49(4), 394-406. (2000).

Petersen, N. et al. "Targeting development of incretin-producing cells increases insulin secretion," *Journal of Clinical Investigation* 125(1), 379-385. (2015).

Vasilyeva, E. et al. "Serum Cytokine Profiles in Children with Crohn's Disease," *Mediators of Inflammation* 2016, 7420127-7420127. (2016).

Wang, X. et al. "Shear stress activation of nuclear receptor PXR in endothelial detoxification," *Proceedings of the National Academy of Sciences* 110(32), 13174. (2013).

Adrian, T. E. et al. "Deoxycholate in an important releaser of peptide YY and enteroglucagon from the human colon," *Gut* 34(9), 1219. (1993).

Chin, A. et al. "The role of mechanical forces and adenosine in the regulation of intestinal enterochromaffin cell serotonin secretion," *American Journal of Physiology Gastrointestinal and Liver Physiology* 302(3), G397-G405. (2011).

Kim, H. J. et al. "Contributions of microbiome and mechanical deformation to intestinal bacterial overgrowth and inflammation in a human gut-on-a-chip," *Proceedings of the National Academy of Sciences* 113(1), E7-E15. (2016).

Ootani, A. et al. "Sustained in vitro intestinal epithelial culture within a Wnt-dependent stem cell niche," *Nature Materials* 15(6), 701-706. (2009).

PCT International Search Report of International Application No. PCT/US2018/052233 dated Dec. 3, 2018.

Parker, et al., "Molecular mechanisms underlying bile acid-stimulated glucagon-like peptide-1 secretion" Br. J. Pharmacol. 165, 414-23, (2012).

* cited by examiner

Fig. 19A-H

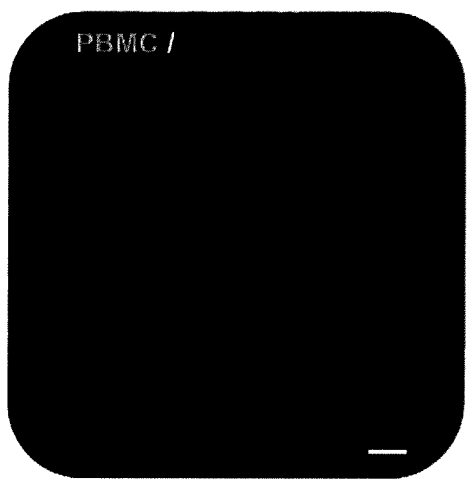 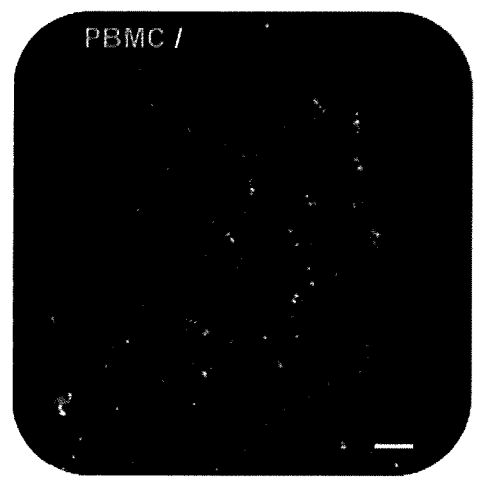
Fig. 20A  Fig. 20C  Fig. 20B
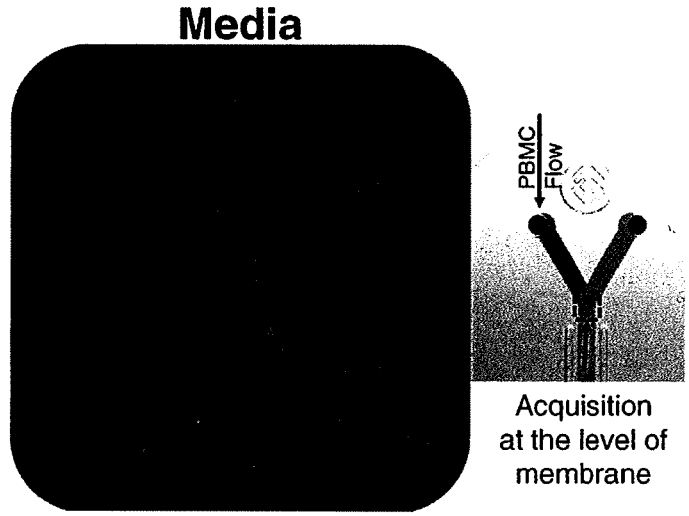
Fig. 20D  Fig. 20E Fig. 24A
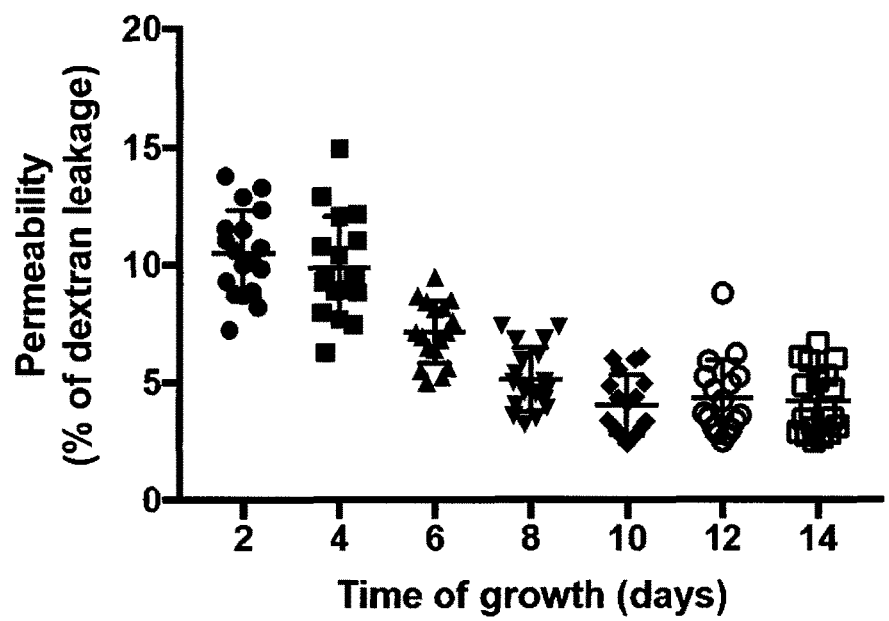
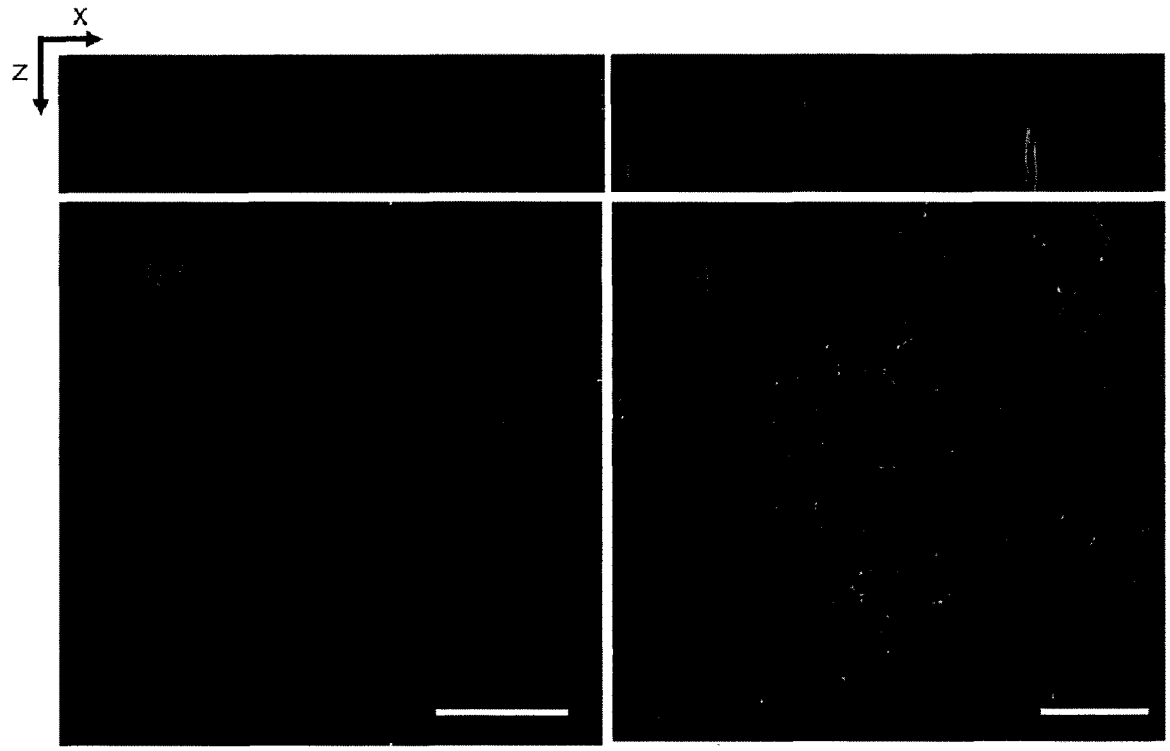
Fig. 24B

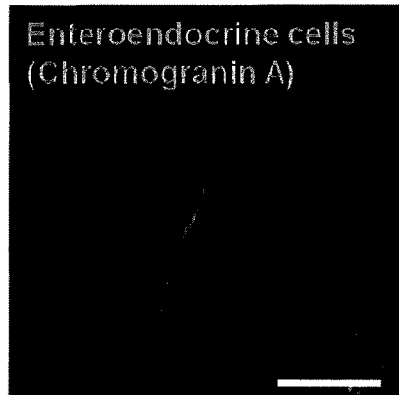 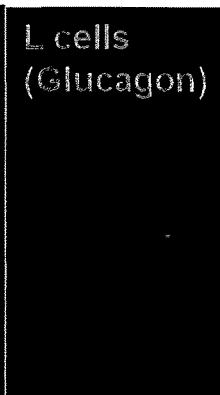 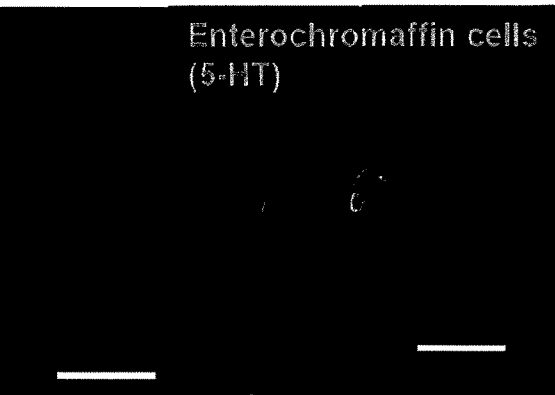
Fig. 25A    Fig. 25B    Fig. 25C
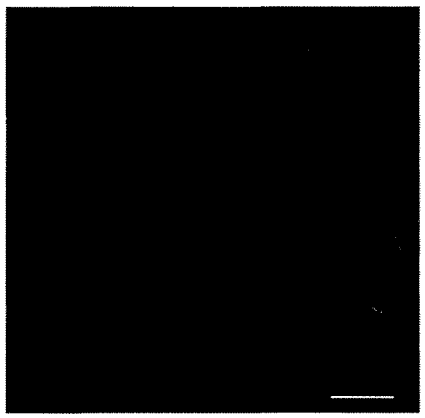 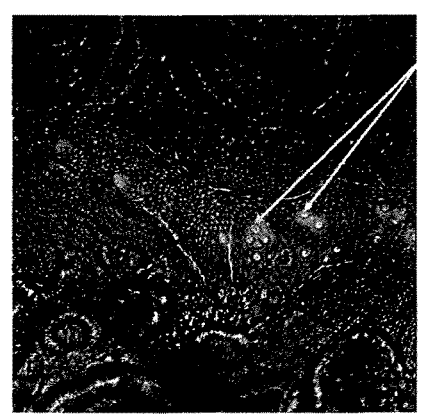
Fi. 25D    Fig. 25E
Fig. 25F

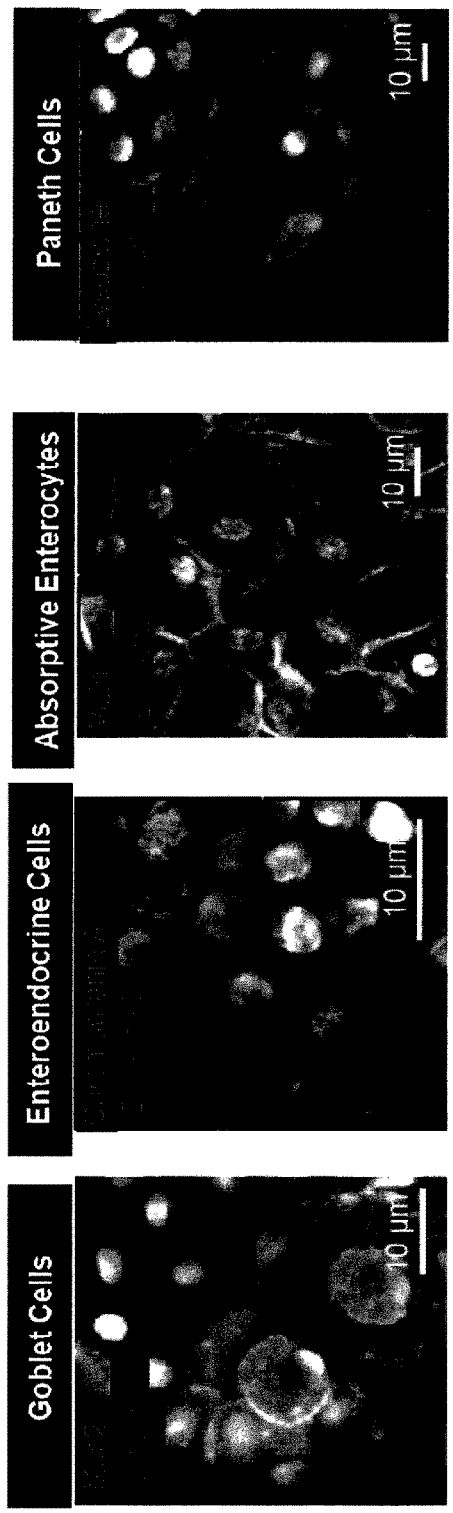
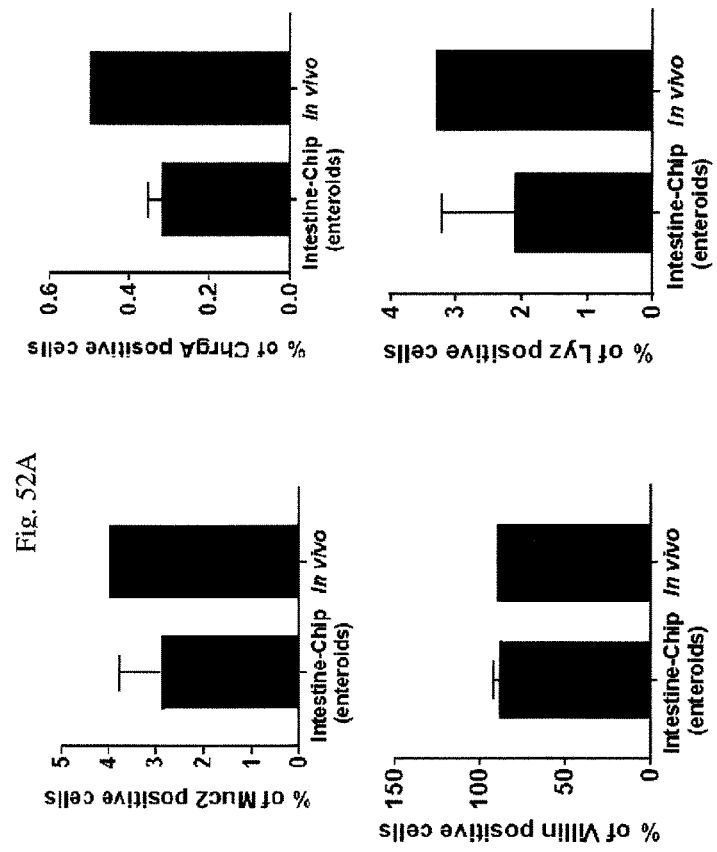
Fig. 52A
Fig. 52B

Fig. 58A
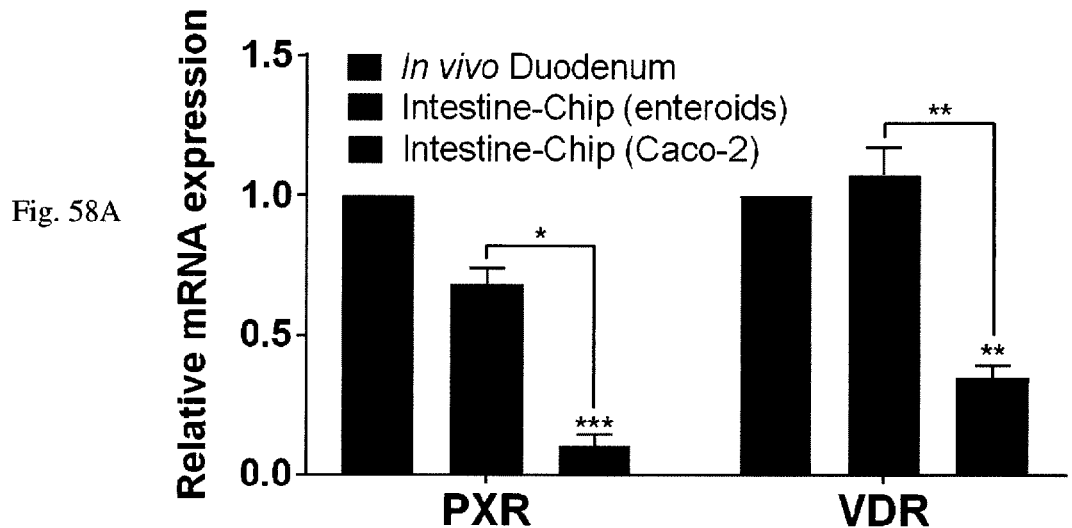
RIF - 20 μM rifampicin
VD3 - 100 nM 1,25-dihidroxyvitamin
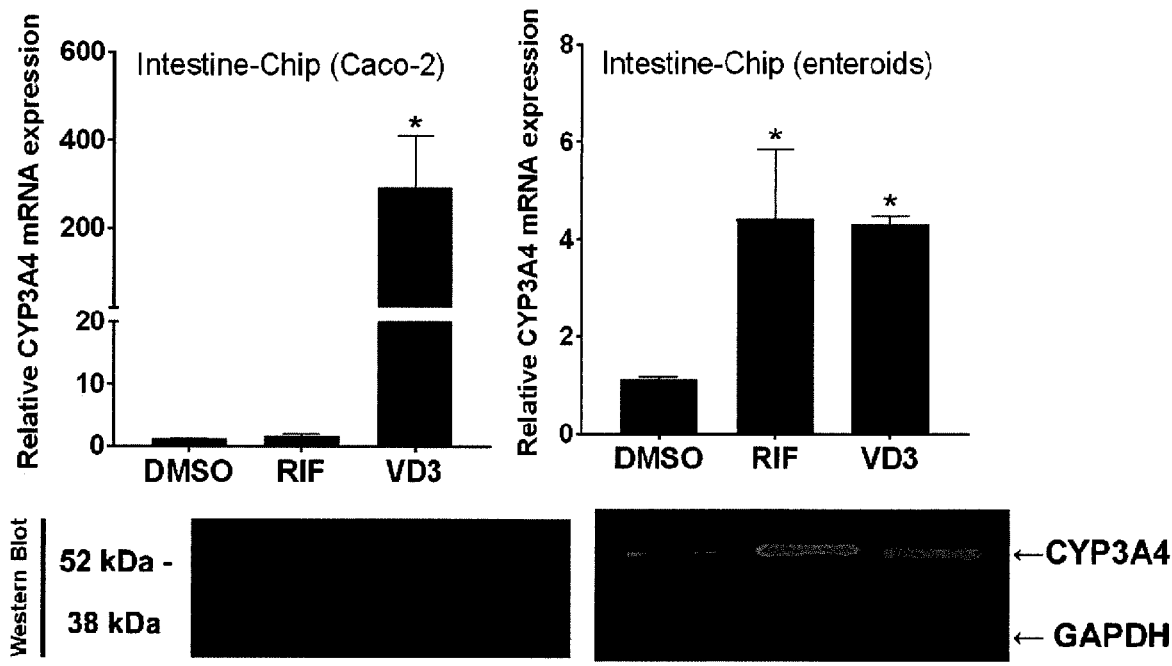
Fig. 58B
Fig. 58C

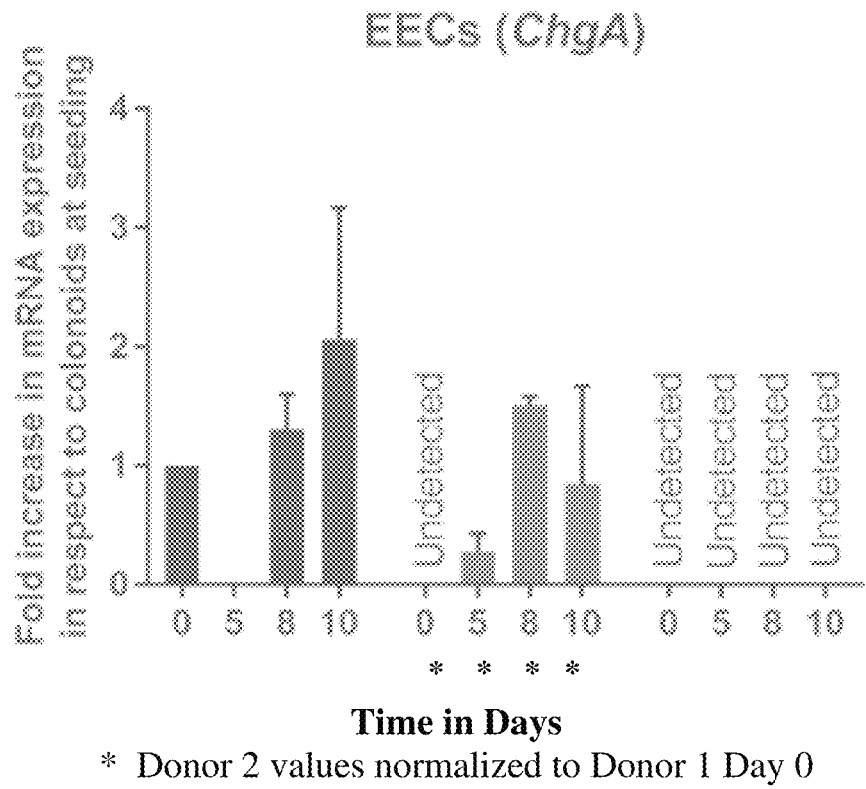
* Donor 2 values normalized to Donor 1 Day 0
Fig. 68F
Fig. 68G
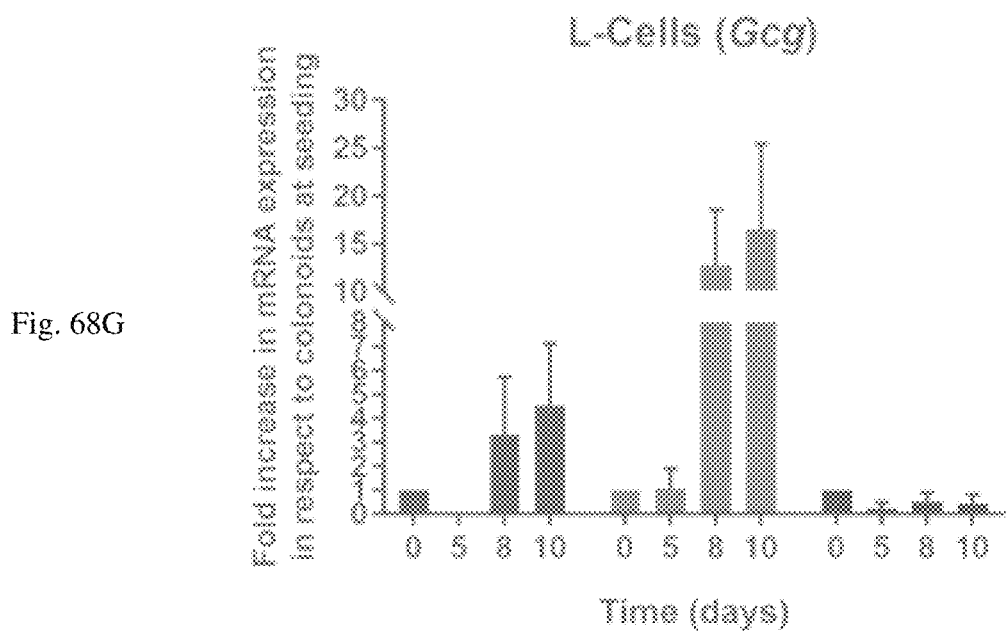

PHYSIOLOGY AND PATHOPHYSIOLOGY OF HUMAN GUT: INTESTINE-ON-CHIP

CROSS-REFERENCE TO RELATED APPLICATIONS

This application is a Continuation of, and claims priority to, patent application Ser. No. 16/825,213, filed Mar. 20, 1920, now Patent Registration U.S. Pat. No. 11,566,231, issued on Jan. 31, 2023, which claims priority to PCT Patent Application Serial No. PCT/US2018/052233, filed Sep. 21, 2018, which claims priority to Provisional Application Ser. No. 62/561,513 filed on Sep. 21, 2017, the contents of which are incorporated herein in their entirety.

FIELD OF THE INVENTION

An in vitro microfluidic intestine on-chip is described herein that mimics the structure and at least one function of specific areas of the gastrointestinal system in vivo. In particular, a multicellular, layered, microfluidic intestinal cell culture, which is some embodiments is derived from patient's enteroids-derived cells, is described comprising L cells, allowing for interactions between L cells and gastrointestinal epithelial cells, endothelial cells and immune cells. This in vitro microfluidic system can be used for modeling inflammatory gastrointestinal autoimmune tissue, e.g., diabetes, obesity, intestinal insufficiency and other inflammatory gastrointestinal disorders. These multicellular-layered microfluidic intestine on-chips further allow for comparisons between types of gastrointestinal tissues, e.g., small intestinal duodenum, small intestinal jejunum, small intestinal ileum, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

BACKGROUND

In vitro gastrointestinal tissue model systems include cell lines, primary cell explant cultures and three-dimensional primary cell organoid culture systems. However, these models have significant limitations. Limitations of both cell lines and primary cell explant cultures are reviewed in part by Pageot, et al. "Human cell models to study small intestinal functions: recapitulation of the crypt-villus axis." Microsc Res Tech.; 49:394-406, 2000.

Explant cultures, which have organotypic properties such as complex 3-dimensional (3D) architecture and cellular heterogeneity are limited in part by their lack of reproducibility of growing conditions between laboratories and their short-term nature.

What is needed is a better in vitro platform for gastrointestinal tissue modeling and drug testing, specifically in combination with modeling gastrointestinal inflammatory diseases.

SUMMARY OF THE INVENTION

An in vitro microfluidic intestine on-chip is described herein that mimics the structure and at least one function of specific areas of the gastrointestinal system in vivo. In particular, a multicellular, layered, microfluidic intestinal cell culture, which is some embodiments is derived from patient's enteroids-derived cells, is described comprising L cells, allowing for interactions between L cells and gastrointestinal epithelial cells, endothelial cells and immune cells. This in vitro microfluidic system can be used for modeling inflammatory gastrointestinal autoimmune tissue, e.g., diabetes, obesity, intestinal insufficiency and other inflammatory gastrointestinal disorders. These multicellular-layered microfluidic intestine on-chips further allow for comparisons between types of gastrointestinal tissues, e.g., small intestinal duodenum, small intestinal jejunum, small intestinal ileum, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

In one embodiment, the present invention contemplates a method of culturing intestinal cells in vitro, comprising: a) providing i) an intestinal epithelial cells, ii) a microfluidic culture device comprising a cell growth region comprising a top and bottom surface; and iii) fibroblasts; b) seeding said fibroblasts on said top or bottom surface of said cell growth region so as to create a cell layer of fibroblasts on said surface, wherein said fibroblasts are mitotically inactivated either at the time of seeding or after seeding; and c) seeding said intestinal epithelial cells on said top surface of said cell growth region. In one embodiment, said fibroblasts are seeded on said top surface of said cell growth region and said intestinal epithelial cells are seeded on top of said fibroblasts. In one embodiment, the method further comprises endothelial cells on said bottom surface of said cell growth region (e.g. seeding endothelial cells prior to seeding the other cells, or after). In one embodiment, said fibroblasts are seeded on said bottom surface of said cell growth region over said endothelial cells.

A variety of device designs are contemplated, as well as a variety of cell growth region types. In one embodiment, said surface of said cell growth region of said microfluidic culture device comprises a membrane. In one embodiment, said membrane is porous. In one embodiment, said microfluidic culture device further comprises a gel. In one embodiment, said gel is positioned on top of said membrane. In one embodiment, said gel is positioned under said membrane. In one embodiment, said membrane is in fluidic communication with a microchannel, said microchannel in fluidic communication with a source of fluid (e.g. a reservoir or other source). In one embodiment, said cell growth region is a chamber or portion thereof. In one embodiment, said chamber comprises a removable lid (e.g. the lid can be removed to create an open-top device, which have certain advantages described below). In one embodiment, said chamber comprises a membrane. In one embodiment, said chamber comprises a gel. In one embodiment, said cell growth region is a microchannel or portion thereof. In one embodiment, said seeded cells are exposed to a flow of fluid at a flow rate. In one embodiment, said fluid comprises culture media. In one embodiment, said fluid comprises blood or one or more blood components (e.g. serum, blood cells, etc.). In one embodiment, said intestinal epithelial cells are Caco-2 cells. In one embodiment, said intestinal epithelial cells are primary intestinal epithelial cells. In one embodiment, said intestinal epithelial cells are derived from intestinal organoids (e.g. organoids from any portion of the intestinal tract, including but not limited to stomach, esophagus, upper intestine, lower intestine, colon, etc.). Such organoids can come from both healthy and sick patients, e.g. from biopsies or other surgical procedures. In one embodiment, said intestinal epithelial cells are derived from enteroid or colonoid fragments. In one embodiment, said enteroid or colonoid fragments on the top of said cell layer of fibroblasts so as to create seeded primary intestinal epithelial cells. In one embodiment, the method further comprises d) expanding said seeded primary intestinal epithelial cells so as to create a monolayer of epithelial cells. In one embodiment, the method further comprises e) differentiating said monolayer of epithelial cells so as to create two or more different differentiated intestinal cell types. In one embodiment, one of said two or more different differentiated intestinal cell types comprises L-cells. In one embodiment, introducing fibroblasts had the unexpected advantages of leading the enteroid-derived cells to generate L-cells (as evidenced by cells with gene expression indicative of L cells). In one embodiment, said L-cells secrete glucagon-like peptide-1 (GLP-1). In one embodiment, one of said two or more different differentiated intestinal cell types is selected from the group consisting of absorptive enterocytes, Paneth cells, goblet cells. In one embodiment, said fibroblasts are Newborn Human Forskin Fibroblasts. In one embodiment, said seeded primary intestinal epithelial cells are exposed to a mechanical force. In one embodiment, said mechanical force causes stretching of said seeded primary intestinal epithelial cells. In one embodiment, said surface of said cell growth region comprises at least one extracellular matrix protein. In one embodiment, said extracellular matrix protein is covalently attached to said surface via a bifunctional cross-linker. In one embodiment, said fibroblasts are covered by a layer, said layer comprising at least one extracellular matrix protein. In one embodiment, said fibroblasts are mitotically inactivated before seeding by irradiation.

The present invention also contemplates devices. In one embodiment, the present invention contemplates a microfluidic culture device, comprising i) a cell growth region comprising a top and bottom surface; ii) a layer of mitotically inactivated human fibroblasts on said top or bottom surface; and iii) human primary intestinal epithelial cells on said top surface. In one embodiment, said fibroblasts are on said top surface and said human primary intestinal epithelial cells are on top of said layer of fibroblasts. In one embodiment the device further comprises endothelial cells on said bottom surface of said cell growth region. In one embodiment, said fibroblasts are seeded on said bottom surface of said cell growth region over said endothelial cells. In one embodiment, said surface of said cell growth region of said microfluidic culture device comprises a membrane. In one embodiment, said membrane is porous. In one embodiment, said microfluidic culture device further comprises a gel. In one embodiment, said gel is positioned on top of said membrane. In one embodiment, said gel is positioned under said membrane. In one embodiment, said membrane is in fluidic communication with a microchannel, said microchannel in fluidic communication with a source of fluid. In one embodiment, said cell growth region is a chamber or portion thereof. In one embodiment, said chamber comprises a removable lid (e.g. where removing the lid creates an open-top device which has advantages described below). In one embodiment, said chamber comprises a membrane. In one embodiment, said chamber comprises a gel. In one embodiment, said cell growth region is a microchannel or portion thereof. In one embodiment, said intestinal epithelial cells are Caco-2 cells. In one embodiment, said intestinal epithelial cells are primary intestinal epithelial cells. In one embodiment, said intestinal epithelial cells are derived from intestinal organoids (e.g. organoids from any portion of the intestinal tract, including but not limited to stomach, esophagus, upper intestine, lower intestine, colon, etc.). Such organoids can come from both healthy and sick patients, e.g. from biopsies or other surgical procedures. In one embodiment, said intestinal epithelial cells are derived from enteroids or colonoids fragments. In one embodiment, said intestinal epithelial cells comprise two or more different differentiated intestinal cell types. In one embodiment, one of said two or more different differentiated intestinal cell types comprises L-cells. In one embodiment, said L-cells secrete glucagon-like peptide-1 (GLP-1). In one embodiment, one of said two or more different differentiated intestinal cell types is selected from the group consisting of absorptive enterocytes, Paneth cells, goblet cells. In one embodiment, said fibroblasts are Newborn Human Forskin Fibroblasts. In one embodiment, said device is configured to expose said intestinal epithelial cells to a mechanical force. In one embodiment, said device is configured to cause stretching of said intestinal epithelial cells. In one embodiment, said surface of said cell growth region comprises at least one extracellular matrix protein. In one embodiment, said extracellular matrix protein is covalently attached to said surface via a bifunctional cross-linker.

The present invention also contemplates methods where cells differentiate in the microfluidic device. In one embodiment, the present invention contemplates a method of culturing intestinal cells in vitro, comprising: a) providing i) an intestinal enteroid or colonoid comprising human primary intestinal epithelial cells, ii) a microfluidic culture device comprising a cell growth region comprising a surface; and iii) human fibroblasts; b) seeding said fibroblasts on said surface of said cell growth region so as to create a cell layer of fibroblasts on said surface, said cell layer comprising a bottom contacting said surface and a top, wherein said fibroblasts are either mitotically inactivated at the time of seeding or mitotically inactivated after seeding; c) disrupting said intestinal enteroid or colonoid comprising human primary intestinal epithelial cells into enteroid or colonoid fragments; d) seeding said enteroid or colonoid fragments on the top of said cell layer of fibroblasts so as to create seeded primary intestinal epithelial cells; e) expanding said seeded primary intestinal epithelial cells so as to create a monolayer of epithelial cells; and f) differentiating said monolayer of epithelial cells so as to create two or more different differentiated intestinal cell types. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, one of said two or more different differentiated intestinal cell types comprises L-cells. In one embodiment, said L-cells secrete glucagon-like peptide-1 (GLP-1). In one embodiment, one of said two or more different differentiated intestinal cell types is selected from the group consisting of absorptive enterocytes, Paneth cells, goblet cells. In one embodiment, said fibroblasts are Newborn Human Forskin Fibroblasts. In one embodiment, said seeded primary intestinal epithelial cells of step (e) are exposed to a flow of fluid at a flow rate. In one embodiment, said seeded primary intestinal epithelial cells of step (e) are exposed to a mechanical force. In one embodiment, said mechanical force causes stretching of said seeded primary intestinal epithelial cells. In one embodiment, said surface of said cell growth region comprises at least one extracellular matrix protein. In one embodiment, said extracellular matrix protein is covalently attached to said surface via a bifunctional crosslinker. In one embodiment, said fibroblasts are mitotically inactivated before seeding by irradiation.

In yet another embodiment, the present invention contemplates a microfluidic culture device, comprising i) a cell growth region comprising a surface; ii) a layer of mitotically inactivated human fibroblasts on said surface; and iii) human primary intestinal epithelial cells on top of said layer of fibroblasts. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said human primary intestinal epithelial cells further comprise two or more different differentiated intestinal cell types. In one embodiment, one of said two or more different differentiated intestinal cell types comprises L-cells. In one embodiment, one of said two or more different differentiated intestinal cell types is selected from the group consisting of absorptive enterocytes, Paneth cells, goblet cells. In one embodiment, said fibroblasts are Newborn Human Forskin Fibroblasts.

In still another embodiment, the present invention contemplates a method of culturing intestinal cells in vitro (and differentiating cells in the microfluidic device), comprising: a) providing i) an intestinal enteroid or colonoid comprising human primary intestinal epithelial cells, and ii) a microfluidic culture device comprising a cell growth region comprising a surface; b) disrupting said intestinal enteroid or colonoid comprising human primary intestinal epithelial cells into enteroid or colonoid fragments; c) seeding said enteroid or colonoid fragments on said surface of said cell growth region so as to create seeded primary intestinal epithelial cells; d) expanding said seeded primary intestinal epithelial cells so as to create a monolayer of epithelial cells; and e) differentiating said monolayer of epithelial cells so as to create two or more different differentiated intestinal cell types, wherein one of said two or more different differentiated intestinal cell types comprises L-cells. In one embodiment, the method further comprises, prior to step c), seeding fibroblasts on said surface of said cell growth region so as to create a cell layer of fibroblasts on said surface, said cell layer comprising a bottom contacting said surface and a top, wherein said fibroblasts are either mitotically inactivated at the time of seeding or mitotically inactivated after seeding, wherein said seeding of step c) comprises seeding said enteroid or colonoid fragments on top of said fibroblast cell layer. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said L-cells secrete glucagon-like peptide-1 (GLP-1). In one embodiment, one of said two or more different differentiated intestinal cell types is selected from the group consisting of absorptive enterocytes, Paneth cells, goblet cells. In one embodiment, said fibroblasts are Newborn Human Forskin Fibroblasts. In one embodiment, said seeded primary intestinal epithelial cells are exposed to a flow of fluid (e.g. a culture fluid, blood or blood components, etc.) at a flow rate. In one embodiment, said seeded primary intestinal epithelial cells are exposed to a mechanical force. In one embodiment, said mechanical force causes stretching of said seeded primary intestinal epithelial cells. In one embodiment, said surface of said cell growth region comprises at least one extracellular matrix protein. In one embodiment, said extracellular matrix protein is covalently attached to said surface via a bifunctional crosslinker.

The present invention also contemplates microfluidic devices comprising differentiated cells, such as L-cells. In one embodiment, the present invention contemplates a microfluidic culture device, comprising i) a cell growth region comprising a surface; and ii) human primary intestinal epithelial cells on said surface, said epithelial cells comprising L-cells. In one embodiment, the device further comprises a layer of mitotically inactivated human fibroblasts on said surface. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said epithelial cells further comprise absorptive enterocytes, Paneth cells, and goblet cells. In one embodiment, said fibroblasts are Newborn Human Forskin Fibroblasts.

The present invention also contemplates exposing differentiated cells in the microfluidic device to a variety of agents, whether naturally occurring on not, including drugs and drug candidates. In one embodiment, the present invention contemplates a method of treating L-cells, comprising: a) providing i) an agent, and ii) a microfluidic culture device, said device comprising a cell growth region comprising a surface, human primary intestinal epithelial cells and L-cells; and b) exposing said L-cells to said agent. In one embodiment, said agent causes said L-cells to release glucagon-like peptide-1 (GLP-1). In one embodiment, said agent is deoxycholic acid. In one embodiment, said agent is an adenylyl cyclase activator. In one embodiment, said adenylyl cyclase activator is forskolin. In one embodiment, L-cells are exposed to forskolin, IBMX or both.

In one embodiment, the present invention contemplates the use of a density-modifying reagent (or a viscosity-modifying reagent or a buoyancy-modifying reagent) in a microfluidic chip to improve cell performance and/or interaction. Thus, in one embodiment, the present invention contemplates a method, comprising: a) providing i) a microfluidic device comprising a body comprising a microchannel therein, said microchannel comprising cells; and ii) a fluid, said fluid comprising a density-modifying reagent; and b) introducing said fluid into said microchannel under conditions such that the density-modifying reagent improves cell performance and/or interaction. In one embodiment, the cells are endothelial cells. In one embodiment, the present invention contemplates a microfluidic device comprising i) a body, said body comprising a microchannel therein, said microchannel comprising cells; and ii) a fluid in said microchannel, said fluid comprising a density-modifying reagent.

In some embodiments, a microfluidic platform for the studies of immune cell recruitment and infiltration (e.g. in the context of chronic intestinal inflammation) is desired. Such a system allows for the assessment of the efficacy of drugs which are targeting important steps and components of this process (MadCAM1, integrins, e.g. alpha4beta7). In one embodiment, the present invention contemplates adhesion of immune cells (e.g. lymphocytes, PBMCs, etc.) to endothelial cells in a microfluidic device (e.g. endos mimicking vascular walls) under flow generated shear forces. In one embodiment, intestine-specific endos (e.g. HIMECs), as opposed to the generic HUVECs used previously, are employed. HIMECs express MadCAM, whereas HUVECs do not. While not limited to any particular theory, it is believed such specific cells are advantageous for drug development, including but not limited to therapies that increase immune recruitment to aid intestinal pathologies. Again, without being limited to any particular theory, it is believed that therapies that target immune recruitment through MadCAM can lead to recruitment that is specific to the intestine and potentially with fewer off target effects/toxicity.

In a preferred embodiment, the immune cell recruitment method employs a liquid with a density-modifying reagent, in order to provide the conditions that allow and even promote immune cells to attach to endothelial cells. Thus, in one embodiment, the present invention contemplates a method comprising a) providing i) a microfluidic device comprising a body comprising a microchannel therein, said microchannel comprising cells (e.g. endothelial cells, and in particular HIMECs); and ii) a fluid, said fluid comprising a density-modifying reagent (or a viscosity-modifying reagent or a buoyancy-modifying reagent) and one or more immune cell types (e.g. lymphocytes, PBMCs, etc.); and b) introducing said fluid into said microchannel under conditions such that the density-modifying reagent (or a viscosity-modifying reagent or a buoyancy-modifying reagent) allows for said one or more immune cell types to interact with said cells in said microchannel (preferably without the use of gravity, e.g. without inverting the microfluidic device). In one embodiment, said density-modifying reagent (or a viscosity-modifying reagent or a buoyancy-modifying reagent) promotes the attachment of one or more immune cell types to said endothelial cells in said microchannel (and in particular HIMECs). In one embodiment, said cells (e.g. endothelial cells) are in a layer on a membrane, the membrane disposed within at least a portion of the microchannel. In one embodiment, the membrane is coated with at least one attachment molecule that supports adhesion of a plurality of living cells. In one embodiment, the membrane is a porous membrane. In one embodiment, the membrane is at least partially flexible. In one embodiment, the membrane is configured to separate the microchannel into first and second microchannels. In one embodiment, the endothelial cells are on the bottom of the membrane (and thus in the second, lower microchannel) with (optionally) epithelial cells on the top of the membrane (and thus in the first, upper microchannel). In one embodiment, the density-modifying reagent (or viscosity-modifying reagent or buoyancy-modifying reagent) is a colloid. In one embodiment, said colloid is a silica-based colloid. In one embodiment, said silica-based colloid is Percoll. In one embodiment, said silica-based colloid is Ficoll.

In one embodiment, the present invention contemplates a microfluidic device comprising i) a body, said body comprising a microchannel therein, said microchannel comprising cells (e.g. endothelial cells); and ii) a fluid in said microchannel, said fluid comprising a density-modifying reagent and one or more immune cell types. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder.

In one embodiment, the present invention provides a method of culturing intestinal cells in vitro, comprising: a) providing, i) an intestinal enteroid or colonoid comprising human primary intestinal epithelial cells, and ii) a microfluidic culture device comprising a cell growth region comprising a surface; b) disrupting said intestinal enteroid or colonoid comprising human primary intestinal epithelial cells into enteroid or colonoid fragments; c) seeding said enteroid or colonoid fragments on said surface of said cell growth region so as to create seeded primary intestinal epithelial cells; d. expanding said seeded primary intestinal epithelial cells so as to create a monolayer of epithelial cells; and e. differentiating said monolayer of epithelial cells so as to create two or more different differentiated intestinal cell types, wherein one of said two or more different differentiated intestinal cell types comprises L-cells. In one embodiment, said method further comprises the step of f) detecting said L-cells. In one embodiment, said method further comprises, prior to step c), seeding fibroblasts on said surface of said cell growth region so as to create a cell layer of fibroblasts on said surface, said cell layer comprising a bottom contacting said surface and a top, wherein said fibroblasts are either mitotically inactivated at the time of seeding or mitotically inactivated after seeding, wherein said seeding of step c) comprises seeding said enteroids or colonoids fragments on top of said fibroblast cell layer. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said L-cells secrete glucagon-like peptide-1 (GLP-1). In one embodiment, one of said two or more different differentiated intestinal cell types is selected from the group consisting of absorptive enterocytes, Paneth cells, and goblet cells. In one embodiment, one of said two or more different differentiated intestinal cell types is selected from the group consisting of enterochromaffin cells and Tuft cells. In one embodiment, said fibroblasts are Newborn Human Forskin Fibroblasts. In one embodiment, said seeded primary intestinal epithelial cells are exposed to a flow of fluid at a flow rate. In one embodiment, said seeded primary intestinal epithelial cells are exposed to a mechanical force. In one embodiment, said mechanical force causes stretching of said seeded primary intestinal epithelial cells. In one embodiment, said surface of said cell growth region comprises at least one extracellular matrix protein. In one embodiment, said extracellular matrix protein is covalently attached to said surface via a bifunctional cross-linker. In one embodiment, said cell growth region comprises a gel. In one embodiment, said gel is positioned on top of a membrane. In one embodiment, said gel is positioned under a membrane. In one embodiment, said membrane has epithelial cells on a first surface (e.g. top surface) and endothelial cells on a second surface (e.g. bottom surface) of the membrane. In one embodiment, the endothelial cells are Human Intestinal Microvascular Endothelial Cells. In one embodiment, said cell growth region is a chamber or portion thereof. In one embodiment, said chamber comprises a removable lid. In one embodiment, said chamber comprises a membrane. In one embodiment, said chamber comprises a gel. In one embodiment, said fluid comprises culture media.

As noted above, in some embodiments, endothelial cells can be cultured on one side of the membrane, while enteroid-derived epithelial cells are cultured on the other side of the membrane. In one embodiment, enteroids derived from biopsies (e.g. of adult ileal tissues or other intestinal tissue) are contemplated as a source of cells for seeding epidermal layers into embodiments of intestine-chips. Both a 1-step embodiment of the method and a 2-step embodiment of the method are contemplated. For the 1-step method, enteroids cells are seeded in one channel on Day 0 while endothelial cells (e.g. HIMECs) are seeded into another channel, separated by a membrane. After seeding, flow of culture fluid is applied at a flow rate over the duration of the 14-day period. For the 2-step method, enteroids cells are seeded in one channel on Day 0, and flow is applied after Day 1. It is preferred that cyclic stretch is applied thereafter (e.g. on day 4). In this 2-step method, the seeding of endothelial cells is delayed, i.e. not done at the same time that the enteroid-derived epithelial cells are seeded; rather, endothelial cells (e.g. HIMECs) are seeded into an opposing channel on the other side of the membrane a number of days after the epithelial cells are seeded (e.g. 1 day, more preferably, 2 days, still more preferably 3 days, and most preferably 4 days or later). After cells attach, flow is applied over the remaining duration of incubation, up to at least Day 14. Flow of culture fluid at a flow rate is an important component of the method. For comparison, organoids cultured under static conditions (e.g. no flow), such as not on chips, create some intestinal differentiated cell types however these cells are in clumps of cells, not monolayers as on-chips, do not provide homogenous and repeatable amounts of differentiated cells and are difficult to access for readouts from within the clumps.

In one embodiment, the present invention provides a microfluidic culture device, comprising i) a cell growth region comprising a surface; and ii) human primary intestinal epithelial cells on said surface, said epithelial cells comprising L-cells. In one embodiment, said device further comprises a layer of mitotically inactivated human fibroblasts on said surface. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said epithelial cells further comprise absorptive enterocytes, Paneth cells, and goblet cells. In one embodiment, said fibroblasts are Newborn Human Forskin Fibroblasts. In one embodiment, said epithelial cells further comprise Tuft cells and enterochromaffin cells.

In one embodiment, the present invention provides a method of treating L-cells, comprising: a) providing, i) an agent, and ii) a microfluidic culture device, said device comprising a cell growth region comprising a surface, human primary intestinal epithelial cells and L-cells; and b) exposing said L-cells to said agent. In one embodiment, said agent causes said L-cells to release glucagon-like peptide-1 (GLP-1). In one embodiment, said agent is deoxycholic acid. In one embodiment, said surface of said cell growth region of said microfluidic culture device comprises a membrane. In one embodiment, said membrane is porous. In one embodiment, said membrane is in fluidic communication with a microchannel, said microchannel in fluidic communication with a source of fluid. In one embodiment, said cell growth region is a chamber or portion thereof. In one embodiment, said cell growth region is a microchannel or portion thereof. In one embodiment, said L-cells secrete glucagon-like peptide-1 (GLP-1).

Definitions

The terms "Intestine on-Chip" and "Gut On-Chip" are used interchangeably herein. A "Gut-On-Chip" or "chip" refers to a "microfluidic device" for modeling any one or more types of gastrointestinal tissue, including but not limited to the small intestine, large intestine, stomach, etc. An "Intestine On-Chip" device is not limited to modeling the upper or lower intestine. In fact, "Intestine On-Chip" refers to a "microfluidic device" for modeling any one or more subtypes of gastrointestinal tissue, including but not limited to the small intestinal ileum, large intestine colon, large intestine rectum, etc. (and this can be done by obtaining primary cells from any of these regions from patients, both healthy and sick, and seeding them on a microfluidic device, including those devices describe herein).

As used herein, the term "Endocrine cells" refers to cells capable of secreting hormones.

As used herein, the term "Peripheral blood mononuclear cells" (or PBMCs) are any peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei.

As used herein, the term "Enteroendocrine Cell" or "EEC" refers to endocrine cells found in gastrointestinal tract, and similar endocrine cells found in other organs including but not limited to pancreas. L-cells refer to a subset of endocrine cells found in vivo within the intestinal lumen.

As used herein, the term "Endocytosis" refers to a process of engulfing molecules, including but not limited to phagocytosis, pinocytosis and receptor-mediated endocytosis.

Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels (and some of these designs are shown by way of example, in the figures).

As used herein, the term "Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. Some embodiments shown in the figures, by way of example, show two microchannels in a microfluidic device.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

Other than in the operating examples, or where otherwise indicated, all numbers expressing quantities of ingredients or reaction conditions used herein should be understood as modified in all instances by the term "about." The term "about" when used to describe the present invention, in connection with percentages means±5%.

As used herein, the term "substantially" is a relative term that can be used to indicate similar dimensions (e.g. height, width, etc.) or similar features (e.g. porosity, linearity, etc.) that need not be identical to a reference, e.g. preferably at least 80% of the dimension or feature, more typically, at least 90%, or at least 95%, or at least 97% or at least 99% or more.

As used herein, the term "biopsy" refers to a sample of the tissue that is removed from a body.

As used herein, the term "inflammation" refers to an in vivo physical condition in which a part of tissue or cells may become activated, reddened, swollen (enlarged), or damaged (ulcerated) especially as a reaction to injury or an irritant. In the body, areas of inflammation can have increased blood flow and capillary permeability, i.e. changes in endothelial cells lining capillaries resulting in capillary dilation and leukocyte infiltration into the irritated and/or inflamed tissues, along with activated immune cells, including white blood cells, leukocytes, lymphocytes, etc., including substances produced by activated immune cells. Inflammation may occur suddenly (acute) or gradually over time (chronic). Inflammation may be local, i.e. in one location as a "patch" or "spot" or may be in several areas as numerous patches, including ulcers, or contiguous involving a large area of tissue. Inflammation may be limited to epithelial regions and underlying endothelium or stromal regions (for example, mucosal areas), or may extend to the submucosa, or extend to the muscularis propria and may further extent to the outermost layer, adventitia, in contact with other parts of the body. Inflammation may also refer to a physiological condition in vitro, as described herein for cells in microfluidic devices.

As used herein, "Caco-2" or "Caco2" refer to a human epithelial intestinal cell line demonstrating a well-differentiated brush border on the apical surface with tight junctions between cells. Although this cell line was originally derived from a large intestine (colon) carcinoma, also called an epithelial colorectal adenocarcinoma, this cell line can express typical small-intestinal microvillus hydrolases and nutrient transporters, see. Meunier, et al., "The human intestinal epithelial cell line Caco-2; pharmacological and pharmacokinetic applications." Cell Biol Toxicol. 11(3-4): 187-94, 1995, abstract. Examples of Caco-2 cell lines include but are not limited to CRL-2102, American Type Culture Collection (Rockville, MD); a BBE subclone of Caco-2 cells; etc.

BRIEF DESCRIPTION OF THE DRAWINGS

FIG. 1A is an exploded view of one embodiment of the perfusion manifold assembly (also called the perfusion disposable or "pod") showing the cover (or cover assembly) off of the reservoirs (the reservoir body can be made of acrylic, for example), the reservoirs positioned above the backplane, the backplane in fluidic communication with the reservoirs, the skirt with a side track for engaging a representative microfluidic device or "chip" (which can be fabricated out of plastic, such as PDMS, for example) having one or more inlet, outlet and (optional) vacuum ports, and one or more microchannels, the chip shown next to (but not in) one embodiment of a chip carrier (which can be fabricated out of a thermoplastic polymer, such as acrylonitrile butadiene styrene (ABS), for example), the carrier being configured to support and carrier the chip, e.g. dimensioned so that the chip fits within a cavity. FIG. 1B shows the same embodiment of the perfusion manifold assembly with the cover on and over the reservoirs, and the chip inside the chip carrier fully linked to the skirt of the perfusion manifold assembly, and thereby in fluidic communication with the reservoirs. In one embodiment, each chip has two inputs, two outputs and (optionally) two connections for the vacuum stretch. In one embodiment, putting the chip in fluidic communication connects all six in one action, rather than connecting them one at a time. FIG. 1C is an exploded view of one embodiment of the perfusion manifold assembly (before the components have been assembled) comprising reservoirs positioned over a fluidic backplane (comprising a fluid resistor), that is fluidically sealed with a capping layer and is positioned over a skirt, with each piece dimensioned to fit over the next. In one embodiment, the skirt comprises structure (e.g. made of polymer) that borders or defines two open spaces, one of the spaces configured to receive the carrier with the chip inside. In one embodiment, the skirt has structure that completely surrounds one open space and two "arms" that extend outwardly that define a second open space for receiving the carrier. In one embodiment, the two arms have sidetracks for slidably engaging the carrier edges.

FIG. 13A shows a morphology timeline after seeding cells. FIG. 13B shows an exemplary method starting by chip activation and ECM coating a day −1 (the day before day 0), cell seeding the chip with HMECs and enteroids in expansion media for 4 days. Day 3 starting flow at 60 ul per hour. Day 4 switching media to differentiation media (e.g. removing Wnt3A) for 4 days. Lower photograph of a chip orientates the Bright-field (Imaging) showing images of cells on chip at Day 0 (seeding) upper channel left and lower channel right. Chips are then imaged at Days 2, 4, 6, and 8 for monitoring cell growth and morphology.

FIG. 15A shows exemplary absorptive enterocytes identified by villin (VIL) stain indicating the honeycombed structures. FIG. 15B shows exemplary enteroendocrine cells identified by chromogranin A (CHGA) stain indicating bring circles. FIG. 15C shows exemplary goblet cells identified by mucin 2 (MUC2) and FIG. 15D shows exemplary Paneth cells identified by lysozyme (LYZ) stain. Stained DNA (Nuclei) are shown indicating the round centers of cells. E-cadherin is also stained indicating the honeycombed structures.

FIG. 16A shows exemplary Absorptive Enterocytes (ALPI). FIG. 16B shows exemplary Enteroendocrine cells identified by chromogranin A (CHGA). FIG. 16C shows exemplary Goblet cells identified by mucin 2 (MUC2) and FIG. 16D shows exemplary Paneth cells identified by lysozyme (LYZ).

FIG. 18A shows images of induced ICAM-1 and nuclei stained channels (left) and under higher magnification (right) for control (upper) and inflamed (lower) channels. FIG. 18B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1β 50 U/ml (approximately 50 pg/ml), IL-6 20 U/ml (approximately 200 pg/ml).

FIG. 18C shows a larger arrow where PBMCs may be added to flow into the main vascular channel. Alternatively, small arrows point to ports where PBMCs may be added to the center area of the channel. Images on the right show white dots representing PBMCs attached to the endothelial layer for no PBMCs added to a chip that was not treated by cytokines, center control with PBMCs but no cytokine treatment and right panel where an inflamed endothelium has numerous attached PBMCs. Attached PBMCs are shown numerically as a total number/chip in an exemplary graph in FIG. 18D.

FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell-endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

FIG. 20A-C shows embodiments of an intestine on chip emulating Immune Cell Recruitment on-Chip through providing physiological level of shear and fluid viscosity to emulate immune cell recruitment at epithelial-endothelial tissue interfaces. Embodiments of intestine on chip showing a florescent micrograph of stained cells FIG. 20A under non-physiological shear in vascular channel and non physiological fluid viscosity. FIG. 20B under physiological shear in vascular channel and physiological fluid viscosity. PBMCs and inflamed HIMEC. FIG. 20C shows flow directions (arrows) on a chip schematic and the acquisition area and level where images were taken. Scale bar=100 micrometers. Physiological levels of shear and fluid viscosity emulate immune cell recruitment at the epithelial-endothelial (tissue-tissue) interface.

FIG. 20D-E shows one embodiment of an intestine on chip where flowing media without the addition of Percoll does not induce PBMC attachment at the same level of imaging as in FIG. 20C.

FIG. 21A is a chart showing relative mRNA expression between standard media (left, bars), viscous media (50% Percoll) (middle bars) and inflammatory inducing media containing Cytomix cytokines (right bars), after 24 hours of treatment. FIG. 21B shows micrographs of cells (left) corresponding to lower power micrographs of the channels (right). Stained ICAM-1 and nuclei. Upper is a control intestine on-chip, middle is an inflamed intestine on-chip and lower is a chip treated with viscous media, 50% Percoll, intestine on-chip.

FIG. 21C shows representative tissues as candidates for white blood cell interactions after diapedesis through the endothelial layer of a blood vessel and FIG. 21D illustrating exemplary cell surface adhesion molecules associated with stages of white blood cell, e.g. lymphocyte, interactions with endothelium. Starting with tethering, rolling, then when inflammatory adhesion molecules are present to trigger activation of the white blood cell, rolling becomes arrest of movement along the endothelial cell(s) the followed by diapedesis through the endothelial layer.

FIG. 22A shows an exemplary schematic representation of one embodiment of a Colon On-Chip, where a long grey arrow points to a layer of colonic epithelium and irradiated fibroblasts. In some embodiments, fibroblasts (e.g. mouse fibroblasts, human fibroblasts) are located underneath epithelial cells seeded from colonoids-enteroids. Short grey arrows point in the direction of fluid flow. FIG. 22B schematic representation of an experimental timeline of Colon On-Chip while FIG. 22C shows bright field micrograph images of cells over times shown on the timeline.

FIG. 23A upper area of epithelial cells, FIG. 23B lower plane of focus closer to fibroblasts, FIG. 23C fibroblasts (long streaks) located at the lower plane of focus. Vimentin staining identifies fibroblast cells (long streaks). E-cadherin and nuclei.

FIG. 24A-B demonstrates exemplary Barrier Function (Permeability) of one embodiment of a Colon On-Chip epithelial cells growing on top of irradiated fibroblasts. FIG. 24A Barrier Function (Permeability) as % of 3 kDa Dextran leakage). FIG. 24B shows exemplary florescent microscope images of the epithelial cell layer. E-cadherin and nuclei, left. ZO-1 and nuclei, right. Upper images show z-stacked side views of the epithelial layer.

FIG. 25A-G demonstrates exemplary florescent microscope images demonstrating subtypes of Enteroendocrine cells. FIG. 25A shows exemplary Enteroendocrine cells identified by chromogranin A (CHGA). FIG. 25B shows exemplary L-cells identified by glucogon. FIG. 25B shows exemplary Enterochromaffin cells identified by 5-HT. Stained DNA (Nuclei) are indicated as is E-cadherin. FIG. 25D shows an exemplary confocal microscope immunostained image over view of epithelial morphology in co-culture with fibroblasts showing goblet cells. E-cadherin, Muc2, nuclei are also shown. FIG. 25E shows an exemplary phase contrast microscope image merged with data from a florescent image of tissue as in FIG. 25D, where goblet cells stained with MUC2 are shown. Goblet cells are forming in between villi-like structures, examples which are indicated with white arrows. FIG. 25F shows an exemplary phase contrast microscope image over the entire main channel showing homogenous 3D villi-like structure formation where epithelium in direct contact with fibroblasts. FIG. 25G shows an exemplary phase contrast microscope image over the entire main channel showing 3D villi-like structures form in scattered areas of the chip where epithelium separated from fibroblasts with the PDMS membrane. The area outlined is enlarged in the lower image.

FIG. 29A shows exemplary fluorescent micrographs of L cells within intestinal epithelial layers on chip. Upper micrograph shows nuclei staining within a microfluidic channel. Middle micrograph shows an epithelial layer within a microfluidic channel at higher magnification. Lower micrographs show an L cell (Glucagon) with Nuclei shown in blue, left, a L-cell (Glucagon), middle, and Nuclei shown, right. FIG. 29B shows a chart of L-cell numbers. FIG. 29C shows comparative charts of L-cell function as exemplary GLP-1 secretion in response to stimulation with 10 μm Fsk/IBMX. L-cells account for 1% (1.67+/−0.89) of intestinal epithelial cells types in Colon On-Chip release GLP-1 in response to Forskolin/IBMX stimulation.

FIG. 37A is one embodiment of a fluidic Ileum Intestine-Chip showing comparative mRNA expression of specialized cell biomarkers for absorptive enterocytes (ALPI); Goblet cells (MUC2); Goblet cells (TFF3); and Paneth cells (LYZ). 1-step; 2-step and in vivo Ileum. FIG. 37B is one embodiment of a fluidic Ileum Intestine-Chip showing comparative mRNA expression of specialized cell biomarkers for enteroendocrine cells (CHGA); L-cells (monoclonal antibody GCG, detects proglucagon, glucagon, GLP-1 and GLP-2); L-cells (PYY); and enterochromaffin cells (TPH1).

FIG. 39A shows an exemplary micrograph representing a cluster of Ileal enteroids embedded in Matrigel in 1 well of a 24-well plate in which organoids were grown embedded in ECM gel and overlaid with IntestiCult™ media. FIG. 39B shows an exemplary micrograph representing endothelial cells grown in flask filled with EGM2-MV media.

FIG. 40A Bright field microscopy image. FIG. 40B confocal microscopy image with stains highlighting F-actin and cell nuclei.

FIG. 41A confocal microscopy images: epithelium without HIMECs, upper images, epithelium with HIMECs with stains highlighting ZO-1 and cell nuclei. FIG. 41B shows exemplary barrier function comparisons between 2 embodiments of Intestin-chips.

FIG. 43A shows one embodiment of an Ileum-Chip (with HIMECs) and FIG. 43B shows exemplary Ileal enteroids. In one embodiment, the Ileum-Chip and Ileal enteroids were analyzed at day 4, 8 and 12 of post-seeding.

FIG. 45A from left to right, by cell type and biomarker: absorptive enterocytes (ALPI); goblet cells (MUC2); Enteroendocrine Cells—EEC (CHGA). FIG. 45B from left to right, by cell type and biomarker: L-cells (GCG); L-cells (PYY); Enterochromaffin Cells (TPH1).

FIG. 48A from left to right, by cell type and biomarker: absorptive enterocytes (ALPI); goblet cells (MUC2); and goblet cells (TFF3). FIG. 48B from left to right, by cell type and biomarker: Enteroendocrine Cells—EEC (CHGA); L-cells (GCG); and Enterochromaffin Cells (TPH1). FIG. 48C from left to right, by cell type and biomarker: Paneth Cells (LYZ); Stem cells (LGR5) and a proliferation biomarker Ki67. FIG. 48D one of the three biomarkers for Tuft Cells (TRPM5); mRNA for the other two markers ChAT and DCLK1 were not detected.

FIG. 49A from left to right, by cell type and biomarker: goblet cells (MUC2); Enteroendocrine Cells—EEC (ChrgA)/L-cells (GLP-1); Enterochromaffin Cells (5HT). FIG. 49B from left to right, by cell type and biomarker: Paneth Cells (LYZ) and absorptive enterocytes (villin). Nuclei are stained.

FIG. 50A shows confocal immunostained images (overview upper panels with side views in the middle panel as z-stacks) demonstrating absorptive enterocytes with stains indicating (villin) and epithelial cells (E-cadherin), and nuclei colored grey-blue. There is less villin staining in the static condition, than in +flow or +flow+stretch conditions. Lower panels show scanning electron micrographs demonstrating contours (3D morphology) of the epithelial layers. FIG. 50B shows an exemplary graph of cell height (micrometers) when epithelial cells undergo exposure to flow (+/−stretch) resulting in columnar morphology and increased cell height. FIG. 50C shows a graph of increasing microvilli density when epithelial cells undergo exposure to flow (+/−stretch).

FIG. 51A shows an exemplary immunofluorescent micrograph of an entire main channel immunostained for ZO-1 and VE-cadherin (vascular endothelial cadherin) also known as CD144) in the upper panel (bar=1000 μm) while the lower right panel shows ZO-1 staining at a higher magnification (bar=100 μm). FIG. 51B shows exemplary induction of barrier function over time for duodenum cells derived from enteroids grown from biopsies obtained from 3 different human adult donors.

FIG. 52A-B shows exemplary duodenum Intestine-Chips possess physiological ratios of major differentiated intestinal cell types shown in immunostained confocal microscopy images and measured by relative mRNA expression compared to a duplicate cell sample used for seeding duodenal enteroids into chips. FIG. 52A shows confocal immunostained images demonstrating cell types and biomarkers from left to right: Goblet Cells (MUC2+) in contrast to epithelial cells (E-cadherin); Enteroendocrine Cells (chromogranin A-CHGA) in contrast to epithelial cells (E-cadherin); absorptive enterocytes (villin) in contrast to epithelial cells (E-cadherin); and Paneth Cells (LYZ) in contrast to epithelial cells (E-cadherin). Nuclei are stained. FIG. 52B shows graphical comparisons of percentages of biomarkers in duodenum Intestine-Chips compared to in vivo amounts (in vivo referenced from: Karam S M. Front Biosci 1999, 4:D286-298). Cell types and biomarkers from left to right: Goblet Cells (MUC2+); Enteroendocrine Cells (chromogranin A-ChrgA); absorptive enterocytes (villin); and Paneth Cells (LYZ).

FIG. 53A shows exemplary absorptive enterocytes (ALPI); goblet cells (MUC2). FIG. 53B shows exemplary Enteroendocrine Cells—EEC (CHGA); Paneth Cells (LYZ). FIG. 53C shows exemplary stem cells (LGR5) and a proliferation biomarker Ki67.

FIG. 55A shows (left) confocal microscopy z-stacks (side views) of monolayers stained for MDR1 (P-gp), villin and merged areas white. Lower panels show villi-like structures. Graphs on the right show comparative biomarker stain intensity from left to right along the x-axis moving away from the membrane. Villi-like structures show strong signal overlap (co-localization) of MDR1 with an apical marker (Villin). FIG. 55 B shows comparative Rhodamine 123 (RFU) accumulation when an inhibitor of MDR1 transport (DMSO) and (DMSO+vinblastine) is used to treat duodenal Intestine-Chips.

FIG. 56A shows (left) confocal microscopy z-stacks (side views) of monolayers stained for PEPT1), villin and merged areas white. Lower panels show villi-like structures. Graphs on the right show comparative biomarker stain intensity from left to right along the x-axis moving away from the membrane. Neither monolayers nor villi-like structures show strong signal overlap (co-localization) of PEPT1 with an apical marker (Villin). FIG. 56B shows (left) confocal microscopy z-stacks (side views) of monolayers stained for BCRP, villin and merged areas white. Lower panels show villi-like structures. Graphs on the right show comparative biomarker stain intensity from left to right along the x-axis moving away from the membrane. Neither monolayers nor villi-like structures show strong signal overlap (co-localization) of BCRP with an apical marker (villin).

FIG. 57A shows relative CYP3A4 expression in vivo duodenum compared to duodenum Intestine-chip (enteroids) and Intestine-Chip (Caco-2). FIG. 57B shows relative protein levels of CYP3A4, using GAPDH as a loading amount control, measured by Western blots.

FIGS. 58A-C shows exemplary in vivo-like Expression of Nuclear Receptors and a Drug Metabolism Enzyme between embodiments of Intestine-Chips. Average expression of nuclear receptors and drug metabolism enzyme CYP3A4 is much closer to in vivo values in Duodenum enteroids-derived Intestine-Chip than in Intestine-Chip based on the use of Caco-2 cells. Furthermore, Rifampicin treatment failed to induce CYP3A4 expression in Caco2 cells. FIG. 58A shows relative mRNA expression of CYP3A4; PXR; and VDR between in vivo Duodenum; Duodenum Intestine-Chip (enteroids); and Intestine-Chip (Caco-2). FIG. 58B shows relative mRNA expression of CYP3A4 in one embodiment of an Intestine-Chip (Caco-2) and FIG. 58C an embodiment of a duodenum Intestine-Chip (enteroids) treated with DMSO: RIF—20 microM rifampicin; VD3—100 nM 1,25-dihidroxyvitamin. GAPDH is a loading amount control.

FIG. 59A shows a confocal micrograph left, showing a z-stack side view below. The graph on the right of fluorescence intensity moving away from the membrane on the x-axis, shows no signal overlap with basolateral marker (E-cadherin). CYP3A4; E-cadherin. FIG. 59B shows a confocal micrograph left, showing a z-stack side view below. The graph on the right of fluorescence intensity moving away from the membrane on the x-axis, shows strong signal overlap with apical marker (Villin). CYP3A4; villin.

FIG. 61A shows exemplary mRNA induction of PXR under a combination of flow and stretch that was decreased by exposure to Rifampicin (Rif).

FIG. 61B shows exemplary mRNA induction of CYP3A4 under a combination of flow and stretch that was decreased by exposure to Rifampicin (Rif). FIG. 61C shows exemplary mRNA induction of MDR1 under a combination of flow and stretch that was decreased by exposure to Rifampicin (Rif).

FIG. 63A shows an exemplary micrograph representing a cluster of human colon enteroids. FIG. 63B shows an exemplary micrograph representing human intestinal microvascular endothelial cells (HIMEC) from colon. FIG. 63C shows an exemplary 2-step timeline for providing one embodiment of a Colon Intestine-Chip.

FIG. 64A shows a confocal microscope image of an overview (looking down) of colonic-enteroids epithelium on-chip demonstrating folds and pouches where Phallodinn (f-actin) is stained and nuclei are stained. FIG. 64B shows a low power micrograph of the epithelial channel, left, where the area outlined in white is shown at higher power to the right. Phallodin (F-actin) staining and nuclei staining.

FIG. 65A shows barrier function comparisons between colonic epithelium without endothelium vs. one embodiment of Colon On-Chip (Colon-Chip seeded with endothelial cells. FIG. 65B shows that Epithelial Barrier Formation in one embodiment of Colon-Chips, where at least one chip was established from each of 3 donors, reached similar levels of intestinal barrier function over time.

FIG. 66A shows exemplary immunostaining of Absorptive enterocytes (Villin); and Goblet cells (MIC2). FIG. 66A shows exemplary immunostaining of EEC (ChgA) and EEC (ChgA)/L-cells immunostained with an anti-glucagon monoclonal antibody (GCG), for detection of proglucagon, glucagon, GLP-1 and GLP-2. DAPI stained nuclei are shown. Insets show areas at a higher magnification.

FIG. 67A shows exemplary goblet cell numbers (MUC2+per DAPI stained nuclei as a percentage, left, and ChgA+ EEC cells per DAPI stained nuclei (percentage), right. FIG. 67B shows exemplary ChgA+ EEC cells/GCG+ cells per DAPI stained nuclei (percentage). Insets show representative confocal images used for providing data, showing representative cell types. In vivo values reference from Karam, Front Biosci 1999, 4:D286-298); Lund, et al. Molecular Metabolism. 2018; 11:70-83; Petersen, et al. The Journal of Clinical Investigation. 2015:125(1):379-385.

FIG. 69A shows levels of mRNA measured from colon epithelial layers on at least 3 chips, each one from one of the 3 donors confirming TRPM5 mRNA expression. FIG. 69B shows that two of the three combined biomarkers for Tuft Cells (TRPM5 and ChAT) were present after immunostaining in confocal microscope images. FIG. 69C shows that Trpm5+/ChAT+ Tuft cells, a Takeda target cell type, are present in the Colon-Chip at physiological levels.

FIG. 70A shows a schematic of an exemplary timeline for evaluating ALI. FIG. 70B shows Human Intestinal Fibroblasts at day 3 of culture, left, and Human Colonic Epithelium at day 4, right.

GENERAL DESCRIPTION OF THE INVENTION

Figure 1A:
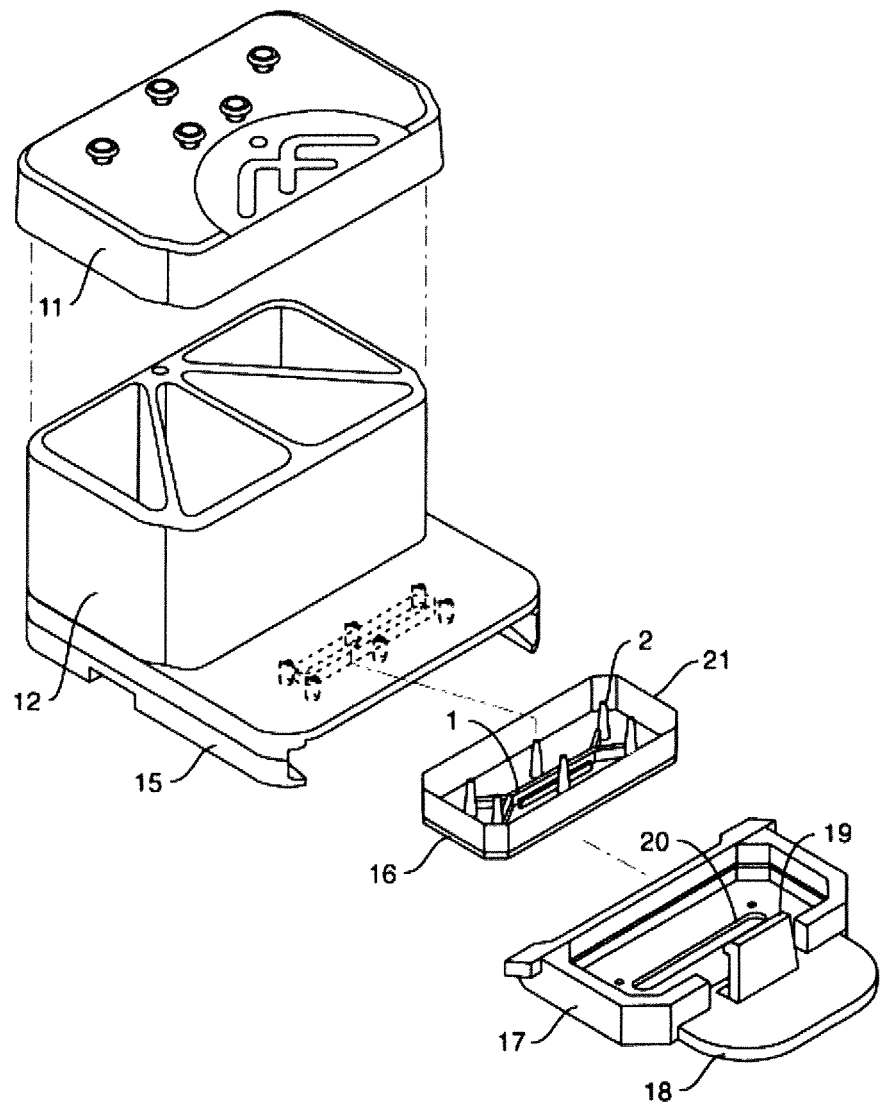
FIG. 1A-C illustrates the perfusion manifold assembly (10) comprises i) a cover or lid (11) configured to serve as to top of ii) one or more fluid reservoirs (12), iii) a capping layer (13) under said fluid reservoir(s), iv) a fluidic backplane (14) under, and in fluidic communication with, said fluid reservoir(s), said fluidic backplane comprising a fluidic resistor, and v) a projecting member or skirt (15) for engaging the microfluidic device (16) or chip which is preferably positioned in a carrier (17), the chip having one or more microchannels (1) and in fluidic communication with one or more ports (2). The assembly can be used with or without the lid or cover. Other embodiments (discussed below) lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels.

An in vitro microfluidic intestine on-chip is described herein that mimics the structure and at least one function of specific areas of the gastrointestinal system in vivo. In particular, a multicellular, layered, microfluidic intestinal cell culture, which is some embodiments is derived from patient's enteroids-derived cells, is described comprising L cells, allowing for interactions between L cells and gastrointestinal epithelial cells, endothelial cells and immune cells. This in vitro microfluidic system can be used for modeling inflammatory gastrointestinal autoimmune tissue, e.g., diabetes, obesity, intestinal insufficiency and other inflammatory gastrointestinal disorders. These multicellular-layered microfluidic intestine on-chips further allow for comparisons between types of gastrointestinal tissues, e.g., small intestinal duodenum, small intestinal jejunum, small intestinal ileum, large intestinal colon, etc., and between disease states of gastrointestinal tissue, i.e. healthy, pre-disease and diseased areas. Additionally, these microfluidic gut-on-chips allow identification of cells and cellular derived factors driving disease states and drug testing for reducing inflammation.

There is a lack of physiologically relevant in vitro system to study the biology and function of small intestinal and colonic enteroendocrine cells, in particular L-cells, as well as therapeutic modulation of the hormone release and production by these cells. Thus, the present inventions overcome these limitations by providing embodiments of an Intestine-Chip device system application to the discovery and development of new drugs for disease, including but not limited to diabetes, obesity and intestinal insufficiency.

As described herein, the present invention provides physiologically relevant models as embodiments of microfluidic intestine on-chip. In part, intestine on-chip was used for the studies of intestinal hormones production and release, including but not limited to chips comprising enteroendocrine cells, such as L-cells that produce glucagon-like peptide (GLP-1), L-cell modulation nutrients, and cellular responses to nonlimiting examples of bile acids, drug therapies and cyclic stretch.

I. Intestine On-Chip System.

A microfluidic chip system that emulates human intestine was developed as described herein, including but not limited to providing microfluidic chips comprising patient-derived primary cells having characteristics mimicking development and function of intestinal cells in vivo. More specifically, microfluidic intestine On-Chips have in vivo-like differentiation demonstrating morphological characteristics, such as cell shapes and cytoarchitecture, as observed in vivo, physiological relevant characteristics, such as strong barrier function, issue-tissue interactions, and responses to: stimulation and test agents, under varying physiological relevant conditions of mechanical stretch & dynamic flow. An Intestine On-Chip system is composed of, but not limited to: human primary intestinal epithelial cells, patient enteroids intestinal epithelial cells, epithelial cells derived from at least three areas of the intestine, endothelial cells, intestinal endothelial cells, etc., Further, a microfluidic intestine on-chip is provided developing at least four intestinal cell types on-chip. An intestine on-chip expresses numerous drug transporters including but not limited to drug related transporters; has reproducibility of cell types and function across multiple donors of cells for enteroids sources; and demonstrates genomic similarity to in vivo tissue with respect to several biological functions.

Thus, in some preferred embodiments, a microfluidic intestine on-chip provides a physiologically relevant microenvironment. It was also discovered that patient-derived cells retain donor phenotype when cultured in microfluidic chips. Thus, in some embodiments, a microfluidic intestine on-chip provides a matching Donor's Genetic Profile. In some embodiments, a microfluidic intestine on-chip enables Precision Medicine Ideal for Mechanistic Studies.

Moreover, microfluidic intestine on-chips were developed for modeling function of circulating immune cells, such as requirement to endothelial cells, i.e. attachment, the migrating through the endothelium of one channel into epithelial layers in a second channel. In some embodiments, Addition of Percoll increases media viscosity and improves immune cells-endothelium interaction.

A comparison was made of advantages of intestine on-chip with other in vitro systems related to intestinal cell in vitro. A microfluidic Intestine On-Chip, and use thereof, overcomes limitations of at least the two systems described below, with additional nonlimiting advantages of having growing intestinal cells from desired regions of the intestine, and further providing culture conditions/uses: intestine dynamic fluid flow; cyclic stretch motions; easy to handle (easy access to apical and basal compartment); versatile and tunable; readily integrated with a multitude of different organs; ideal for mechanistic studies; and allows personalized medicine using minimal sample size, e.g. small biopsy, small numbers of cells.

Figure 9:
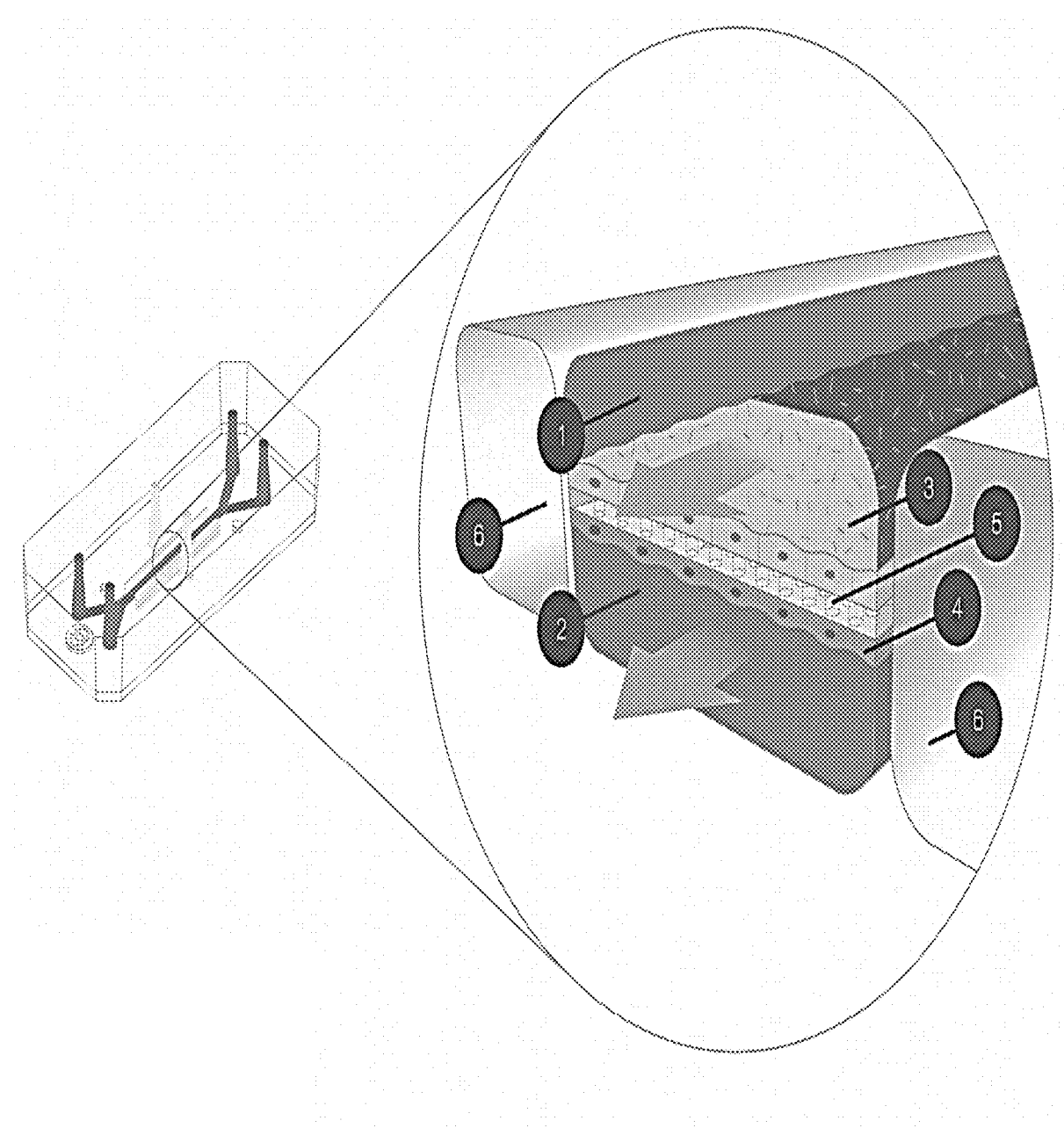
FIG. 9 shows an exemplary schematic representation of one embodiment of a microfluidic chip: 1. Epithelial Channel; 2. Vascular Channel; 3. Human Primary Intestinal Epithelial Cells; 4. Human Intestinal Microvascular Endothelial Cells (HIMEC) or iHIMEC, etc.); 5. Membrane; and 6. Vacuum Channels.

FIG. 9 shows an exemplary schematic representation of one embodiment of a microfluidic chip: 1. Epithelial Channel; 2. Vascular Channel; 3. Human Primary Intestinal Epithelial Cells; 4. Human Intestinal Microvascular Endothelial Cells (HIMEC); 5. Membrane; and 6. Vacuum Channels.

Figure 10:
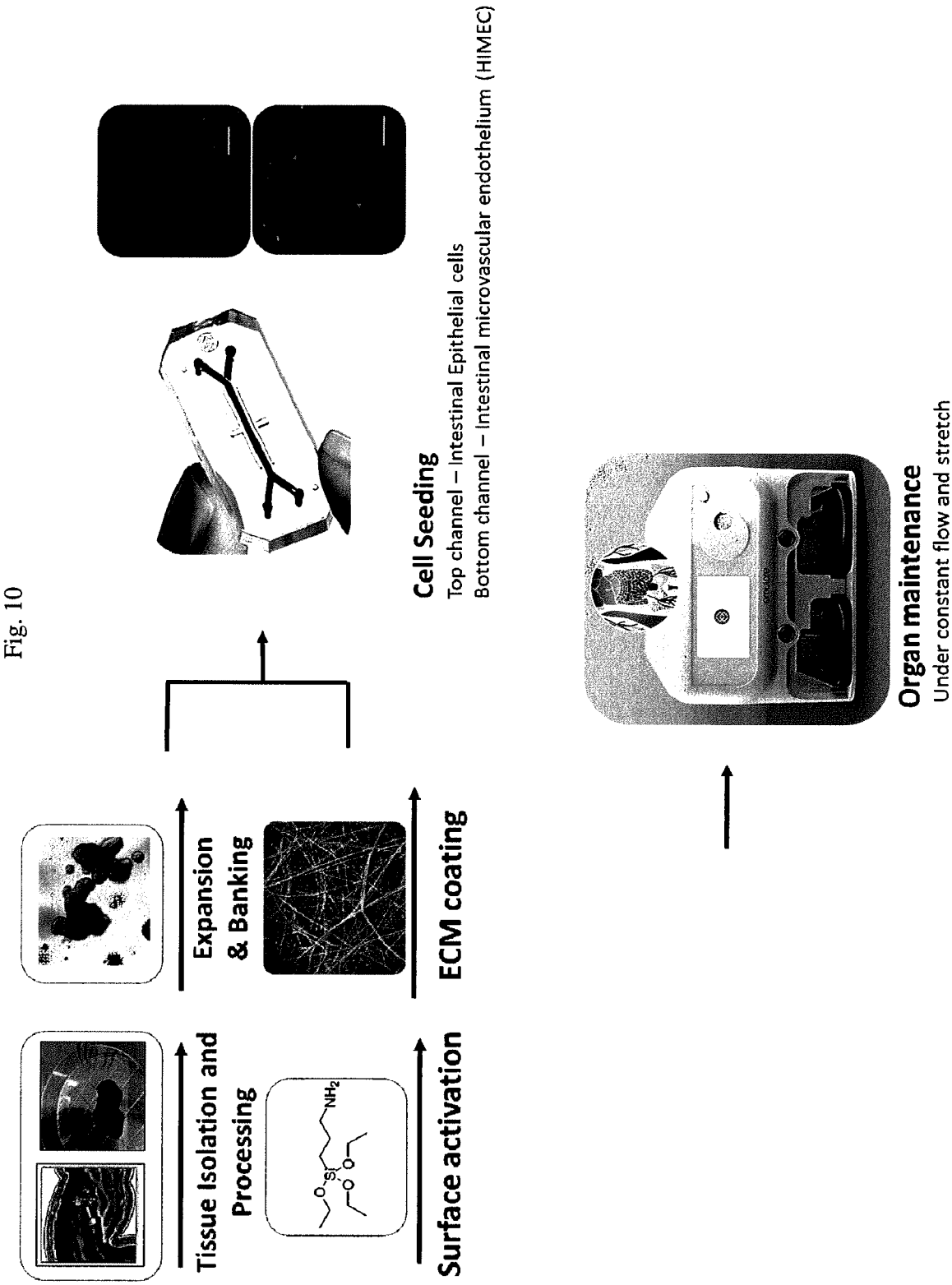
FIG. 10 shows an exemplary schematic representation along with representative photographs and micrographs for preparing one embodiment of a microfluidic Intestine-Chip where methods of (left to right) tissue isolation and processing; expansion & banking provide cells used to seed: a Top channel—Intestinal Epithelial cells forming an epithelium and Bottom channel—Intestinal microvascular endothelium (HIMEC) incubated (organ maintenance) under constant flow and certain membrane stretch conditions. Prior to cell seeding, the chip membrane was surface activated then ECM coated. Lower images show morphology of the epithelial cell layer exposed to flow over time (left 3 images) compared to the same time period, 12 days of incubation, under static culture. Thus, in this co-culture setup we observed the spontaneous 3D villi formation that doesn't occur in the static culture. We have successfully maintained this microfluidic co-cultures for over 3 wk with no loss of phenotype.
Figure 10:
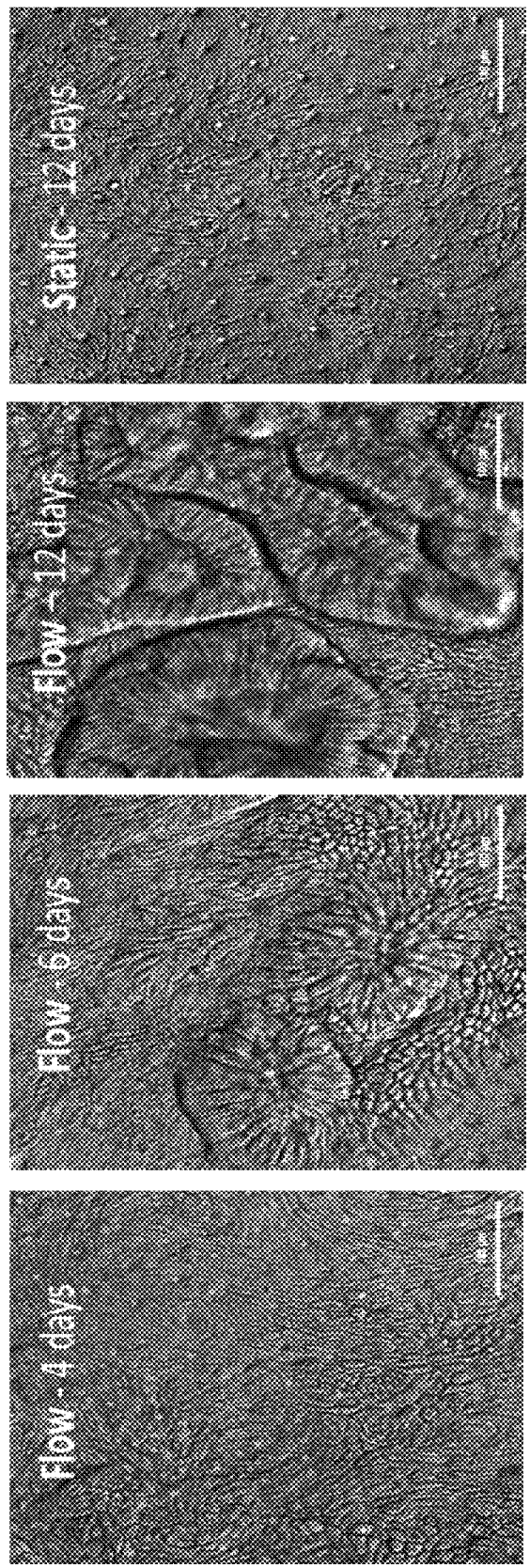

FIG. 10 shows an exemplary schematic representation along with representative photographs and micrographs for preparing one embodiment of a microfluidic Intestine-Chip where methods of (left to right) tissue isolation and processing; expansion & banking provide cells used to seed: a Top channel—Intestinal Epithelial cells forming an epithelium and Bottom channel—Intestinal microvascular endothelium (HIMEC) incubated (organ maintenance) under constant flow and certain membrane stretch conditions. Prior to cell seeding, the chip membrane was surface activated then ECM coated. Lower images show morphology of the epithelial cell layer exposed to flow over time (left 3 images) compared to the same time period, 12 days of incubation, under static culture. Thus, in this co-culture setup we observed the spontaneous 3D villi formation that doesn't occur in the static culture. We have successfully maintained this microfluidic co-cultures for over 3 wk with no loss of phenotype.

In contrast, Caco-2 cells, although easy to use and providing reproducible data, (and are cost effective and used extensively for ADME/Tox screening and drug response assays, and are useful for prototyping), have numerous disadvantages. Disadvantages include but are not limited to: being tumor derived cells from one region of the intestinal tract, i.e. human epithelial colorectal adenocarcinoma cells, that under certain culture conditions differentiate into a polarized monolayer containing small intestinal enterocyte-like cells. However in contrast to human primary epithelium, Caco-2 cells nor their differentiated cell layers, do not possess functional intestinal cell types such as goblet cells, enteroendocrine cells, Paneth cells etc. Thus, Caco-2 cells do not provide healthy cells representing regions of the intestinal tract, and are not applicable for personalized medicine, in part due to differences between these Caco-2 tumor cells from the colorectal region in a cancer patient, compared to intestinal cells provided by patients with differences in genotypes and phenotypes, differences in cells between regions of the intestinal tract, etc. Further, when growing these cancer cells in a Transwell culture, as a representative static system, this system has additional limitations when used for growing and testing Caco-2 Cells (tumor cells) due in part to a lack of mechanoactive environment, e.g. lack of fluid flow, stretch, etc.

Figure 11A:
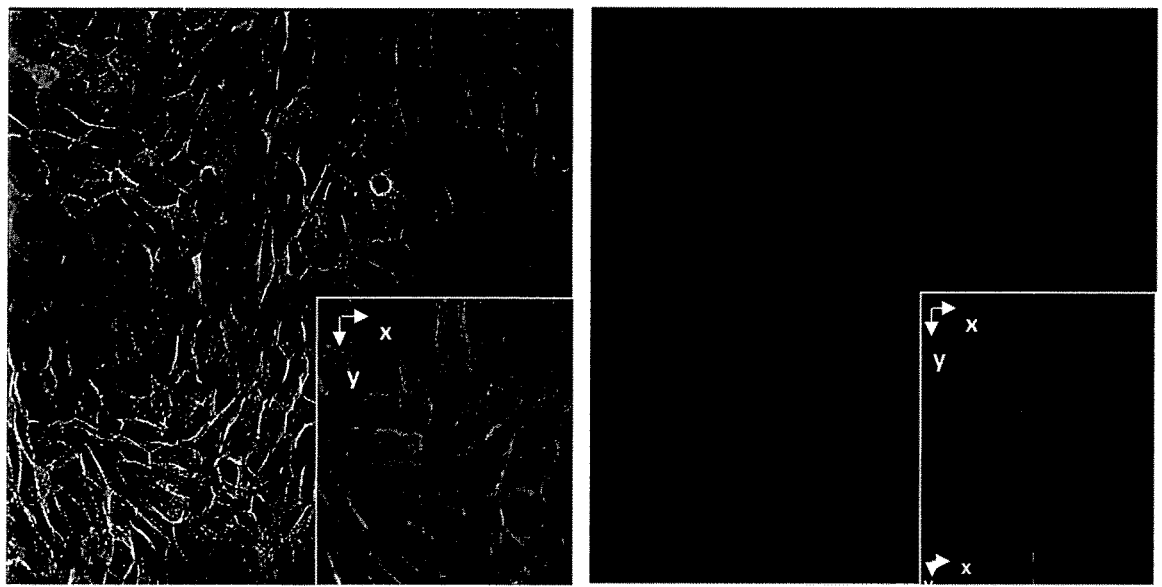
FIG. 11A-B shows exemplary fluorescent micrographs of an intestinal cell layer grown without flow on-chip vs. under flow on-chip (stained at the same time) demonstrating that epithelial morphology is improved by dynamic culture, i.e. microenvironment. Cultures grown without flow are shown in FIG. 11A where squamous cell morphology is flat and has a poorly polarized epithelial monolayer; weakly defined cell-cell junctions; and have an average cell height 10.42±0.8 μm. Actin stains indicating cell structures and E-cadherin stains indicating string like structures. Cultures grown with flow are shown in FIG. 11B where cells form a highly polarized dense epithelial monolayer; have strongly delineated cell-cell junctions; have an average cell height 23.55±0.7 μM. E-cadherin stains indicating string like structures and nuclei stains highlighting cell centers. Cultures were assessed at 24 hours after initiation of flow. Insets show confocal microscopic images at a higher magnification.
Figure 11B:
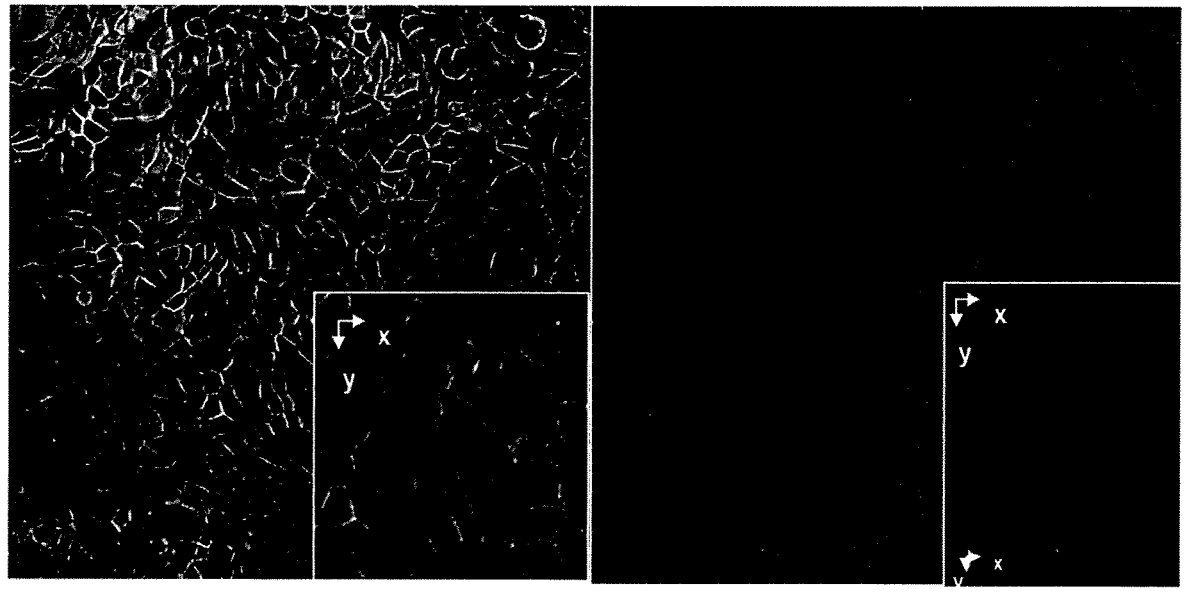

FIG. 11A-B shows exemplary fluorescent micrographs of an intestinal cell layer grown without flow on-chip vs. under flow on-chip (stained at the same time) demonstrating that epithelial morphology is improved by dynamic culture, i.e. microenvironment. Cultures grown without flow are shown in A where squamous cell morphology is flat and has a poorly polarized epithelial monolayer; weakly defined cell-cell junctions; and have an average cell height $10.42\pm0.8$ μm. Actin E-cadherin. Cultures grown with flow are shown in B where cells form a highly polarized dense epithelial monolayer; have strongly delineated cell-cell junctions; have an average cell height $23.55\pm0.7$ μm. E-cadherin and nuclei. Cultures were assessed at 24 hours after initiation of flow. Insets show confocal microscopic images at a higher magnification.

Also in contrast, 3D enteroid cultures derived from human primary cells has advantages, in part, of providing cells isolated from different intestinal regions, capable of use in personalized medicine, has cells showing In vivo-like differentiation, and a transcriptional profile enabling studies of stem cell activity has limitations, in part, of a lack of accessible lumen; lack of mechanoactive environment for growing/culturing cells, a lack of tissue-tissue interface, and reduced ability to increase complexity, such as described herein in numerous embodiments.

Figure 12:
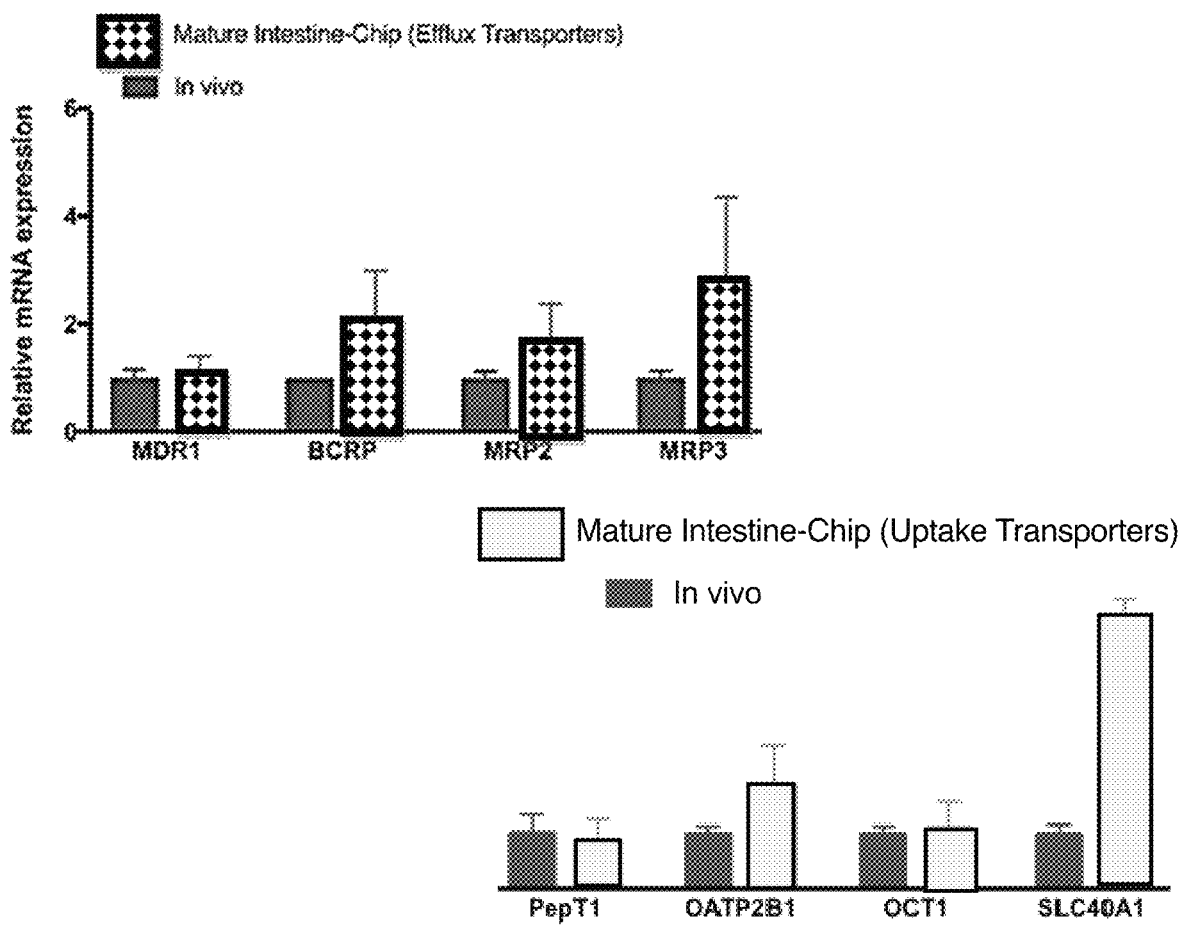
FIG. 12 shows exemplary comparative charts of epithelial cell drug transporter molecules demonstrating that drug transporter are present in the cells in the microfluidic device at the levels observed in in vivo tissue. Average expression of major intestinal drug transporters reached similar levels in Intestine-Chips as in native human intestine. Left, Efflux transporter (pink) and left uptake transports (blue). The lower schematic shows apical and basal expression of transporter molecules in an intestinal epithelial cell. Intestinal epithelia contain in their apical (luminal) membrane several uptake transporters including one or more members of the organic anion transporting polypeptide (OATP) family; peptide transporter 1 (PEPT1; SLC15A1); ileal apical sodium/bile acid co-transporter (ASBT; SLC10A2); and monocarboxylic acid transporter 1 (MCT1; SLC16A1). The apical ATP-dependent efflux pumps include multidrug resistance protein 2 (MRP2; ABCC2); breast cancer resistance protein (BCRP; ABCG2); and P-glycoprotein (P-gp; MDR1, ABCB1). The basolateral membrane of intestinal epithelia contains organic cation transporter 1 (OCT1; SLC22A1); heteromeric organic solute transporter (OSTα-OSTβ); and MRP3 (ABCC3).
Figure 12:
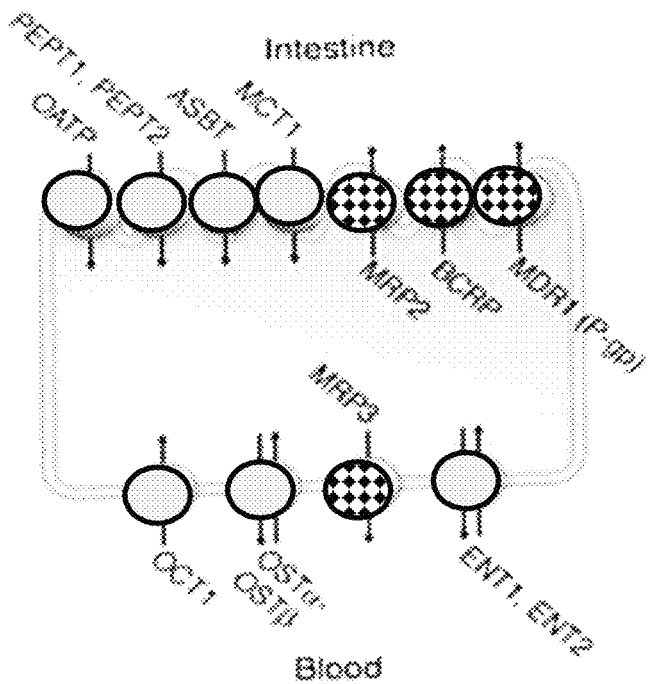

Moreover, FIG. 12 shows exemplary comparative charts of epithelial cell drug transporter molecules demonstrating that drug transporter are present in one embodiment of an intestine on-chip at the levels observed in in vivo tissue. Average expression of major intestinal drug transporters reached similar levels in Intestine-Chips as in native human intestine. Left, Efflux transporter (pink) and left uptake transports (blue). The lower schematic shows apical and basal expression of transporter molecules in an intestinal epithelial cell. Intestinal epithelia contain in their apical (luminal) membrane several uptake transporters including one or more members of the organic anion transporting polypeptide (OATP) family; peptide transporter 1 (PEPT1; SLC15A1); ileal apical sodium/bile acid co-transporter (ASBT; SLC10A2); and monocarboxylic acid transporter 1 (MCT1; SLC16A1). The apical ATP-dependent efflux pumps include multidrug resistance protein 2 (MRP2; ABCC2); breast cancer resistance protein (BCRP; ABCG2); and P-glycoprotein (P-gp; MDR1, ABCB1). The basolateral membrane of intestinal epithelia contains organic cation transporter 1 (OCT1; SLC22A1); heteromeric organic solute transporter (OSTα-OSTβ); and MRP3 (ABCC3).

Thus, human intestine is a site for the absorption and metabolism of orally applied medications. We showed that Intestine-Chip (describe herein) can be used as a powerful tool in drug development since major drug transporters are present at the levels observed in in vivo tissue. One function intestine is to absorb nutrients, passive and active transport. Shows expression of transporters shows utility in improved absorption assays, so methods to measure intestinal absorption by active transport, nutrients and drugs, efflux of drugs, possibly prevention of drug absorption, e.g. MRP2 as an efflux transporter.

Therefore, additional embodiments of intestine on-chips described herein, may be used for drug transporter and efflux evaluation. In particular, such use may be used in personal medicine, where such intestinal transporter molecules functioning individually or in combination epithelial cell layers may be different from person to person.

II. Intestine On-Chip.

In some embodiments, a microfluidic intestine on-chip comprises epithelium including but not limited to epithelial cells derived from: healthy cells, tumor-derived cells, biopsy-derived cells, enteroids derived cells, Caco2 cells, etc. In some embodiments, a microfluidic intestine on-chip comprises endothelial cells including but not limited to: Human Umbilical Vein Endothelial Cells (HUVEC), Human Intestinal Microvascular Endothelial Cells (HIMEC), healthy cells, tumor-derived cells, biopsy-derived cells, etc. In yet further embodiments, a microfluidic intestine on-chip additionally comprises Human Intestinal Fibroblasts, Immune Cell, ENS, Microbiome cells, etc. In particular, differences between HIMECs and HUVECs include but are not limited to HIMEC expression of MadCAM, unlike HUVECs which do not express MadCAM.

In some preferred embodiments for providing an intestine on-chip comprising L-cells, fibroblasts are added to chips comprising enteroids cells and HIMECs. In some embodiments for providing an intestine on-chip, chips comprise tumor-derived epithelium and human umbilical vein endothelial cells, as one example, chips comprising Caco2 cells and HUVECs.

In some embodiments, epithelial cells were cultured under Liquid-Liquid culture conditions. In some embodiments, epithelial cells were cultured under Air-Liquid culture conditions. In preferred embodiments, cells were cultured under fluid flow. In preferred embodiments, cells were cultured under stretch conditions.

A. Exemplary Embodiments of Small Intestine On-Chip.

In one embodiment, microfluidic chips are seeded with Enteroids, obtained from biopsied tissues of different intestinal regions through collaboration with hospitals (Adult tissue), See, Table 1, HUVEC and HIMEC, human small intestinal endothelial cells (Human Primary Umbilical Vein Endothelial Cells; Human Primary Small Intestinal Microvascular Endothelial Cells, respectively: commercially obtained from Cell Biologics).

TABLE 1

Sources of Enteroids.

| Number* | Intestinal Region | Age | Gender |
|---|---|---|---|
| 1 | Duodenum | 27 | F |
| 2 | Duodenum | 25 | F |
| 3 | Jejunum | 25 | F |
| 4 | Jejunum | 30 | F |
| 5 | Colon | 66 | M |

*Each number represents a different patient.

1. Cell Preparation for Experiments Unless Otherwise Described.
   a. For the Intestine-Chip (Enteroids), Human Small Intestinal Microvascular Endothelial Cells (HIMECs) are seeded into the bottom channel and allowed to attach prior to seeding the primary enteroids.
   b. Prepare cell suspension and count cell number.
   c. Seeding density is specific to the cell type.
      i. HIMECs: 9 million cells/nil.
      ii. After counting cells, adjust cell suspension to the appropriate density for seeding.
1. Bottom Channel Seeding (HIMECs)
Use ONE chip first—confirm seeding density before seeding other Chips
   a. Prior to seeding, wash each channel with 200 ul of cell culture medium.
   b. Pipette 30 cell culture media and insert in bottom inlet (Tips inserted).
   c. Agitate cell suspension gently before seeding each Chip to ensure a homogenous cell suspension.
   d. Pipette 30 ul of the cell suspension and seed into the top channel inlet (Tips inserted).
   e. Place Chip on a Petri dish and transfer to the microscope to check the density
   f. After confirming the cell density, seed cells in the rest of the Chips.
   g. Incubate inverted at 37 C for 30-45 min.
   h. After confirming good cell attachment wash bottom channel with 200 ul of cell culture medium.
3. Enteroids Preparation
   a. Recover enteroids.
      i. Transfer 24-well plate containing enteroids into hood.
      ii. Carefully aspirate media from each well without disturbing enteroids.
      iii. Pipette 500 ul Cell Recovery Solution (CRS) to each well.
      iv. Use a mini cell scrapper and mix the matrigel with the CRS to collect the enteroids.
      v. Use a 10 ml pipette and collect cells from 3 wells and transfer to a labeled 15 ml conical (Tube 1)—these cells will be used as your Cell at Seeding Control.
      vi. Use the same pipette and collect cells from appropriate number of wells (we suggest use of two wells of enteroids for seeding one chip) and transfer to a different 15 ml conical (Tube 2).
      vii. Incubate on ice for 45 min with frequent tube inversion every 10 minutes to dissolve Matrigel.
Chill the centrifuge to 4° C. before beginning
      viii. Centrifuge at 300 G, 5 min, 4° C.
      ix. Aspirate supernatant from 15 ml conical without disturbing pellet.
      x. Tap the conical to break the pellet and add the following to each tube:
         1. Tube 1: 300 ul Lysis Buffer and transfer to 1.5 ml Eppendorf tube (Store −80° C.).
         2. Tube 2: 2 ml Digestion Solution and transfer to water bath for 3-6 minutes with frequent tapping every 1 minute to break up enteroids.
      xi. After digestion, add 8 ml Advanced DMEM/F12 to Tube 2, invert, and centrifuge at same settings above.
      xii. Aspirate supernatant and resuspend enteroids in Expansion Media containing Rock Inhibitor (1:1000) and CHIR (1:2000) (EM+): The volume is determined by 35 ul of media used per one chip×n, where n is the number of chips.
4. Top Channel Seeding (Enteroids)
One chip was used first to confirm seeding density before seeding other Chips.
   a. Prior to seeding, wash each channel twice with 100 μl EM+.
   b. Pipette 35 μl of EGM2-MV and insert in bottom inlet (Tips inserted).
   c. Agitate Enteroids suspension gently before seeding each Chip to ensure a homogenous cell suspension.
   d. Pipette 35 μl of the Enteroids suspension and seed into the top channel inlet (Tips inserted).
   e. Place Chip on a petri dish and transfer to the microscope to check the density.
   f. After confirming the cell density, seed Enteroids in the rest of the Chips.
   g. Incubate at 37° C. overnight.
Expansion Medium (with ROCK and CHIR) in both input Reservoirs of each Pods for 3 days, then only Expansion Medium for remaining days.
Recommend changing medium every 24-48 hours, depending on cell type once flow is started.
5. Enteroid Expansion after Seeding into Chip.
Formulation for Expansion (EM; EM+) Table 2, and Differentiation media (DM) Table 3: Abbreviations: CM—Conditioned media, for use with enteroids, including colonoids.

TABLE 2

Expansion Media.

| Component | Volume (for 100 ml total) | Dilution factor | Final Concentration |
|---|---|---|---|
| EXPANSION MEDIA (EM) | | | |
| Wnt3A CM | 50 ml | 2x | 50% |
| Noggin CM | 10 ml | 10x | 10% |
| R-spondin CM | 20 ml | 5x | 20% |
| Advanced DMEM/F12 | 14.55 ml | — | — |
| Glutamax | 1 ml | 100x | 1x (2 mM glutamine) |
| HEPES | 1 ml | 100x | 10 mM (stock 1M; 100x) |
| Primocin | 200 μl | 500x | 0.1 mg/ml (stock 50 mg/ml) |
| B27 | 2 ml | 50x | 1x (stock 100x) |
| N2 | 1 ml | 100x | 1 x (stock 50x) |
| N-acetyl cysteine | 200 μl | 500x | 1 mM (stock 500 mM) |
| EGF | 10 μl | 10,000x | 50 ng/ml (stock 500 ug/ml) |

TABLE 2-continued

Expansion Media.

| Component | Volume (for 100 ml total) | Dilution factor | Final Concentration |
|---|---|---|---|
| Gastrin | 10 µl | 10,000x | 10 nM (stock 100 uM) |
| A-83-01 | 10 µl | 10,000x | 500 nM (stock 5 mM) |
| SB2001190 | 20 µl | 5,000x | 10 uM (stock 50 mM) |
| Total | 100 ml | — | — |
| ADDITIONAL COMPONENTS (EM+) | | | |
| ROCK inhibitor (Y27632) | 100 µl | 1,000x | 10 uM (stock 10 mM) |
| CHIR 99021 | 50 µl | 2,000x | 5 uM (stock 10 mM) |

6. Enteroid Differentiation.
   a. At day 4, aspirate media from both input Reservoirs and add 3 ml Differentiation Media.
   b. At day 6, replenish Differentiation Media in both input Reservoirs.

Formulation for Expansion (EM; EM+) and Differentiation media (DM): Abbreviations: CM—conditioned media.

Differentiation Medium (100 ml total), Table 3: In order to differentiate cells the following media components are removed: Wnt3A, SB2001190 and the concentration of R-spondin and Noggin C M (conditioned media) needs to be reduced to 10% and 5%, respectively. Notch inhibitor (DAPT) can be added to further enhance differentiation.

TABLE 3

Differentiation Medium.
DIFFERENTIATION MEDIA (DM)

| Component | Volume (for 100 ml total) | Dilution factor | Final Concentration |
|---|---|---|---|
| Noggin CM | 5 ml | 20x | 5% |
| R-spondin CM | 10 ml | 10x | 10% |
| Advanced DMEM/F12 | 79.57 ml | — | — |
| Glutamax | 1 ml | 100x | 1x (2 mM glutamine) |
| HEPES | 1 ml | 100x | 10 mM (stock 1M; 100x) |
| Primocin | 200 µl | 500x | 0.1 mg/ml (stock 50 mg/ml) |
| B27 | 2 ml | 50x | 1x (stock 100x) |
| N2 | 1 ml | 100x | 1 x (stock 50x) |
| N-acetyl cysteine | 200 µl | 500x | 1 mM (stock 500 mM) |
| EGF | 10 µl | 10,000x | 50 ng/ml (stock 500 µlg/ml) |
| Gastrin | 10 µll | 10,000x | 10 nM (stock 100 uM) |
| A-83-01 | 10 µll | 1,000x | 500 nM (stock 0.5 mM) |
| Total | 100 ml | — | — |

Figure 13A:
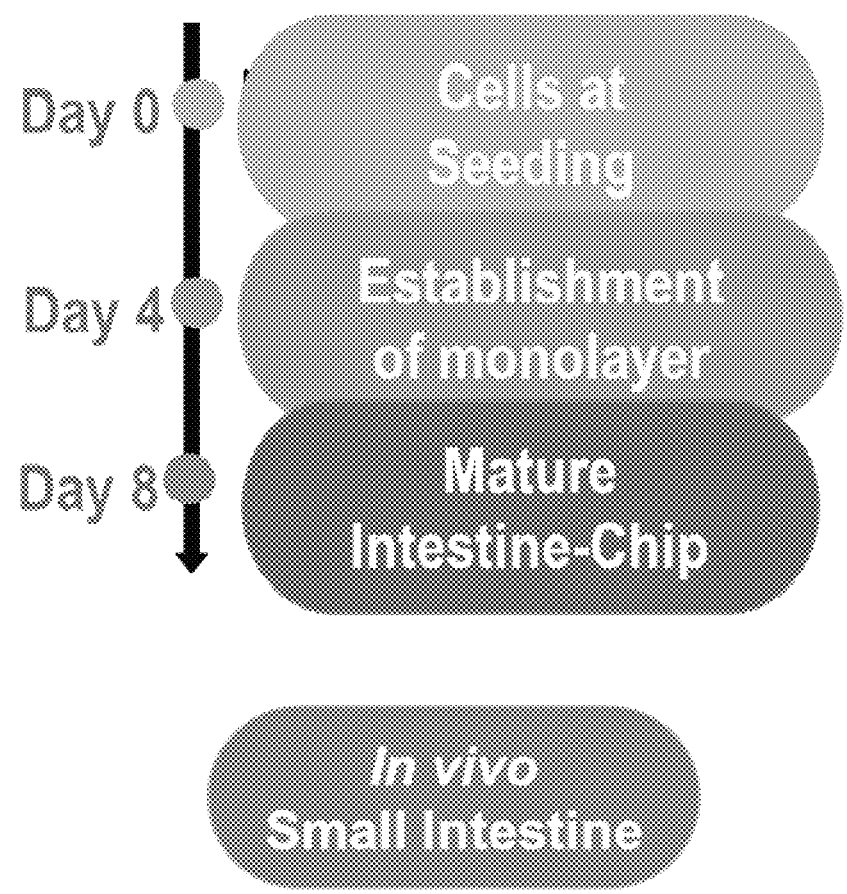
FIG. 13A-B shows an exemplary schematic representation of a timeline for seeding and growing cells (e.g. enteroids) in an intestine on-chip microfluidic device.
Figure 13B:
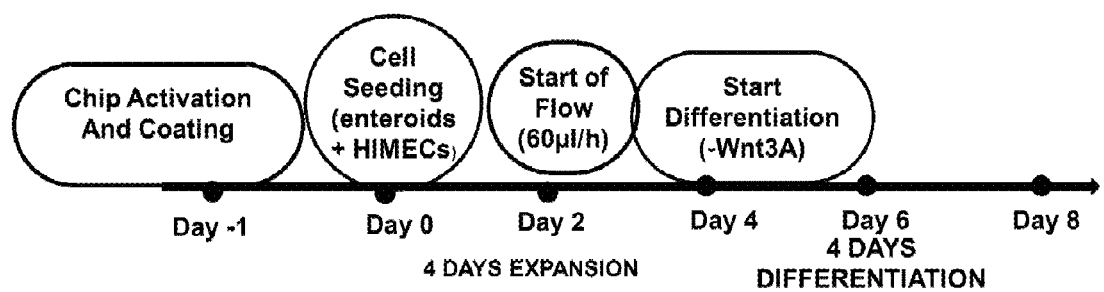
Figure 13B:
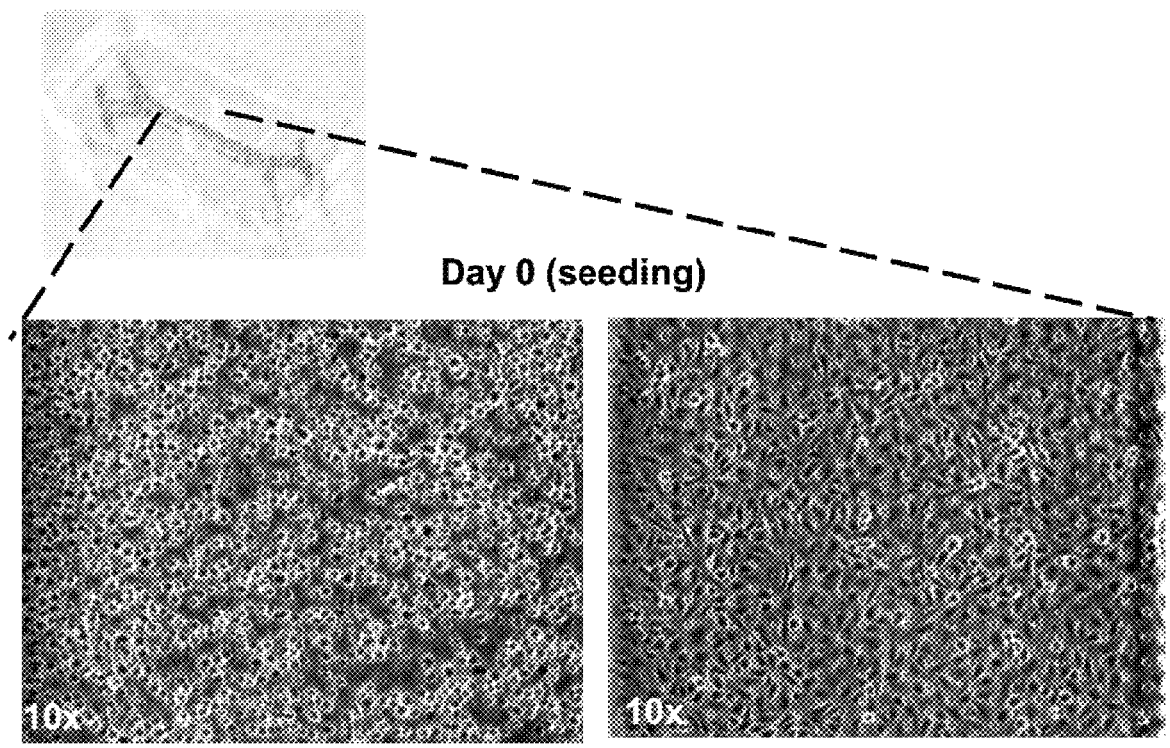

FIG. 13 shows an exemplary schematic representation of a timeline for seeding and growing cells (e.g. enteroids) in an intestine on-chip. A shows a morphology timeline after seeding cells. B shows an exemplary method starting by chip activation and ECM coating a day ~1 (the day before day 0), cell seeding the chip with HMECs and enteroids in expansion media for 4 days. Day 3 starting flow at 60 ul per hour. Day 4 switching media to differentiation media (e.g. removing Wnt3A) for 4 days. Lower photograph of a chip orientates the Bright-field (Imaging) showing images of cells on chip at Day 0 (seeding) upper channel left and lower channel right. Chips are then imaged at Days 2, 4, 6, and 8 for monitoring cell growth and morphology.

Figure 14:
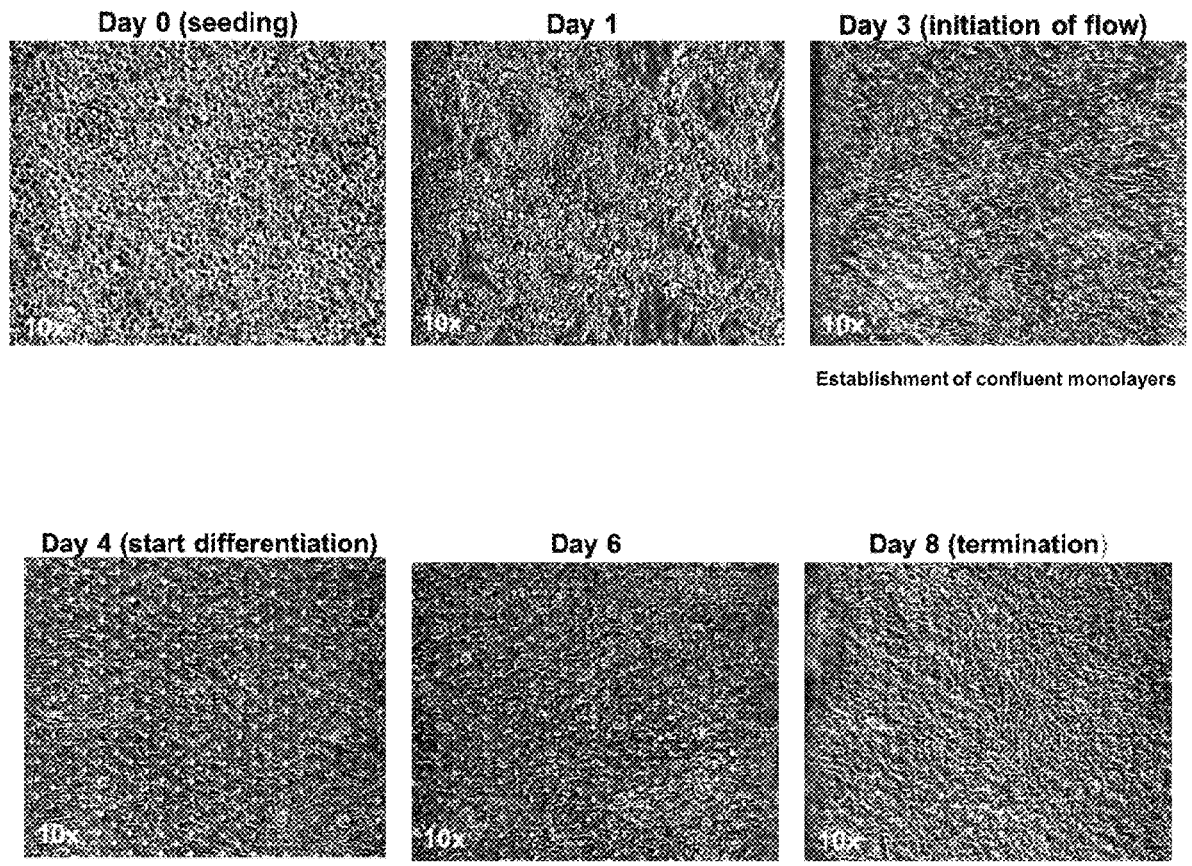
FIG. 14 shows bright-field micrographs over time, from the upper left panel at Day 0 to the lower right panel at Day 8, demonstrating development of a monolayer of cells in one embodiment of a microfluidic device. Initiation of flow is on Day 3 and observations of differentiation are on Day 4.

FIG. 14 shows bright-field micrographs over time, from the upper left panel at Day 0 to the lower right panel at Day 8, demonstrating development of a monolayer of cells in one embodiment of a microfluidic device. Initiation of flow is on Day 3 and observations of differentiation are on Day 4.

Figure 15A:
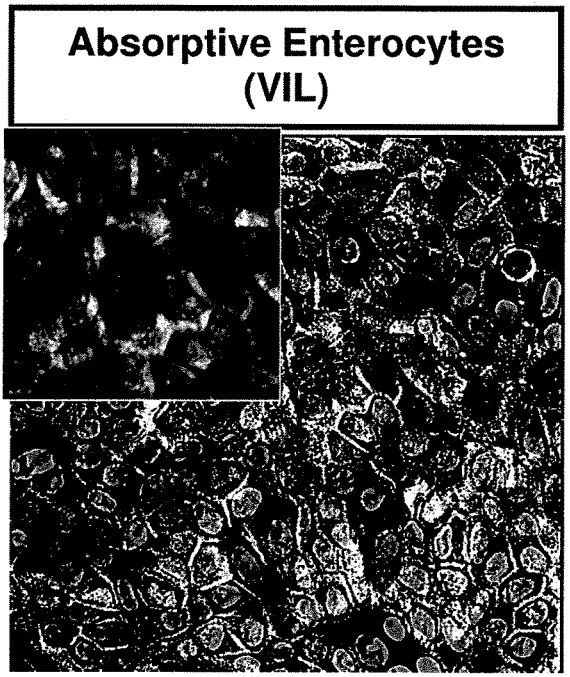
FIG. 15A-D shows exemplary colored fluorescent micrographs of an intestinal cell layer in a microfluidic device comprising at least 4 types of intestinal cells present by Day 8 after 4 days in differentiation media.
Figure 15B:
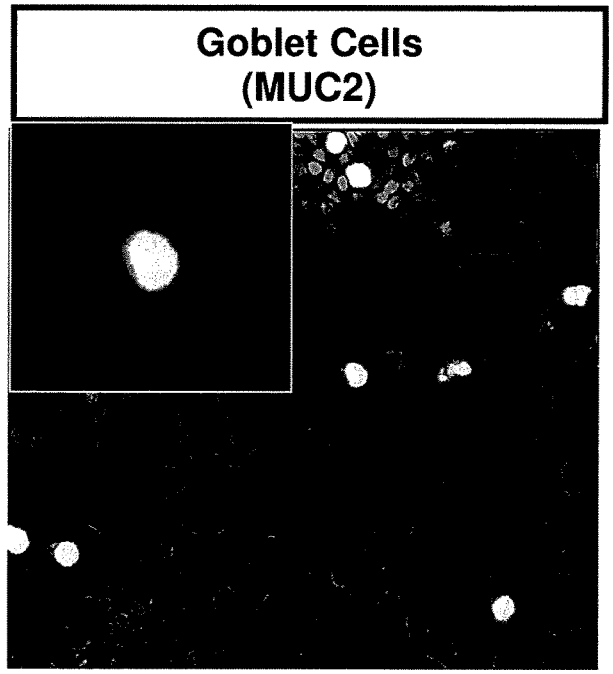
Figure 15C:
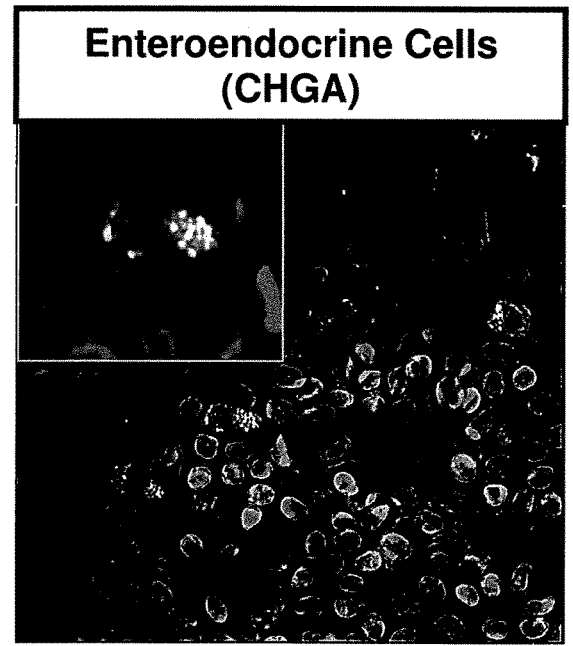
Figure 15D:
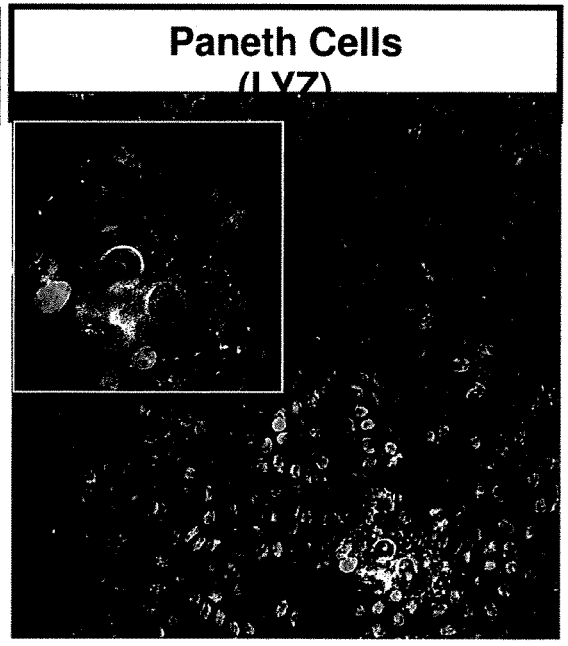

FIG. 15A-D shows exemplary fluorescent micrographs of an intestinal cell layer in a microfluidic device comprising at least 4 types of intestinal cells present by Day 8 after 4 days in differentiation media. FIG. 15A shows exemplary absorptive enterocytes identified by villin (VIL). FIG. 15B shows exemplary enteroendocrine cells identified by chromogranin A (CHGA). FIG. 15C shows exemplary goblet cells identified by mucin 2 (MUC2) and FIG. 15D shows exemplary Paneth cells identified by lysozyme (LYZ). Stained DNA (Nuclei) and E-cadherin are indicated.

Figure 16A:
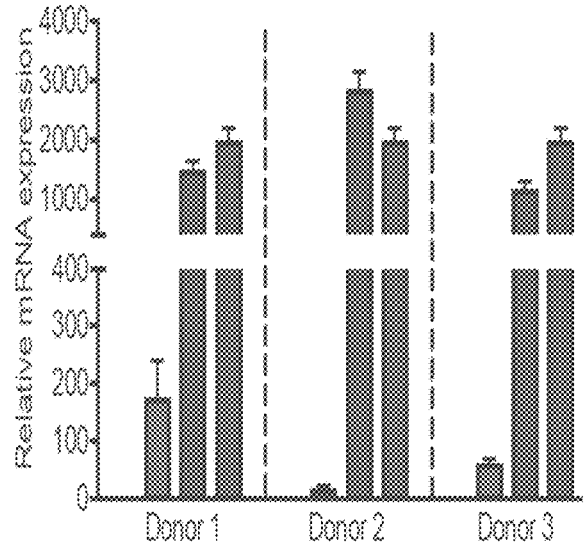
FIG. 16A-D shows Tissue Maturation by graphical comparison of development over time, left to right bars within each cell grouping, also across multiple different donors comparing development of cell types from 3 human donors. Enteroids derived from donor Biopsies were seeded onto chips showed physiologically relevant level of maturation in Intestine-Chip. Graphs represent mRNA expression levels of intestinal cell-type specific markers assessed at different days of Intestine-Chip growth (Day 4 and Day 8) in respect to the cells used for the Chip seeding. Commercially available RNA isolated from native human tissue (supplied by Amsbio) was used as a reference for In vivo Small Intestine.
Figure 16B:
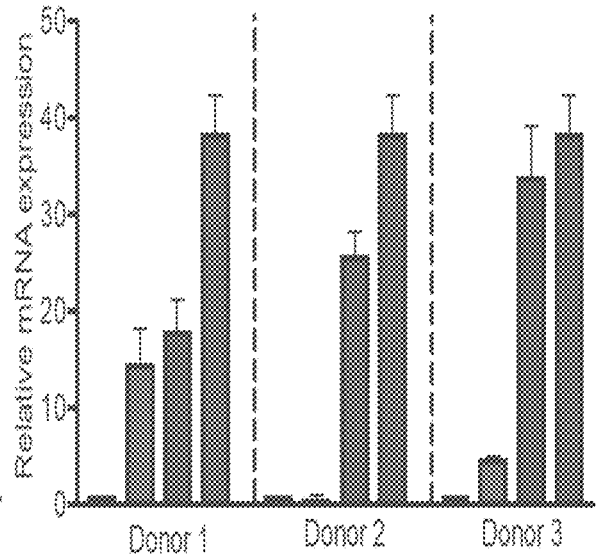
Figure 16C:
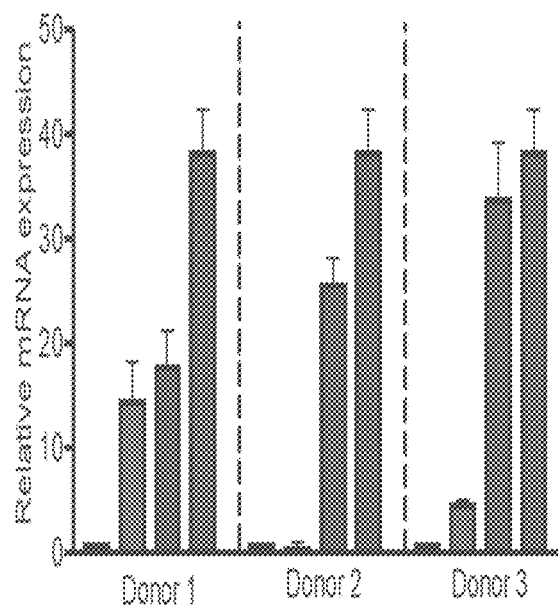
Figure 16D:
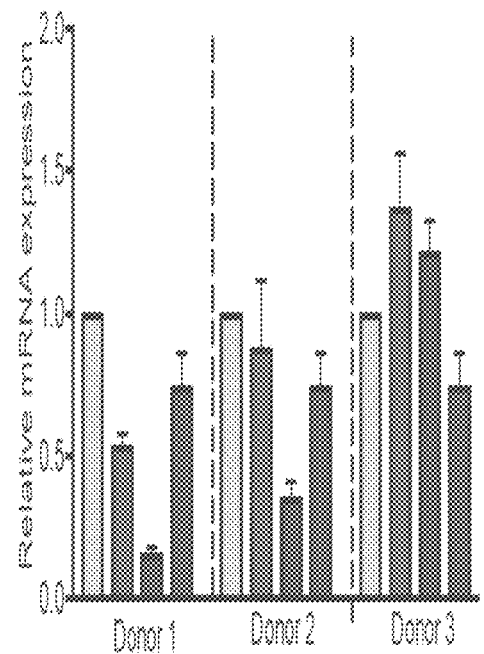

FIG. 16A-D shows Tissue Maturation by graphical comparison of development over time, left to right bars within each cell grouping, also across multiple different donors comparing development of cell types from 3 human donors. Enteroids derived from donor Biopsies were seeded onto chips showed physiologically relevant level of maturation in Intestine-Chip. Graphs represent mRNA expression levels of intestinal cell-type specific markers assessed at different days of Intestine-Chip growth (Day 4 and Day 8) in respect to the cells used for the Chip seeding. Commercially available RNA isolated from native human tissue (supplied by Amsbio) was used as a reference for In vivo Small Intestine. FIG. 16A shows exemplary Absorptive Enterocytes (ALPI). FIG. 16B shows exemplary Enteroendocrine cells identified by chromogranin A (CHGA). FIG. 16C shows exemplary Goblet cells identified by mucin 2 (MUC2) and FIG. 16D shows exemplary Paneth cells identified by lysozyme (LYZ). Absorptive Enteroendocrine cells do not develop as quickly as other intestinal cell types growing on-chip.

Produce antimicrobial peptides; secrete a wide range of peptide hormones; Release mucus protecting against chemical and biological Stress; Responsible for absorption of water, electrolytes and nutrients.

Figure 17:
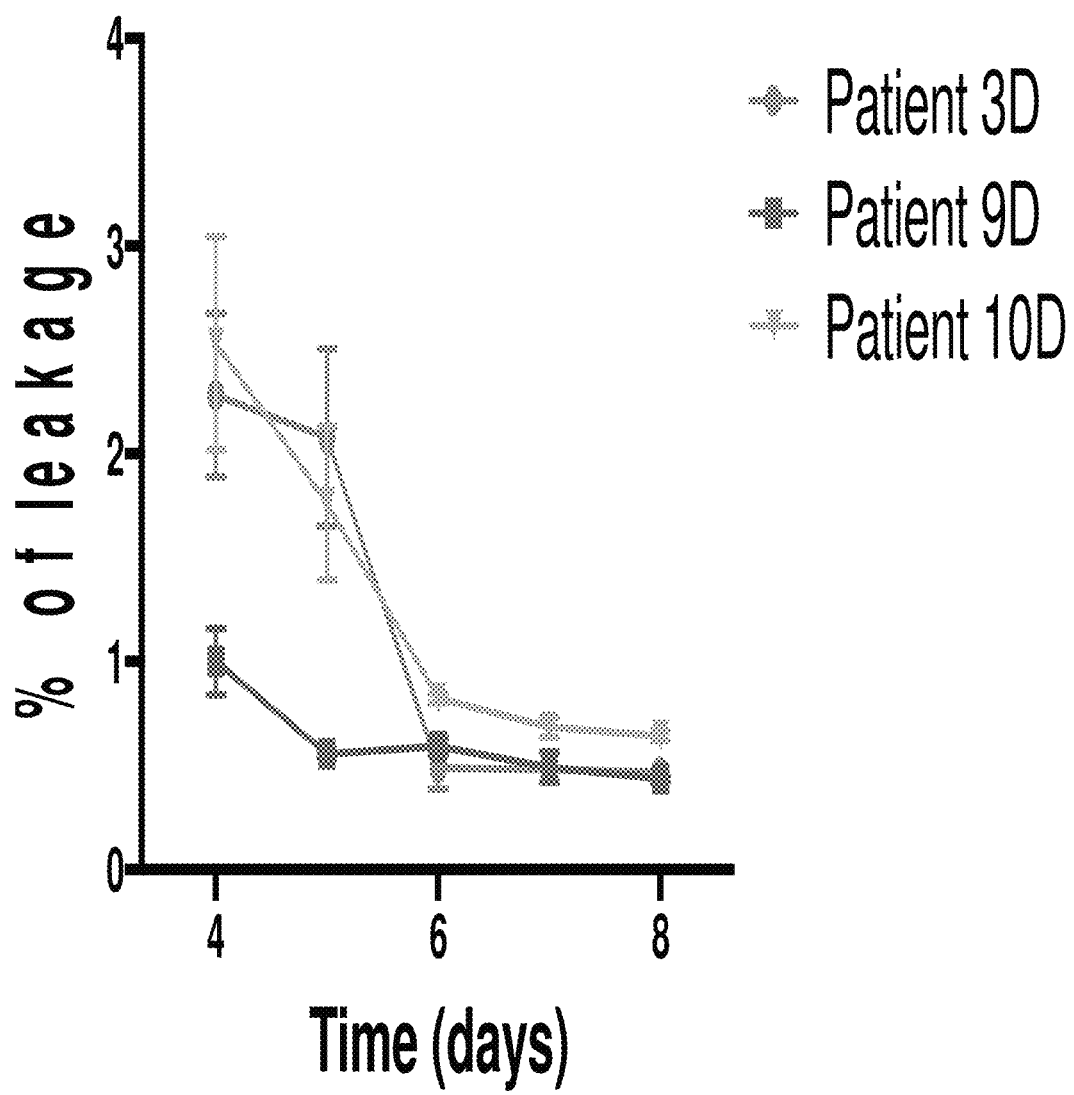
FIG. 17 shows the Formation of Intestinal Barrier Function in a microfluidic device confirmed Across Different Donors showing a graph of permeability changes over time, day 3-day 8. Intestine-Chips derived from biopsy of 3 independent donors achieved comparable levels of intestinal barrier function to Lucifer Yellow (~450 Da). Thus, an intact barrier is formed by day 6 of culture. Step A—at Day 3, include a dye molecule, e.g. Dextran (Cascade Blue) or Lucifer Yellow (~450 Da) in media of top input Reservoirs. Step B—At days 4, 5, 6, 7, and 8, collect a 250 μl sample from each output reservoirs of each chip for barrier function of an intestine on-chip.

FIG. 17 shows the formation of Intestinal Barrier Function in a microfluidic device Confirmed Across Different Donors showing a graph of permeability changes over time, day 3-day 8. Intestine-Chips derived from biopsy of 3 independent donors achieved comparable levels of intestinal barrier function to Lucifer Yellow (~450 Da). Thus, an intact barrier is formed by day 6 of culture. Step a. At Day 3, include a dye molecule, e.g. Dextran (Cascade Blue) or Lucifer Yellow (~450 Da) in media of top input Reservoirs. Step b. At days 4, 5, 6, 7, and 8, collect a 250 µl sample from each output Reservoirs of each Chip for Barrier Function of an Intestine On-Chip.

III. Immune Cell Requirement.

In some embodiments, a fluidic platform for the studies of immune cell recruitment and infiltration in the context of chronic intestinal inflammation is desired. Such a system would allow for the assessment of the efficacy of drugs which are targeting important steps and components of this process (MadCAM1, integrins, e.g. alpha4beta7).

Preclinical in-vitro systems of the human intestinal tissue are desired, because of a lack of these characteristics in other systems, that would employ the use of: gut-tissue specific microvascular endothelial cells (relevant for MadCAM1 expression); physiologically relevant fluid flow and shear stress (relevant for immune cells-endothelium interaction) and patient-derived tissue (relevant for the assessment of donor-donor variability|normal vs diseased state|normal vs inflamed regions) for the studies of immune cells recruitment and infiltration and drug efficacy testing. The following embodiments of intestine non-chip were developed in part to have these characteristics. Further, the following embodiments may be combined with other embodiments described herein.

In part, challenges to developing WBCs (white blood cell) adhesion to vascular walls under flow is due to the flow generated shear forces, in liquid without a density-modifying reagent, preventing immune cells from attaching or by knocking immune cells off of the endothelium while cells are beginning to attach before they attach strongly enough to migrate through the cell layer. However, because shear rates induced by flow Recruitment of Circulating Immune Cells into Intestine-Chip are affected by viscosity of the liquid, shear was altered with the addition of a "density-modifying reagent" or "thickening agent" as described herein.

It was discovered during the development of the present inventions, that addition of Percoll as one example of a density-modifying reagent increased media viscosity and improved immune cell-endothelium interaction.

A. Shear.

Without being bound by theory, shear rate is a functional of geometry, flow rate and fluid viscosity. Accordingly, one of the challenges is that requiring higher shear typically means increasing flow. However, in the absence of recirculating the media (which is not preferred in some embodiments because we often want to assess the single-pass effect of the Chip), the higher flow rate means going through too much media. This can be problematic because: a) large volumes of liquid can be challenging in terms of reservoir and instrument design; b) the media can be expensive (e.g. media used for enteroids); c) large volumes of liquid into which signals dilute—can harm autocrine signaling, make pharmacokinetic experiments difficult, etc.

In one embodiment, the present invention contemplates increasing shear independently of flow rate by supplementing the liquid used with a viscosity-modifying reagent. In one embodiment, the viscosity-modifying reagent comprises a gel (whether wholly or partially gelled) or gel precursors (e.g. alginate, polyacrylamide, agar), polymers (silicone), proteins (e.g. albumin), and thickeners such as xanatham gum. They can also comprise colloids, such as silica-based colloids, and in particular Percoll, Ficoll, etc.

A desirable feature of the viscosity-modifying reagent is that it should not lead to toxicity or inflammation. Identifying viscosity-modifying reagents that cause little to no inflammation is very important since a) we are looking for the most physiological system, and b) inflammation is often one of our readouts. We currently know that alginate, while useful for some purposes, is associated with unacceptable inflammation (e.g. looking at cytokine expression). By contrast, Percoll does not cause inflammation. This is an unexpected advantage of Percoll.

In one embodiment, the present invention contemplates immune-cell (e.g. neutrophils, PBMCs, T cells) recruitment. In a preferred embodiment, immune-cell recruitment work best when operating in a certain range of shear rate in order to produce physiological results. Additionally, we found that gravity affects the immune cells, and in turn, the effectiveness of the recruitment. Specifically, we typically use our Chip's bottom channel as the vascular channel. Accordingly, to be recruited to the endothelium, the immune cells have to interact with the channel's top wall (where the endothelial cells lie, coating the bottom of our membrane). This means that the immune cells have gravity work against them, which we believe makes the process inefficient. In support of this hypothesis, we have found that recruitment assays work much better with the Chip inverted, when gravity helps the immune cells reach the membrane. Flipping chips has been part of our standard protocol for immune-cell recruitment assays before the present invention.

We have considered several ways to better address recruitment without the need to invert the Chip. We have found that immune-cell recruitment assays function better (e.g. enhanced recruitment after inflammation, particularly compared to a Chip that wasn't flipped) when the fluid used incorporates a density-modifying reagent. The density-modifying reagent can comprise soluble dense materials (e.g. polymers), sugars (e.g. dextrans), starches, cellulose, dense proteins, or colloids. In one embodiment, silica colloids are contemplated. In another embodiment, nanoparticle suspensions (e.g. gold nanoparticle) are contemplated. In a preferred embodiment, the present invention contemplates Percoll or Ficoll (the last two were developed by separating cells or cell parts based on their density during centrifugation).

Without being bound by theory, increasing the density of a fluid carrying immune cells increases the buoyancy of these cells. Specifically, once a certain density is reached, the cells become buoyant, meaning that they float upwards in the channel. Accordingly, cells floating upwards can better interact with the endothelial cells present at the top of the channel (under the membrane). The end result is a protocol that, amongst other advantages, allows for effective immune-cell recruitment and specifically without needing to flip Chips. The latter part is especially an advantage in the context of our culture module (which does not easily permit inverting the Chip).

Dilution of Percoll is meant to match closely the specific density of the cells are suspended into it. Several ratios of Percoll/Medium are contemplated. The blood substitute is used for two different types of applications: In the first type of application, it is added to the fluid (i.e. Blood, Serum, Medium) to keep particles/particulates in it dispersed to be in suspension and flowed in a continuously manner. In this application the relative ratio Percoll/Fluid (i.e. Blood, Serum, Medium), which correspond to a specific density can be varied to adapt to the specific particle/particulates in it dispersed. In this application is also contemplated the use of fluorescent dies, antibodies or other detection solution to better image the blood substitute or the particle/particulates suspended into it. In this second type of application is also contemplated the use of fluorescent dies, antibody or other detection solution to better image the blood substitute. In the second type of application, the blood substitute is flowed into the micro-channel to mimic physiological relevant blood flow shear stresses with the ultimate goal to stimulate the endothelium to fully mature. In this application the relative ratio Percoll/Fluid (i.e. Blood, Serum, Medium) can be varied to adapt the viscosity of the blood substitute to the specific geometry or the specific dimensions of the micro-channel and the working range of the pump in use. So that it is possible to have some flexibility in the use of it to achieve the desired shear.

The blood substitute is designed to perfuse different fluid such as blood, plasma and medium; the blood substitute can flow in channels lined with endothelial cells without generating inflammation.

In some embodiment, increase viscosity to mimic physiological relevant shear stress at low flow rate.

In some embodiment, increase viscosity to keep particles/particulates in suspension.

Substitute of Percoll by Ficoll, for one example, could be used in similar or the same method.

B. Exemplary Methods of Immune Cell Recruitment.

The following Sections (i.e. steps) were used for providing immune cell recruitment assays on-chip using intestine on-chip. In some embodiments, inflammation is induced in a microfluidic intestine on-chip by inducing inflammation with cytokines.

Section 1: Inflammatory Stimulation of Intestine-Chip: Cytokine Induced Inflammation.

Seed Intestine-Chip following general protocol; At day 5, divide all of the chips into at least two subgroups: 1) Controls—which will not be treated with the inflammatory stimuli, and 2) Inflamed by treatment for 4-24 hours with an inflammatory stimuli such as TNFalpha, IL-1beta or LPS. Then, aspirate the media in both output Reservoirs and input Reservoir of the Bottom Channel; Induce vascular inflammation in the Intestine-chip. In one embodiment, vascular inflammation is triggered by perfusing fresh EGM2-MV media, with an inflammatory stimuli added, through the Bottom Channel. Perfuse EGM2-MV media+/−inflammatory stimuli through the Bottom Channel of Intestine-Chip at 60 ul/h for 4-24 hours. In one preferred embodiment, stimulation is 24 hours. For the control, media without an inflammatory stimuli is used instead. In one embodiment to induce vascular inflammation in the Intestine-Chip a mix of cytokines at the clinically relevant concentrations (Cytomix (e.g. Miltenyi Biotec, Cambridge, Massachusetts, USA): 50 pg/ml, IL-1B, 215 pg/ml, TNFalpha and 200 pg/ml IL-6) similar to the levels observed in the blood of chronically diseased patients is used. The choice of the inflammatory stimulus, composition of Cytomix and their concentrations can be adjusted dependently on the needs of the specific application.

Figure 18A:
FIG. 18A-B shows exemplary florescent microscope images and graphs demonstrating induction of adhesion molecule expression in intestinal endothelial cells on-chip 24 hours after induction of inflammation using clinically relevant levels of cytokines.
Figure 18B:
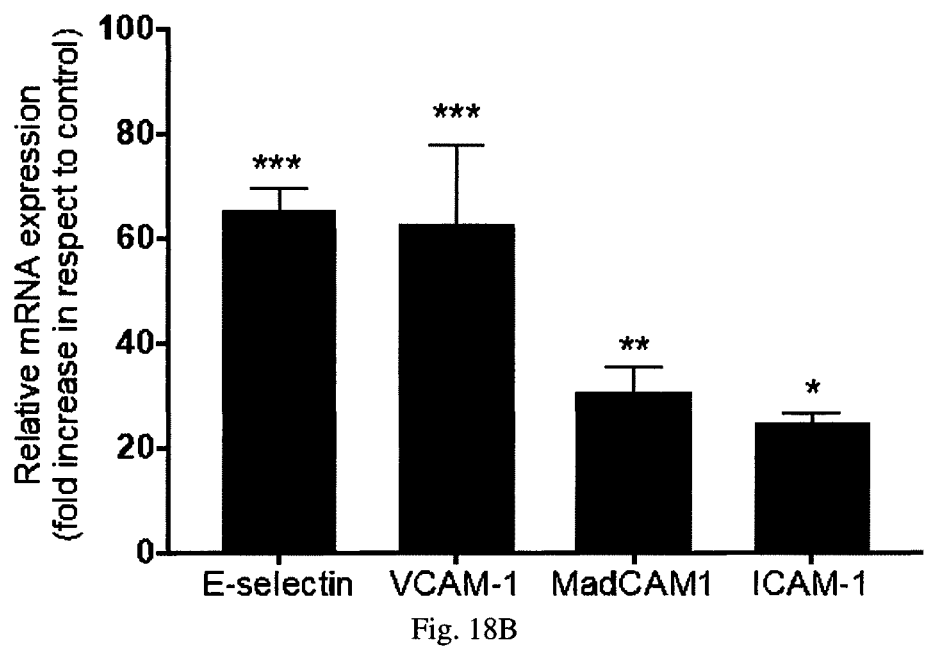

FIG. 18A-B shows exemplary florescent microscope images and graphs demonstrating induction of adhesion molecule expression in intestinal endothelial cells on-chip 24 hours after induction of inflammation using clinically relevant levels of cytokines. FIG. 18A shows images of induced ICAM-1 and nuclei stained channels (left) and under higher magnification (right) for control (upper) and inflamed (lower) channels. FIG. 18B shows a graphical comparison of relative mRNA expression for E-selectin, VCAM1, Mad-CAM1 and ICAM-1. Cells on-chip were treated for 24 hours with a Cytomix Formulation: TNF-alpha 10 U/ml (approximately 215 pg/ml), IL-1β 50 U/ml (approximately 50 pg/ml), IL-6 20 U/ml (approximately 200 pg/ml).

Figure 18C:
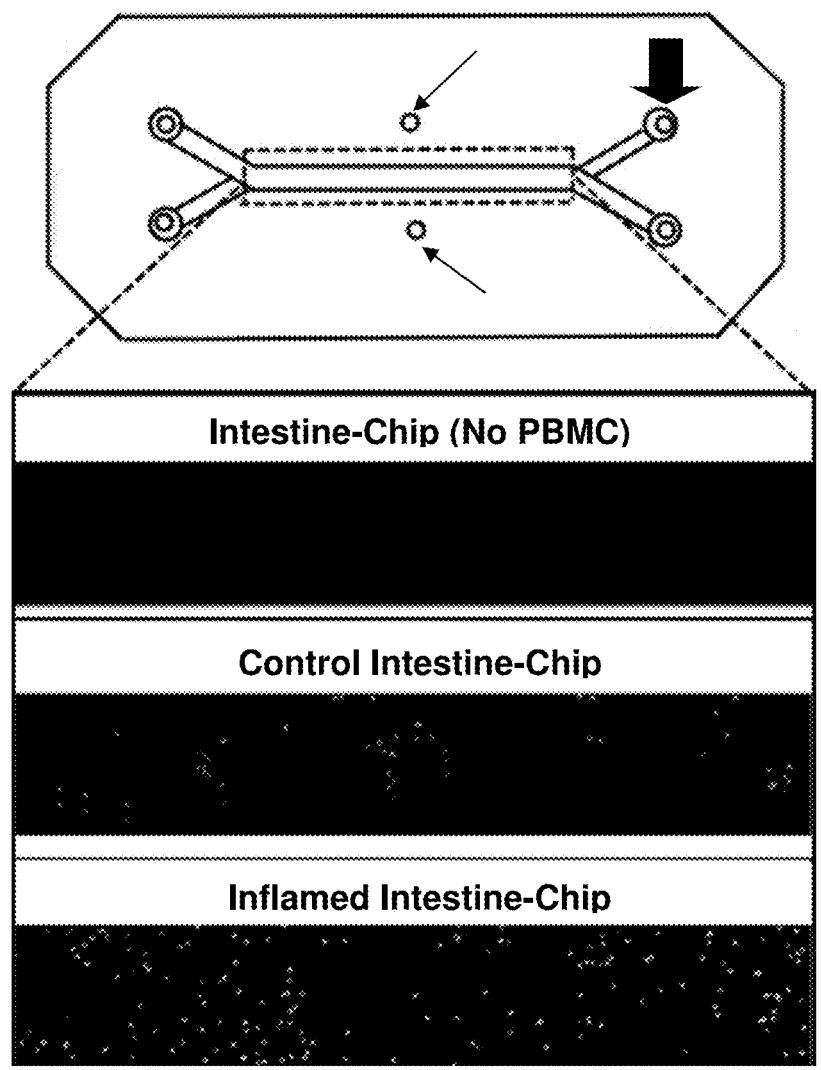
FIG. 18C-D shows exemplary increased PBMC recruitment after cytokines-induce inflammation of the endothelium of an inflamed intestine-Chip.
Figure 18D:
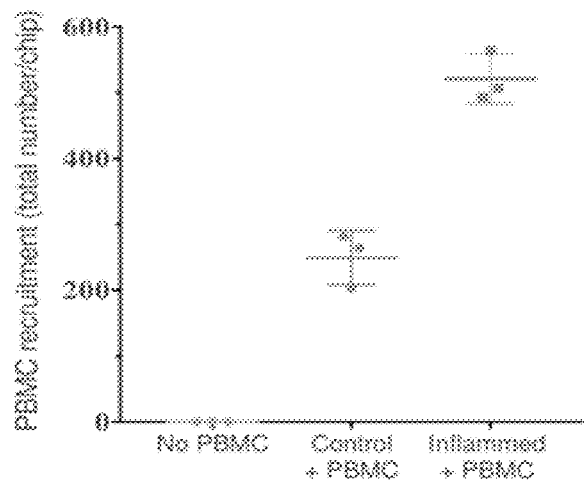

FIG. 18C-D shows exemplary increased PBMC recruitment after cytokines-induce inflammation of the endothelium of an inflamed intestine-Chip. FIG. 18C shows a larger arrow where PBMCs may be added to flow into the main vascular channel. Alternatively, small arrows point to ports where PBMCs may be added to the center area of the channel. Images on the right show white dots representing PBMCs attached to the endothelial layer for no PBMCs added to a chip that was not treated by cytokines, center control with PBMCs but no cytokine treatment and right panel where an inflamed endothelium has numerous attached PBMCs. Attached PBMCs are shown numerically as a total number/chip in an exemplary graph in FIG. 18D.

Figures 19A, 19B, 19C, 19D, 19E, 19F, 19G, 19H:
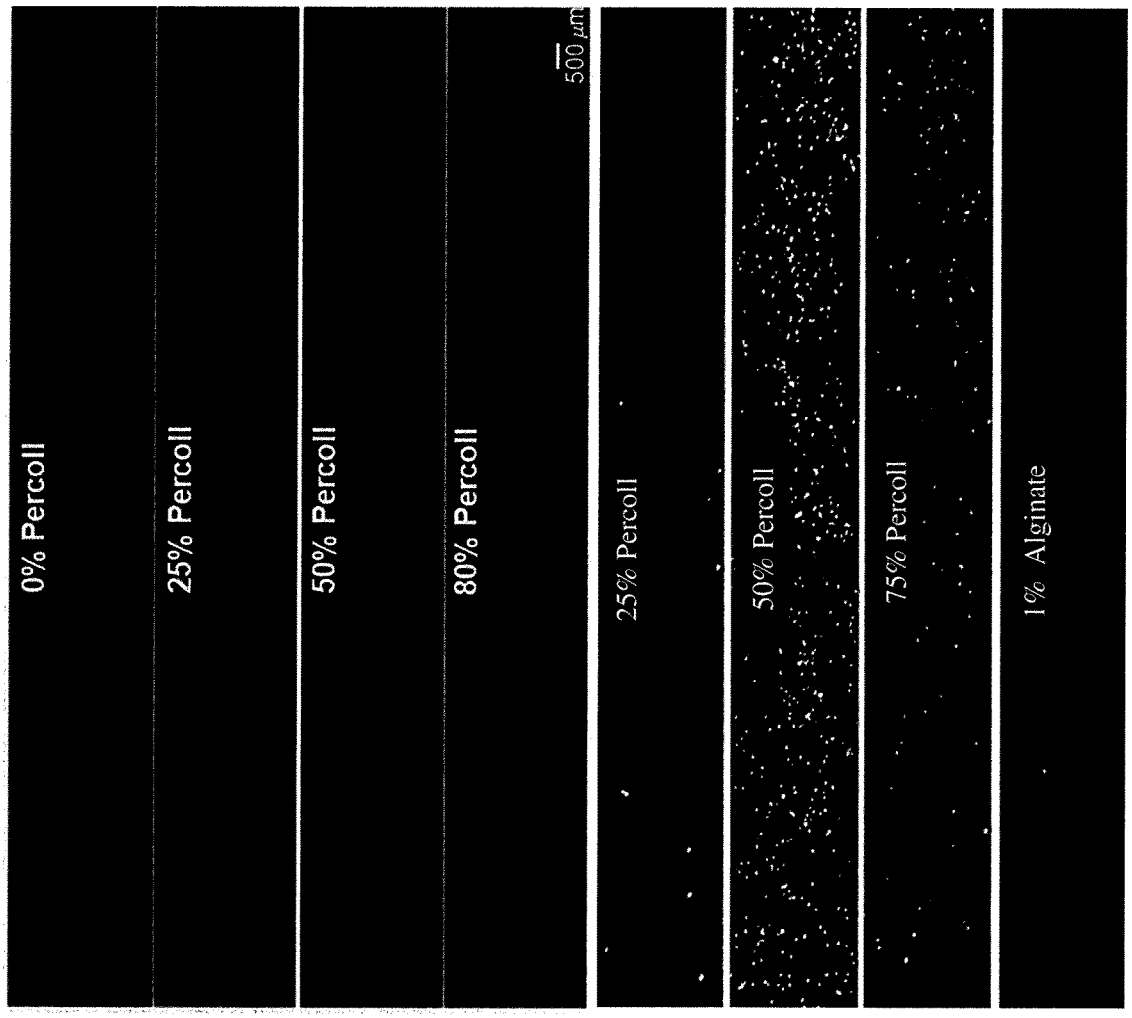
FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing labeled PBMC (peripheral mononuclear blood cells) (each shaded dot or white dot represents one cell) attached to inflamed endothelium, under liquid flow where the liquid contained FIG. 19A 0% Percoll.
Figure 19I:
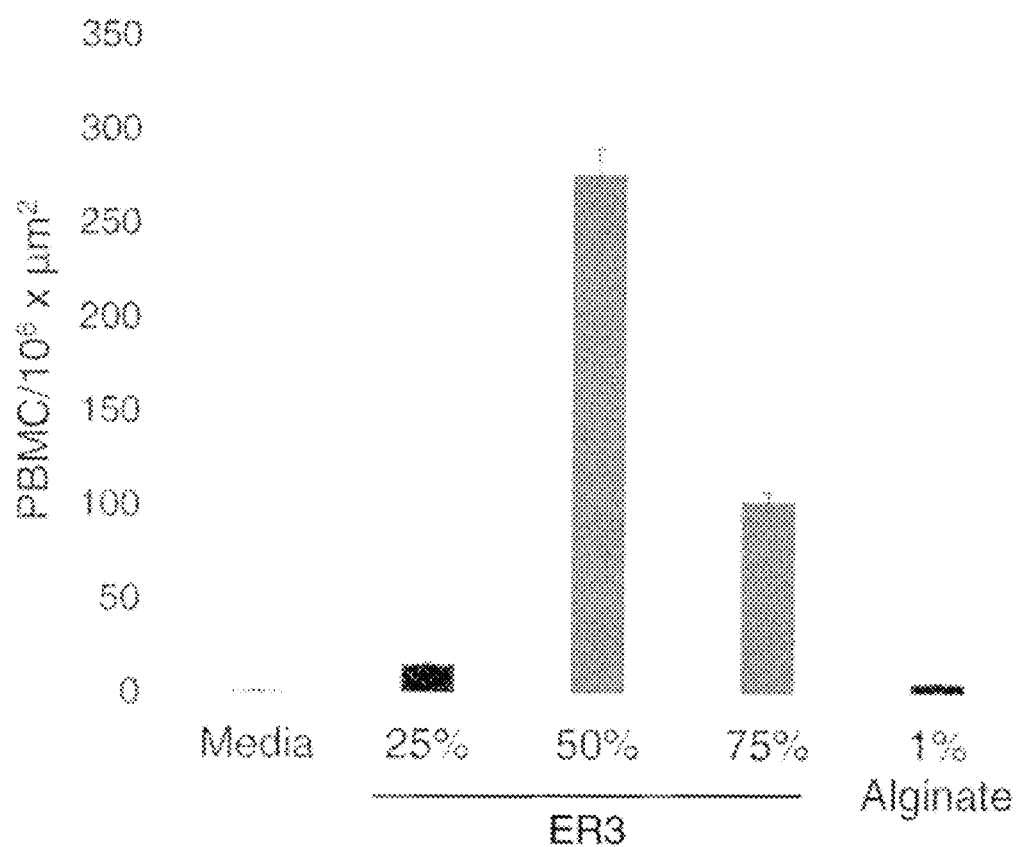

FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing labeled PBMC (peripheral mononuclear blood cells) (each dot or white dot represents one cell) attached to inflamed endothelium, under liquid flow where the liquid contained FIG. 19A 0% Percoll; FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell-endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

In other embodiments, Intestine On-Chip responds to low levels of cytokines present in the blood of chronically diseased patients by increased expression of adhesion molecules, See Table 4.

TABLE 4

Induction of Inflammation Using Clinically Relevant Levels of Cytokines: Experimental conditions vs. clinical relevance.

|  | Serum Concentration [pg/ml] | | Chip Stimulation |
| --- | --- | --- | --- |
| Cytokine | Healthy | Crohn's Disease | [pg/ml] |
| IL-1β | 17.4 [11-26] | 47.1 [32-87] | 50 |
| IL-6 | 120.3 [110-128] | 177.4 [131-297] | 200 |
| TNFα | 179.2 [144-196] | 193.0 [179-221] | 215 |

* Vasilyeva et al. Mediators of Inflammation. 2016 for off chip results.

Luminal stimulation with a stimuli is another embodiment for inducing an Inflamed Intestine-Chip. As one non-limiting example cholera toxin is added into the epithelial cell media.

Section 2: Preparation of Immune Cells:

Thaw the frozen vial containing PBMC's ($3\times10^6$ cells for 24 chip experiment) in the water bath. Resuspend the cells in 10 ml of media, spin down at 400×g/5 min/RT Remove the supernatant and resuspend the cells in 5 uM Cell Tracker Red CMPTX (Cat #C34552) staining solution prepared by diluting 10 ul of 5 mM stock solution in 10 ml of RPMI media (with 5% FBS). Incubate the cells at 37° C. (in a water bath) for 15-20 min protected from light. Add 40 ml of RPMI media to absorb any unload dye. Incubate for additional 5 min at 37° C. (in a water bath) protected from light. Spin down the cells at 400×g/5 min/RT.

In some embodiments, an inflammatory intestine on-chip prepared in Section 1 and Section 2, combined with methods in Section 4, is used for modeling inflammation. However, in part due to challenges with controlling shear forces and rates, as described herein, in addition to the discovery that a 50% Percoll liquid allowed increased attachment in a manner allowing maximal attachment of white blood cells, as opposed to 15% and 75% Percoll liquid solutions. Therefore, a 50% Percoll solution (step) was added to immune cell recruitment assays. In one embodiment, a 50% Percoll solution (step) was added to immune cell recruitment assays in place of flipping (inverting) chips (i.e. in place of using gravity to cause the immune cells to settle on the endothelial cells) to allow white blood cell interaction with endothelial cells on the lower surface of the membrane separating the endothelial channel from the epithelial channel.

FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing labeled PBMC (peripheral mononuclear blood cells) (each dot or white dot represents one cell) attached to inflamed endothelium, under liquid flow where the liquid contained FIG. 19A 0% Percoll; FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell-endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

Section 3: Addition of the Percoll Solution to Immune Cells (PBMC's):

Prepare 50% Percoll solution in RPMI media by mixing stock Percoll solution and RPMI media 1:1 (vol/vol) e.g. 10 ml of Percoll with 10 ml of RPMI media; in some embodiment, degass solutions using a steri-flip. Add 50% Percoll/RPMI solution to the cells to achieve final cell concentration of $2 \times 10^6$ cells/ml.

Section 4: Recruitment Assay:

Add PBMC's as a cell suspension in 50% Percoll/RPMI into the Input Reservoir of the Bottom Channel, while in the Input Reservoir of the Top Channel add appropriate epithelial cell media (see Protocol for Small Intestine-Chip). Perfuse the immune cell solution through the Bottom Channel at the Shear Stress of ~2dyn/cm2 (flow rate ~1200 ul/h) for 15 min. Aspirate media in both output Reservoirs. Add fresh RPMI media of Input Reservoirs of the Bottom Channel. Perfuse the Bottom Channel with RPMI media for additional 15 min at high flow rate of 1200 µl/h to remove cells that didn't adhere to the endothelial cell surface.

Section 5: Assessment of the Immune Cells Recruitment:

As one example of a readout, imaging the cells that attached to endothelial cells using immunofluorescent staining by immunofluorescent microcopy or by confocal microscope (endothelial cells can be co-stained using Wheat Germ Agglutinin (WGA), if assessment needs to be performed in the live cells or VE-cadherin or other staining specific for endothelial cells, if post-fixation assessment is preferred). Immune Cells can be co-stained for CD14 or CD3 markers in order to differentiate them into different subpopulations of monocytes and lymphocytes, respectively. Chips can be lysed in order to assess endothelial or immune cells gene expression. Effluents can be collected from the Top and Bottom Output Reservoirs in order to assess cytokines and chemokines released by the cells.

After assessment of immune cell recruitment chips can be terminated by the fixation with 4% PFA or can be maintained in culture under the normal flow conditions of 60 ul/h for their further assessment, including studies of immune cell translocation into the epithelial channel, contribution of immune cells to Intestine-Chip response to luminally applied stimuli etc.

FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing labeled PBMC (peripheral mononuclear blood cells) (each dot or white dot represents one cell) attached to inflamed endothelium, under liquid flow where the liquid contained FIG. 19A 0% Percoll; FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell-endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

FIG. 20A-C shows embodiments of an intestine on chip emulating Immune Cell Recruitment on-Chip through providing physiological level of shear and fluid viscosity to emulate immune cell recruitment at epithelial-endothelial tissue interfaces. Embodiments of intestine on chip showing a florescent micrograph of stained cells FIG. 20A under Non physiological Shear in Vascular Channel and Non physiological Fluid Viscosity. FIG. 20B under Physiological Shear in Vascular Channel and Physiological Fluid Viscosity. PBMCs and inflamed HIMEC. FIG. 20C shows flow directions (arrows) on a chip schematic and the acquisition area and level where images were taken. Scale bar=100 micrometers. Physiological levels of shear and fluid viscosity emulate immune cell recruitment at the epithelial-endothelial (tissue-tissue) interface.

FIG. 20D-E shows one embodiment of an intestine on chip where flowing media without the addition of Percoll does not induce PBMC attachment at the same level of imaging as in FIG. 20C.

Figure 21A:
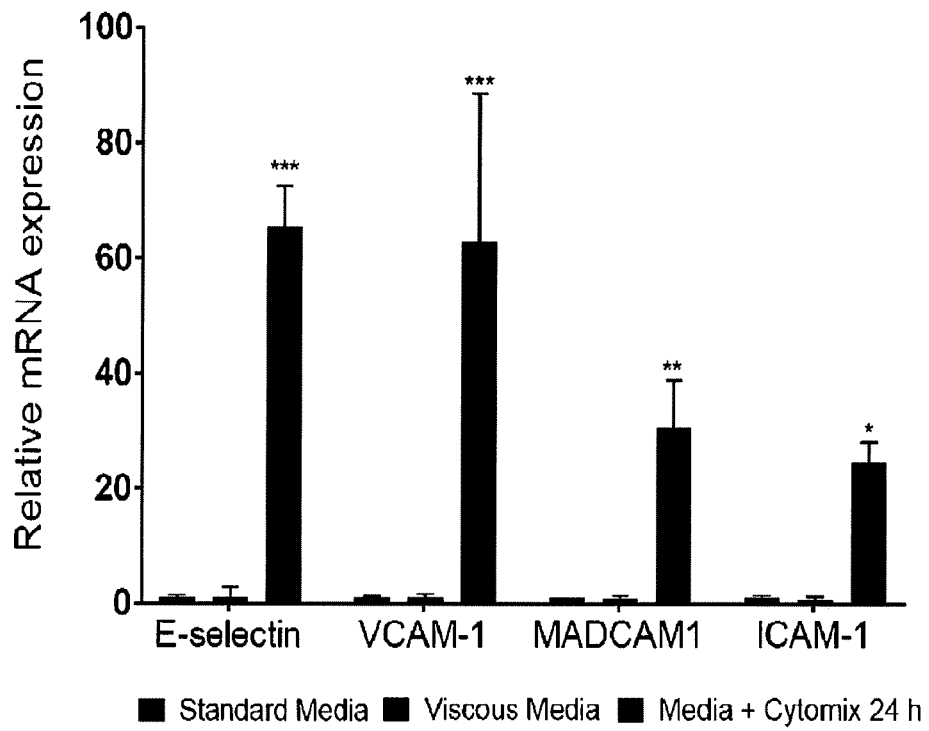
FIG. 21A-B shows that a change in the media viscosity does not affect the expression of adhesion molecules on endothelial cells (vascular compartment) on-chip.
Figure 21B:
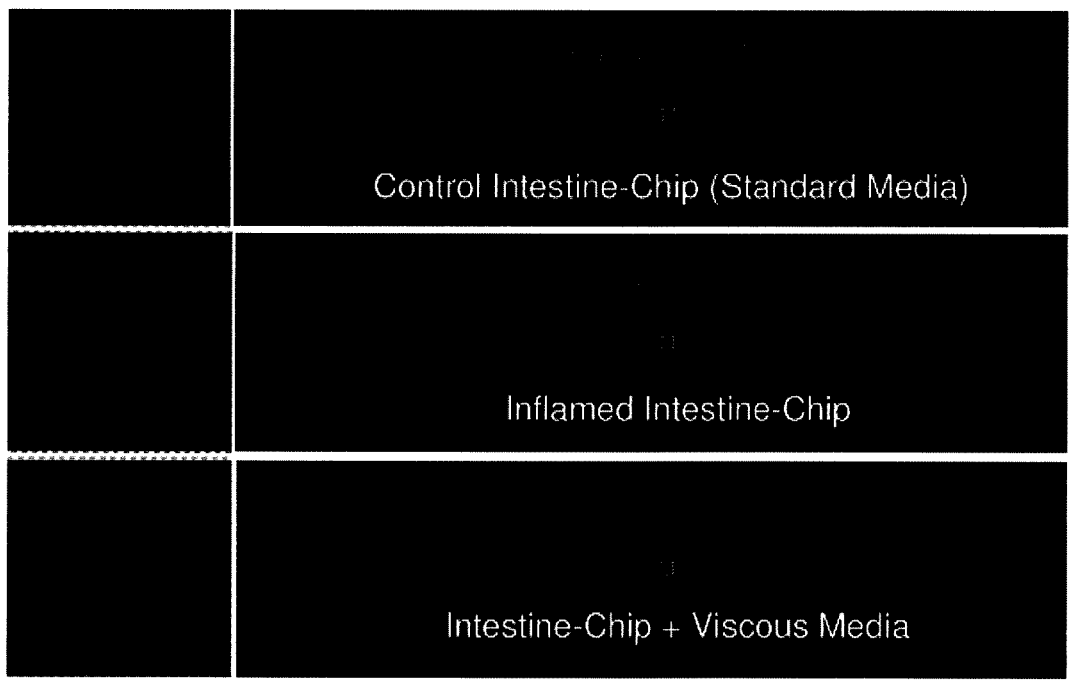

FIG. 21A-B shows that a change in the media viscosity does not affect the expression of adhesion molecules on endothelial cells (vascular compartment) on-chip. FIG. 21A is a chart showing relative mRNA expression between standard media (left, grey bars), viscous media (50% Percoll) (blue, middle bars) and inflammatory inducing media containing Cytomix cytokines (right, bars), after 24 hours of treatment.

FIG. 21B shows micrographs of cells (left) corresponding to lower power micrographs of the channels (right). Stained ICAM-1 and nuclei. Upper is a control intestine on-chip, middle is an inflamed intestine on-chip and lower is a chip treated with viscous media, 50% Percoll, intestine on-chip.

Figure 21C:
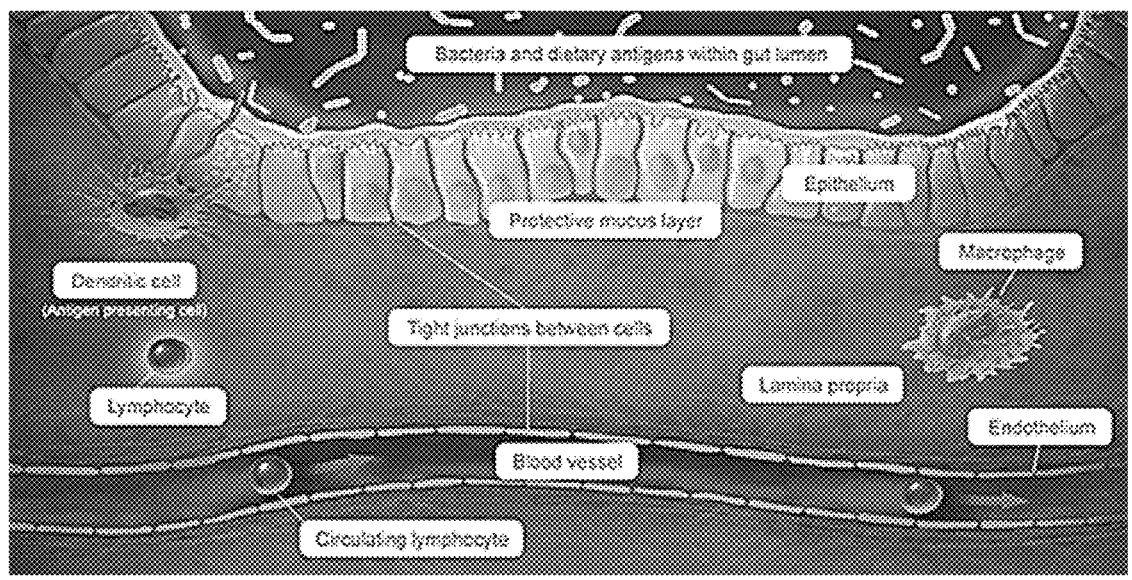
FIG. 21C-D shows schematic images of intestinal tissue where
Figure 21D:
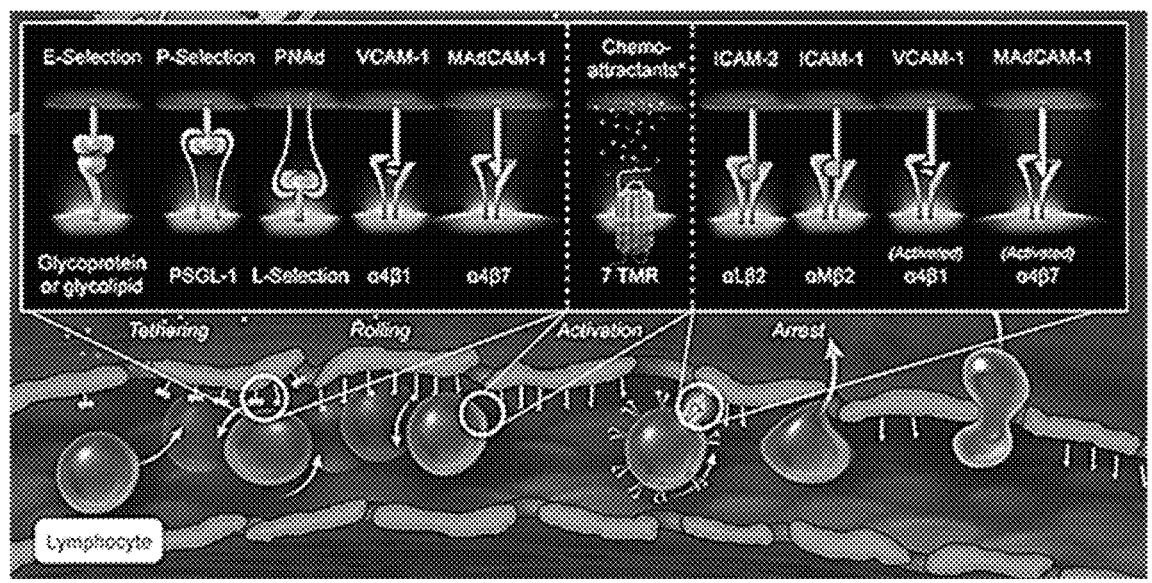

FIG. 21C-D shows schematic images of intestinal tissue where FIG. 21C shows representative tissues as candidates for white blood cell interactions after diapedesis through the endothelial layer of a blood vessel and FIG. 21D illustrating exemplary cell surface adhesion molecules associated with stages of white blood cell, e.g. lymphocyte, interactions with endothelium. Starting with tethering, rolling, then when inflammatory adhesion molecules are present to trigger activation of the white blood cell, rolling becomes arrest of movement along the endothelial cell(s) the followed by diapedesis through the endothelial layer.

II. Fibroblasts Induce L-Cell Differentiation on Colon-Chip.

In some embodiments, a Colon on-chip comprises Enteroids/Colonoids and irradiated fibroblasts. Exemplary colonoids were obtained from biopsied tissues through collaboration with hospitals. Irradiated Fibroblasts were obtained from commercial sources, e.g. NuFF Fibroblasts Human Fibroblasts (NuFF) Irradiated Donor 11 (Neonatal human foreskin fibroblasts. From human Foreskin tissue, 24 hour newborn human, donor 11 (D11)). Cryopreserved vial. 4-5 million cells/vial MTI GlobalStem Cat #GSC-3001).

In one embodiment, a "sandwich method" of ECM coatings is used, where the chip membrane is first coated with ECM on the side facing the upper channel, then irradiated fibroblasts were then added. After fibroblast cell attachment, another coating of ECM was applied on top of the attached fibroblast cells before adding enteroids-colonoids. Prior to adding fibroblasts, coat membrane of chip with ECM. Both Collagen IV and Matrigel coatings were compared. Matrigel showed greater cell attachment of the fibroblasts. In other embodiments, a sandwich method is used to place irradiated fibroblasts on the lower channel, using endothelial cells instead of colonoids. In yet other embodiments, irradiated fibroblasts are located within gels in either channel.

A. Colon-Chip Comprising Fibroblast Co-Cultures Show Development of Intestinal Differentiated Cells.

Figure 25G:
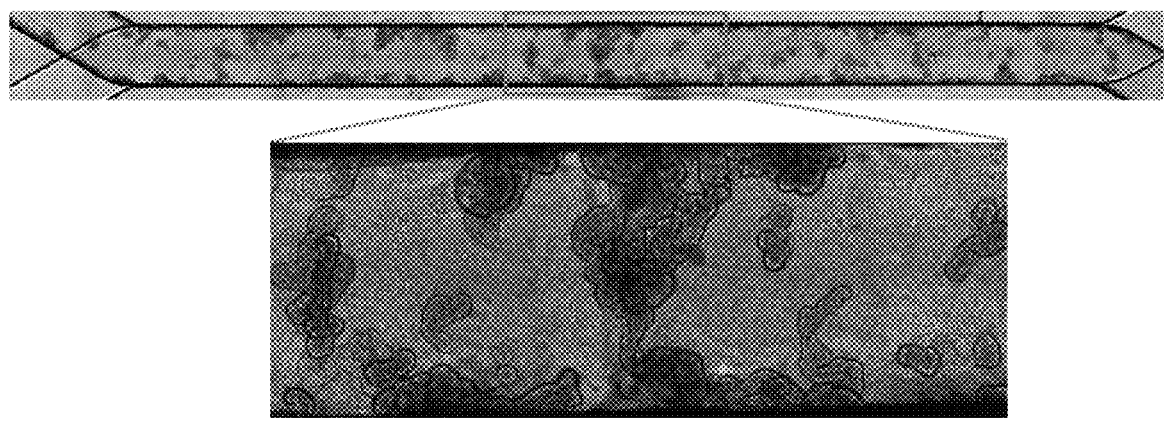

FIG. 25A-G demonstrates exemplary florescent microscope images demonstrating subtypes of Enteroendocrine cells. FIG. 25A shows exemplary Enteroendocrine cells identified by chromogranin A (CHGA). FIG. 25B shows exemplary L-cells identified by glucogon. FIG. 25B shows exemplary enterochromaffin cells identified by 5-HT. Stained DNA (Nuclei) are shown as is E-cadherin. FIG. 25D shows an exemplary confocal microscope immunostained image over view of epithelial morphology in co-culture with fibroblasts showing goblet cells. E-cadherin Muc2nuclei. FIG. 25E shows an exemplary phase contrast microscope image merged with data from a florescent image of tissue as in FIG. 25D, where goblet cells stained with MUC2. Goblet cells are forming in between villi-like structures.

B. The Location of Fibroblasts in Relation to Epithelial Cells Matters.

FIG. 25F shows an exemplary phase contrast microscope image over the entire main channel showing homogenous 3D villi-like structure formation where epithelium in direct contact with fibroblasts. FIG. 25G shows an exemplary phase contrast microscope image over the entire main channel showing 3D villi-like structures form in scattered areas of the chip where epithelium separated from fibroblasts with the PDMS membrane. Area outlined in blue is enlarged in the lower image.

C. Exemplary Method of Providing One Embodiment of a Colon On-Chip.

The following is an exemplary method of providing one embodiment of a Colon on-chip.

1. Cell Preparation
  a. For the Intestine-on-Chip (Colonoids), irradiated Newborn Human Foreskin Fibroblast (NUFFs) were seeded into the top channel and allowed to attach prior to seeding the primary enteroids
  b. Prepare cell suspension and count cell number. Seeding density is specific to the cell type. For example, NUFFs: 3 million cells/ml.
  c. After counting cells, adjust cell suspension to the appropriate density for seeding.
2. Top Channel Seeding (NUFFs)
Use ONE chip first to confirm seeding density before seeding other Chips.
  a. Prior to seeding, wash each channel with 200 ul of cell culture medium
  b. Pipette 30 cell culture media and insert in bottom inlet (Tips inserted)
  c. Agitate cell suspension gently before seeding each Chip to ensure a homogenous cell suspension
  d. Pipette 30 ul of the cell suspension and seed into the top channel inlet (Tips inserted)
  e. Place Chip on a petri dish and transfer to the microscope to check the density
  f. After confirming the cell density, seed cells in the rest of the Chips
  g. Incubate at 37° C. for 3-5 h.
3. Top Channel Seeding (Colonoids)
Reminder: Use ONE chip first—confirm seeding density before seeding other Chips
  a. Prior to seeding, wash each channel twice with 100 ul EM+
  b. Pipette 35 EM+ and insert in bottom inlet (Tips inserted)
  c. Agitate Enteroids suspension gently before seeding each Chip to ensure a homogenous cell suspension
  d. Pipette 35 ul of the Enteroids suspension and seed into the top channel inlet (Tips inserted)
  e. Place Chip on a Petri dish and transfer to the microscope to check the density
  f. After confirming the cell density, seed Enteroids in the rest of the Chips
  g. Incubate at 37° C. overnight.

Incubate Expansion Medium (with ROCK and CHIR) in both input Reservoirs of each Pod for 3 days, then Expansion Medium (without ROCK and CHIR) for remaining days.

Expansion Medium (Top Channel) may contain 100 ug/ml Dextran, Cascade Blue, 3000 MW, Anionic, Lysine Fixable (ThermoFisher Scientific Catalog Number D7132) for barrier evaluation.

D. Colon-Chip (Colonoids) Experimental Timeline (FIG. 1) and Data Collection:

1. Bright-Field Imaging (FIG. 22):
  a. Follow Steps Described for preparing and seeding enteroids.
  b. Capture representative images along the length of chip (e.g. Inlet Junction, Outlet Junction, and Center of Chip) at the following exemplary time points: Day −1, 0, 1, 4, 6, 8, 10, 14.

Figure 22A:
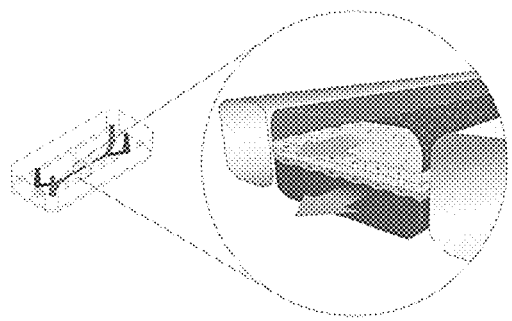
FIG. 22A-C shows differentiation of enteroendocrine cells achieved in Colon-Chips.
Figure 22B:
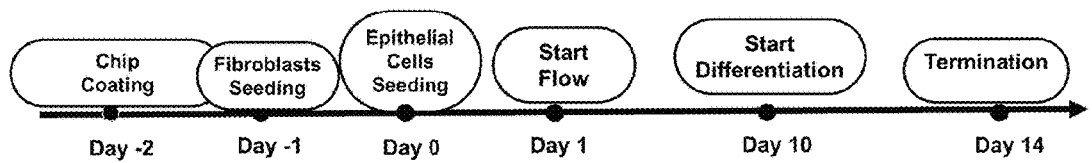
Figure 22C:
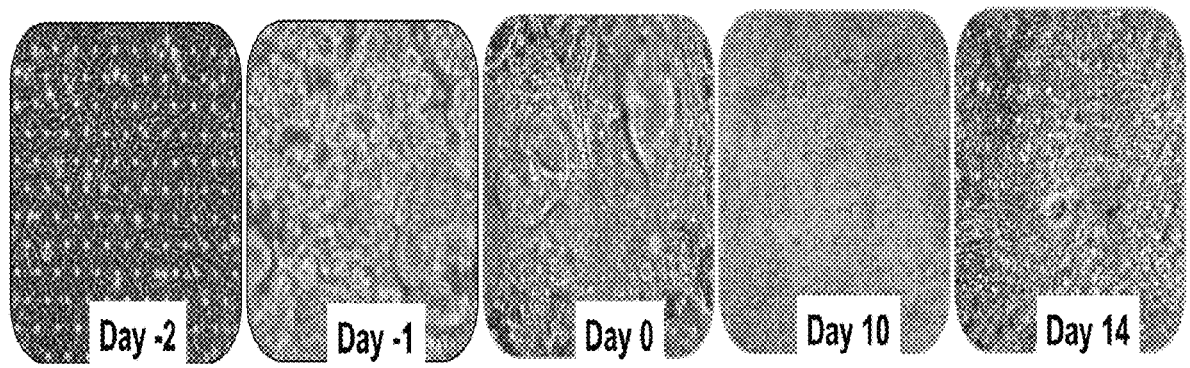

FIG. 22A-C Differentiation of Enteroendocrine Cells Achieved in Colon-Chips. FIG. 22A schematic representation of one embodiment of a Colon on-chip, irradiated. Fibroblasts (e.g. mouse fibroblasts, human fibroblasts) underneath epithelial cells seeded from colonoids-enteroids. FIG. 22B schematic representation of an Experimental timeline of Colon On-Chip while FIG. 22C shows bright field micrograph images of cells over times shown on the timeline.

Figure 23A:
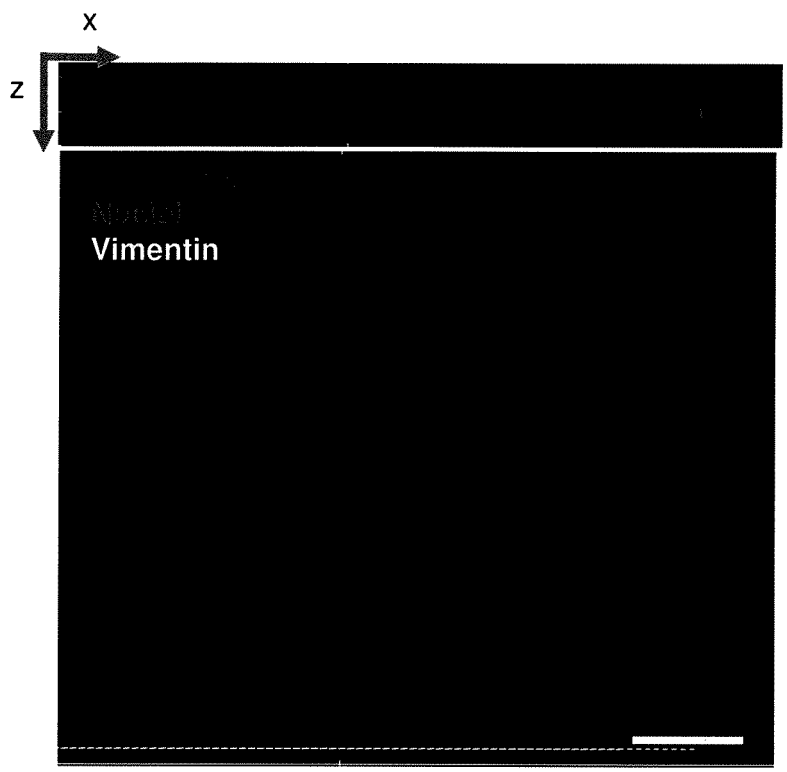
FIG. 23A-C shows exemplary florescent microscope images, focused on three different planes showing epithelial-fibroblast tissue interfaces.
Figure 23B:
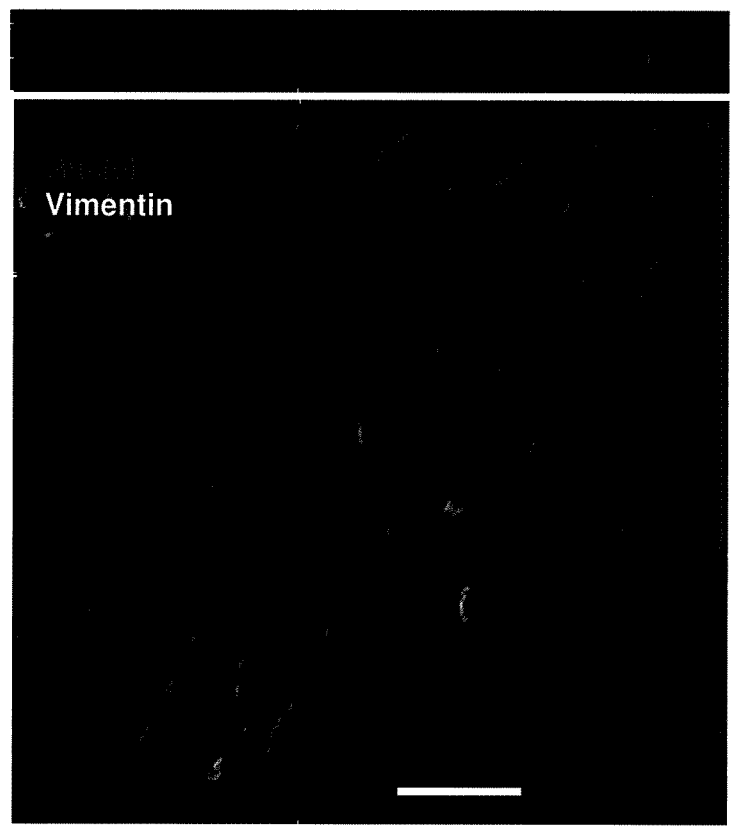
Figure 23C:
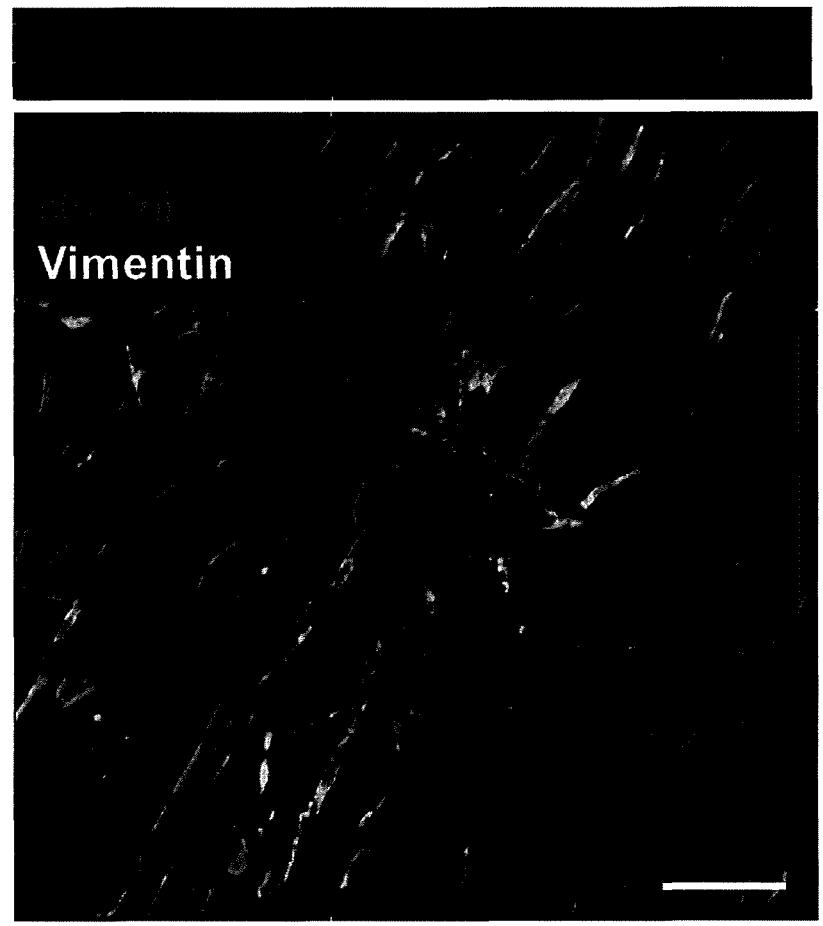

FIG. 23A-C shows exemplary florescent microscope images, focused on three different planes showing Epithelial-Fibroblast Tissue Interfaces. FIG. 23A upper area of epithelial cells, FIG. 23B lower plane of focus closer to fibroblasts, FIG. 23C fibroblasts located at the lower plane of focus. Vimentin staining identifies fibroblast cells. E-cadherin and nuclei.

2. Barrier Function (FIG. 24):
   a. Collect 250 µl effluent samples from both output Reservoirs of each Chip for Barrier Function:
      i. Add a dye or barrier test compound, e.g. as described herein, to flow media.
      ii. Collect at time points: Day 2, 4, 6, 8, 10, 12, 14.
      iii. Include in the plate set up: Standard Curve, Apical Blank, and Basal Blank Prior to collecting effluent samples, aspirate to remove media from the Outlet Reservoirs, without touching the port, at the following exemplary time points: Day 3, 5, 7, 9, 11, 13.

FIG. 24A-B demonstrates exemplary Barrier Function (Permeability) of one embodiment of a colon on-chip epithelial cells growing on top of irradiated fibroblasts. FIG. 24A Barrier Function (Permeability) as % of 3 kDa Dextran leakage). FIG. 24B shows exemplary florescent microscope images of the epithelial cell layer. E-cadherin and nuclei, left. ZO-1 and nuclei, right. Upper images show z-stacked side views of the epithelial layer.

3. Differentiation
   a. At day 10, aspirate media from both input Reservoirs and add 3 ml of Differentiation Media). Differentiation Medium (Top Channel) may contain 100 ug/ml Dextran, Cascade Blue, 3000 MW, Anionic, Lysine Fixable (ThermoFisher Scientific Catalog Number D7132).
   b. At day 12, replenish Differentiation Media in both input Reservoirs E. Intestine On-Chip System Comprising Enteroendocrine Cell Subsets.

Enteroendocrine cells produce and secretes a variety of hormones or signaling molecules, including but not limited to the following cells and an exemplary secretary molecule: gastrin (G cells), ghrelin (P or X cells), somatostatin (D cells), cholecystokinin (CCK) (I cells), serotonin (enterochromaffin cells), glucose-dependent insulinotropic peptide (GIP) (K cells), glucagon-like peptides (GLPs) and peptide YY (PYY) (L cells).

Enteroendocrine cells in part may have immunoreactivity in addition to having other types of responses. Enteroendocrine cells can be distinguished morphologically in micrographs of epithelial layers as 'open cells' with microvilli extending to the lumen, and 'closed cells' that do not reach the lumen. Their secretory products accumulate in secretory granules for secretion upon stimulation by exocytosis at the basolateral membrane into the interstitial space, where they can act locally or on distant targets through the bloodstream. In this respect, enteroendocrine cells can be regarded as primary chemoreceptors, capable of responding to luminal constituents by releasing secretory products that activate neuronal pathways, nearby cells or distant targets through different mechanisms. This model is particularly suitable for the 'open cells' that reach the luminal surface. 'Closed cells', however, can be regulated by luminal content indirectly through neural and humoral mechanism.

The presence of Enteroendocrine Cells (EEC) and several subsets were confirmed by gene expression analysis and immunofluorescence staining for EEC specific markers in colon on-chip.

F. Microfluidic Intestine (Colon) On-Chip Comprises Enteroendocrine Cells (EEC) Subsets Including L-Cells.

It is not meant to limit the source of L-cells used in any of the microfluidic chips, individually, or linked, such that L-cells may be induced to differentiate on-chip, e.g. by the addition of irradiated fibroblast cells for generating L-cells, or by the addition of L-cells isolated from biopsies, or L-cells added as an L-cell line.

1. Exemplary Generation of L-Cells in Colon-Chips.

In particular for L cells, Nutrients, free fatty acids and bile components stimulate release of L-cell contents including but not limited to: GLP-1, GLP-2, PYY, which mediates pleiotropic effects via a combination of endo-, para-, and neurocrine pathways. Thus, in some embodiments, assays for measuring release of molecules includes but is not limited to release of one or more GLP-1, GLP-2, PYY, etc.

Because L-cell release of endocrine signals, L-cell function is related to diseases, including but not limited to Type 1 and Type II diabetes.

As described herein, it was discovered that by introducing fibroblasts into intestinal enteroids/colonoids seeded microfluidic chips, an unexpected result was inducing the enteroids-derived cells to generate L-cells (or at least cells with gene expression indicative of L-type cells). This was surprising because physiologically relevant numbers of L cells were not observed in in vitro intestinal cell cultures derived from enteroids.

Figure 26:
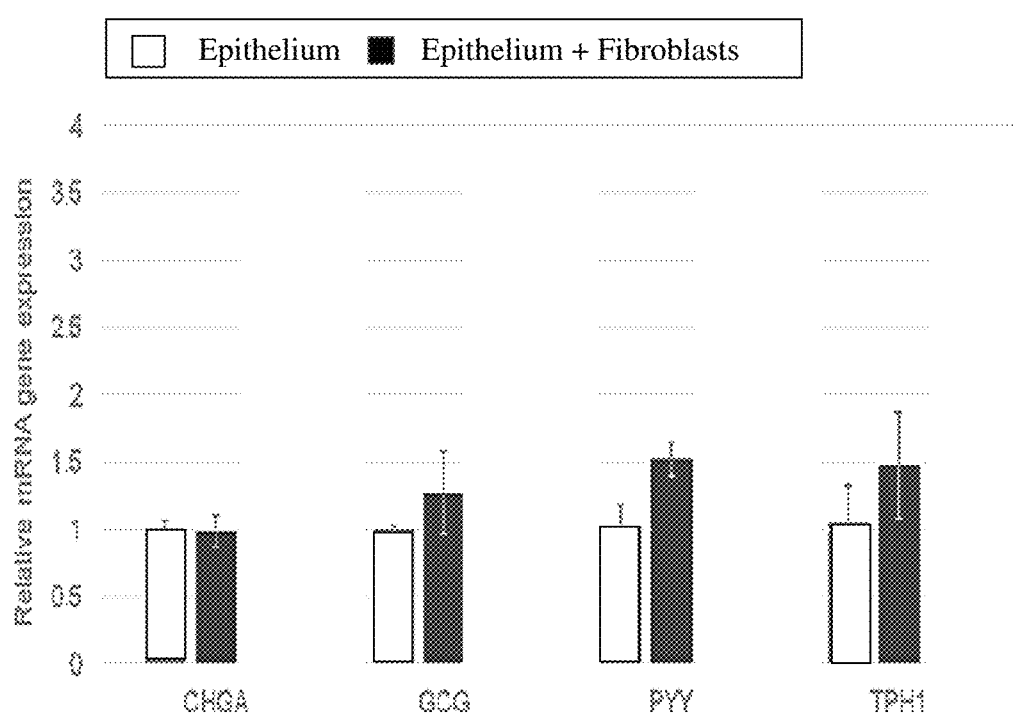
FIG. 26 shows relative mRNA expression for L-cells markers including GCG and PYY, that are increased in co-cultures of epithelium and irradiated fibroblasts (pink bar) compared to epithelium alone (grey bar), in addition to other subtype markers Enteroendocrine cells identified by chromogranin A (CHGA) and THP1.

FIG. 26 shows relative mRNA expression for L-cells markers including GCG and PYY, that are increased in co-cultures of epithelium and irradiated fibroblasts (pink bar) compared to epithelium alone (grey bar), in addition to other subtype markers Enteroendocrine cells identified by chromogranin A (CHGA) and THP1.

Figure 27A:
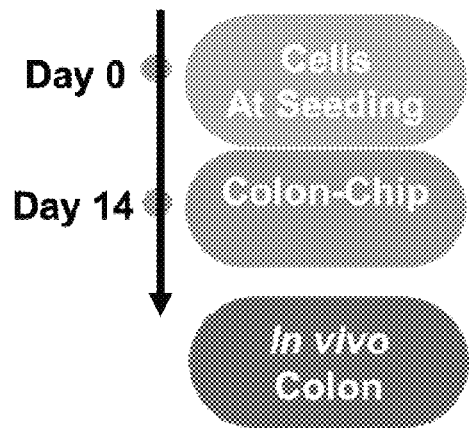
FIG. 27A-B shows exemplary schematic diagrams of FIG. 27A an experimental timeline and FIG. 27B relative mRNA expression for L-cells markers including GCG and PYY, that are expressed in co-cultures of epithelium and irradiated fibroblasts (blue bar) compared to in vivo colon (biopsies).
Figure 27B:
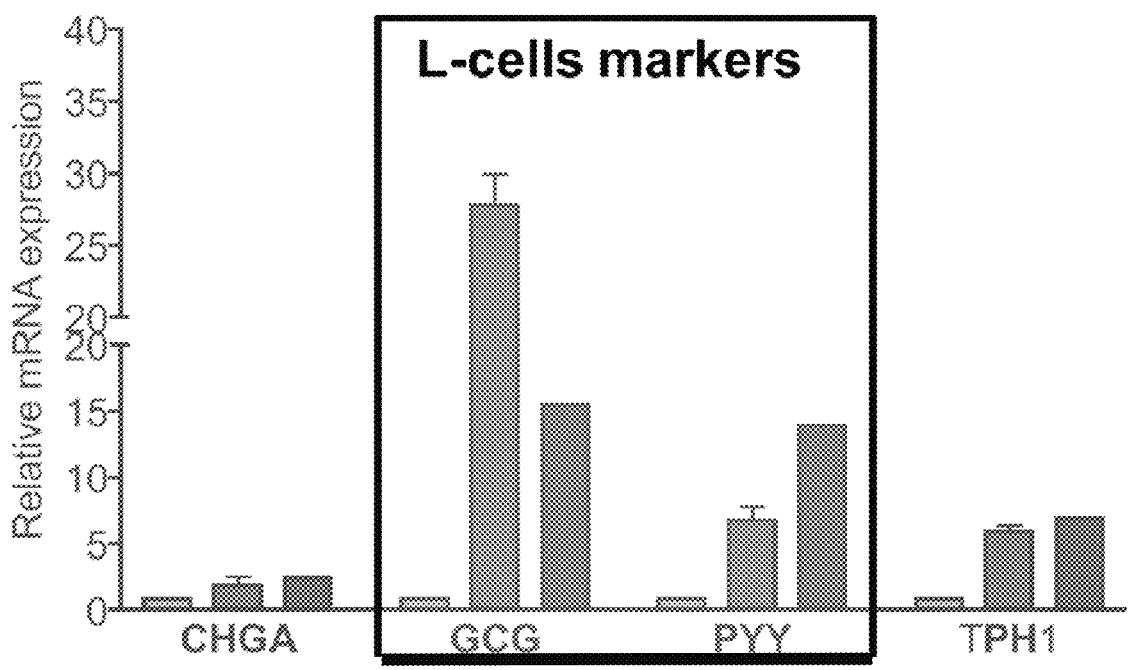

FIG. 27A-B shows exemplary schematic diagrams of 27A an experimental timeline and 27B relative mRNA expression for L-cells markers including GCG and PYY, that are expressed in co-cultures of epithelium and irradiated fibroblasts (blue bar) compared to in vivo colon (biopsies).

2. Biologically Active L-Cells in Colon Chips.

In particular, microfluidic intestine on chip was provided composed of primary human colonic epithelium and fibroblasts grown in direct contact. These cells growing on chip formed cell-cell junctions and a strong intestinal barrier. The epithelial layer comprised enteroendocrine cells, including L-cells. L-cells accounting for 1% (1.67+/−0.89) of intestinal epithelial cell types in Colon On-Chip, as described herein.

One of the molecules secreted by L-cells, GLP-1, has pleiotropic actions in peripheral tissues. The majority of the effects of GLP-1 are mediated in some embodiments by direct interaction with GLP-1Rs on specific tissues. Further, in other embodiments, the actions of GLP-1 in liver, fat, and muscle occur through indirect mechanisms.

Thus, in some embodiments, molecular and other signals generated by the presence of L cells may be identified. In some embodiments, responses of other cells on chip to such L-cell generated molecular signals may be observed/measured, including but not limited to production of secreted molecules, degradation of such molecules, on chips, e.g. GLP-1 production and degradation.

Figure 28:
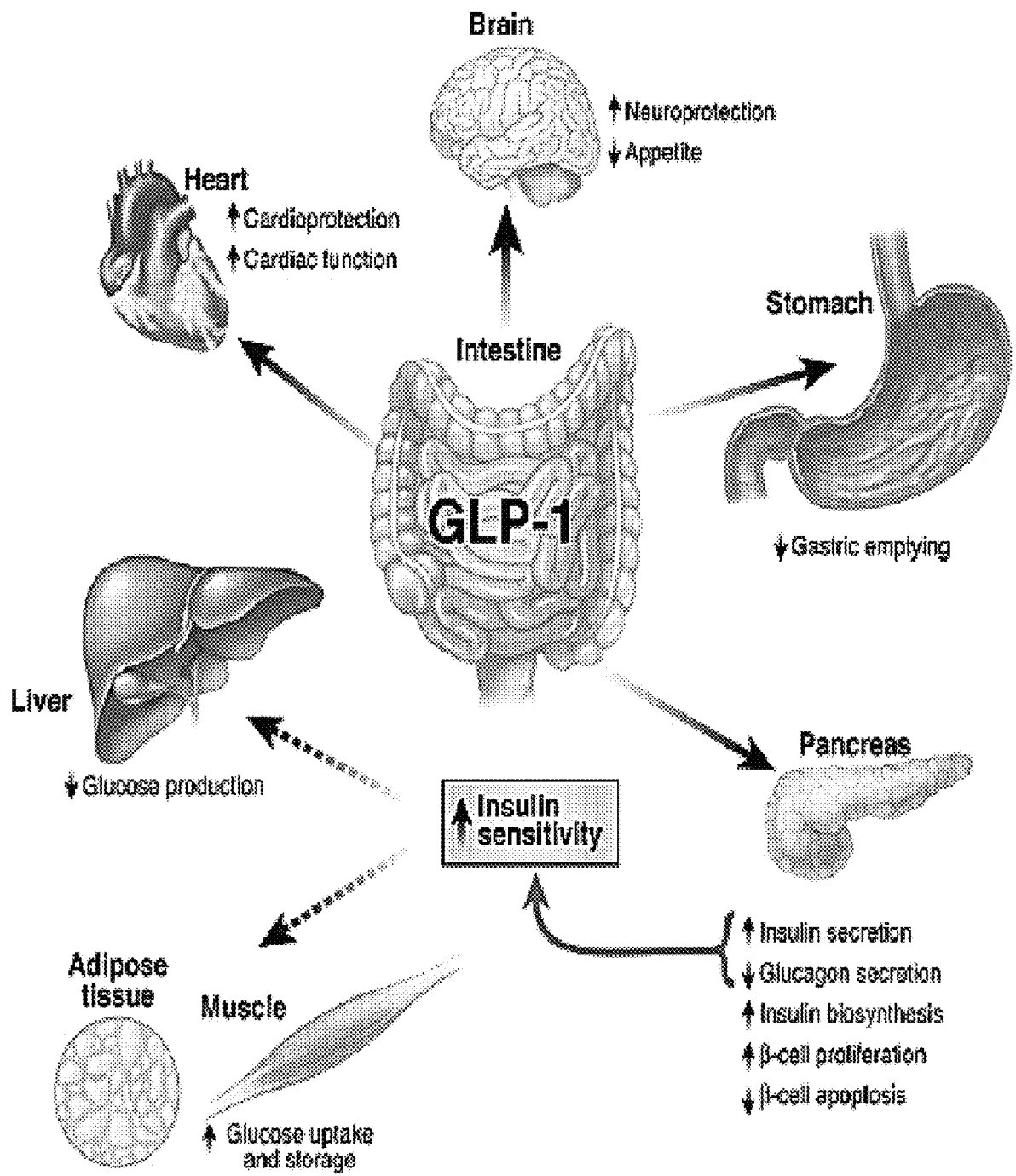
FIG. 28 shows an exemplary schematic of GLP-1, an L-cell produced and secreted hormone with multiple direct effects on human physiology. Adapted from: Baggio L L, Drucker D J (2007) Biology of incretins: GLP-1 and GIP. Gastroenterology 132(6):2131-57. In other words, L-cells have pleiotropic actions in peripheral tissues.

FIG. 28 shows an exemplary schematic of GLP-1, an L-cell produced and secreted hormone with multiple direct effects on human physiology. Adapted from: Baggio L L, Drucker D J (2007) Biology of incretins: GLP-1 and GIP. Gastroenterology 132(6):2131-57. In other words, L-cells have pleiotropic actions in peripheral tissues.

In one embodiment of an intestine (colon) on chip, L-cells release GLP-1 in response to Forskolin/IBMX stimulation. Thus, in one embodiment of an intestine on chip recapitulated L-cell response to forskolin/IBMX and physiological stimulation with bile acids by the release of GLP-1.

Figure 29A:
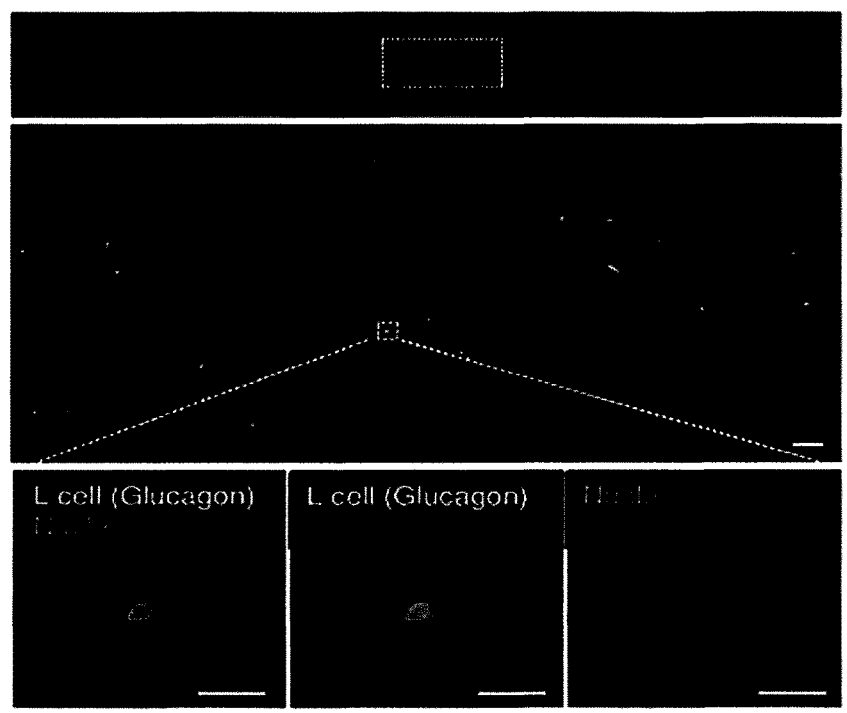
FIG. 29A-C demonstrates that L-cells present in Colon On-Chips are Biologically Active.
Figure 29B:
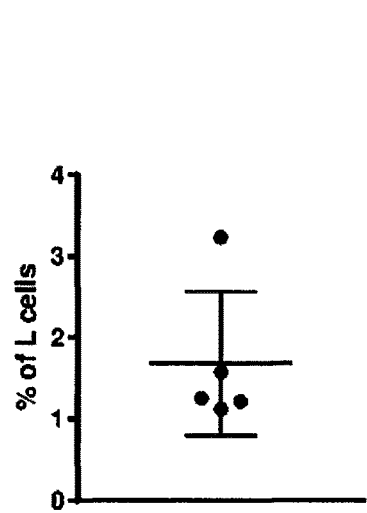
Figure 29C:
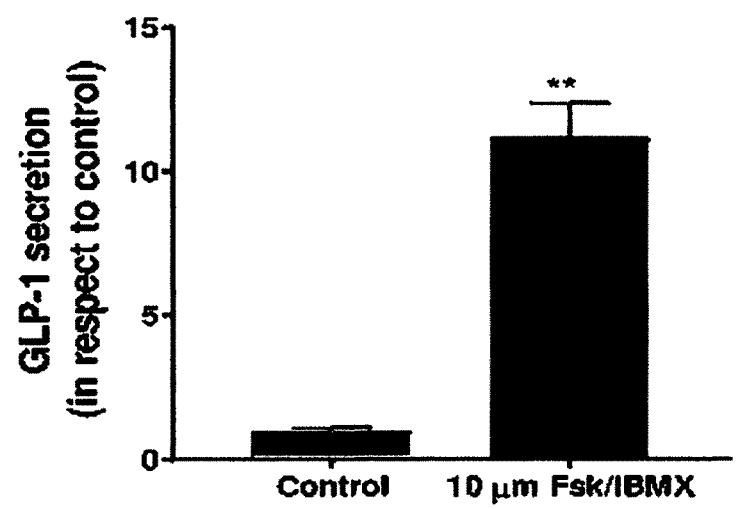

FIG. 29A-C demonstrates that L-cells present in Colon On-Chips are Biologically Active. FIG. 29A shows exemplary fluorescent micrographs of L cells within intestinal epithelial layers on chip. Upper micrograph shows nuclei staining within a microfluidic channel. Middle micrograph shows an epithelial layer within a microfluidic channel at higher magnification. Lower micrographs show an L cell (Glucagon) with Nuclei stained, left, a L-cell (Glucagon), middle, and Nuclei stained, right. FIG. 29B shows a chart of L-cell numbers. FIG. 29C shows comparative charts of L-cell function as exemplary GLP-1 secretion in response to stimulation with 10 μM Fsk/IBMX. L-cells account for 1% (1.67+/−0.89) of intestinal epithelial cells types in Colon-Chip release GLP-1 in response to Forskolin/IBMX stimulation.

In some embodiments of intestine on chip, it was discovered that L cells respond to mechanical stretch while growing in microfluidic chips. Therefore, in some embodiments of intestine on chip, L cell release of signal molecules triggered by the mechanical forces is contemplated. In some embodiments of intestine on chip, L cell release of signal molecules in response to a calcium influx is contemplated. In some embodiments of intestine on chip, L cell release of signal molecules in response to neuronal stimulation is contemplated. In other embodiments, neural-intestinal interaction with L-cells is contemplated for study in relation to health and disease. Thus providing additional advantages of using intestine on chip comprising L-cells.

Figure 30:
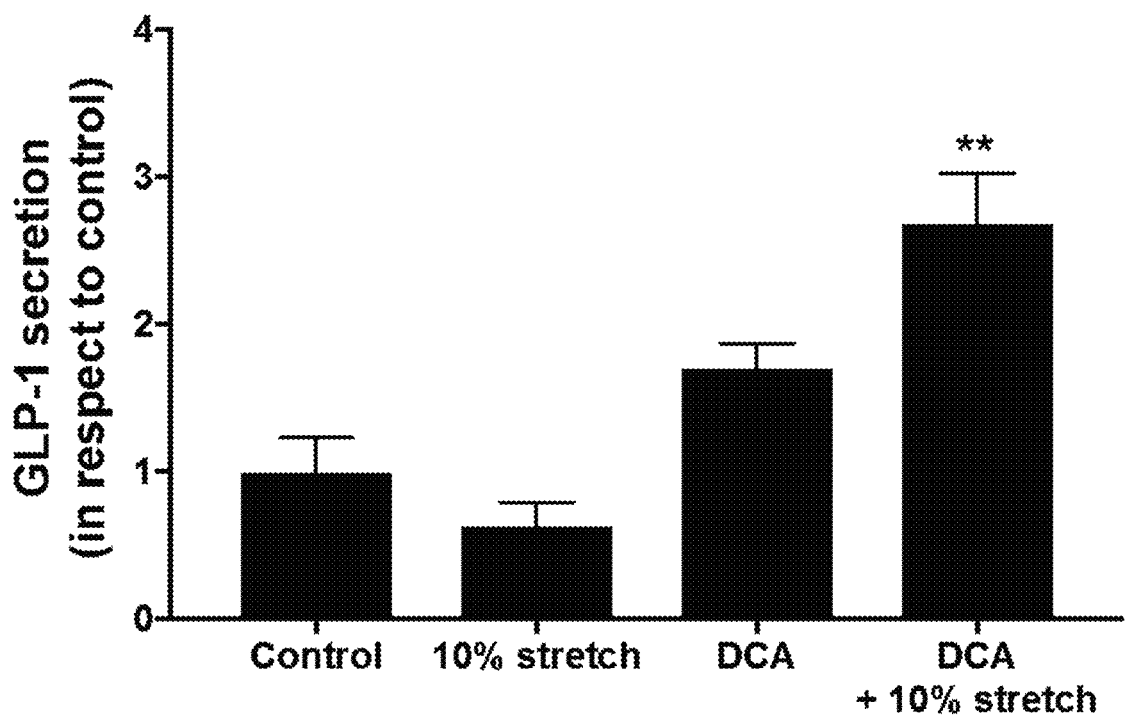
FIG. 30 shows an exemplary demonstration that L-cells respond to bile acid stimulation and stretching as shown by a graphical corporation of increased GLP-1 secretion. L-cells release GLP-1 into the vascular channel upon stimulation with bile acid (30 µM deoxycholic acid) and stretching.
Figure 31A:
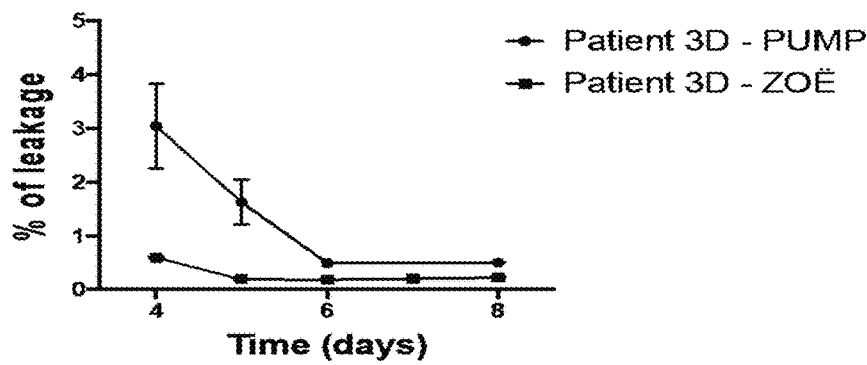
FIG. 31A-G shows an exemplary demonstration of faster establishment of intestinal permeability with lower chip to chip variability and faster development of cell types in maturing epithelial layers when using the culture module (described herein and shown in the figures), including but not limited to Epithelial cells identified by EpCAM, Paneth cells identified by lysozyme (LYZ), Absorptive Enterocytes identified by ALPI, Goblet cells identified by mucin 2 (MUC2), Enteroendocrine cells identified by chromogranin A (CHGA) and quiescent stem cells identified by (BMI1).
Figure 31B:
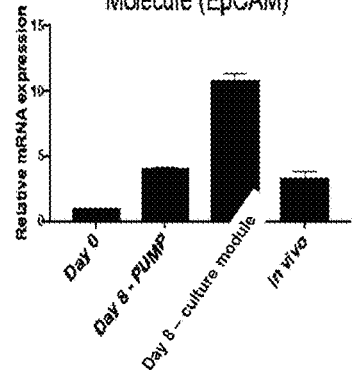
Figure 31C:
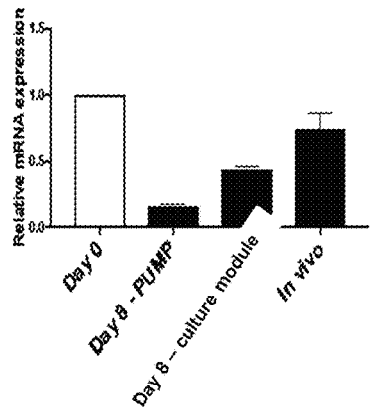
Figure 31D:
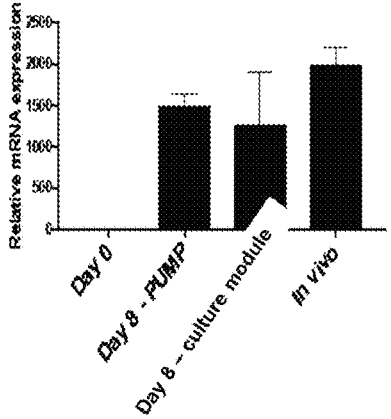
Figure 31E:
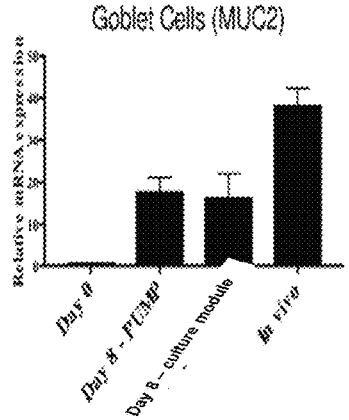
Figure 31F:
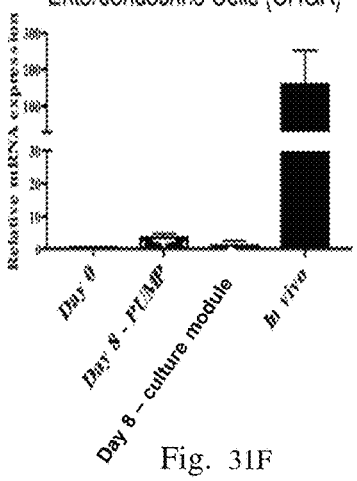
Figure 31G:
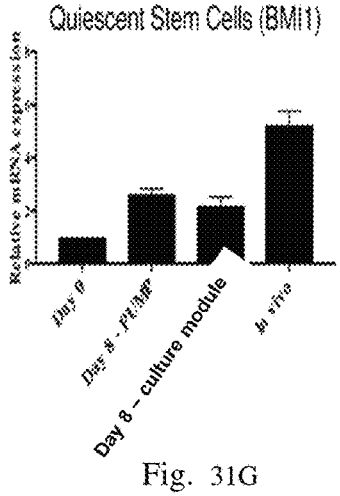

FIG. 30 L-cells Respond to Bile Acid Stimulation and Stretching as shown by a graphical corporation of increased GLP-1 secretion. L-cells release GLP-1 into the vascular channel upon stimulation with bile acid (30 μM deoxycholic acid) and stretching.

Diabetes—GLP-1 increases insulin secretion from pancreas and regulates blood glucose levels. There is a potential to develop orally active, luminally restricted compounds that target the receptors present on the L-cells to cause release of GLP-1. As one example, an effective therapy for T2D is direct targeting of GLP-1 receptors on pancreatic β cells with exenatide. Thus, targeting GLP-1 receptors in gastrointestinal cells is contemplated for an additional therapy for Type II diabetes (T2D).

Another target receptor contemplated for therapeutic targeting is GPR119, which is expressed by L cells and pancreatic β cells. In the pancreas, GPR119 agonists both increase GLP-1 release and act directly on pancreatic islets to release insulin. Therapeutics that specifically release endogenous GLP-1 from L cells are not yet available, although a luminally restricted GPR119 agonist is contemplated as a selective for incretin secretion.

Obesity—In other embodiments, target receptors for free fatty acids on enteroendocrine cells in the intestine are contemplated to increase satiety and combat obesity. SGLT1 or mechanisms through which its expression is regulated are also contemplated antidiabetic targets. SGLT1 is rapidly upregulated in T2D and its overexpression causes substantial obesity in mice.

Inflammatory Bowel Disease—Enteroendocrine cells were shown to have direct proinflammatory effect on disease progression (for one example, through secretion of IL-17) and anti-inflammatory effects through neuroimmune interaction. Thus, testing of therapies involving L-cells are contemplated.

Endocrine involvement in the context of the Intestine On Chip may be further used for linked-organ configurations. For one example, linking the endocrine-active Intestine On Chip with a Liver On Chip enables identifying energy metabolism alterations in health and disease, such as for diabetes. Thus, testing of therapies involving L-cells in multiple organs are contemplated.

Therefore, L-cells and the their surface receptors are considered herein as targets for novel therapies against disease including but not limited to type-2-diabetes, obesity, inflammatory bowel disease and cancer.

G. Exemplary Methods for Assessment of the Enteroendocrine Activity of Colon On-Chip (e.g. Release of GLP-1 from L-Cells):

a. At day 14, include a hormone release stimulant in the media of top input Reservoirs together with Dipeptidyl Peptidase IV Inhibitor (Diprotin A: Sigma D3822) to prevent GLP-1 degradation. Stimulants include but not limited to:
   i. Forskolin (coleonol) and/or IBMX (3-isobutyl-1-methylxanthine)—increase cyclic AMP (cAMP) inside the cells to release hormones (both used at 10 um)
   ii. Deoxycholic acid (DCA Sigma D2510) at the concentrations of 30 uM or other secondary bile acids, including but not limited to Lithocholic acid (LCA)
   iii. Compounds such as INT-777.
   iv. Free Fatty Acids (FFA) such as linolenic acid.
b. Stimulate for 2.5 hours at a flow rate of 200 ul/h (we are currently optimizing this condition)+/−10% stretch (to assess the effects of cyclic stretch motions on GLP-1 release)
c. Collect 400 ul sample from both output Reservoirs of each Chip for assessment of GLP-1 content
d. Centrifuge the samples at 400 G, 5 min, 4 C, aliquot and transfer the supernatant into labeled Eppendorf tubes, snap freeze, and store at −80 C before assessment
e. Measure GLP-1 content using Meso Scale Discovery Multi-Array Assay System for Active GLP-1 (ver. 2) (Cat #K150JWC-1) (see GLP-1 release, exemplary FIGS. 29 and 30).

III. Overcoming Day 10 Decline in Intestinal Layer Quality: Fluidic Ileum Intestine-Chip.

One observation of Intestine Chips related to a Day 10 observation of the beginning of a loss of intestinal epithelial layer quality when using adult derived cell sources. As one example, starting from day 10, barrier function begins to decline in the majority of embodiments of intestinal chips. Thus readouts for the majority of end of study results were obtained on Day 10.

However, longer experimental time-lines were desired. Therefore, a method was developed for overcoming the fluidic Intestine Chip Day 10 barrier. After numerous types of alterations, a 2-step seeding procedure is discovered to provide a longer time frame for observations of a healthy intestinal layer on-chip. This 2-step seeding method was developed using Ileal-derived enteroids in combination with adult derived HIMECs. Then the 2-step seeding method was applied to other embodiments of fluidic devices comprising: Ileal-derived cells; duodenum-derived cells; and colon-derived cells.

Moreover, desired features of fluidic intestine devices include, but are not limited to, having a strong intestinal barrier function lasting over a time period to provide a sufficient experimental window for observations and collecting data for readouts, i.e. longevity, such as for providing medically relevant readouts; having correct tissue maturation along with 3D (three-dimensional) tissue architecture for replicating in vitro the desired embodiment, such as duodenum, ileum, colon, etc., under healthy, compromised or certain stages of disease conditions, e.g. epithelial layers having percentages of specialized cells matching (or physiologically relevant) with 3D architecture observed in vivo. Read-outs include but are not limited to: barrier function; qRT-PCR; bright-field microscopy; and confocal microscopy.

A. Two-Step Seeding for Embodiments of Fluidic Ileum Intestine-Chip/Ileum-Chip.

The ileum refers to the third portion of the small intestine, between the jejunum and the cecum. Biopsies were obtained from ileal areas of human small intestine then used for providing enteroids.

I. A Two-Step Seeding Method.

Embodiments of fluidic devices for testing conditions leading to a 2-step seeding method included using cyclic stretch, applied on day 4, and culturing under Liquid-Liquid culture conditions.

Enteroids derived from biopsies of adult ileal tissues were used to provide cells for seeding epidermal layers into embodiments of intestine-chips. For the 1-step method, ileal enteroids cells were seeded in one channel on Day 0 while HIMECs were seeded into another channel, separated by a membrane. After seeding, flow was applied over the duration of the 14-day observation period. After testing several variables, a 2-step method was developed then compared to the standard 1-step method used for embodiments of Intestine-chips, such as embodiments comprising pediatric sources of HIMECs. For the 2-step method ileal enteroids cells were seeded in one channel on Day 0, flow was applied after Day 1, cyclic stretch was applied on day 4, then HIMECs were seeded into an opposing channel on the other side of the membrane. After cells attached, flow was applied over the remaining duration of incubation, up to at least Day 14. For comparison, organoids cultured under static conditions, such as not on chips, create some intestinal differentiated cell types however these cells are in clumps of cells, not monolayers as on-chips, do not provide homogenous and repeatable amounts of differentiated cells and are difficult to access for readouts from within the clumps.

Figure 33:
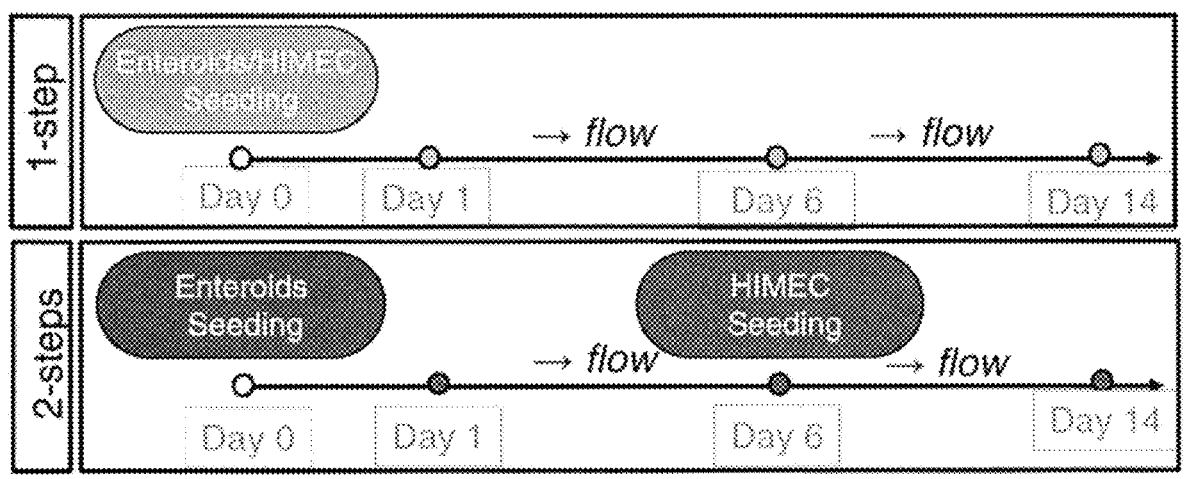
FIG. 33 is a schematic illustration comparing two types of seeding methods used for seeding ileal intestinally derived enteroids cells into fluidic devices under flow: a 1-step method vs. a 2-step method.

FIG. 33 is a schematic illustration comparing two types of seeding methods used for seeding ileal intestinally derived enteroids cells into fluidic devices under flow: a 1-step method vs. a 2-step method.

Although 1-step seeding protocol allows faster establishment of strong intestinal barrier functions it fails to support its maintenance for longer than 10 days. A 2-step seeding procedure allows longer maintenance of high barrier function, i.e. low Papp values ($-0.5$-$1\times10^6$ cm/s) increasing time window available for experimentation.

Figure 34:
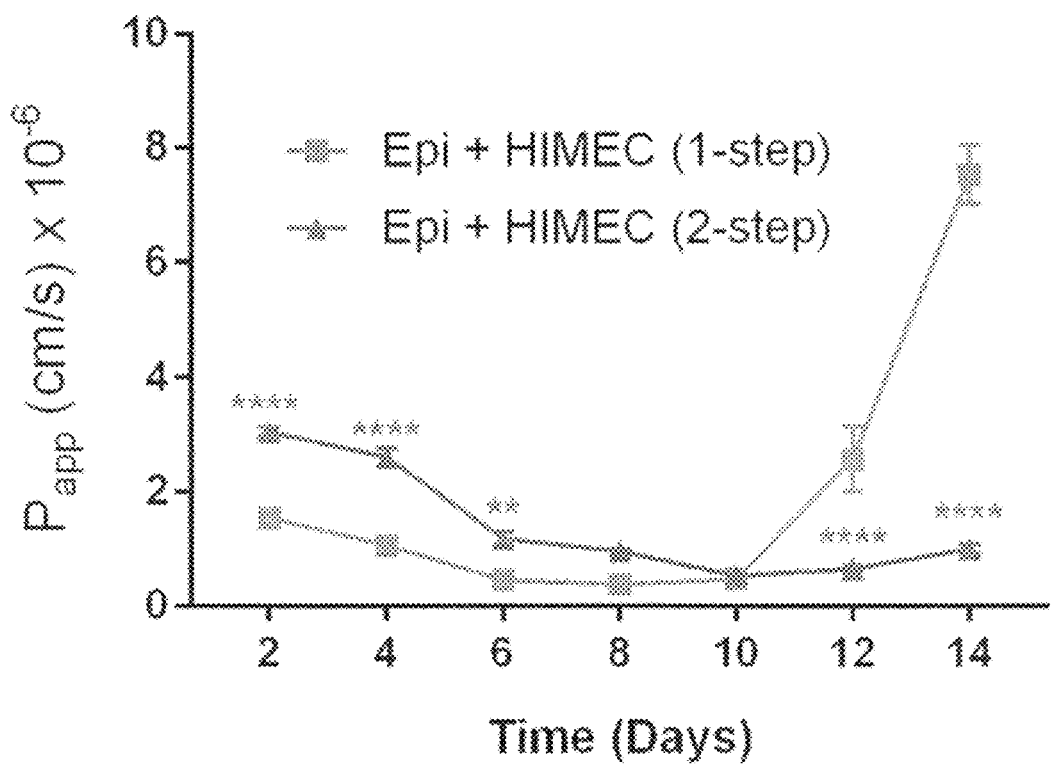
FIG. 34 is one embodiment of a fluidic Ileum Intestine-Chip showing maintenance of barrier function up to at least 14 days using one embodiment of a 2-step as opposed to a loss of barrier function by day 12 using one embodiment of a 1-step method.

FIG. 34 is one embodiment of a fluidic Ileum Intestine-Chip showing maintenance of barrier function up to at least 14 days using one embodiment of a 2-step as opposed to a loss of barrier function by day 12 using one embodiment of a 1-step method.

Surprisingly, when using adult sources of cells, as opposed to pediatric sources, an abundance of morphogenesis of villi-like structures was observed in ileal epithelium in the 2-step seeding protocol. 3D villi-like structures are formed across the entire length of the inlet as well as the middle channel of the ileal Intestine-Chip platform in 2-step seeding protocol. In comparison, villi-like structures are present in the inlet of 1-step seeding protocol but not in the main middle culture channel.

Figure 35:
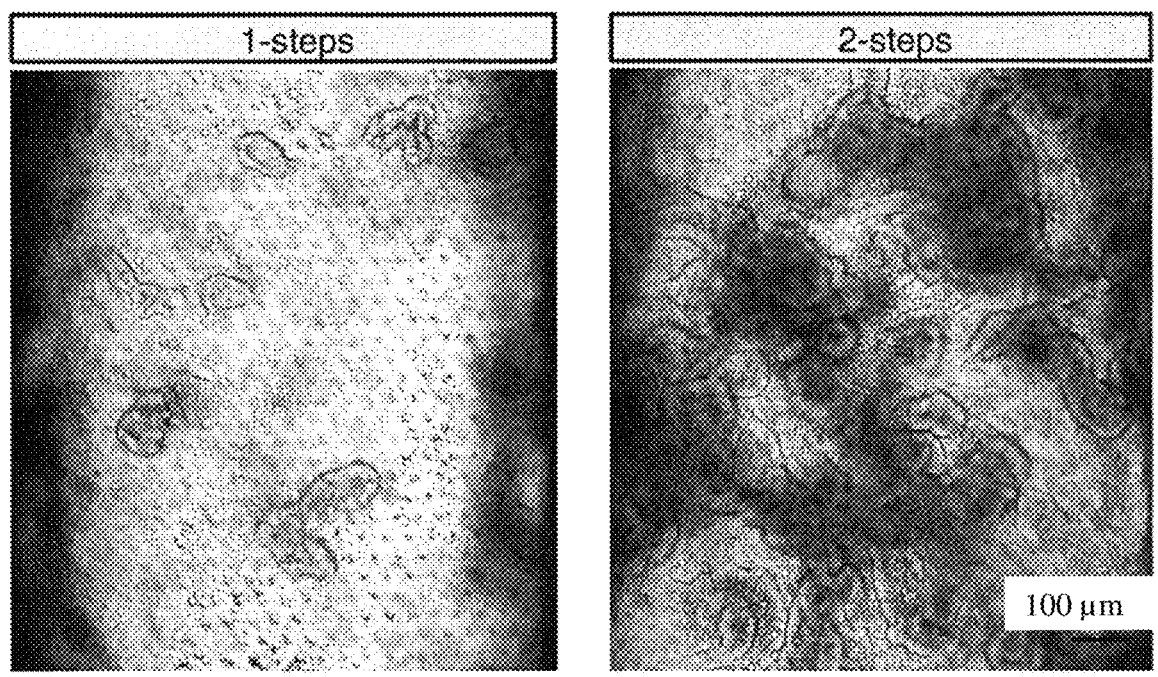
FIG. 35 is one embodiment of a fluidic Ileum Intestine-Chip showing morphogenesis of villi-like structures in ileal epithelium after using a 1-step method (left) compared to a 2-step seeding protocol (right). Representative images from day 8 of seeding are shown.

FIG. 35 is one embodiment of a fluidic Ileum Intestine-Chip showing morphogenesis of villi-like structures in ileal epithelium after using a 1-step method (left) compared to a 2-step seeding protocol (right). Representative images from day 8 of seeding are shown.

F-Actin staining allowed the visualization of differences in general morphology of the epithelial tissue between the two seeding methods.

Figure 36:
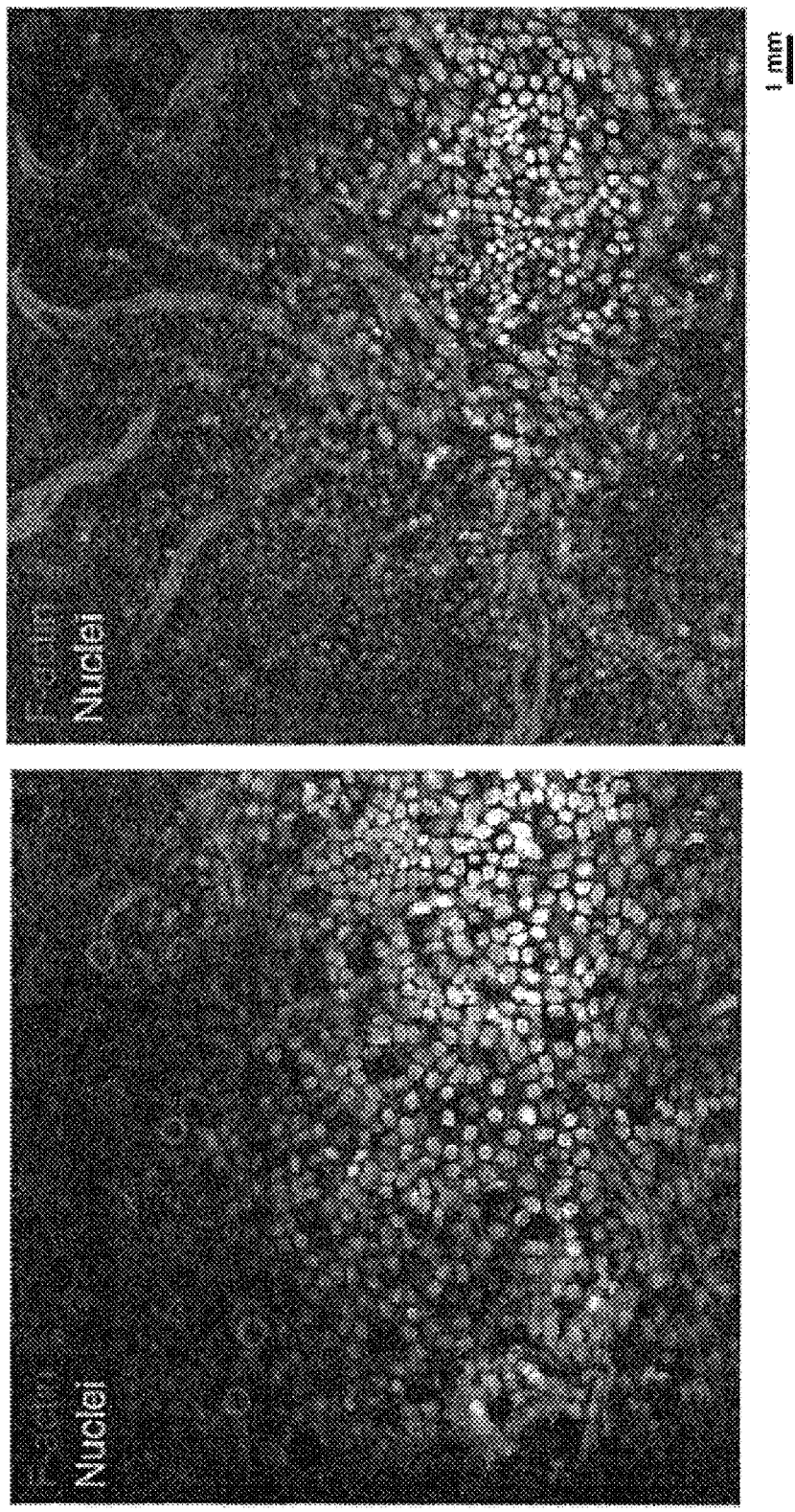
FIG. 36 is one embodiment of a fluidic Ileum Intestine-Chip showing homogenous 3D tissue morphology observed using one embodiment of a 2-step protocol (right) in contrast to a 1-step method (left). F-actin; stained nuclei indicated in white-grey in black and white image.

FIG. 36 is one embodiment of a fluidic Ileum Intestine-Chip showing homogenous 3D tissue morphology observed using one embodiment of a 2-step protocol (right) in contrast to a 1-step method (left). F-actin (stained); stained nuclei colored white-grey in black and white image.

2. Intestinal Tissue Maturation: Specialized Cells.

Embodiments of fluidic devices comprising enteroid derived cells from biopsies of adult ileal tissues were evaluated for intestinal tissue maturation. In part, tissue maturation in the epithelial layer was measured by comparative mRNA expression of specialized cell biomarkers, between a 1-step method; a 2-step method and in vivo ileum.

Figure 37A:
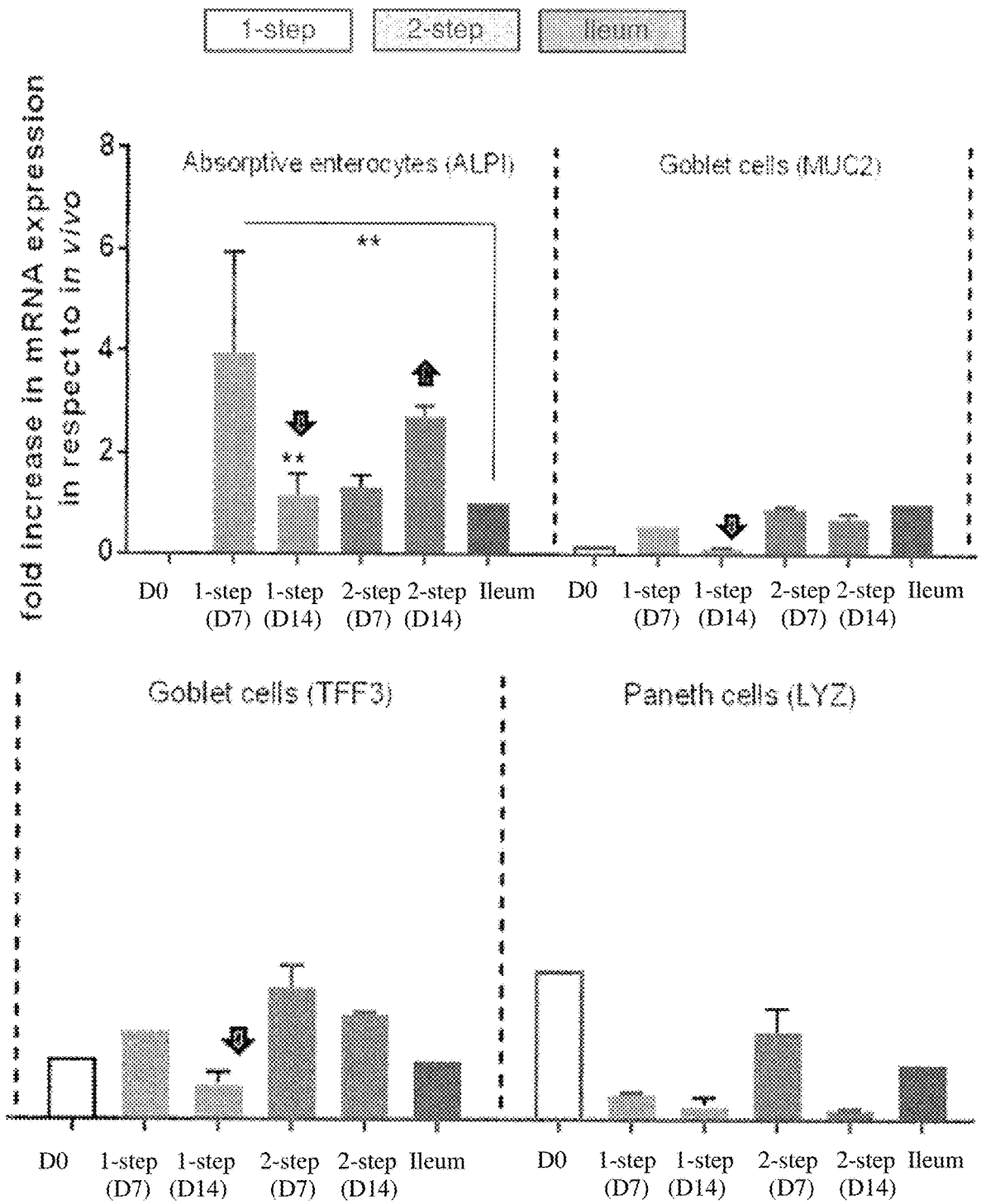
FIG. 37A-B showing one embodiment of a fluidic Ileum Intestine-Chip showing comparative mRNA expression of specialized cell biomarkers comparing a 1-step; a 2-step and in vivo ileum.
Figure 37B:
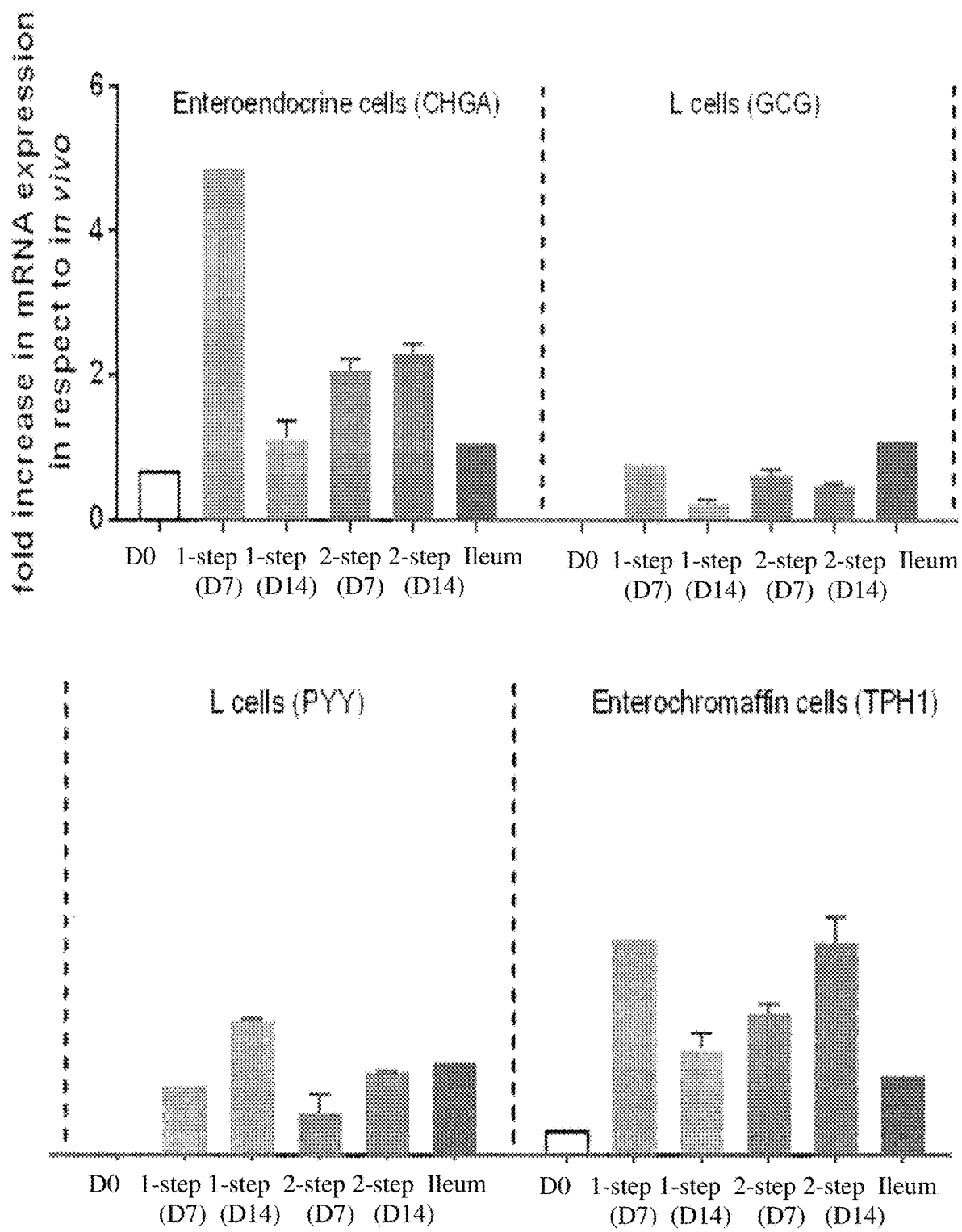

As shown in FIG. 37A-B, successful differentiation of enteroendocrine cells maturation was observed using both seeding procedures. Thus, Ileum derived epithelial cell layers showed expression of cell type specific biomarkers for absorptive enterocytes, Paneth cells, goblet cells, enteroendocrine cells, L-cells and enterochromaffin cells, for both methods. Expression levels of biomarkers in cells cultured using one embodiment of a 2-step method showed expression levels similar to levels observed in adult in vivo ileal tissue for the majority of cell types. Gene expression levels of adult in vivo tissue were obtained from the RNA samples that were isolated directly from human ileal tissue.

FIG. 37A-B showing one embodiment of a fluidic Ileum Intestine-Chip showing comparative mRNA expression of specialized cell biomarkers comparing a 1-step; a 2-step and in vivo ileum. FIG. 37A is one embodiment of a fluidic Ileum Intestine-Chip showing comparative mRNA expression of specialized cell biomarkers for absorptive enterocytes (ALPI); Goblet cells (MUC2); Goblet cells (TFF3); and Paneth cells (LYZ). 1-step; 2-step and in vivo Ileum. FIG. 37B is one embodiment of a fluidic Ileum Intestine-Chip showing comparative mRNA expression of specialized cell biomarkers for enteroendocrine cells (CHGA); L-cells (monoclonal antibody GCG, detects proglucagon, glucagon, GLP-1 and GLP-2); L-cells (PYY); and enterochromaffin cells (TPH1).

Tuft cells, sometimes referred to as brush cells, are microvilli+ chemosensory-secretory cells observed in certain areas of the epithelial lining of the small intestine and colon. Collectively, expression of three genes, Transient Receptor Potential Cation Channel Subfamily M Member 5 (TRPM5); Choline acetyl transferase (ChAT or CHAT) and Doublecortin-like kinase 1 protein (DCLK1, identify populations of Tuft intestinal cells. Their presence was monitored in embodiments of fluidic Ileum Intestine-Chips. Expression of Tuft cells specific markers was very low or undetectable in several embodiments of an ileum-Chip (independently of protocol). IN particular, Trpm5 mRNA was detected at low levels, while protein was not detected by immunofluorescence in one embodiment of a fluidic Ileum Intestine-Chip (Trpm5−, ChAT−, DCLK1−).

Figure 38:
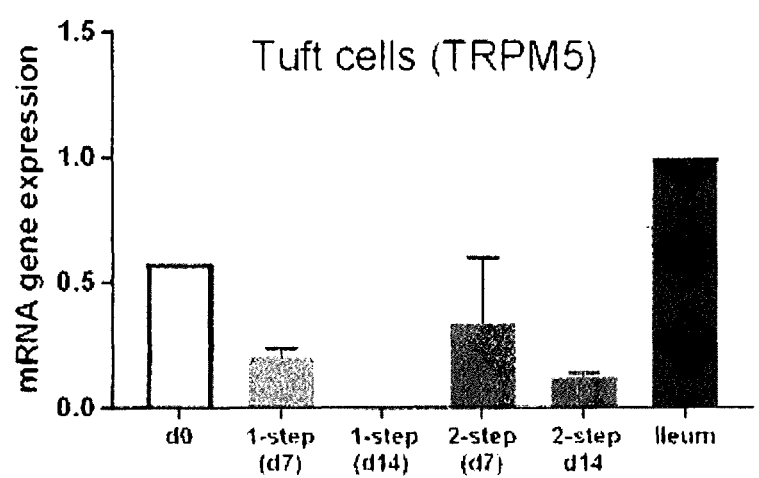
FIG. 38 is one embodiment of a fluidic Ileum Intestine-Chip showing comparative mRNA expression levels for one of the Tuft cell markers TRPM5. Other Tuft cell biomarkers ChAT and DCLK1 were not detected in these samples, except for the mRNA isolated from the in vivo levels in isolated ileal tissue. Sample dates: day (d)O; 1-step (d7); 1-step (d14); 2-step (d7); 2-step (d14); and Ileum (isolated).

FIG. 38 is one embodiment of a fluidic Ileum Intestine-Chip showing comparative mRNA expression levels for one of the Tuft cell markers TRPM5. Other Tuft cell biomarkers ChAT and DCLK1 were not detected in these samples, except for the mRNA isolated from the in vivo levels in isolated ileal tissue. Sample dates: day (d)O; 1-step (d7); 1-step (d14); 2-step (d7); 2-step (d14); and Ileum (isolated).

In summary, two seeding protocols were compared for establishing an ileum-Chip model. For modeling embodiments of Intestine-chips having intact barrier function, up to at least Day 14, one exemplary embodiment of a 2-step seeding protocol was chosen that supports development of desired features of an ileum-Chip, including: A strong intestinal barrier function; correct tissue maturation, as in comparison to representing a specific area in vivo, showing development and successful maintenance of major differentiated cell types; 3D tissue architecture as shown by successful formation of homogenous intestinal "villi-like structure"; and a sufficient experimental time window, at least 1 week along with high longevity, i.e. at least up to 14 days from seeding an epithelial layer.

IV. Fluidic Ileal Intestine-Chip/Ileal-Chip Enteroids.

In some embodiments, human ileal areas of the small intestine are modeled in fluidic devices using a fluidic Intestine-Chip seeded with Ileal Enteroids cells obtained from adult patient biopsies.

Figure 39A:
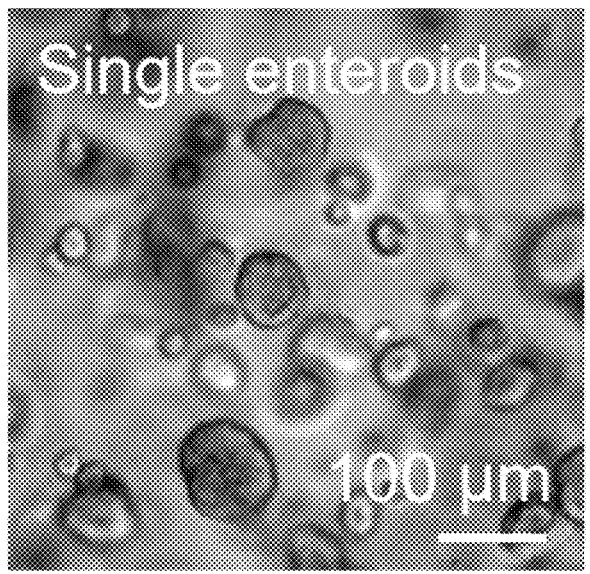
FIG. 39A-B shows exemplary micrographs (bright-field microscopy) of cells used for seeding Intestine-Chips.
Figure 39B:
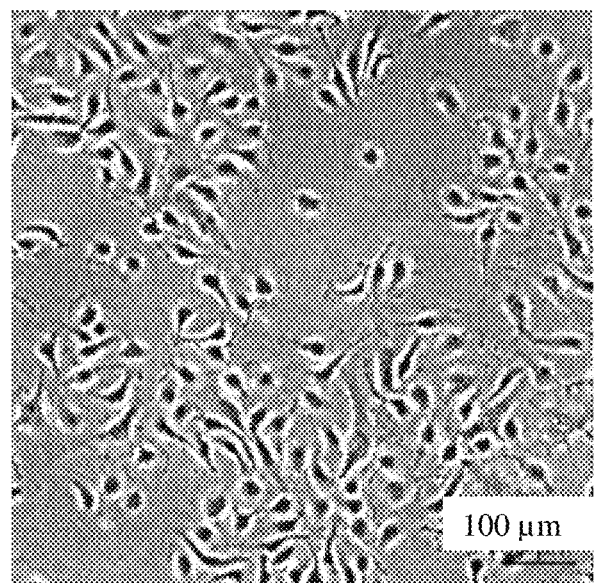
Figure 39C:
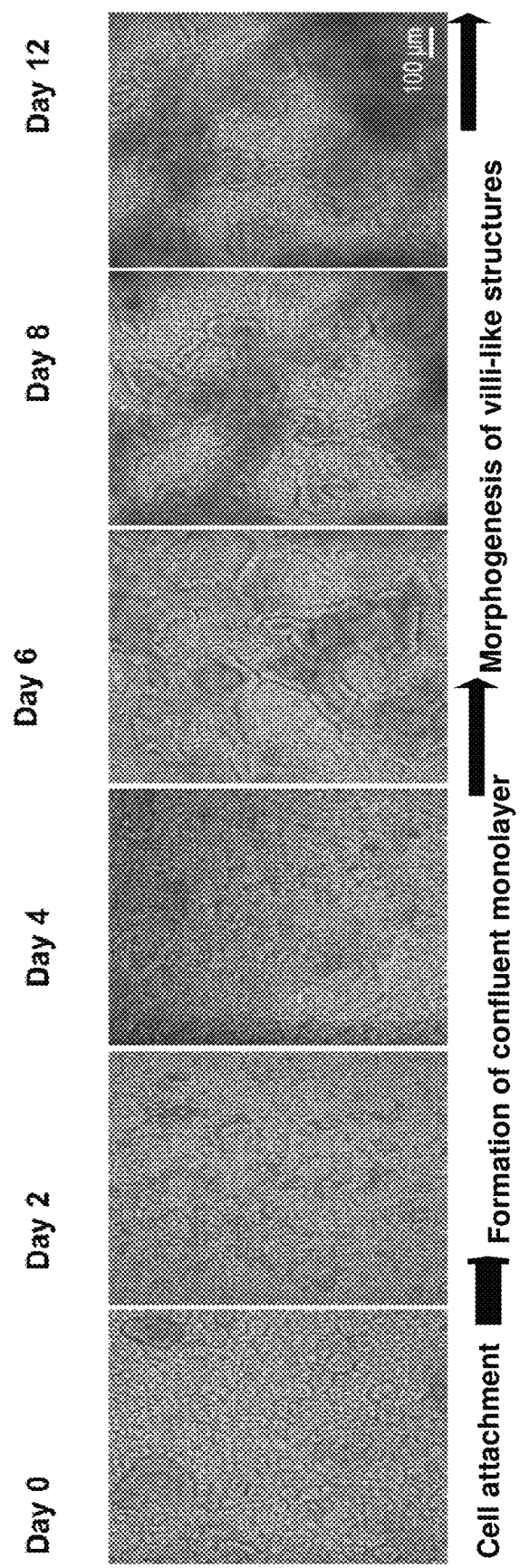
FIG. 39C shows exemplary micrographs over time of intestinal cells cultured in fluidic chips. From left to right, Day 0 cell attachment, Day 2-Day 4 formation of a confluent monolayer: Day 6: HIMEC seeding, under flow and stretch, morphogenesis of villi-like structures through Day 8 and up to Day 12.

Examples of cells used for seeding fluidic devices are shown in FIG. 39A-B with results of seeding cells after specified days of culture shown in FIG. 39C.

FIG. 39A-B shows exemplary micrographs (bright-field microscopy) of cells used for seeding Intestine-Chips. FIG. 39A shows an exemplary micrograph representing a cluster of Ileal enteroids embedded in Matrigel in 1 well of a 24-well plate in which organoids were grown embedded in ECM gel and overlaid with IntestiCult™ media. FIG. 39B shows an exemplary micrograph representing endothelial cells grown in flask filled with EGM2-MV media.

One embodiment of an experimental timeline for providing an ileum intestine-chip. Day −1: chip surface activation and coating. Day 0: seeding enteroids. Day 1: begin culturing under flow conditions. Day 4: observations and readouts. Day 6: HIMEC seeding; culturing under flow and stretch conditions. Day 14 (or later): observations and readouts.

FIG. 39C shows exemplary micrographs over time of intestinal cells cultured in fluidic chips. From left to right, Day 0 cell attachment, Day 2-Day 4 formation of a confluent monolayer; Day 6: HIMEC seeding, under flow and stretch, morphogenesis of villi-like structures through Day 8 and up to Day 12.

In some embodiments, fluidic devices using a fluidic Intestine-Chip seeded with Ileal Enteroids cells show intestinal 3D Tissue Architecture representative of the ileum, for example, formation of Intestinal Villi-like Structures during epithelial layer formation.

Figure 40A:
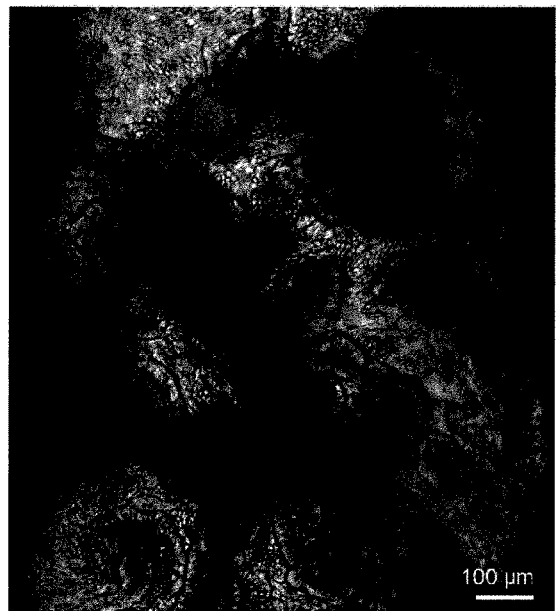
FIG. 40A-B is one embodiment of a fluidic Ileum Intestine-Chip showing morphogenesis of villi-like structures in ileal epithelium across entire length of the epithelial channel. Representative images from day 8 of growth are shown.
Figure 40B:
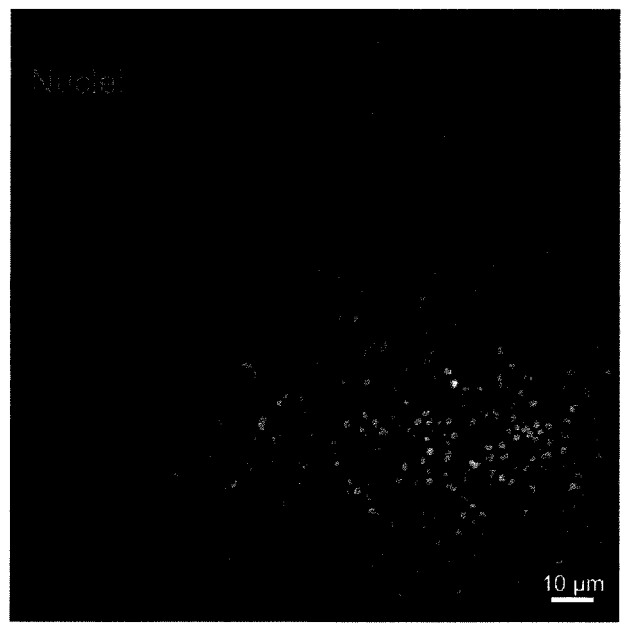

FIG. 40A-B is one embodiment of a fluidic Ileum Intestine-Chip showing morphogenesis of villi-like structures in ileal epithelium across entire length of the epithelial channel. Representative images from day 8 of growth are shown. FIG. 40A Bright field microscopy image. FIG. 40B confocal microscopy image. F-actin and nuclei are stained.

One surprising result discovered during the development of the present inventions was the presence of endothelial cells rescues epithelial layers from a loss of intestinal barrier function. In other words, the presence of HIMEC in vascular channel improves maintenance of intestinal barrier functions.

Figure 41A:
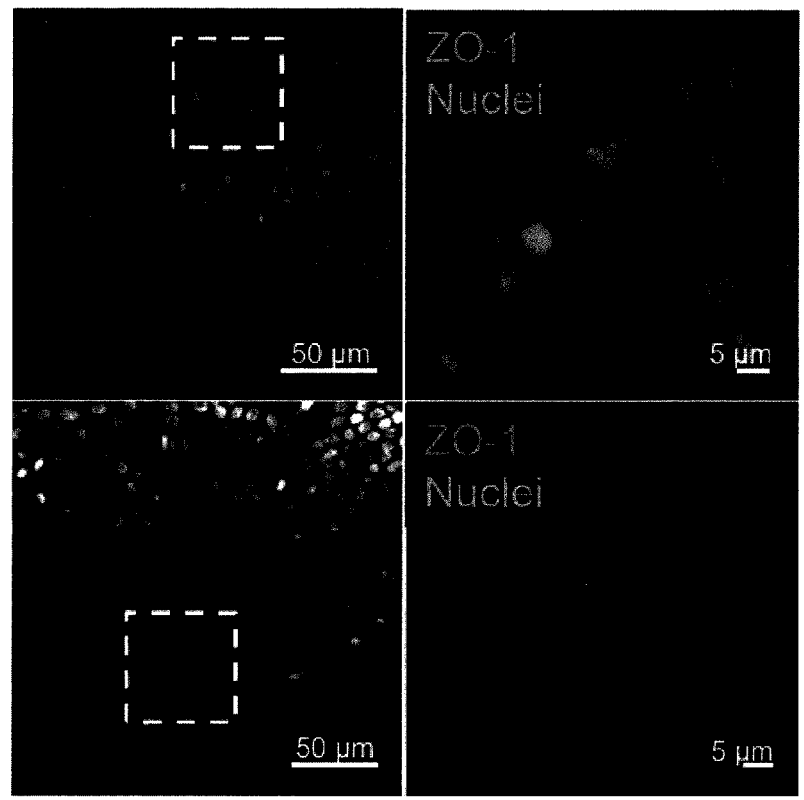
FIG. 41A-B shows two embodiments of a fluidic Ileum Intestine-Chip, one with HIMEC and one without, showing presence of HIMEC in the vascular channel improves maintenance of intestinal barrier functions. Representative images from day 14 of growth are shown.
Figure 41B:
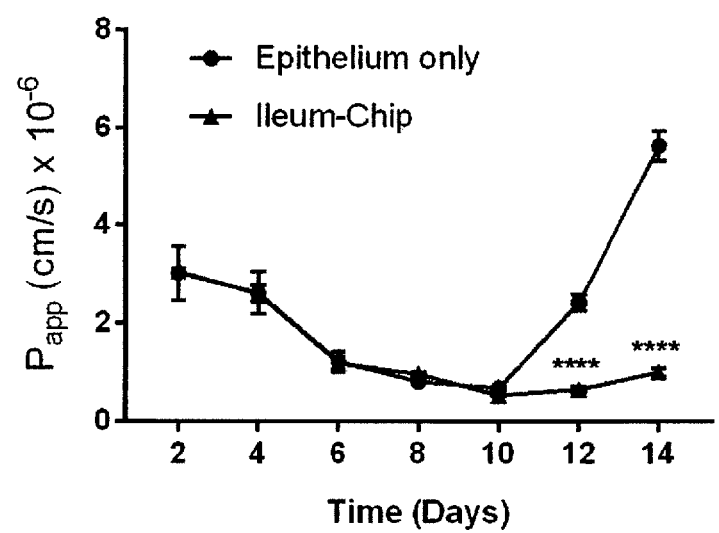

FIG. 41A-B shows two embodiments of a fluidic Ileum Intestine-Chip, one with HIMEC and one without, showing presence of HIMEC in the vascular channel improves maintenance of intestinal barrier functions. Representative images from day 14 of growth are shown. FIG. 41A confocal microscopy images: epithelium without HIMECs, upper images, epithelium with HIMECs. ZO-1 (stained) and nuclei (stained). FIG. 41B shows exemplary barrier function comparisons between 2 embodiments of Intestin-chips.

In some embodiments, in part for identifying differences between ileal enteroids and embodiments of an Ileum-Chip (with HIMECs), imaging (microscopic observations) and gene expression analysis were compared. In particular, Ileal enteroids and one embodiment of an Ileum-Chip (with HIMECs) were cultured up to 12 days in the presence of IntestiCult™ Organoid Growth Medium (Human) (STEMCELL Technologies Inc., 2323-222 Third Street, Cambridge, MA 02142).

Figure 42A:
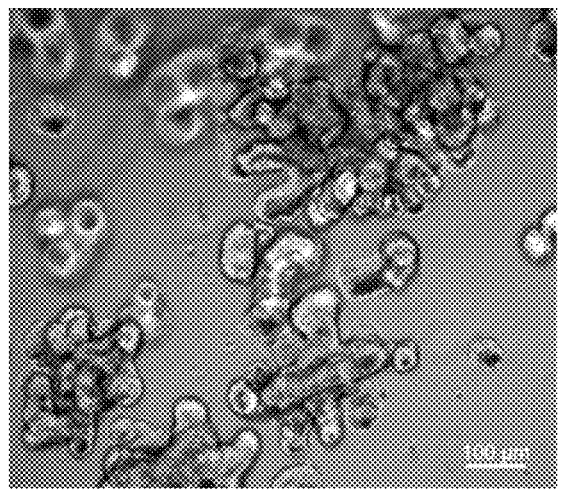
FIG. 42A-B shows bright field microscopy image comparisons between FIG. 42A showing exemplary 3D Ileal Organoids and FIG. 40A showing one embodiment of an Ileum-Chip (with HIMECs). Ileal enteroids and Ileum-Chip was cultured up to 4, 8 and 12 days in the presence of IntestiCult™ Media and compared using imaging and gene expression analysis.
Figure 42B:
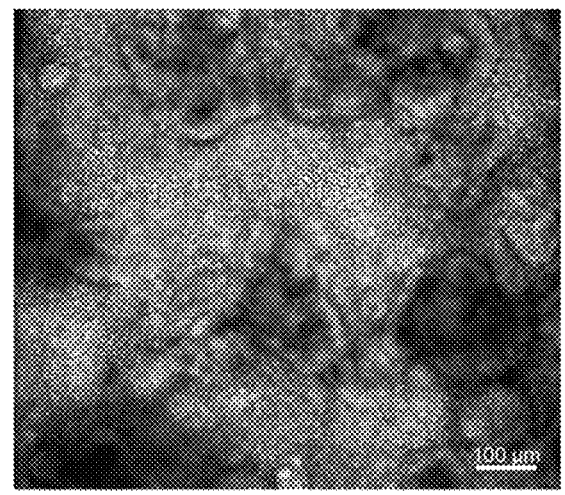

FIG. 42A-B shows bright field microscopy image comparisons between FIG. 42A showing exemplary 3D Ileal Organoids and FIG. 40A showing one embodiment of an Ileum-Chip (with HIMECs). Ileal enteroids and Ileum-Chip was cultured up to 4, 8 and 12 days in the presence of IntestiCult™ Media and compared using imaging and gene expression analysis.

Figure 43A:
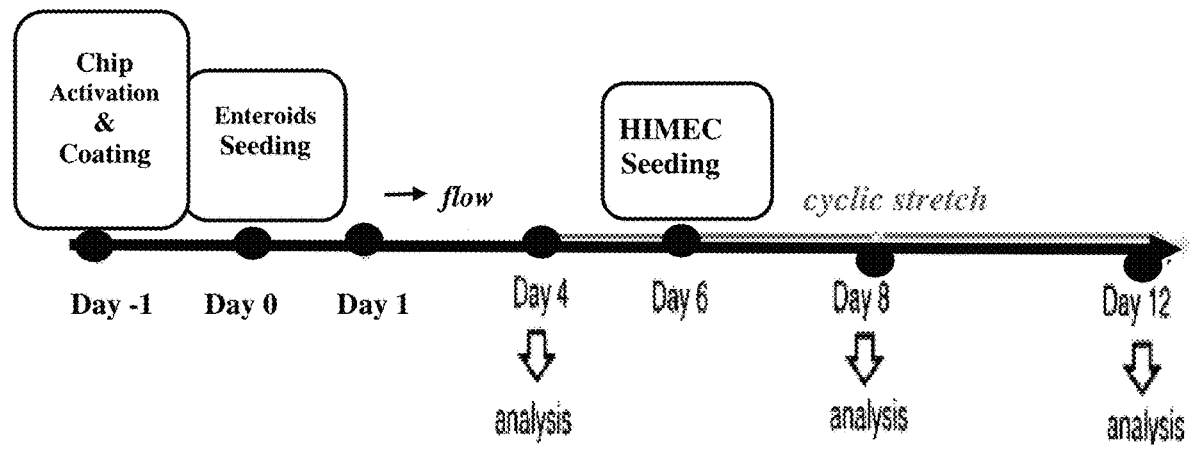
FIG. 43A-B shows schematic illustrations of exemplary experimental timelines for culturing
Figure 43B:
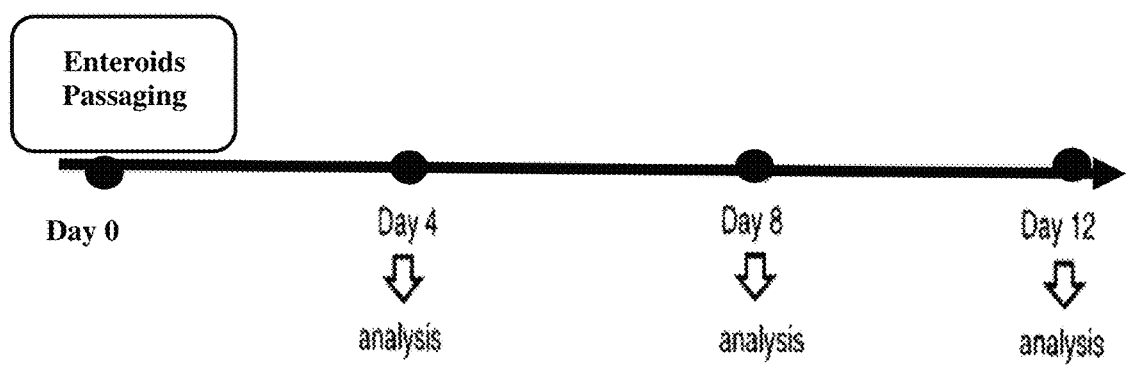

FIG. 43A-B shows schematic illustrations of exemplary experimental timelines for culturing FIG. 43A shows one embodiment of an Ileum-Chip (with HIMECs) and FIG. 43B shows exemplary Ileal enteroids. In one embodiment, the Ileum-Chip and Ileal enteroids were analyzed at day 4, 8 and 12 of post-seeding.

In some embodiments, intestinal cell types were identified in and compared between ileal enteroids cultured as described herein, and one embodiment of an Ileum Intestine-Chip (with HIMECs). The presence of major intestinal cell types, such as goblet cells; Enteroendocrine Cells—EEC; L-cells; enterochromaffin Cells; Paneth Cells (LYZ) and absorptive enterocytes were detected with the exception of tuft cells in 3D ileal enteroids and one embodiment of an Ileum Intestine-Chip (with HIMECs).

Figure 44A:
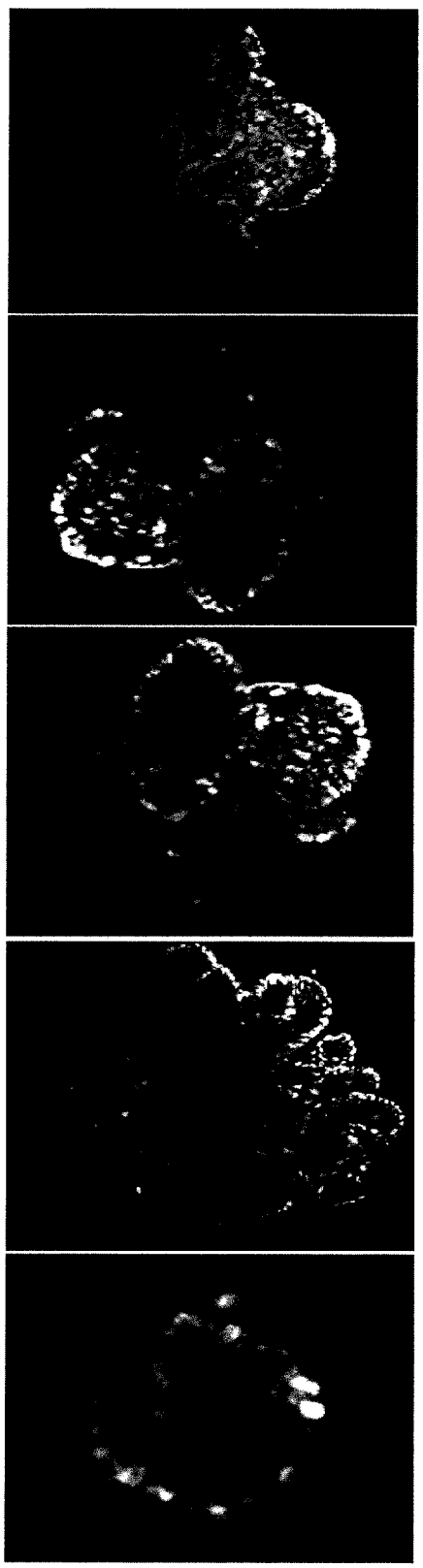
FIG. 44A-B shows exemplary cell types detected in FIG. 44A shows exemplary 3D ileal enteroids and FIG. 44B shows exemplary confocal images of Ileum-Chip (with HIMECs). Representative images from day 8 of growth are shown, from left to right, by cell type and immunostained biomarker: goblet cells (MUC2); Enteroendocrine Cells—EEC (CHGA)/L-cells (GLP-1); Enterochromaffin Cells (5HT); Paneth Cells (LYZ) and absorptive enterocytes (villin). Nuclei are stained.
Figure 44B:
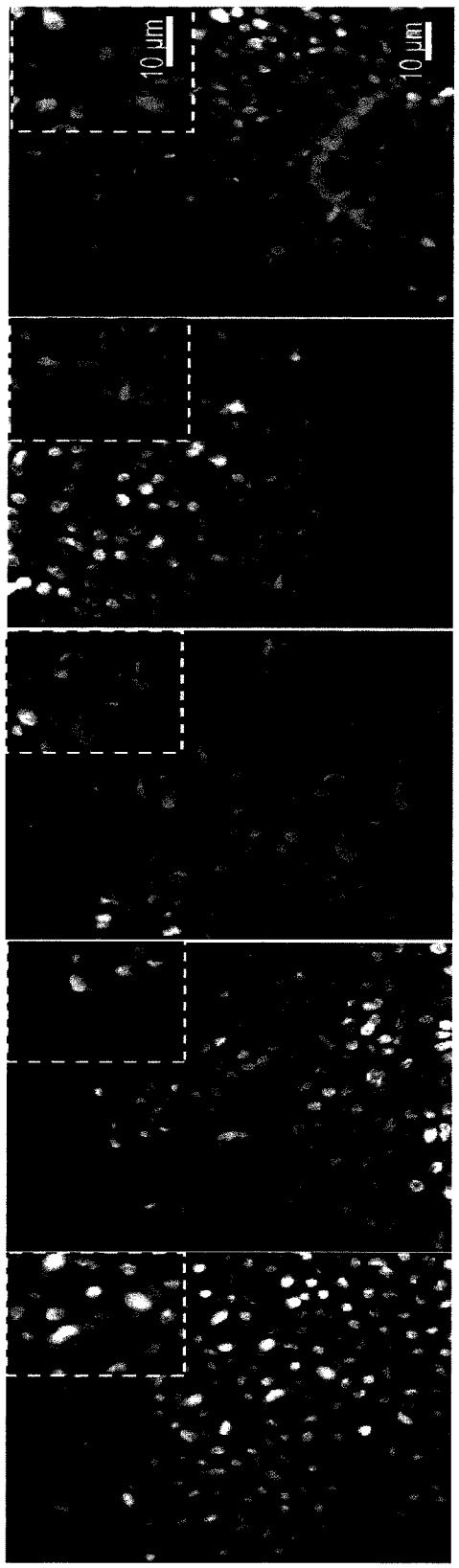

FIG. 44A-B shows exemplary cell types detected in FIG. 44A shows exemplary 3D ileal enteroids and FIG. 44B shows exemplary confocal images of Ileum-Chip (with HIMECs). Representative images from day 8 of growth are shown, from left to right, by cell type and immunostained biomarker: goblet cells (MUC2); Enteroendocrine Cells—EEC (CHGA)/L-cells (GLP-1); enterochromaffin Cells (5HT); Paneth Cells (LYZ) and absorptive enterocytes (villin). Nuclei are stained.

Although mature major cell types were detected in both enteroids and in epithelial layers derived from enteroids, there were significant differences between comparative amounts as indicated by differences in mRNA expression for intestinal cell type biomarkers. As one example, On-Chip Culture of enteroids into epithelial layers Improves Maturation of Intestinal Cells shown by significant differences in expression levels of mRNA in respect to enteroids cell samples used for seeding fluidic chips. In particular, on-chip cultures at Day 4, Day 6 and Day 8, showed significantly increased expression (in comparison to 3D enteroids cultures) of markers specific for absorptive enterocytes, goblet cells and enteroendocrine cells. One embodiment of the Ileum-Chip showed improved maturation of enteroendocrine cell population, including L-cells and enterochromaffin cells in comparison to 3D ileal enteroids. Moreover, one embodiment of an Ileum-Chip showed improved maturation of enteroendocrine cell population, including L-cells and enterochromaffin cells in comparison to 3D enteroids.

Figure 45A:
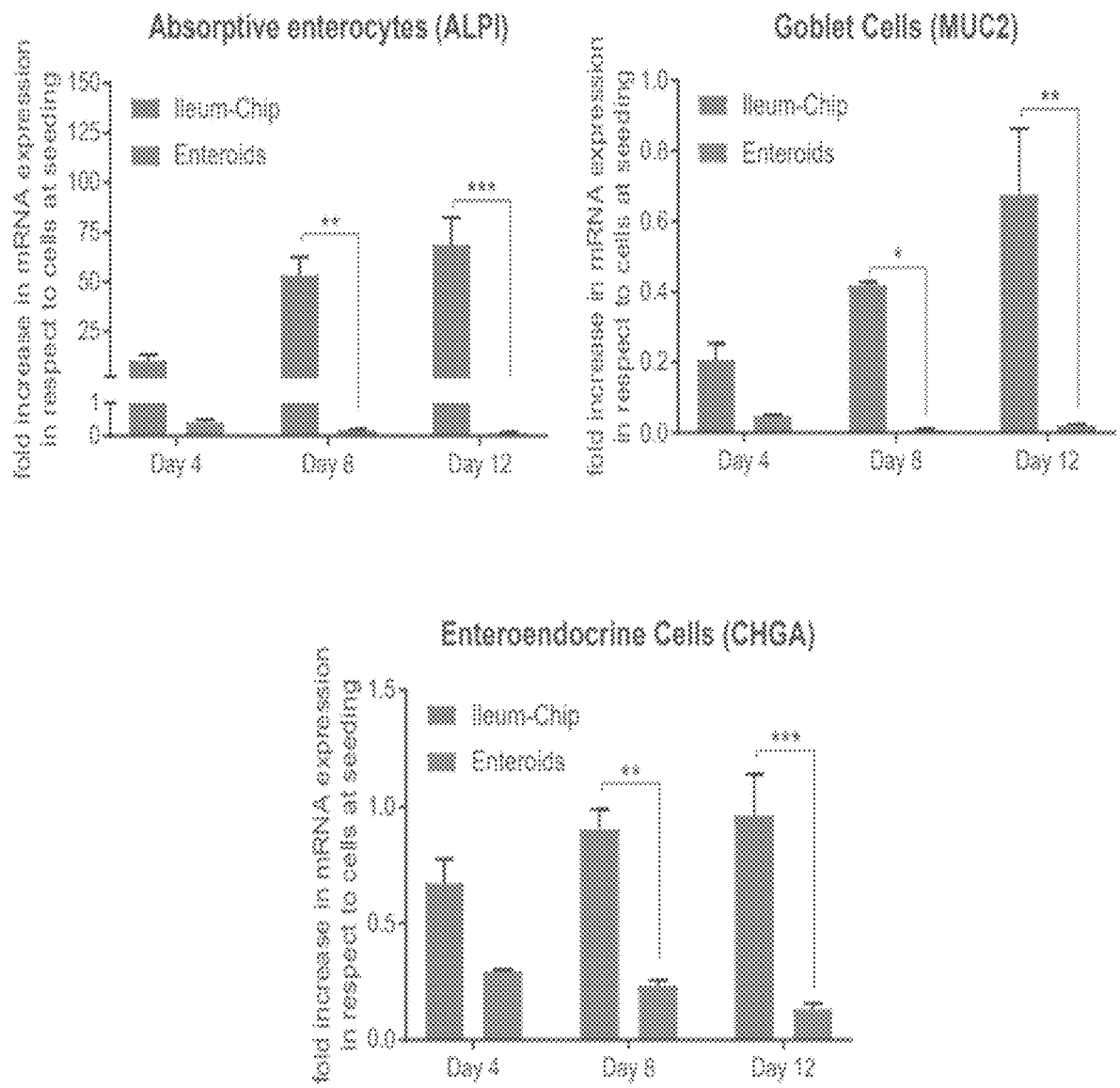
FIG. 45A-B shows exemplary cell types detected in larger amounts in one embodiment of Ileum On-Chip (Ileum-Chip in respect to enteroids cell samples used for seeding fluidic chips. Representative data from Ileum-Chip (left bar) and enteroids (right bar) from days, 4, 8, and 12 of culture On-Chip are shown.
Figure 45B:
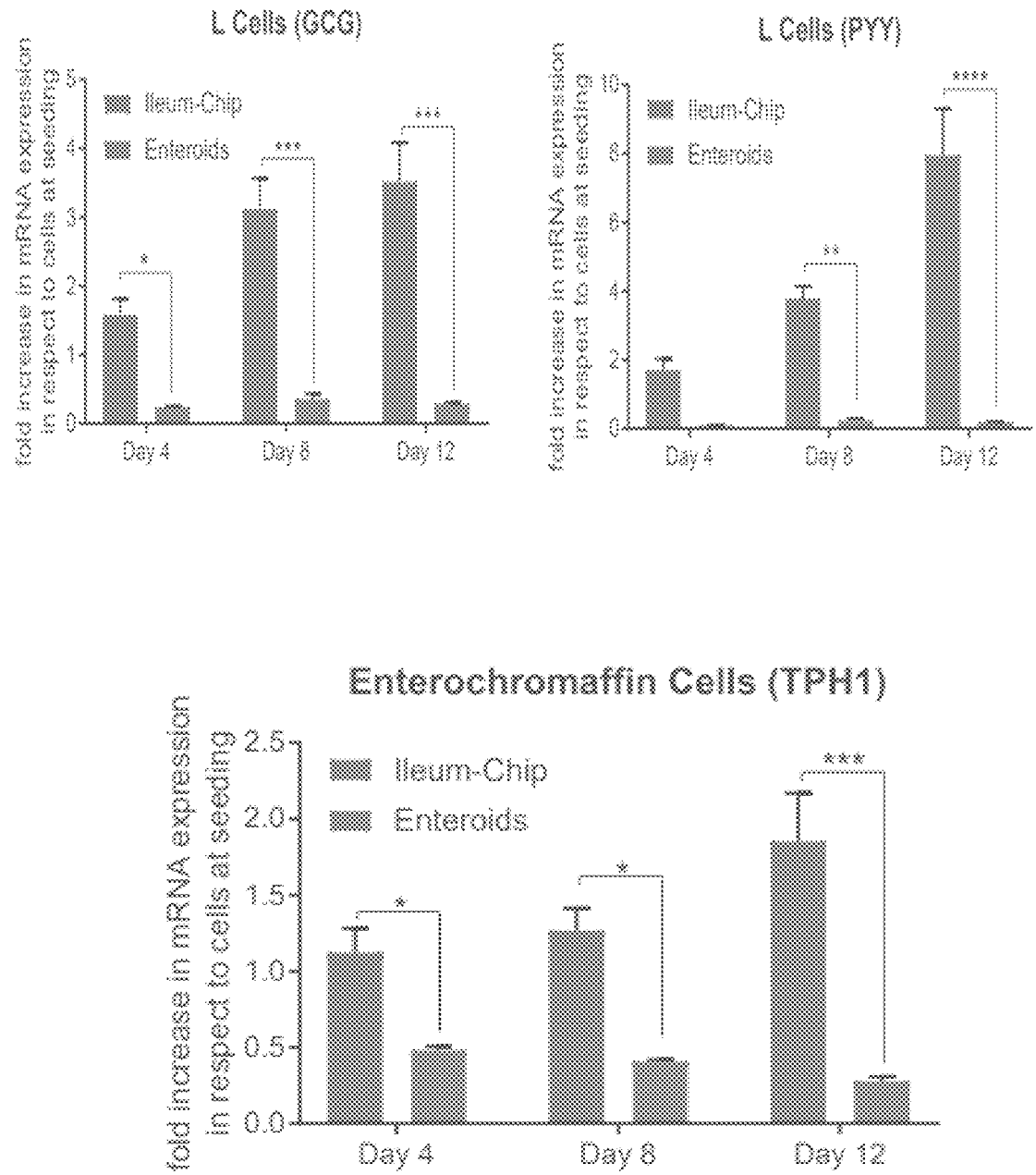

FIG. 45A-B shows exemplary cell types detected in larger amounts in one embodiment of Ileum-Chip in respect to enteroids cell samples used for seeding fluidic chips. Representative data from Ileum-Chip (left bar) and enteroids (right bar) from days, 4, 8, and 12 of culture on-chip are shown. FIG. 45A from left to right, by cell type and biomarker: absorptive enterocytes (ALPI); goblet cells (MUC2); Enteroendocrine Cells-EEC (CHGA). FIG. 45B from left to right, by cell type and biomarker: L-cells (GCG); L-cells (PYY); Enterochromaffin Cells (TPH1).

Further, higher expression of mRNA of lysozyme and Trpm5, markers specific for Paneth and Tuft cells, respectively, was measured in enteroids cultures. Decreased levels of stem cell marker LGR5 on-chip was shown in comparison to 3D enteroids.

Figure 46:
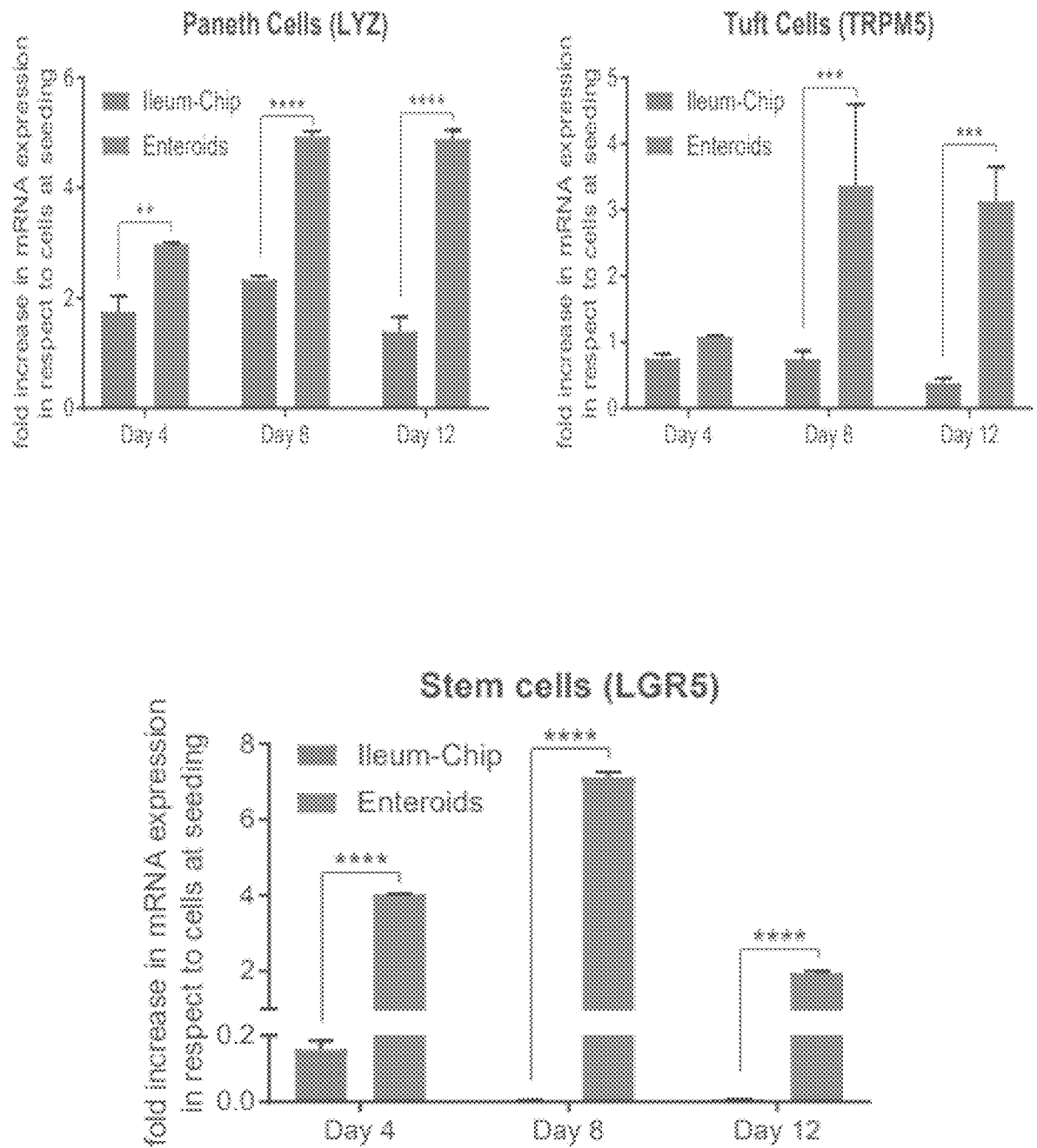
FIG. 46 shows exemplary cell types and biomarker detected in one embodiment of Ileum-Chip in respect to enteroids cell samples used for seeding fluidic chips showing highly proliferative cultures rich in Paneth and Tuft Cells. From left to right: Paneth Cells (LYZ); Tuft Cells (TRPM5); and Stem cells (LGR5). Representative data from Ileum-Chip (left bar) and enteroids (right bar) from days, 4, 8, and 12 of culture On-Chip are shown.

FIG. 46 shows exemplary cell types and biomarker detected in one embodiment of Ileum-Chip in respect to enteroids cell samples used for seeding fluidic chips showing highly proliferative cultures rich in Paneth and Tuft Cells. From left to right: Paneth Cells (LYZ); Tuft Cells (TRPM5); and Stem cells (LGR5). Representative data from Ileum-Chip (left bar) and enteroids (right bar) from days, 4, 8, and 12 of culture on-chip are shown.

In summary, some embodiments of Ileum-Chip (in the presence of microvasculature endothelial cells) revealed: Improved maintenance of barrier function over 2 weeks of fluidic culture in comparison to ileal tissue grown alone; Increased expression of the genes specific for differentiated cell lineages (absorptive enterocytes, goblet cells, enteroendocrine cells) in respect to 3D ileal organoids; Increased differentiation was counterbalanced by the decrease in the sternness and cell proliferation; Presence of all major intestinal cell types, including absorptive enterocytes, goblet cells, Paneth cells, enteroendocrine cells and their subpopulations (L-cells, enterochromaffin cells). Surprisingly, Tuft cells were not detected (at the level of immunostaining) in 3D ileal organoids nor in one embodiment of an Ileum-Chip.

In relation to barrier functions of Ileum-Chips established from the organoids, replicate chips each using 1 of 3 individual donors reached similar levels of intestinal impermeability to 3 kDa dextran.

Figure 47:
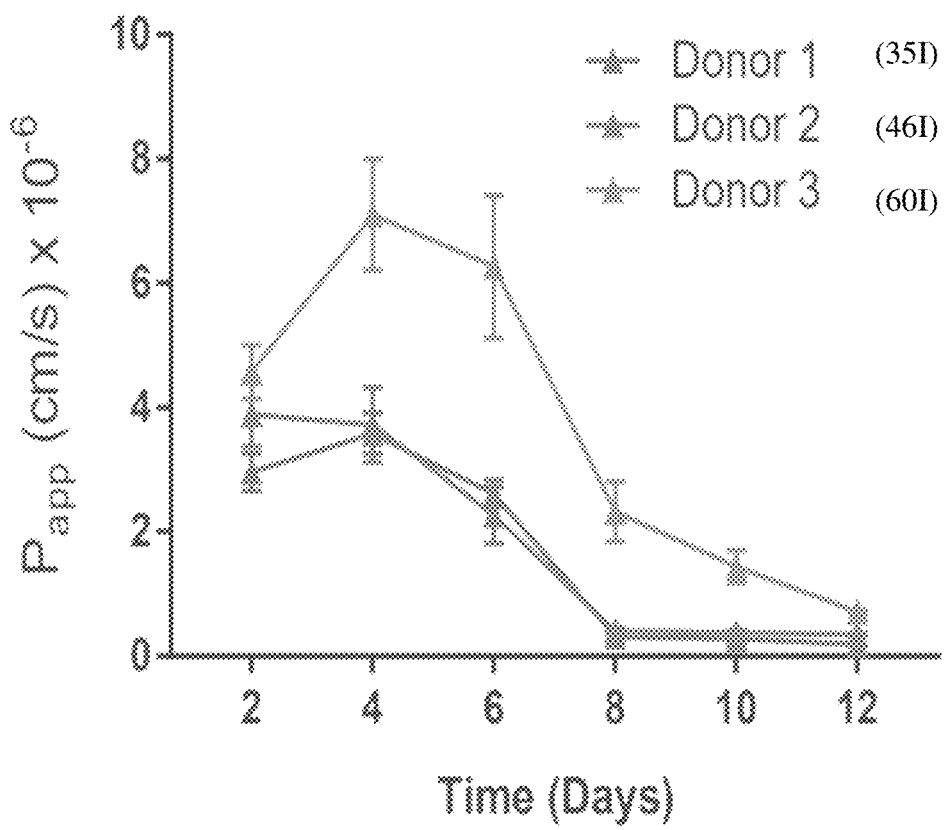
FIG. 47 shows exemplary barrier function in relation to impermeability of 3 kDa dextran over time (days after seeding enteroids) for enteroids seeded into Ileum-Chips for replicate chips each using 1 of 3 individual donor cells.

FIG. 47 shows exemplary barrier function in relation to impermeability of 3 kDa dextran over time (days after seeding enteroids) for enteroids seeded into Ileum-Chips for replicate chips each using 1 of 3 individual donor cells.

Markers specific for different sub-populations of enteroendocrine were detected in Ileum-Chips established from the enteroids of 3 different donors. Successful Differentiation of Enteroendocrine Cells in Ileum-Chips.

Time-dependent Increases in Differentiation of Enterocytes and Goblet Cells. Time-dependent decreases in populations of Paneth cells and cycling Lgr5+ stem cells was observed across different donors. This observation suggested increased differentiation balanced by decrease in proliferation and sternness, i.e. cells expressing stem cell biomarkers, such as lrg5.

Figure 48A:
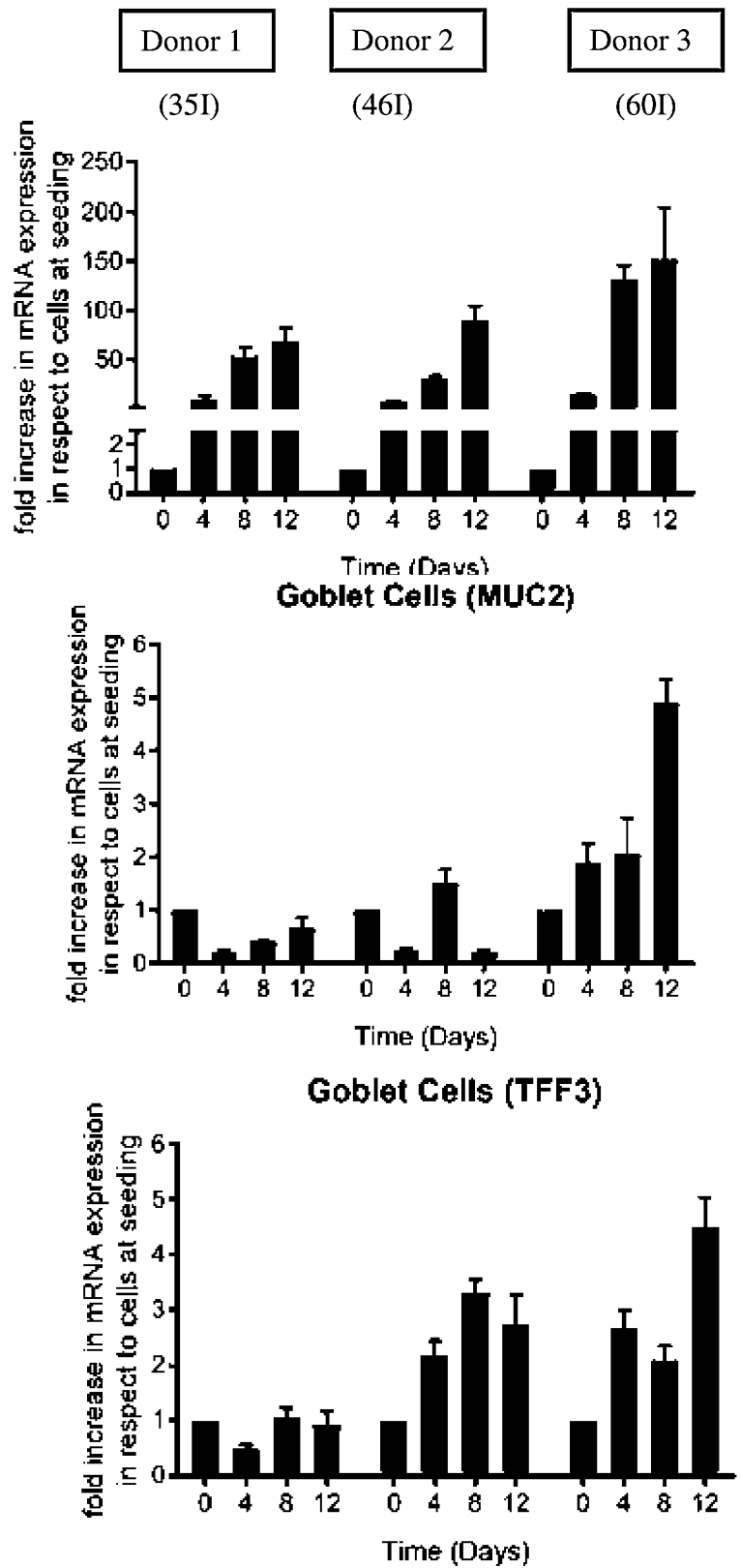
FIG. 48A-D shows exemplary cell types detected over time in one embodiment of Ileum-Chip, by mRNA expression in respect to enteroids cell samples used for seeding fluidic chips. Data from at least 3 replicate chips, each receiving enteroids cells from a different donor, as representative data from days 0, 4, 8, and 12 are shown.
Figure 48B:
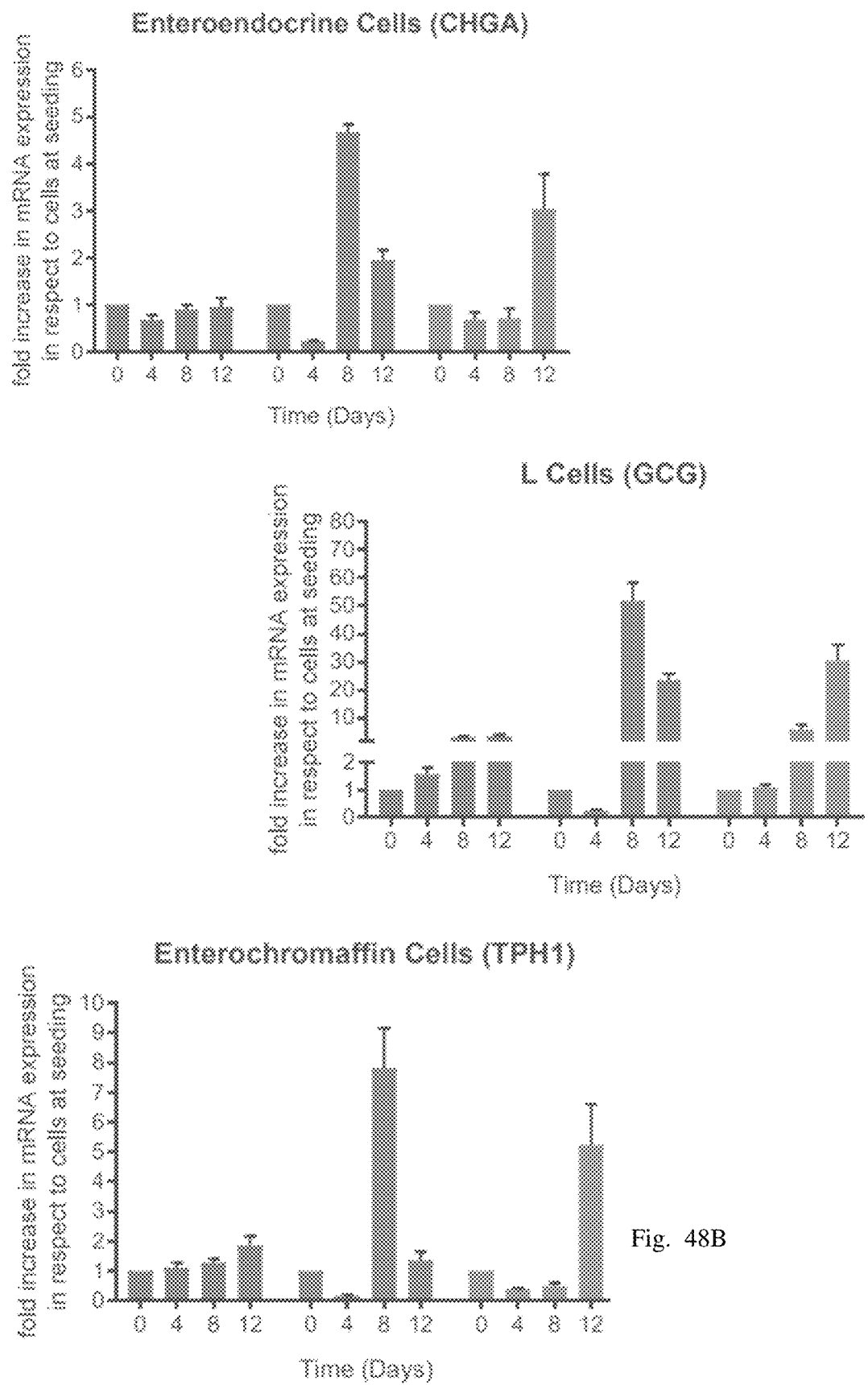
Figure 48C:
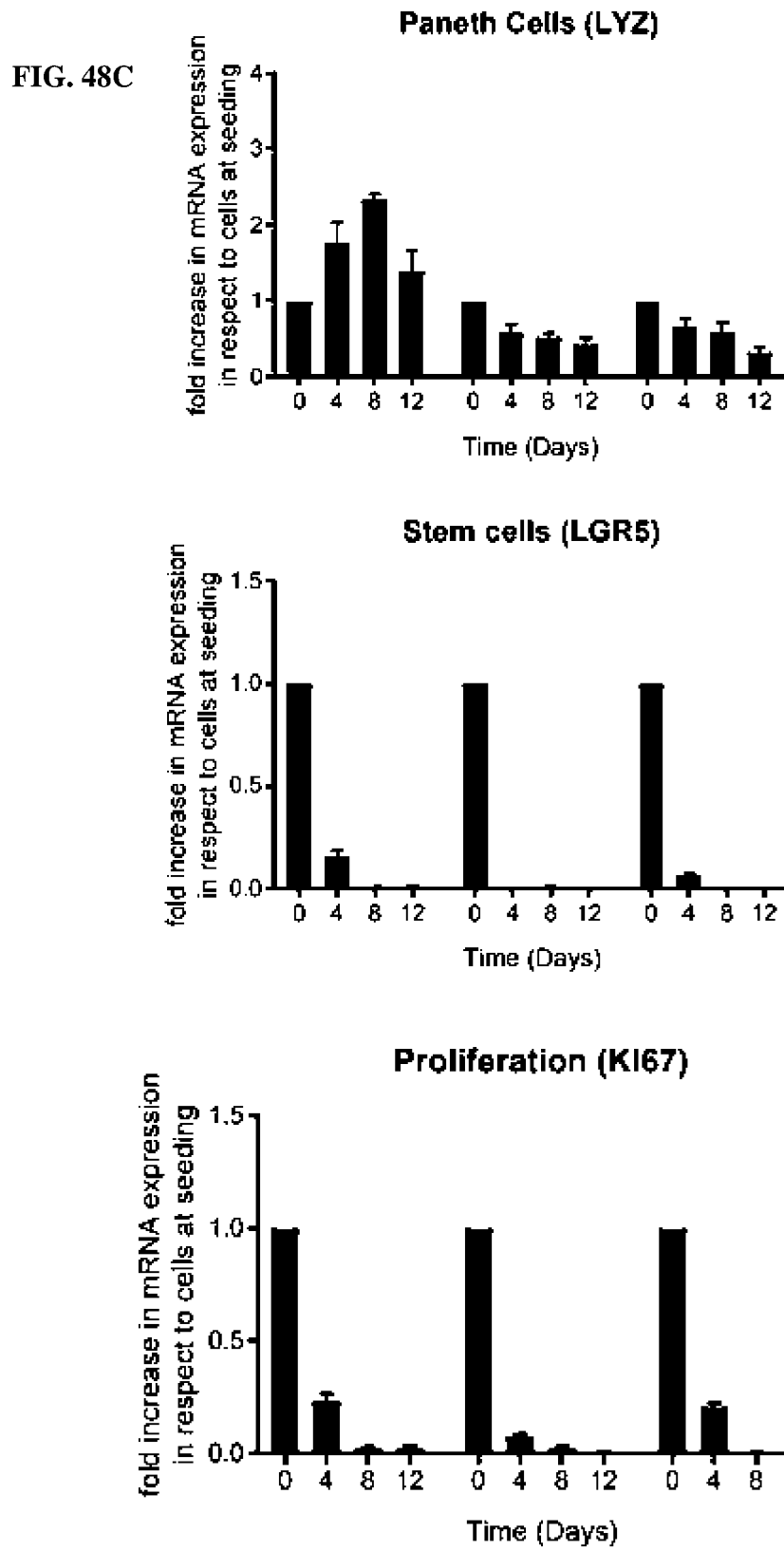

FIG. 48A-D shows exemplary cell types detected over time in one embodiment of Ileum-Chip, by mRNA expression in respect to enteroids cell samples used for seeding fluidic chips. Data from at least 3 replicate chips, each receiving enteroids cells from a different donor, as representative data from days 0, 4, 8, and 12 are shown. FIG. 48A from left to right, by cell type and biomarker: absorptive enterocytes (ALPI); goblet cells (MUC2); and goblet cells (TFF3). FIG. 48B from left to right, by cell type and biomarker: Enteroendocrine Cells—EEC (CHGA); L-cells (GCG); and Enterochromaffin Cells (TPH1). FIG. 48C from left to right, by cell type and biomarker: Paneth Cells (LYZ); Stem cells (LGR5) and a proliferation biomarker Ki67.

Collectively, expression of three genes, ChAT, DCLK1 and Trpm5, identify populations of tuft cells. Their presence was monitored in embodiments of readouts from Ileum-Chip and Colon-Chip. While their presence was confirmed in one embodiment of the Colon-Chip system at the level of immunofluorescence staining (Trpm5+, ChAT+) and qRT-PCR (Trpm5+), these biomarkers were undetectable in one embodiment of the Ileum-Chip at the level of protein (Immunofluorescence (IF) Trpm5−, ChAT−, DCLK1−) with low expression of mRNA (Trpm5+) was measured.

Thus, expression of Tuft Cells specific marker in Ileum-Chips, i.e. ChAT and DCLK1 were not detected. TRPM5 mRNA expression showed donor-specific fluctuations. Expression of CHAT and DCLK1 mRNA were undetectable.

Figure 48D:
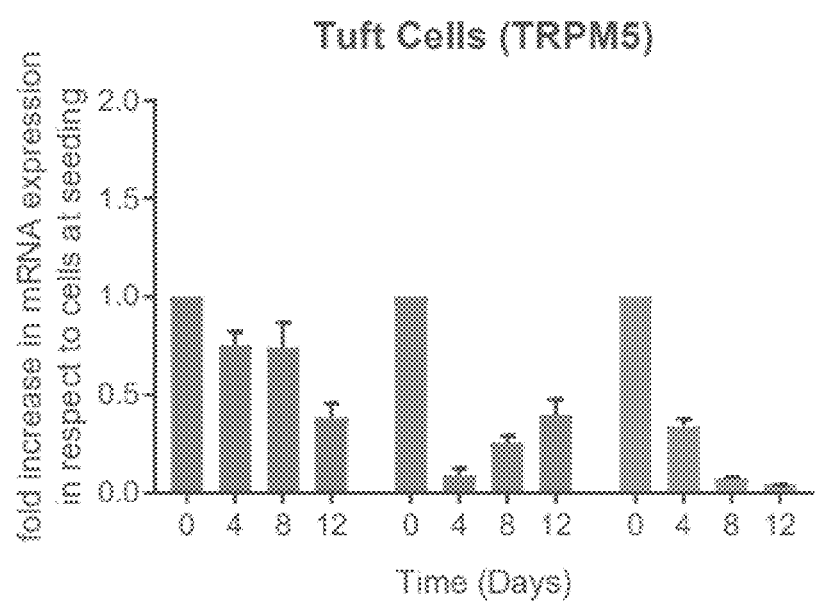

FIG. 48D one of the three biomarkers for Tuft Cells (TRPM5); mRNA for the other two markers ChAT and DCLK1 were not detected.

The majority of major intestinal cell types were identified in Ileum-Chip at physiologically-relevant ratios compared to in vivo measurements. In vivo values referenced from: Karam, et al. Front Biosci 1999. 4:D286-298; Lund, et al. Molecular Metabolism. 2018; 11:70-83; Petersen, et al. The Journal of Clinical Investigation. 2015:125(1):379-385. Quantification performed across 3 donor samples at day 8 of fluidic culture. Thus, Physiological Ratios of Major Intestinal Cell Types are present in Ileum-Chip.

Figure 49A:
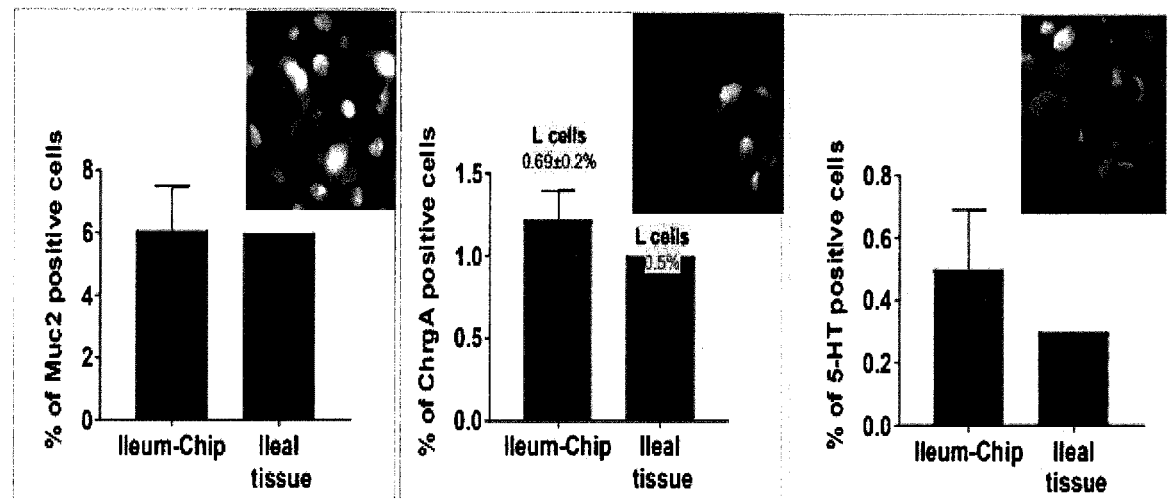
FIG. 49A-B shows exemplary physiological ratios of major intestinal cell types present in Ileum-Chip measured by percentage of biomarker positive cells compared to immunostained ileal tissue.
Figure 49B:
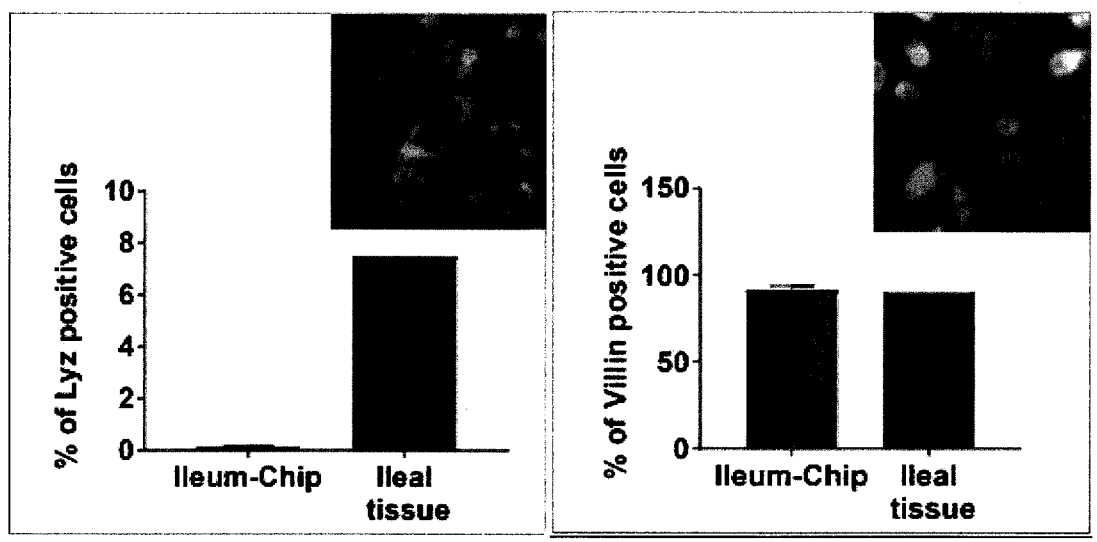

FIG. 49A-B shows exemplary physiological ratios of major intestinal cell types present in Ileum-Chip measured by percentage of biomarker positive cells compared to immunostained ileal tissue. FIG. 49A from left to right, by cell type and biomarker: goblet cells (MUC2); Enteroendocrine Cells—EEC (ChrgA)/L-cells (GLP-1); Enterochromaffin Cells (5HT). FIG. 49B from left to right, by cell type and biomarker: Paneth Cells (LYZ) and absorptive enterocytes (villin), while nuclei are stained.

Summary: Characterization of Ileum-Chip across 3 donors confirmed: Formation of intact barrier function across all 3 donors tested; Time-dependent increase in differentiation of absorptive enterocytes and goblet cells balanced by decreased proliferation and disappearance of Lgr5 expression; Presence of all major intestinal cell types, including absorptive enterocytes, goblet cells, Paneth cells, enteroendocrine cells and their subpopulations (L-cells, enterochromaffin cells) confirmed by gene expression analysis and confocal imaging. Most of these cells (except for Paneth cells) showed to be present in Ileum-Chip at the physiologically-relevant ratios.

Although the presence of Tuft cells-specific transcript Trpm5 was detected by qPCR, the identification of these cells was not confirmed by immunofluorescence staining.

V. Fluidic Duodenum Intestine-Chip/Duodenal-Chip Enteroids.

The duodenum attaches, at its proximal end, to the stomach, normally a J-shaped sac, which in turn connects to the esophagus at its other end. Ingested fluids and liquids enter the small intestine through a pyloric sphincter (a band of smooth muscle) which functions as a valve to control the flow of partially digested food from the stomach into the small intestine. In turn, the duodenum area precedes the jejunum area, which in turn is followed by the proximal ileal area of the small intestine. The distal ileum at the distal end of the small intestine is connected with the large intestine by an ileocecal sphincter muscle.

In some embodiments, human duodenum areas of the small intestine are modeled in fluidic devices using a fluidic Intestine-Chip seeded with duodenum enteroids cells. In some embodiments, cells for providing enteroids were obtained from adults. In preferred embodiments duodenum enteroids cells are grown as described for ileal enteroids. In preferred embodiments duodenum enteroids cells are seeded into fluidic devices following one embodiment of a two-step method as described for Ileal Intestine chips where duodenum Enteroids cells are seeded at Day 0 followed by HIMECs seeding on Day 6, under flow and stretch as described. In some embodiments, cultures are liquid-liquid cultures.

Figure 50A:
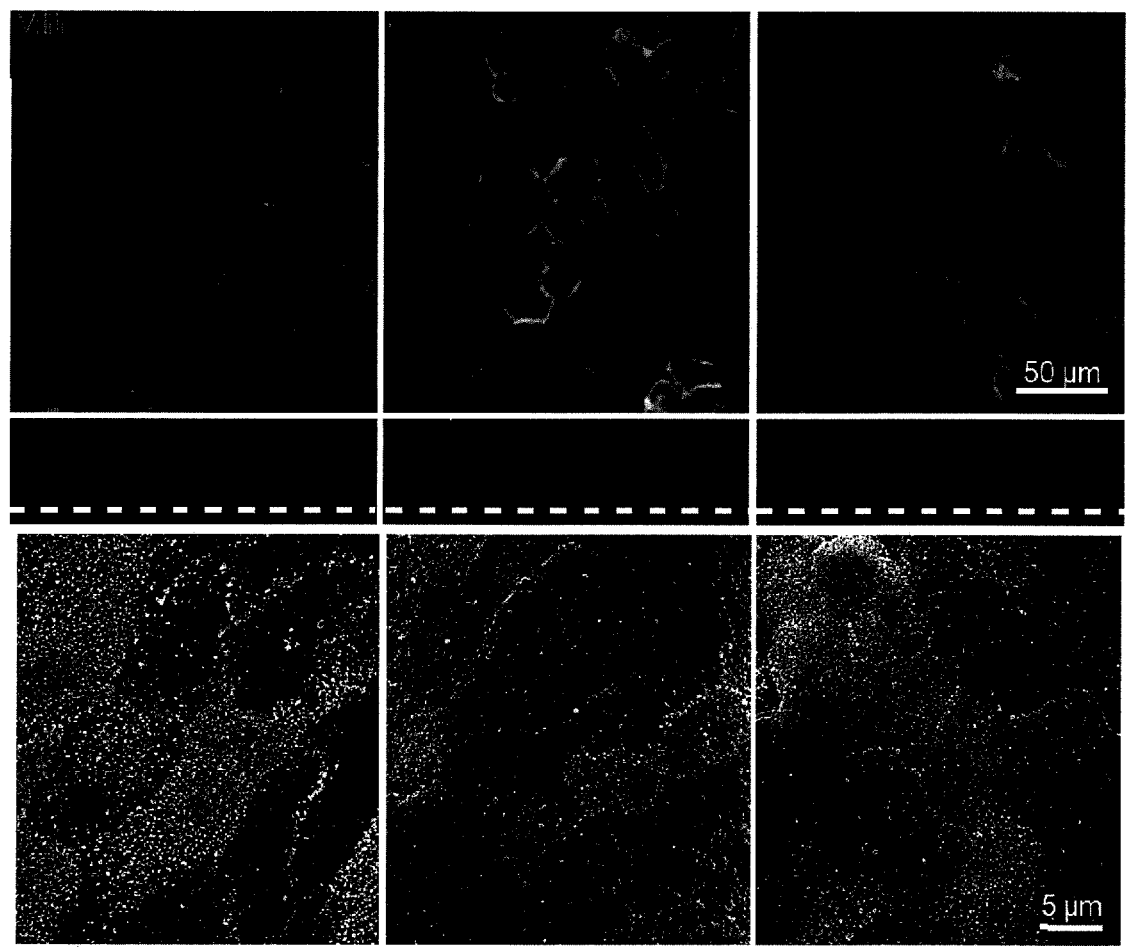
FIG. 50A-C shows duodenal epithelial morphology is improved by use of a dynamic microenvironment. Static cultures (left panels) are compared to cultures under flow (middle panels) and combined Flow+Stretch (right panels). Flow increases formation of intestinal duodenum microvillus on the apical surface of absorptive enterocytes.
Figure 50B:
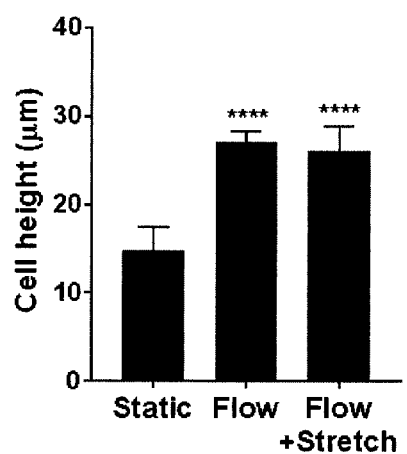
Figure 50C:
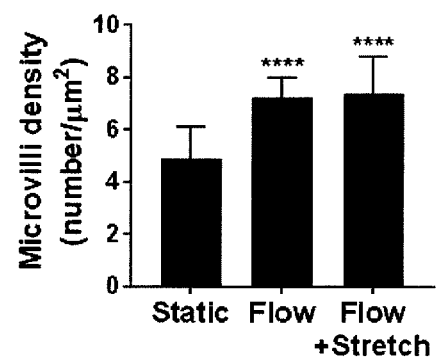

FIG. 50A-C shows duodenal epithelial morphology is improved by use of a dynamic microenvironment. Static cultures (left panels) are compared to cultures under flow (middle panels) and combined Flow+Stretch (right panels). Flow increases formation of intestinal duodenum microvillus on the apical surface of absorptive enterocytes. FIG. 50A shows confocal immunostained images (overview upper panels with side views in the middle panel as z-stacks) demonstrating absorptive enterocytes with stain indicating villin and epithelial cells with stain indicating E-cadherin, and nuclei stained. There is less villin staining in the static condition, than in +flow or +flow+stretch conditions. Lower panels show scanning electron micrographs demonstrating contours (3D morphology) of the epithelial layers. FIG. 50B shows an exemplary graph of cell height (micrometers) when epithelial cells undergo exposure to flow (+/−stretch) resulting in columnar morphology and increased cell height. FIG. 50C shows a graph of increasing microvilli density when epithelial cells undergo exposure to flow (+/−stretch).

In some embodiments, fluidic devices using a fluidic duodenum Intestine-Chip seeded with HIMECs show strong intestinal barrier function.

Figure 51A:
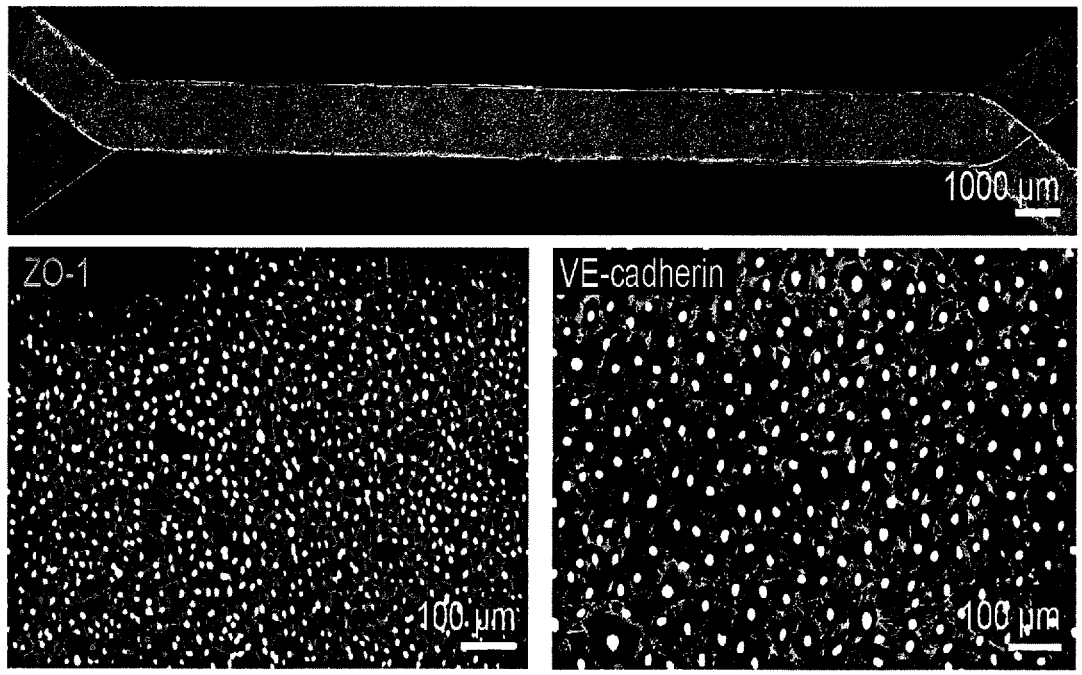
FIG. 51A-B shows exemplary micrographs and barrier function for one embodiment of a duodenum Intestine-Chip derived from a biopsy obtained from three independent donors, one donor's cells per chip, emulating a duodenum tissue-tissue interface and strong intestinal barrier function (measured using 3 kDa dextran) (approximately $1\times10^6$ cm/s).
Figure 51B:
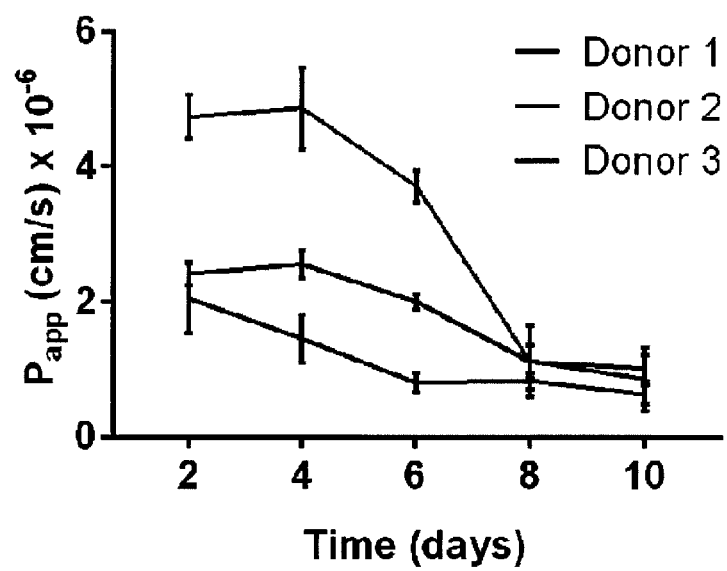

FIG. 51A-B shows exemplary micrographs and barrier function for one embodiment of a duodenum Intestine-Chip derived from a biopsy obtained from three independent donors, one donor's cells per chip, emulating a duodenum tissue-tissue interface and strong intestinal barrier function (measured using 3 kDa dextran) (approximately $1 \times 10^6$ cm/s). FIG. 51A shows an exemplary immunofluorescent micrograph of an entire main channel immunostained for ZO-1 and VE-cadherin (vascular endothelial cadherin) also known as CD144) in the upper panel (bar=1000 µm) while the lower right panel shows ZO-1 staining at a higher magnification (bar=100 µm). FIG. 51B shows exemplary induction of barrier function over time for duodenum cells derived from enteroids grown from biopsies obtained from 3 different human adult donors.

A. Tissue Maturation.

Embodiments of fluidic devices comprising enteroids-derived cells from biopsies of adult duodenum tissues were evaluated for intestinal tissue maturation. In part, tissue maturation in the epithelial layer was measured by relative mRNA expression of specialized cell biomarkers compared to in vivo duodenum biopsies.

FIG. 52A-B shows exemplary duodenum Intestine-Chips possess physiological ratios of major differentiated intestinal cell types shown in immunostained confocal microscopy images and measured by relative mRNA expression compared to a duplicate cell sample used for seeding duodenal enteroids into chips. FIG. 52A shows confocal immunostained images demonstrating cell types and biomarkers from left to right: Goblet Cells (MUC2+) in contrast to epithelial cells (E-cadherin); Enteroendocrine Cells (chromogranin A-CHGA) in contrast to epithelial cells (E-cadherin); absorptive enterocytes (villin) in contrast to epithelial cells (E-cadherin); and Paneth Cells (LYZ) in contrast to epithelial cells (E-cadherin). Nuclei are stained and indicated in grey. FIG. 52B shows graphical comparisons of percentages of biomarkers in duodenum Intestine-Chips compared to in vivo amounts (in vivo referenced from: Karam S M. Front Biosci 1999, 4:D286-298). Cell types and biomarkers from left to right: Goblet Cells (MUC2+); Enteroendocrine Cells (chromogranin A-ChrgA); absorptive enterocytes (villin); and Paneth Cells (LYZ).

On-Chip Culture of duodenum enteroids into epithelial layers results in maturation of major intestinal cell types representative of in vivo duodenum shown by comparative expression levels of mRNA in respect to enteroids cell samples used for seeding fluidic chips.

Figure 53A:
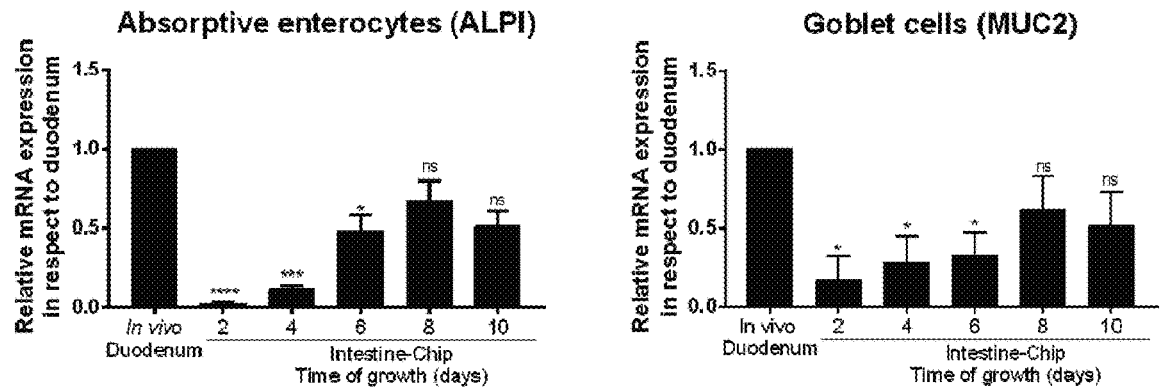
FIG. 53A-C shows exemplary duodenum Intestine-Chips mature cell types and overall growth activity identified by relative mRNA expression of biomarkers at Days 2, 4, 6, 8 and 10. From left to right, by cell type and biomarker.
Figure 53B:
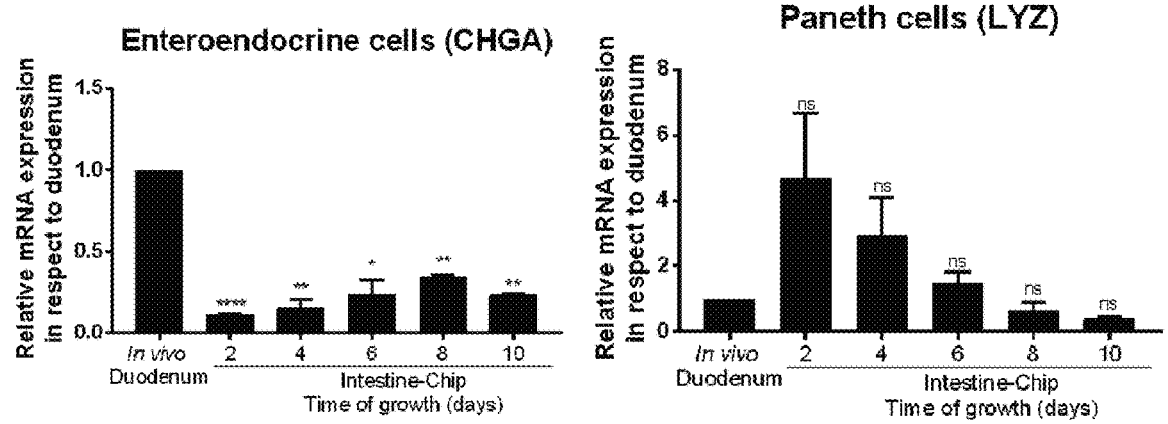
Figure 53C:
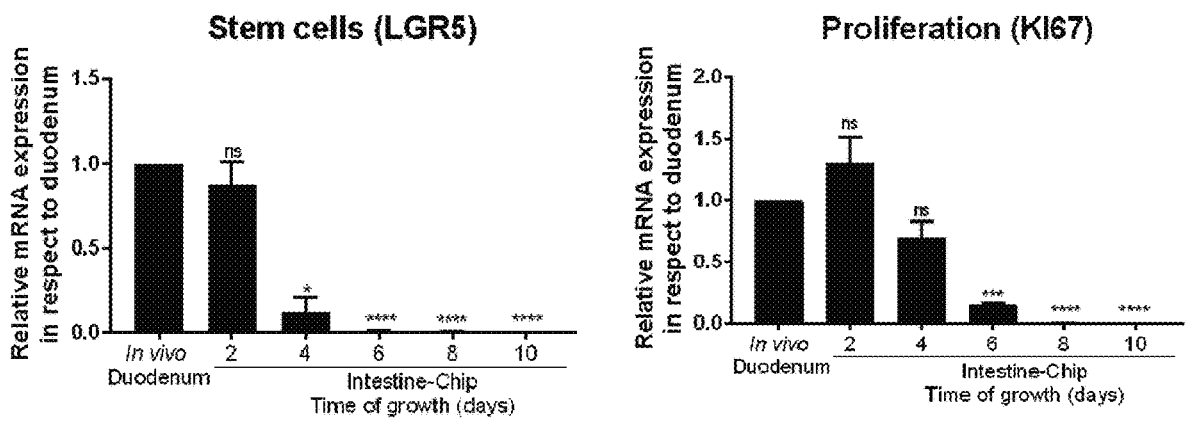

FIG. 53A-C shows exemplary duodenum Intestine-Chips mature cell types and overall growth activity identified by relative mRNA expression of biomarkers at Days 2, 4, 6, 8 and 10. From left to right, by cell type and biomarker. FIG. 53A shows exemplary absorptive enterocytes (ALPI); goblet cells (MUC2). FIG. 53B shows exemplary Enteroendocrine Cells—EEC (CHGA); Paneth Cells (LYZ). FIG. 53C shows exemplary stem cells (LGR5) and a proliferation biomarker Ki67.

B. Drug Uptake and Efflux Transporters in Duodenum-Chip.

In some embodiments, methods comprising fluidic devices described herein include measuring expression of drug uptake and efflux transporters in relation to drug treatments. Embodiments of Intestine-Chips exhibit expression of major intestinal drug transporters, including but not limited to efflux transporters, such as MDR1, BCRP, MRP2, MRP3, etc., and drug uptake transporters, such as PepT1, OATP2B1, OCT1, SLC40A1, etc. In particular, one embodiment of Duodenum enteroids derived Intestine-Chip showed average expression of uptake transporters OATP2B1 and OCT1 that is closer to in vivo than observed in Intestine-Chips based on Caco-2 cell line, See FIG. 54.

As demonstrated herein, Intestine-Chips (enteroids-derived) show correct localization and function of MDR-1 (P-gp) efflux transporter and Intestine-Chip (enteroids) exhibits correct luminal localization of BCRP and PEPT1.

Figure 54:
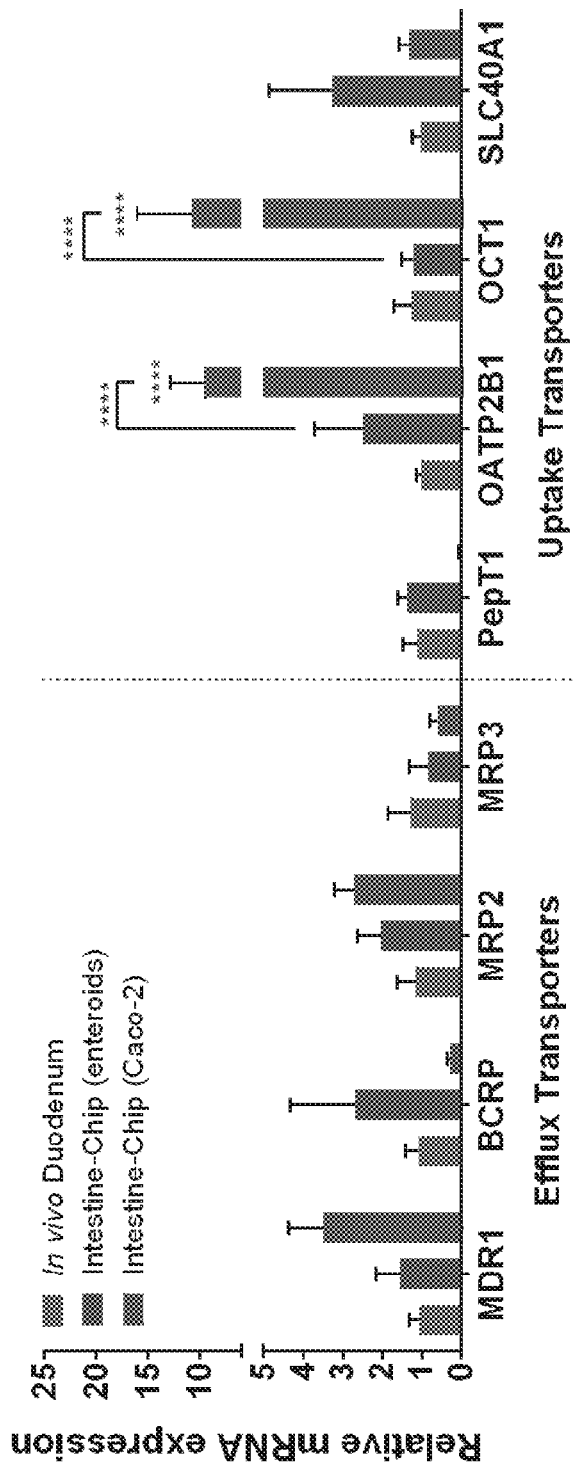
FIG. 54 shows exemplary embodiments of duodenal Intestine-Chips (enteroids-derived) exhibiting expression of major intestinal drug efflux transporters MDR1, BCRP, MRP2, MRP3, and drug uptake transporters, such as PepT1, OATP2B1, OCT1, and SLC40A1.

FIG. 54 shows exemplary embodiments of duodenal Intestine-Chips (enteroids-derived) exhibiting expression of major intestinal drug efflux transporters MDR1, BCRP, MRP2, MRP3, and drug uptake transporters, such as PepT1, OATP2B1, OCT1, and SLC40A1.

Figure 55A:
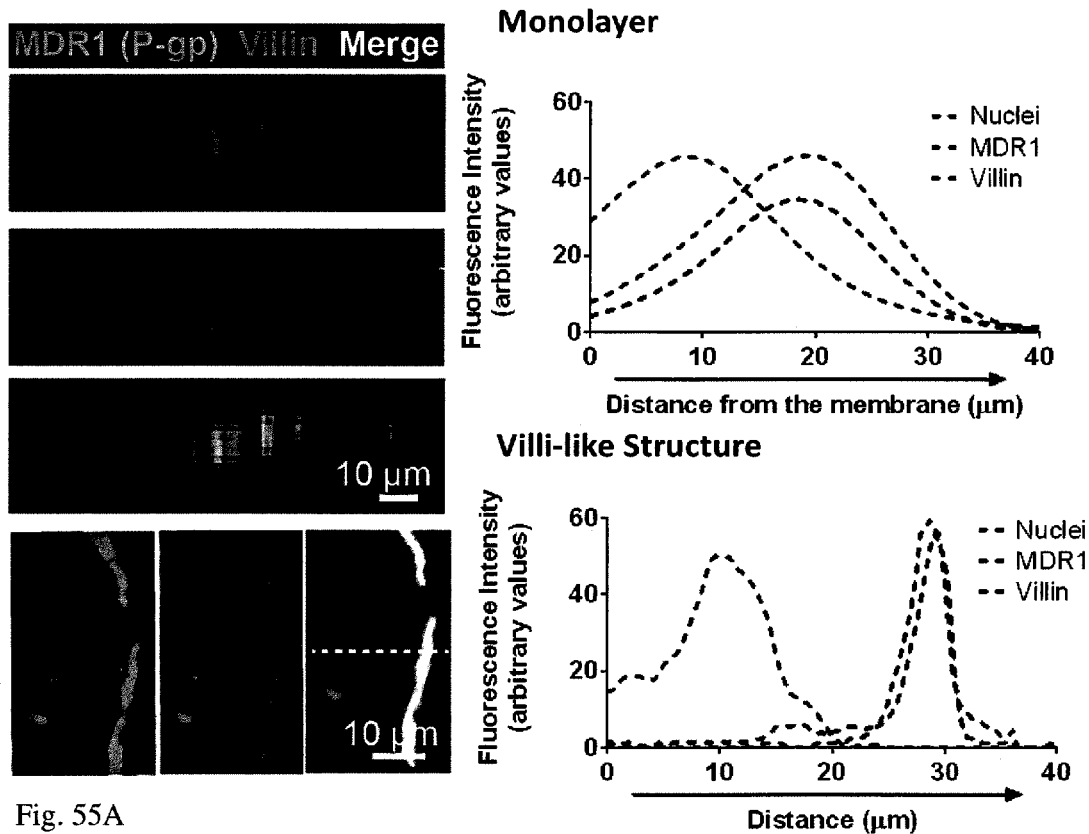
FIG. 55A-B shows exemplary embodiments of duodenal Intestine-Chips (enteroids-derived) having correct localization and function of MDR-1 (P-gp) efflux transporter as compared to in vivo localization and function.
Figure 55B:
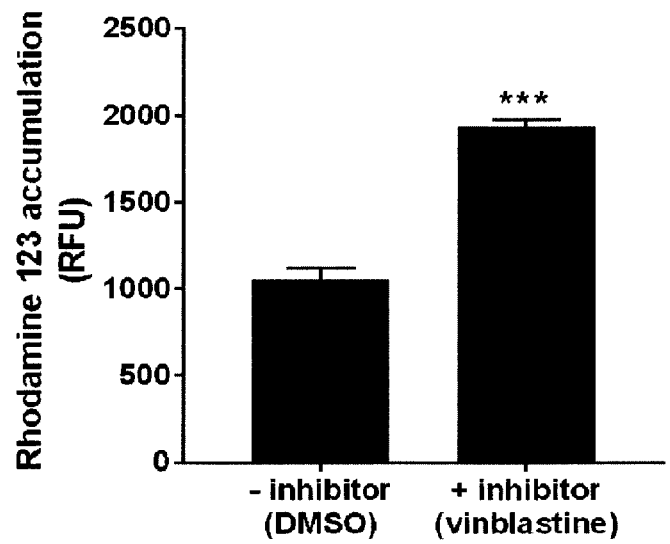

FIG. 55A-B shows exemplary embodiments of duodenal Intestine-Chips (enteroids-derived) having correct localization and function of MDR-1 (P-gp) efflux transporter as compared to in vivo localization and function. FIG. 55A shows (left) confocal microscopy z-stacks (side views) of monolayers stained for MDR1 (P-gp), villin and merged areas white. Lower panels show villi-like structures. Graphs on the right show comparative biomarker stain intensity from left to right along the x-axis moving away from the membrane. Villi-like structures show strong signal overlap (co-localization) of MDR1 with an apical marker (Villin). FIG. 55 B shows comparative Rhodamine 123 (RFU) accumulation when an inhibitor of MDR1 transport (DMSO) and (DMSO+vinblastine) is used to treat duodenal Intestine-Chips.

Figure 56A:
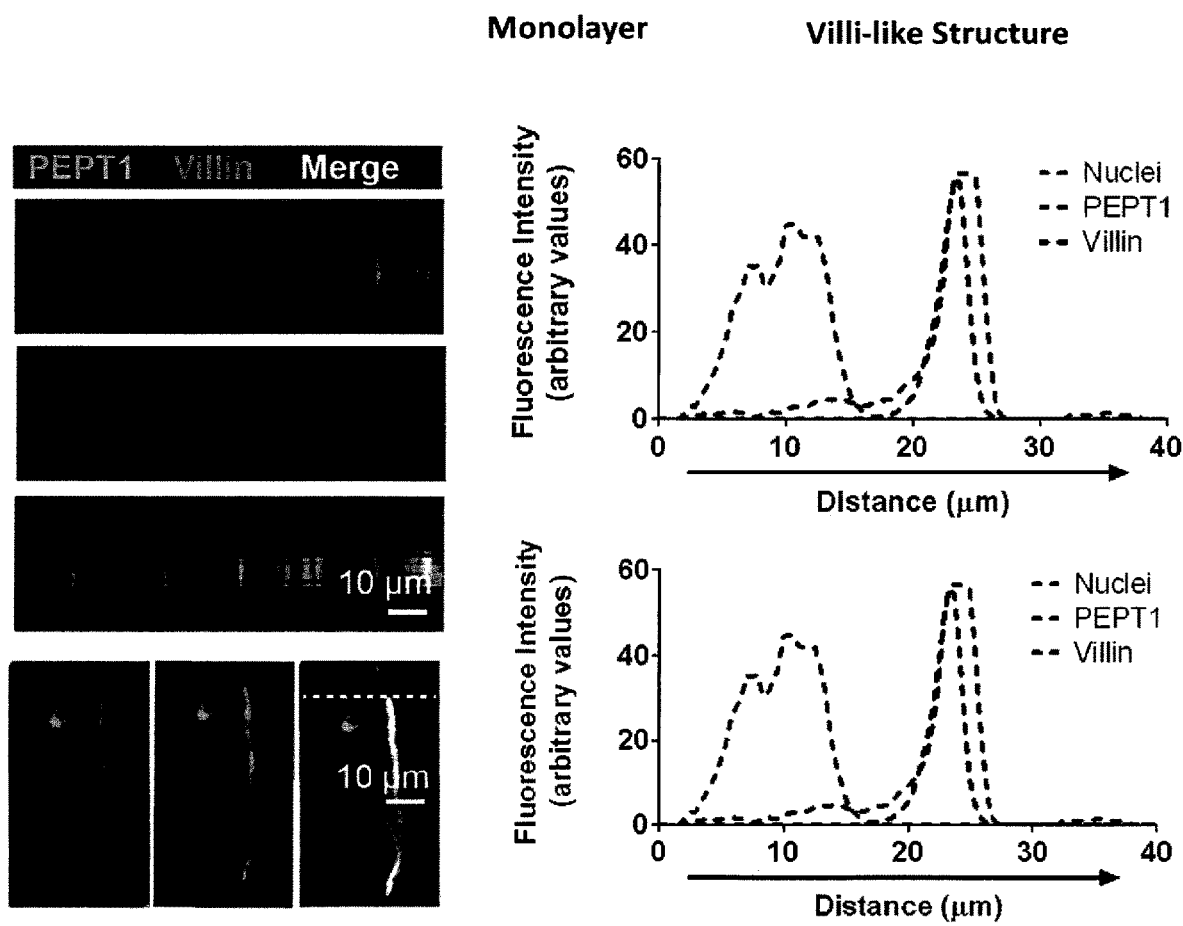
FIG. 56A-B shows exemplary embodiments of duodenal Intestine-Chips (enteroids-derived) having correct luminal localization of PEPT1 and BCRP as compared to in vivo localization and function.
Figure 56B:
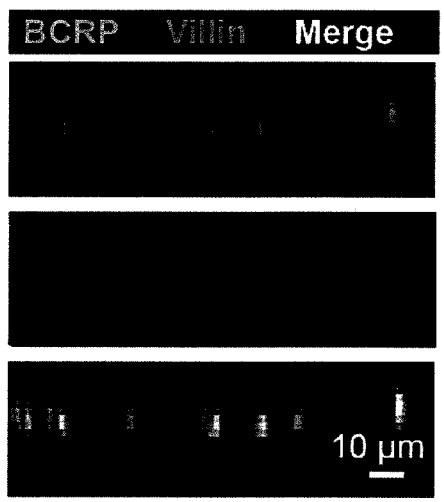
Figure 56B:
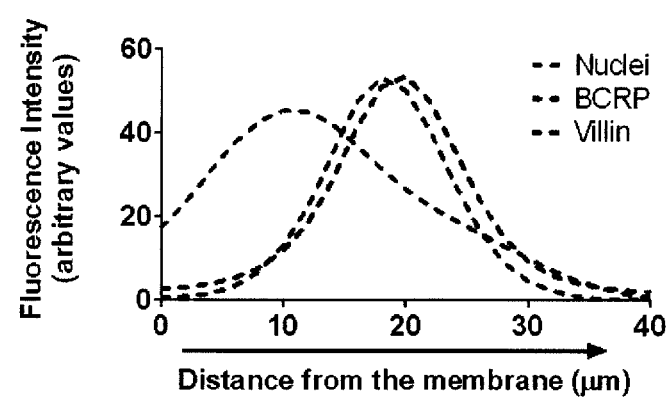
Figure 56B:
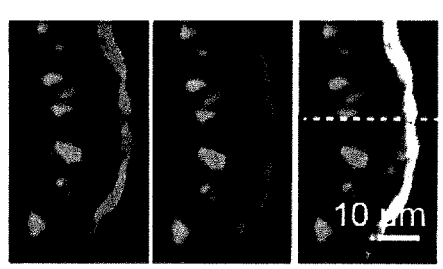
Figure 56B:
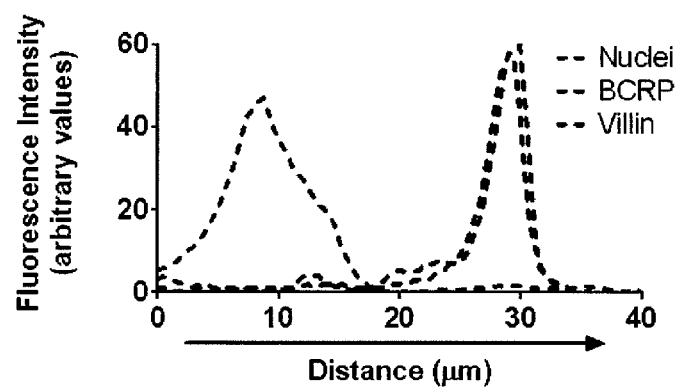

FIG. 56A-B shows exemplary embodiments of duodenal Intestine-Chips (enteroids-derived) having correct luminal localization of PEPT1 and BCRP as compared to in vivo localization and function. FIG. 56A shows (left) confocal microscopy z-stacks (side views) of monolayers stained for PEPT1, villin and merged areas white. Lower panels show villi-like structures. Graphs on the right show comparative biomarker stain intensity from left to right along the x-axis moving away from the membrane. Neither monolayers nor villi-like structures show strong signal overlap (co-localization) of PEPT1 with an apical marker (Villin). FIG. 56B shows (left) confocal microscopy z-stacks (side views) of monolayers stained for BCRP, villin and merged areas white. Lower panels show villi-like structures. Graphs on the right show comparative biomarker stain intensity from left to right along the x-axis moving away from the membrane. Neither monolayers nor villi-like structures show strong signal overlap (co-localization) of BCRP with an apical marker (villin).

C. Embodiments of Intestine-Chips Derived from Enteroids Show Higher Expression of Certain Uptake Transporters and Enzymes than that is Closer to In Vivo Levels than Measured in Caco-2 Cells Based Intestine-Chips.

Figure 57A:
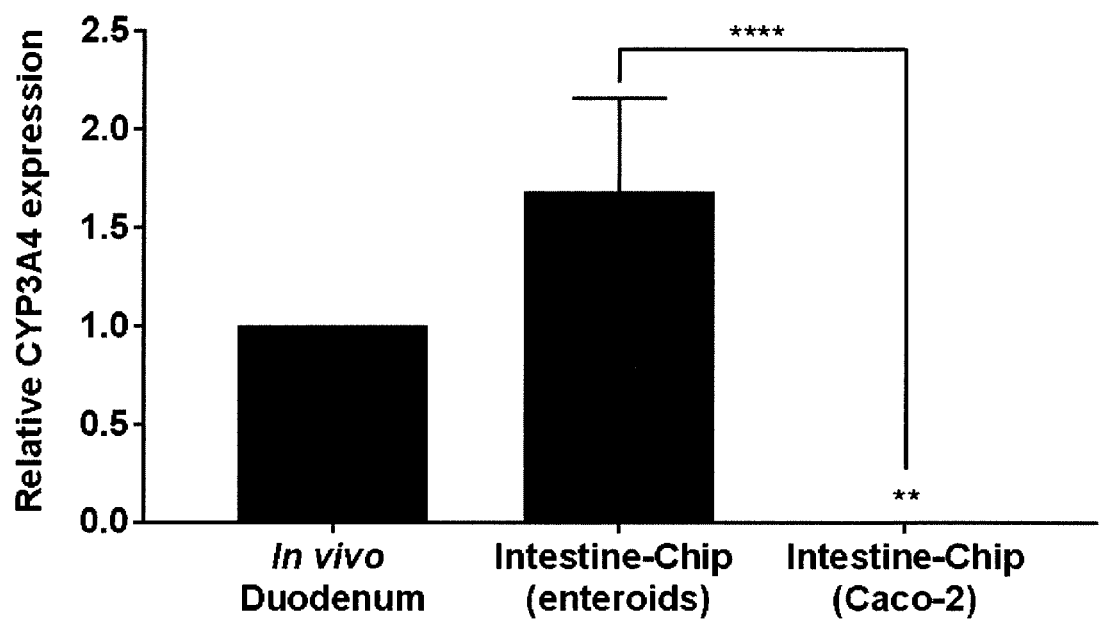
FIGS. 57A-B shows exemplary embodiments of duodenum Intestine-Chips (enteroids-derived) demonstrating an average expression of drug metabolism enzyme CYP3A4 in Intestine-Chip derived from duodenum enteroids that is much higher and closer to in vivo measurements than in Caco-2 cells based Intestine-Chip.
Figure 57B:
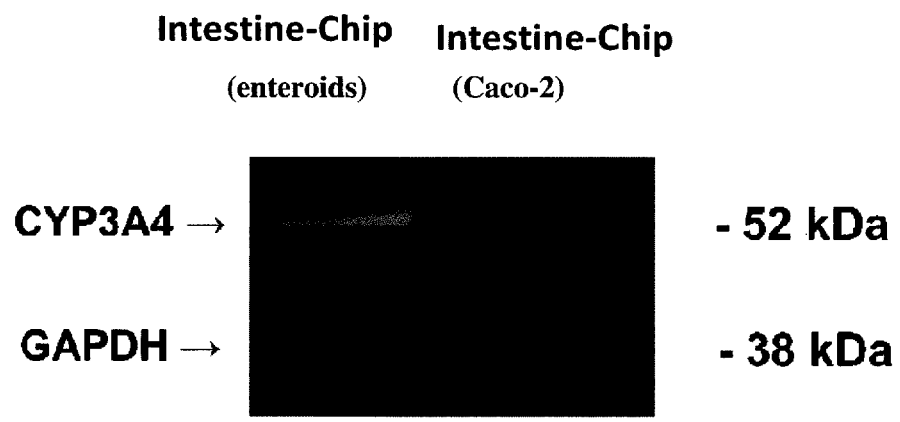

In particular, average expression of a drug metabolism enzyme CYP3A4 in one embodiment of a duodenal Intestine-Chip derived from enteroids is much higher and closer to in vivo levels than in Caco-2 cells based Intestine-Chip, see FIG. 57A-B.

FIGS. 57A-B shows exemplary embodiments of duodenum Intestine-Chips (enteroids-derived) demonstrating an average expression of drug metabolism enzyme CYP3A4 in Intestine-Chip derived from duodenum enteroids that is much higher and closer to in vivo measurements than in Caco-2 cells based Intestine-Chip. FIG. 57A shows relative CYP3A4 expression in vivo duodenum compared to duodenum Intestine-chip (enteroids) and Intestine-Chip (Caco-2). FIG. 57B shows relative protein levels of CYP3A4, using GAPDH as a loading amount control, measured by Western blots.

CYP3A4 is expression is regulated by nuclear receptors. Therefore, nuclear receptors in addition to CYP3A4 were evaluated, in particular for use in biomarker identification and drug testing.

1. Nuclear Receptors.

Nuclear receptors involved in the induction of drug metabolizing enzymes include but are not limited to pregnane X receptor (PXR), aryl hydrocarbon receptor (AhR), and constitutive androstane receptor (CAR), which are involved in regulating CYP3A4, CYP1A2 and CYP2B6, respectively. PXR activation in particular is associated with increases in drug metabolism and decreases in inflammation. Thus, in some embodiments, compositions and methods include fluidic devices, such as described herein, for use in screening for drug interactions with cells and tissues in fluidic devices. In further embodiments, such compositions and methods include determining drug-drug interactions. In some embodiments, drugs; therapeutics, such as small molecules; and potential therapeutics are tested on fluidic devices for monitoring effects on PXR.

In vitro studies using human cells shows that following stimulation of the human PXR with rifaximin, expression of a variety of PXR-regulated genes, including CYP3A4 and MDR1 were enhanced. Further, NFkB-dependent cytokine production is attenuated, whereas this effect is lost in models of PXR knock down.

Nuclear receptor expression and functions are altered in tissues associated with intestinal inflammation. As one example, inflammation leads to downregulation of PXR and decrease in drug metabolism shown by the loss of CYP3A4 activity, i.e. markedly lower in patients with Crohn's disease (CD)). In other examples, such as in animal models of Inflammatory Bowel Disease (IBD), activation of the PXR attenuates colonic inflammation, tissue damage, and accelerates mucosal healing following a bout of colitis.

There are significant differences in the expression of nuclear receptors between embodiments of Intestine-chips. As with enteroid-derived intestine-chips showing improved expression of several uptake transporters, enteroid-derived intestine-chips are superior to Caco-2 derived chips for expressing enteroid nuclear receptors, and their targets, involved in sensing of xenobiotics and organisms protection from chemical insults. In particular, asteroid-derived Intestine-Chip shows improved CYP3A4 induction in comparison to Caco-2 based system revealed by significant increases in CYP3A4 mRNA and protein expression (Western Blots) upon stimulation with PXR and a calcitriol receptor, vitamin D receptor (VDR) ligands, see FIGS. 58A-B.

Furthermore, intestine-Chips derived from enteroids demonstrates improved CYP3A4 induction potential in comparison to Caco-2 based system revealed by significant increase in mRNA and protein expression upon stimulation with PXR and VDR ligands.

Therefore, embodiments of enteroids-derived intestine-chips, e.g. duodenum, are used for drug interaction and drug-drug interaction evaluations.

FIGS. 58A-C shows exemplary in vivo-like Expression of Nuclear Receptors and a Drug Metabolism Enzyme between embodiments of Intestine-Chips. Average expression of nuclear receptors and drug metabolism enzyme CYP3A4 is much closer to in vivo values in Duodenum enteroids-derived Intestine-Chip than in Intestine-Chip based on the use of Caco-2 cells. Furthermore, Rifampicin treatment failed to induce CYP3A4 expression in Caco2 cells. FIG. 58A shows relative mRNA expression of CYP3A4; PXR; and VDR between in vivo Duodenum; Duodenum Intestine-Chip (enteroids); and Intestine-Chip (Caco-2). FIG. 58B shows relative mRNA expression of CYP3A4 in one embodiment of an Intestine-Chip (Caco-2) and FIG. 58C an embodiment of a duodenum Intestine-Chip (enteroids) treated with DMSO: RIF—20 microM rifampicin; VD3—100 nM 1,25-dihidroxyvitamin. GAPDH is a loading amount control.

Figure 59A:
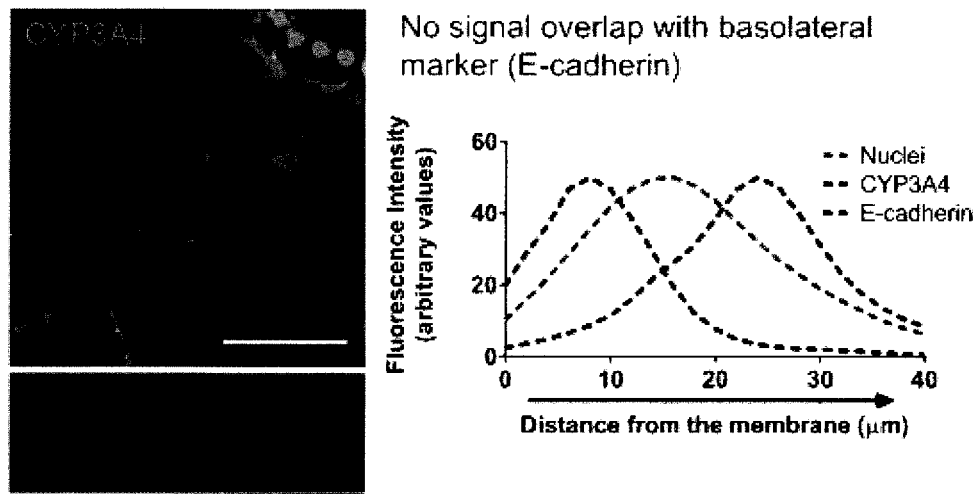
FIGS. 59A-B shows exemplary localization of CYP3A4 on the apical side (luminal region) of the epithelial layer.
Figure 59B:
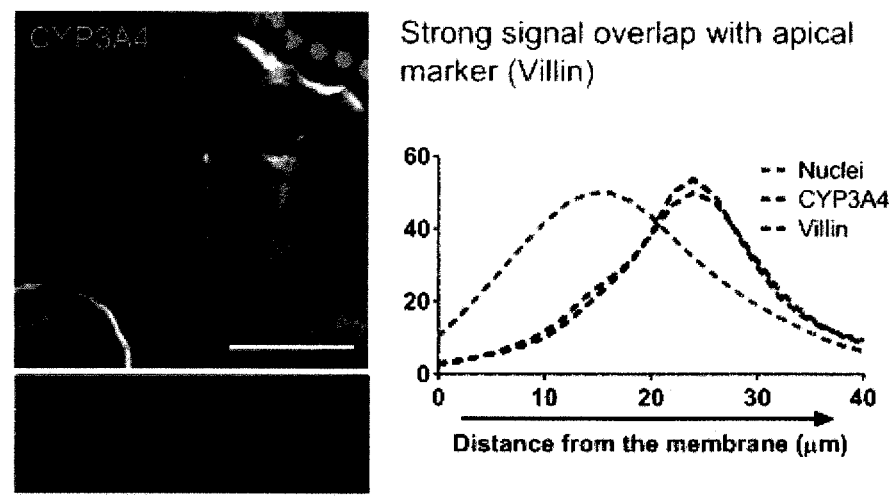
Figure 60:
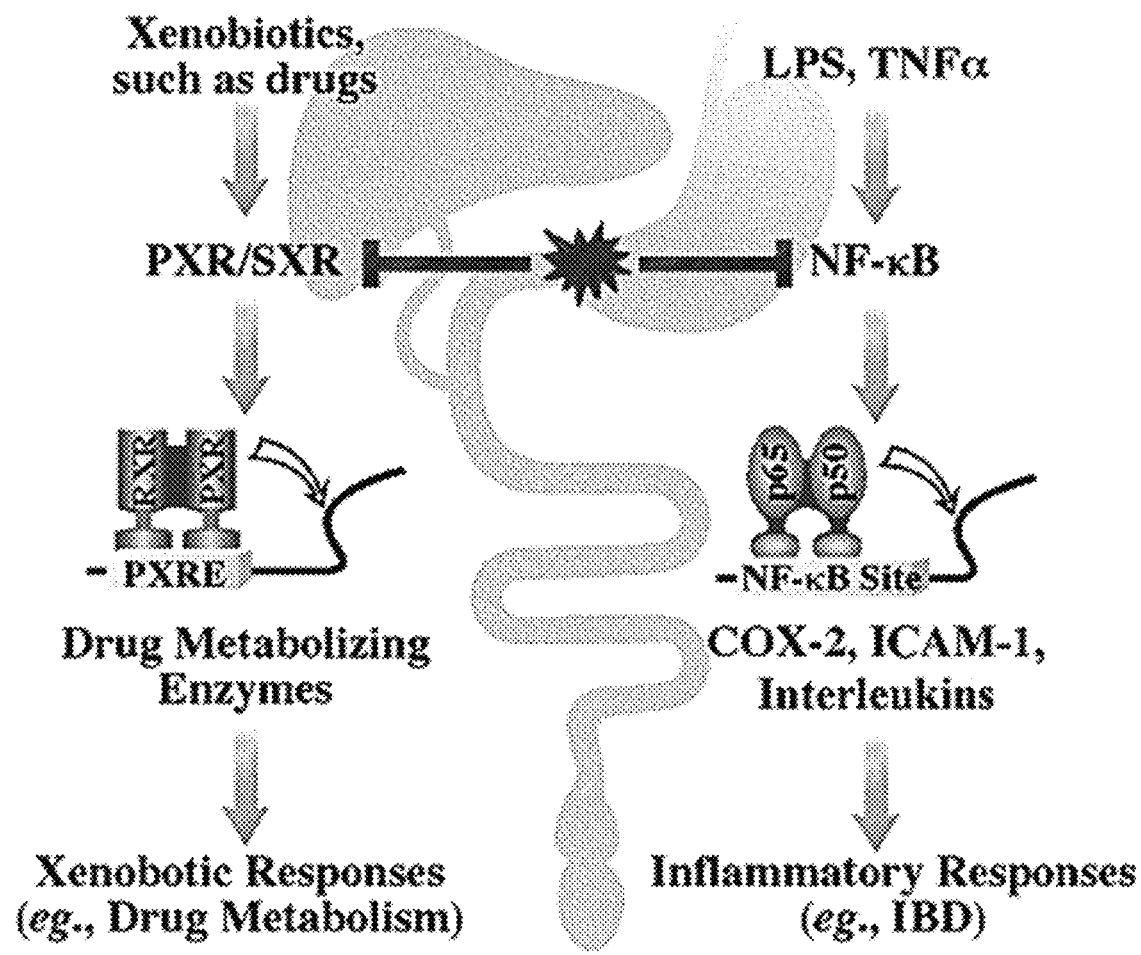
FIG. 60 shows an illustration of an exemplary PXR pathway. Xie and Tian, Xenobiotic receptor meets NF-kappaB, a collision in the small bowel, Cell Metab, 4:177-178, (2006).

FIGS. 59A-B shows exemplary localization of CYP3A4 on the apical side (luminal region) of the epithelial layer. FIG. 59A shows a confocal micrograph left, showing a z-stack side view below. The graph on the right of fluorescence intensity moving away from the membrane on the x-axis, shows no signal overlap with basolateral marker (E-cadherin). CYP3A4; E-cadherin. FIG. 59B shows a confocal micrograph left, showing a z-stack side view below. The graph on the right of fluorescence intensity moving away from the membrane on the x-axis, shows strong signal overlap with apical marker (Villin). CYP3A4; villin FIG. 60 shows an illustration of an exemplary PXR pathway. Xie and Tian, Xenobiotic receptor meets NF-kappaB, a collision in the small bowel, Cell Metab, 4:177-178, (2006).

2. Effects of Fluidic Culture Conditions and Exemplary Drugs on Nuclear Receptor Expression: Cyclic Strain Activates PXR in Intestine-Chip In some embodiments, a fluidic duodenum Intestine-Chip is used for identifying nuclear receptor changes in response to fluidic device culture conditions, e.g. stretch, flow, etc. Thus, in some embodiments, a fluidic intestine-chip under stretch, i.e. cyclic strain, and flow is used for identifying nuclear receptor changes in response to exposure to exemplary test compounds, including antibiotics, e.g. Rifampicin (Rif), a PXR agonist.

Figure 61A:
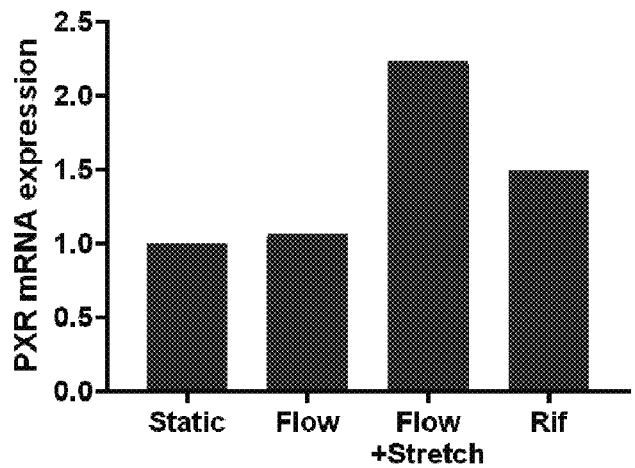
FIG. 61A-C shows exemplary mRNA induction of a nuclear receptor PXR along with PXR transcriptional targets a CYP3A4 enzyme and an ATP transporter MDR1 in one embodiment of an Intestine-Chip under stretch and flow. mRNA expression increased by a combination of flow and stretch was reduced by exposure to Rifampicin (Rif), a PXR agonist.

An exemplary fluidic Intestine-Chip as described herein, was used for identifying any changes in PXR expression related to culture conditions under flow combined with stretch, see, FIG. 61A. Additionally, expression of exemplary PXR transcriptional targets: a Cytochrome P450 Family metabolic enzyme, CYP3A4, and an example of an ATP-binding cassette (ABC) transporters, Multidrug resistance protein 1 (MDR1) expressed by the abcb gene in humans were tested by RNAseq analysis. See, FIG. 61B-C.

Increased expression of a nuclear receptor PXR in addition to increased CYP3A4 and increased MDR1 was observed under a combination of flow and stretch in one embodiment of an Intestine-Chip. Intestinal tissue from at least 3 donors was tested, +/−stretch. Please add a more detailed description of the Intestine-chip as now there are numerous embodiments of Intestinal chips.

Although PXR was induced under laminar shear stress when measured in bovine aortic cells cultured on collagen-coated glass slides, additional effects of cyclic strain was unknown. For example, see, Wang, et al., "Shear stress activation of nuclear receptor PXR in endothelial detoxification." Proceedings of the National Academy of Sciences. 6; 110(32):13174-9, 2013, bovine aortic ECs (BAECs), seeded on collagen-coated glass slides, were exposed to a physiological level of laminar shear stress (LSS; 12 dyn/cm$^2$), oscillatory shear stress (OSS; 0.5±4 dyn/cm$^2$, 1 Hz), or static condition for 18 hours. Luciferase assay showed that PXR activity was significantly increased by LSS but decreased by OSS compared with static control. Unlike Wang, et al., at least in one embodiment of a fluidic Intestine-Chips under flow alone did not increase PXR expression above static culture conditions, see, FIG. 62A.

Furthermore, embodiments of fluidic Intestine-Chips under flow and stretch were additionally tested by an exemplary drug, a PXR agonist Rifampicin.

Figure 61B:
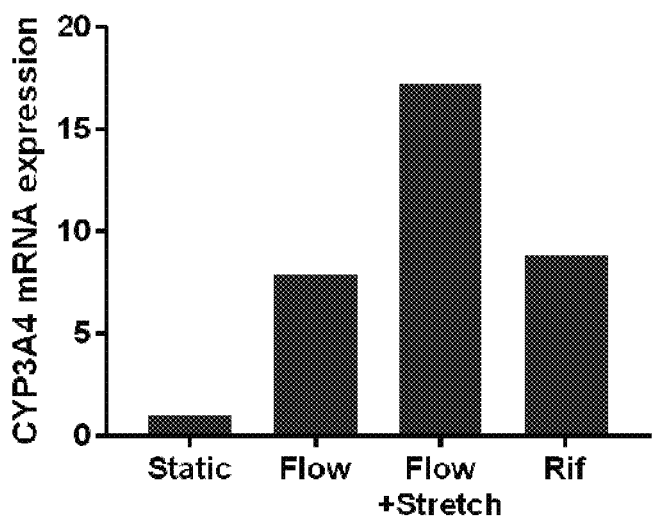
Figure 61C:
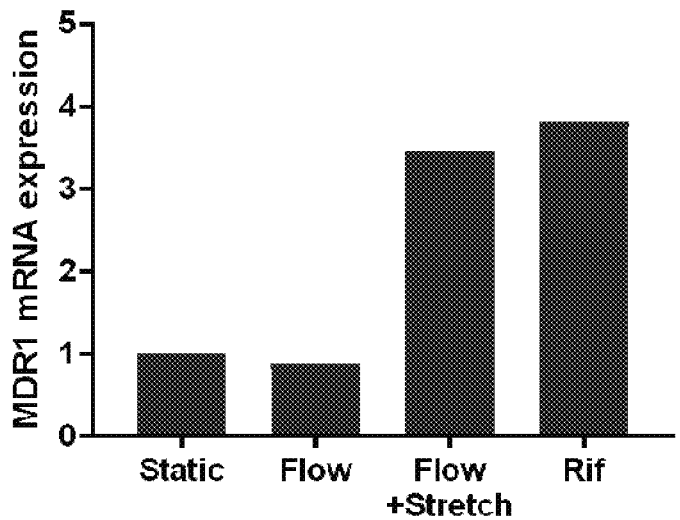

FIG. 61A-C shows exemplary mRNA induction of a nuclear receptor PXR along with PXR transcriptional targets a CYP3A4 enzyme and an ATP transporter MDR1 in one embodiment of an Intestine-Chip under stretch and flow. mRNA expression increased by a combination of flow and stretch was reduced by exposure to Rifampicin (Rif), a PXR agonist. FIG. 61A shows exemplary mRNA induction of PXR under a combination of flow and stretch that was decreased by exposure to Rifampicin (Rif). FIG. 61B shows exemplary mRNA induction of CYP3A4 under a combination of flow and stretch that was decreased by exposure to Rifampicin (Rif). FIG. 61C shows exemplary mRNA induction of MDR1 under a combination of flow and stretch that was decreased by exposure to Rifampicin (Rif).

Thus, as shown herein, a combination of flow and stretch, i.e. cyclic strain, induces PXR mRNA expression in one embodiment of an Intestine-Chip. In contrast, when duplicate intestinal devices are exposed to Rifaximin, here used as an example of a control drug (i.e. antibiotic), PXR is reduced.

3. Stretch-Induced PXR Activation Suppresses Proinflammatory Response in Intestine-Chip Models of Bacteria Induced Inflammation.

Intestinal inflammation is frequently associated with the presence of increased amounts of Lipopolysaccharide (LPS). Lipopolysaccharide (LPS), a component of the cell wall of Gram-negative bacteria, induces inflammation in intestinal tissues associated with IL-8 production. IL-8 may act as a chemotactic factor that attracts neutrophils, basophils, and T-cells, to sites of inflammation.

When LPS was used to induce inflammation in one embodiment of an Intestine-Chip, without stretch, in the presence of Rifaximin, here used as an example of a control drug (i.e. antibiotic) there was a decrease in IL-8. The addition of cyclic strain, i.e. stretch, in place of Rifaximin resulted in a more significant reduction of IL-8 production.

Thus, cyclic strain attenuates LPS-induced inflammation in Intestine-Chip whereas Rifaximin (antibiotic) was able to decrease the release of pro-inflammatory cytokines through a PXR-dependent mechanism.

Figure 62:
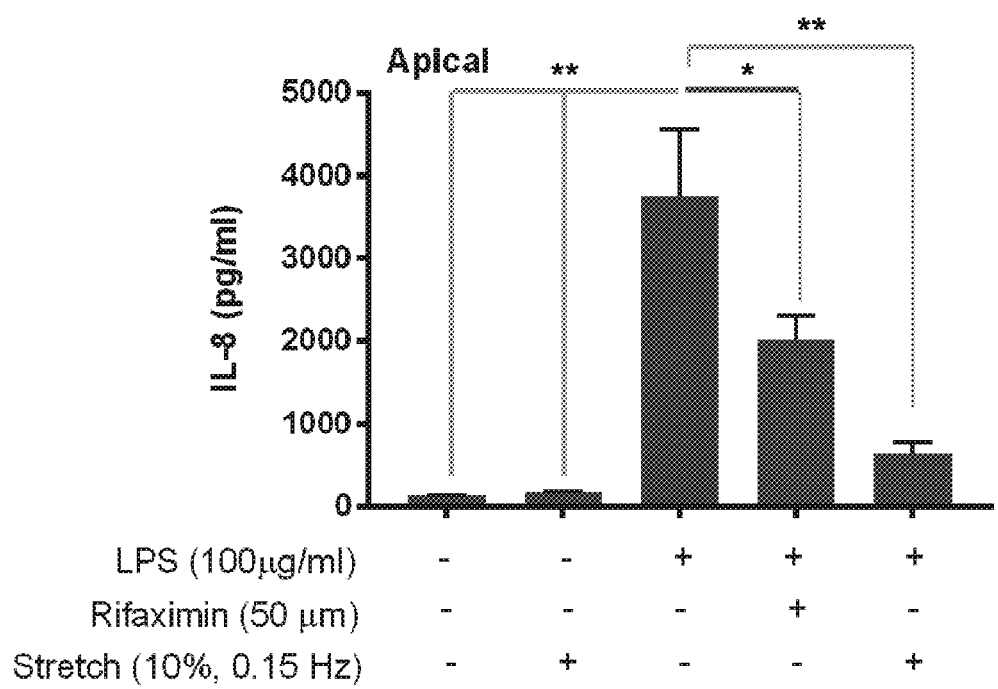
FIG. 62 shows exemplary stretch-induced PXR activation suppression of IL-8 as representative of a proinflammatory response in one embodiment of an Intestine-Chip. Lipopolysaccharide (LPS) (100 µg/ml); Rifaximin (50 µg/ml); and Stretch (10%, 0.15 Hz).

FIG. 62 shows exemplary stretch-induced PXR activation suppression of IL-8 as representative of a proinflammatory response in one embodiment of an Intestine-Chip. Lipopolysaccharide (LPS) (100 µg/ml); Rifaximin (50 µg/ml); and Stretch (10%, 0.15 Hz).

Summary: In some embodiments, duodenum-enteroids derived Intestine-Chip recreates tissue-tissue interfaces and strong intestinal barrier function as in vivo duodenal tissue when incorporating mechanical forces for improve intestinal tissue architecture. Duodenum-enteroids derived Intestine-Chip have major intestinal cell types at physiological ratios with reproducible results across multiple donors of duodenum tissues. Duodenum-enteroids derived Intestine-Chip shows genomic similarity to in vivo tissue with respect to biological functions enabling studies of drug transport and modeling of drug-induced metabolism. Furthermore, a surprising discovery demonstrated that cyclic strain has a role in inflammation.

VI. Fluidic Colon Intestine-Chip/Colon-Chip.

In some embodiments, areas of the human colon are modeled in fluidic devices using a fluidic Intestine-Chip seeded with colonoids cells and human colonic microvascular endothelial cells (cHIMECs) obtained from adult patient biopsies.

Figures 63A, 63B:
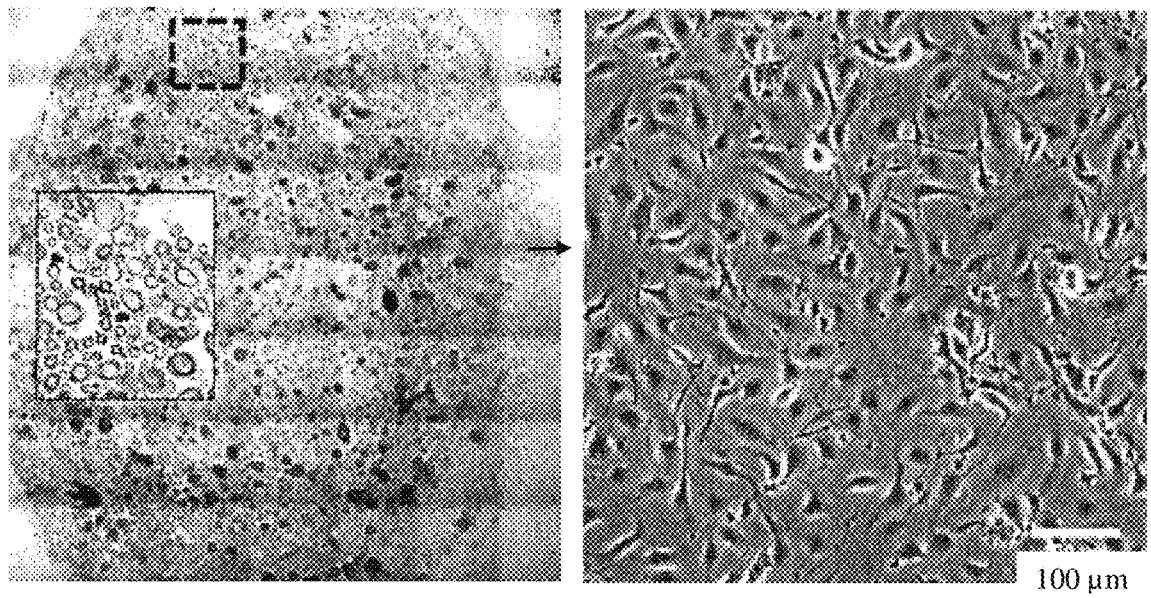
FIG. 63A-C shows exemplary micrographs (bright-field microscopy) of cells used for seeding one embodiment of Colon Intestine-Chips.
Figure 63C:
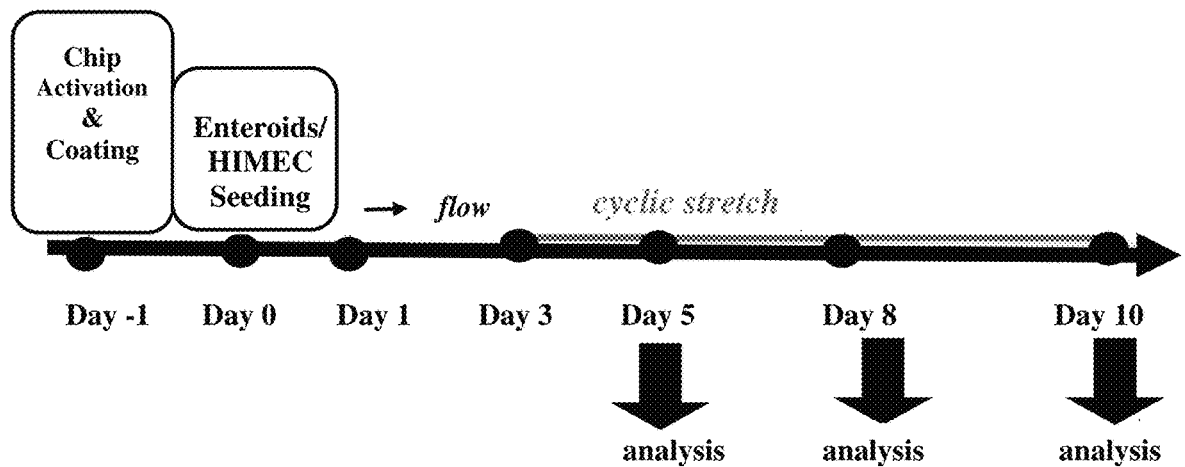

Examples of cells used for seeding embodiments of fluidic devices are shown in FIG. 63A-B with an exemplary timeline for providing one embodiment of a Colon Intestine-Chip shown in FIG. 63C. In some embodiments, Liquid-Liquid culture conditions were used. In some embodiments, an Air-Liquid Interface is contemplated for use. In some embodiments, colonoids were cultures under flow and stretch conditions. In some embodiments, a 1-step method of seeding colonoids was used. In some embodiments, a 2-step method of seeding colonoids is contemplated for use.

FIG. 63A-C shows exemplary micrographs (bright-field microscopy) of cells used for seeding one embodiment of Colon Intestine-Chips. FIG. 63A shows an exemplary micrograph representing a cluster of human colon enteroids. FIG. 63B shows an exemplary micrograph representing human intestinal microvascular endothelial cells (HIMEC) from colon. FIG. 39C shows exemplary micrographs over time of intestinal cells cultured in fluidic chips. From left to right, Day 0 cell attachment, Day 2-Day 4 formation of a confluent monolayer: Day 6: HIMEC seeding, under flow and stretch, morphogenesis of villi-like structures through Day 8 and up to Day 12. FIG. 63C shows an exemplary 2-step timeline for providing one embodiment of a Colon Intestine-Chip.

A. Tissue Differentiation in Colonoids Seeded Colon-Chips.

In some embodiments, colonic epithelium forms distinct morphological features in Colonoids Seeded Colon-Chips including folds and pouches such as found in the human colon in vivo.

Figure 64A:
FIG. 64A-B shows exemplary confocal microscopy micrographs showing colonic epithelium forming distinct morphological features as folds and pouches in one embodiment of an enteroids-derived Colon On-Chip.
Figure 64B:
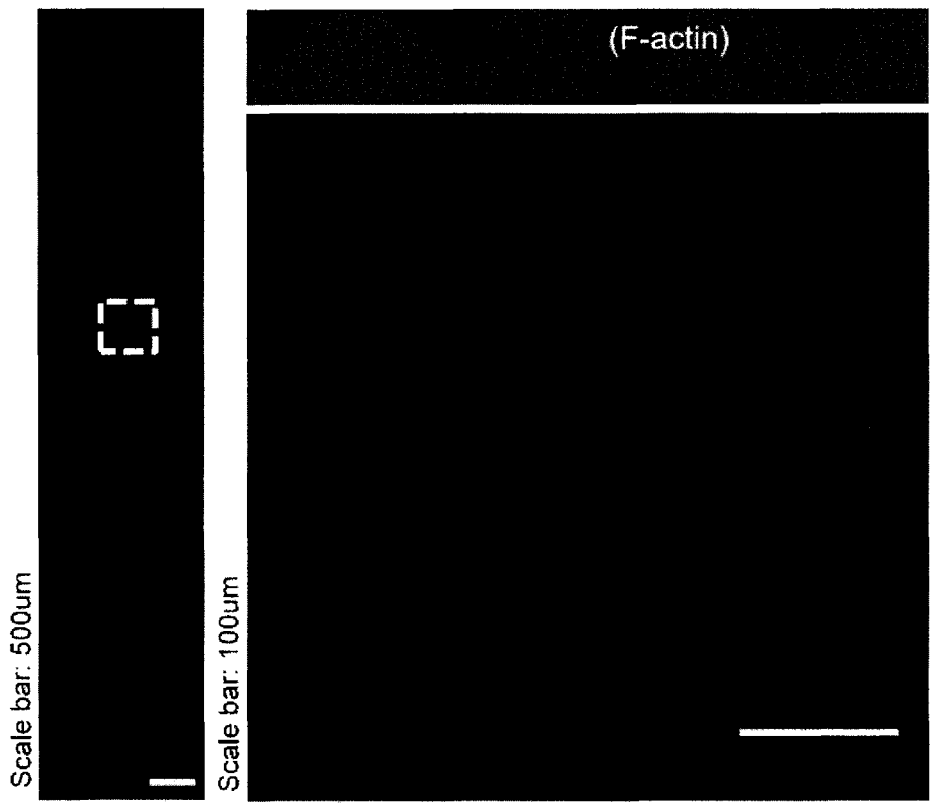

FIG. 64A-B shows exemplary confocal microscopy micrographs showing colonic epithelium forming distinct morphological features as folds and pouches in one embodiment of an enteroids-derived Colon-chip. FIG. 64A shows a confocal microscope image of an overview (looking down) of colonic-enteroids epithelium on-chip demonstrating folds and pouches where Phallodinn (f-actin) and nuclei are stained. FIG. 64B shows a low power micrograph of the epithelial channel, left, where the area outlined in white is shown at higher power to the right. Phallodin (F-actin) and nuclei are stained.

Figure 65A:
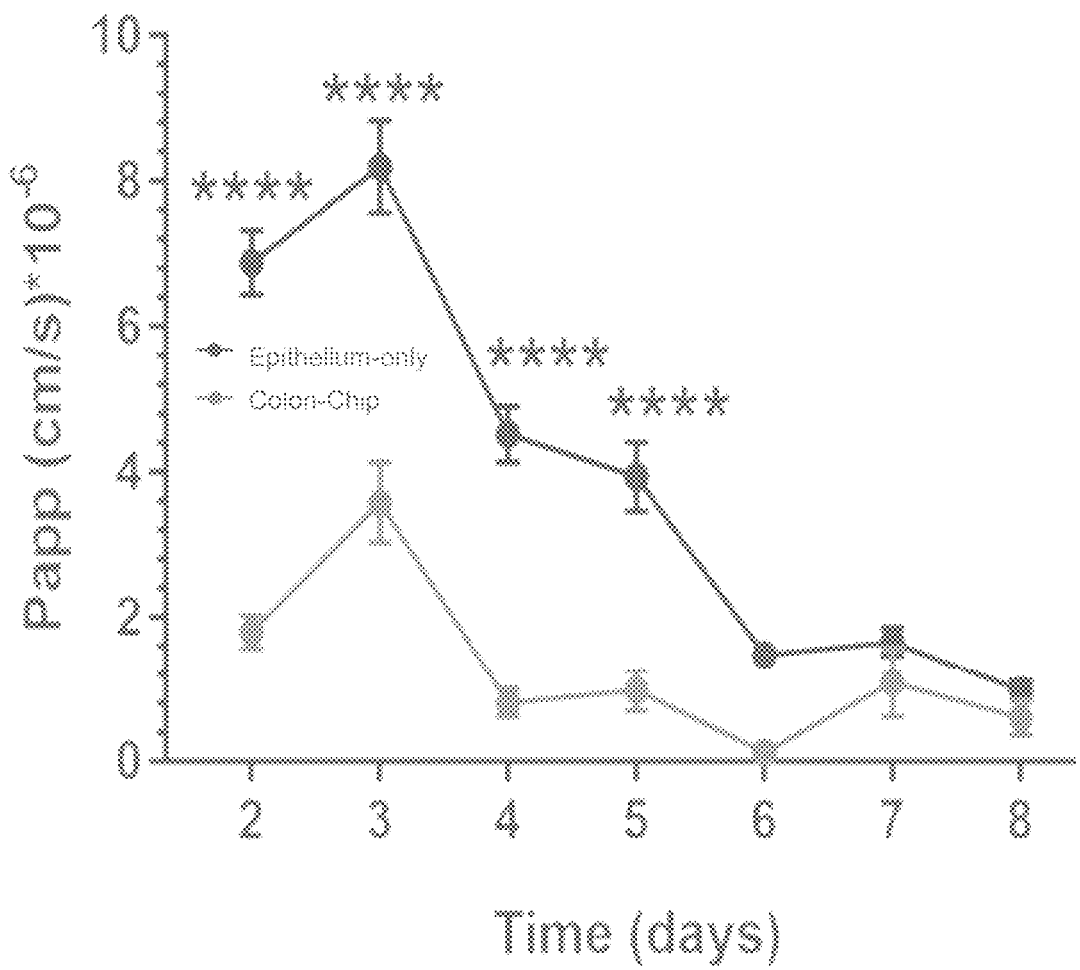
FIG. 65A-B shows exemplary barrier formation accelerated by the presence of Endothelial Cells.
Figure 65B:
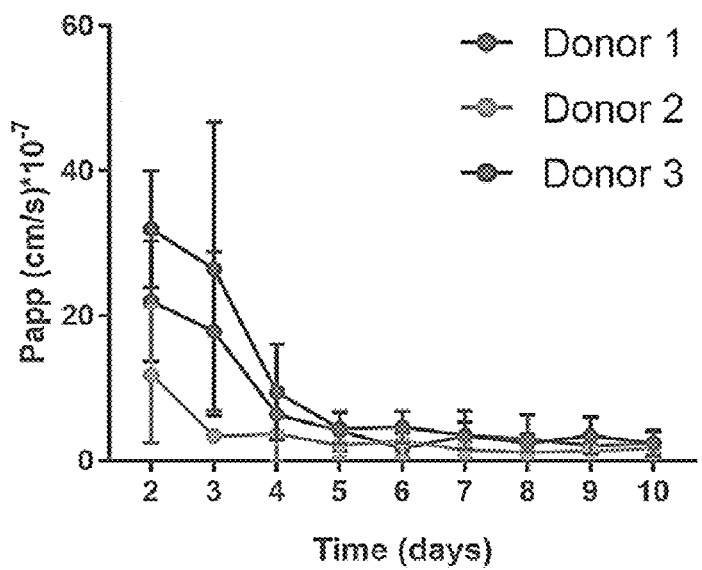

Surprisingly, presence of endothelial cells accelerates barrier formation in the epithelium of one embodiment of Colon-Chip. In other words, colonic endothelial cells decrease the time required for epithelial barrier formation in one embodiment of Colon-Chips FIG. 65A-B shows exemplary barrier formation accelerated by the presence of Endothelial Cells. FIG. 65A shows barrier function comparisons between colonic epithelium without endothelium vs. one embodiment of Colon-Chip seeded with endothelial cells. FIG. 65B shows that Epithelial Barrier Formation in one embodiment of Colon-Chips, where at least one chip was established from each of 3 donors, reached similar levels of intestinal barrier function over time.

In some embodiments, colonoids-derived Colon Intestine-Chip shows development of major intestinal cell types similar to colonic tissue in vivo.

Figure 66A:
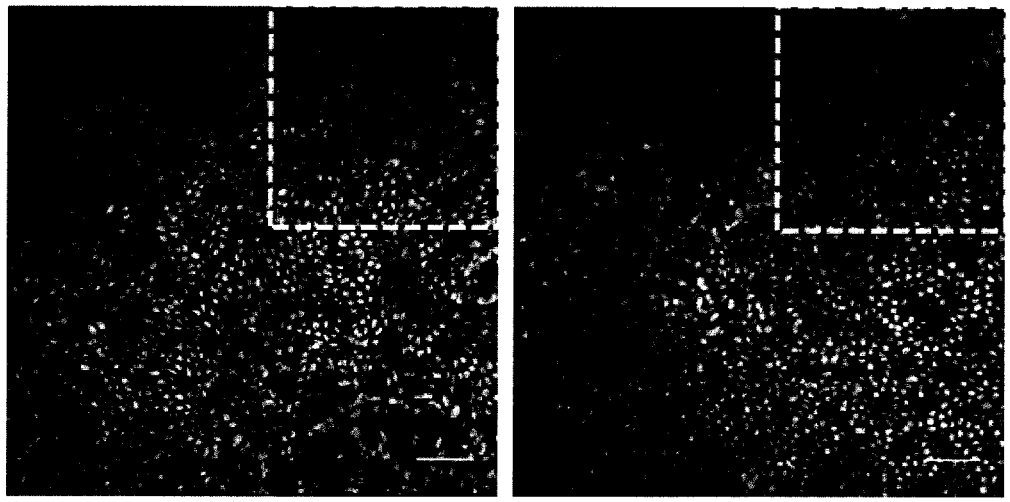
FIG. 66A-B shows exemplary immunostaining of major intestinal cell types similar to colonic tissue in vivo. Representative images at Day 8 of culture.
Figure 66B:
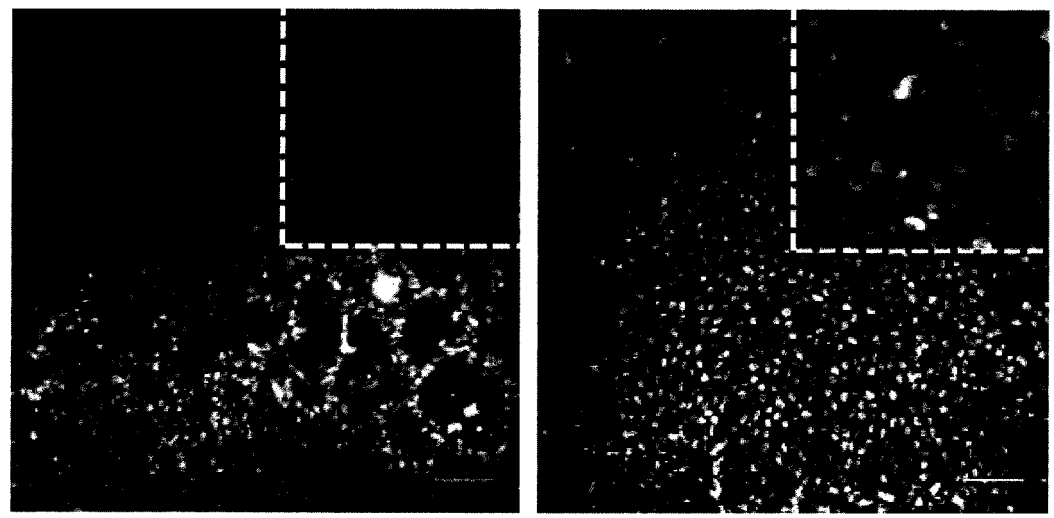

FIG. 66A-B shows exemplary immunostaining of major intestinal cell types similar to colonic tissue in vivo. Representative images at Day 8 of culture. FIG. 66A shows exemplary immunostaining of Absorptive enterocytes (Villin); and Goblet cells (MIC2). FIG. 66A shows exemplary immunostaining of EEC (ChgA) and EEC (ChgA)/L-cells immunostained with an anti-glucagon monoclonal antibody (GCG), for detection of proglucagon, glucagon, GLP-1 and GLP-2. DAPI stained nuclei are indicated in grey. Insets show areas at a higher magnification.

In some embodiments, colonoids-derived Colon Intestine-Chip underwent quantification of major intestinal cell types. In vivo values reference from Karam S M. Front Biosci 1999, 4:D286-298); Lund M L, etal. Molecular Metabolism. 2018; 11:70-83; Petersen N, et al. The Journal of Clinical Investigation. 2015:125(1):379-385.

Figure 67A:
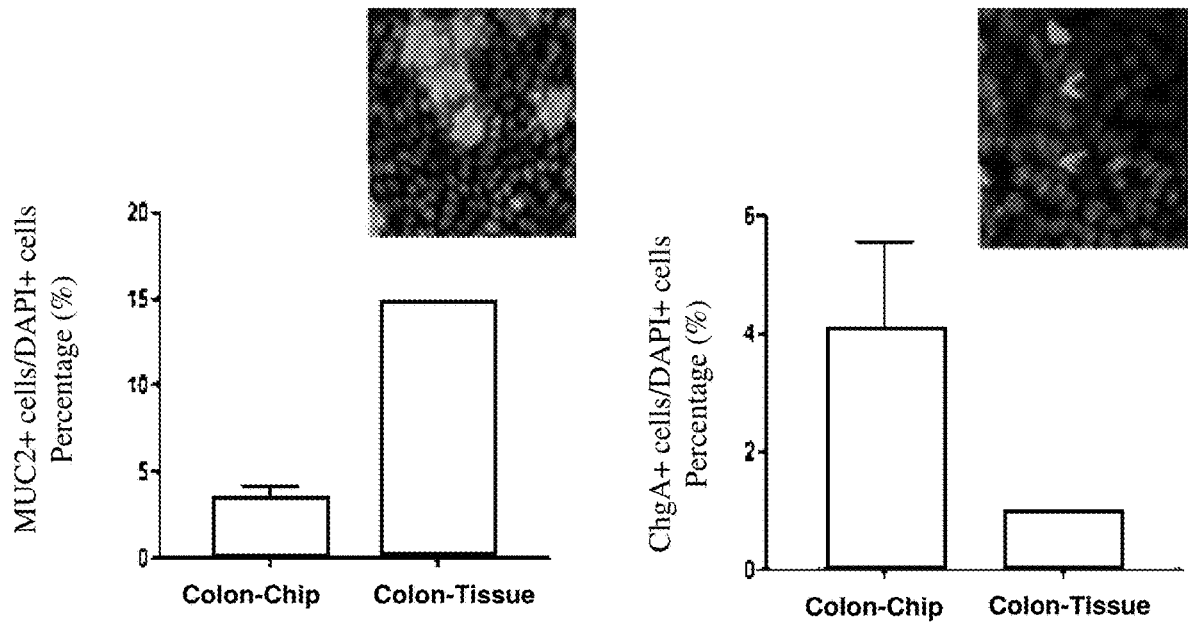
FIG. 67A-B shows quantification of the major intestinal cell types in one embodiment of Colon-Chip. Bar graphs show colon-chip values on the left, and in vivo colonic tissue values shown as bars on the right, of each box.
Figure 67B:
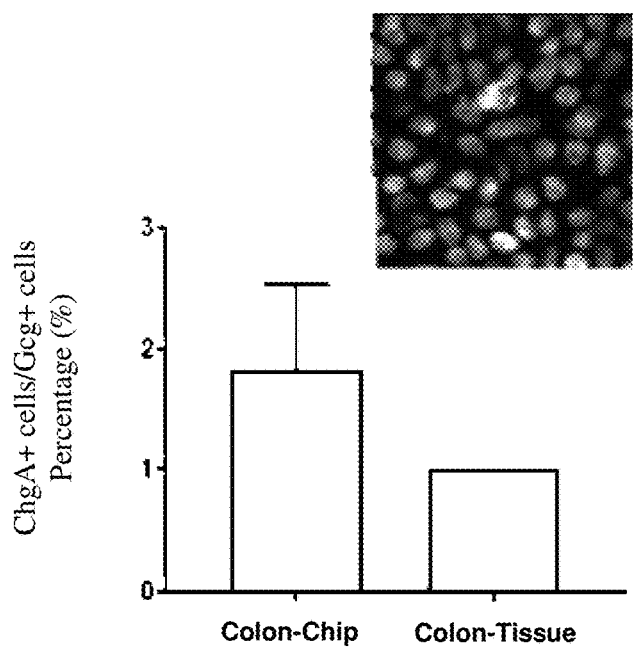
Figure 68A:
FIG. 68 shows tissue maturation by graphical comparison of development over time, left to right bars within each cell grouping, also across multiple different donors comparing development of cell types from 3 human donors. Colonoids derived from donor biopsies seeded onto chips showed physiologically relevant level of maturation in Colon Intestine-Chip. Graphs represent fold increases in mRNA expression levels of intestinal cell-type specific markers in respect to duplicate colonoids samples at the time of seeding. Intestinal cell-type specific markers were assessed at different days of Intestine-Chip growth (Day 0, 5, 8, and Day 10). * designates RNA samples from the day 5 time point used for RNA-seq analysis. Shows exemplary Absorptive Enterocytes (ALPI); Goblet cells identified by mucin 2 (MUC2); Paneth cells identified by lysozyme (LYZ); in addition to Stem cells (LGR5+); a proliferating cell biomarker, Ki67; and differentiation of enteroendocrine cell subtypes in colon-chips: EECs (ChgA); L-cells (Gcg) and Enterochromaffin Cells (Tph1).
Figure 68A:
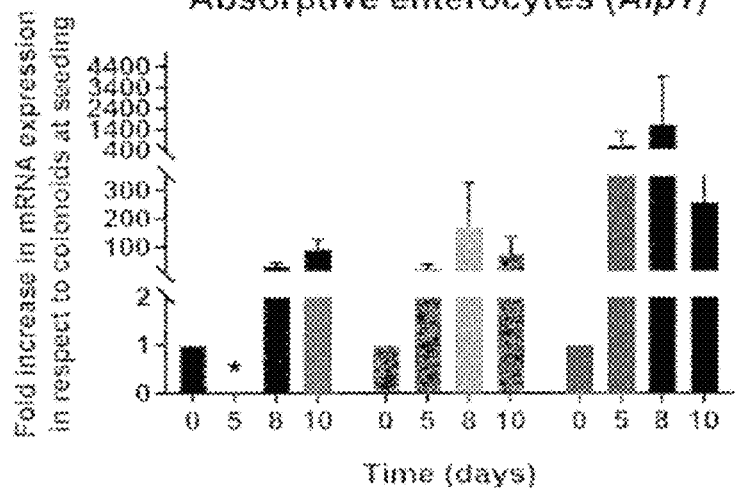
Figure 68B:
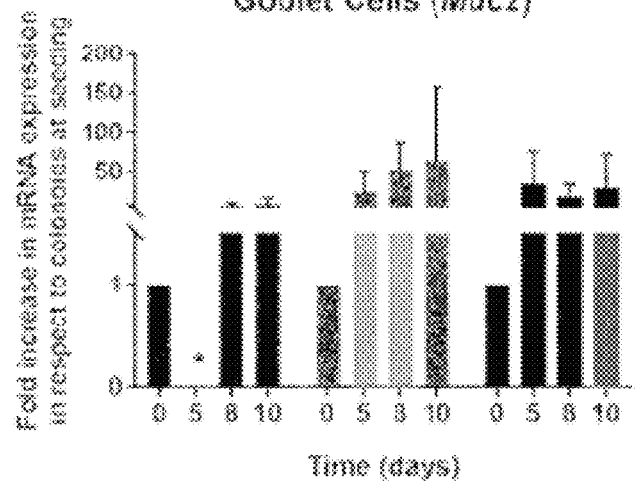
Figure 68C:
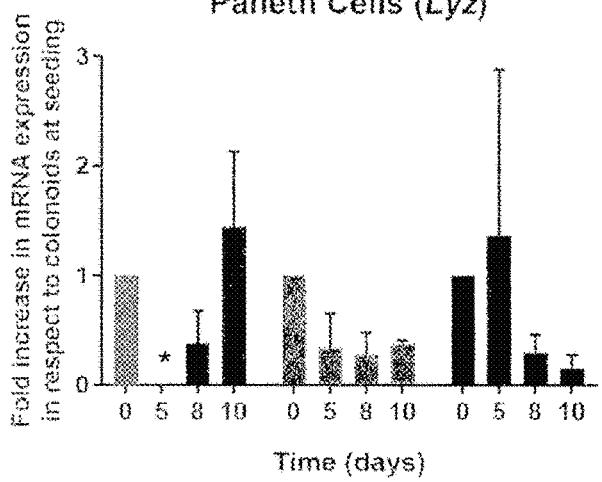
Figure 68D:
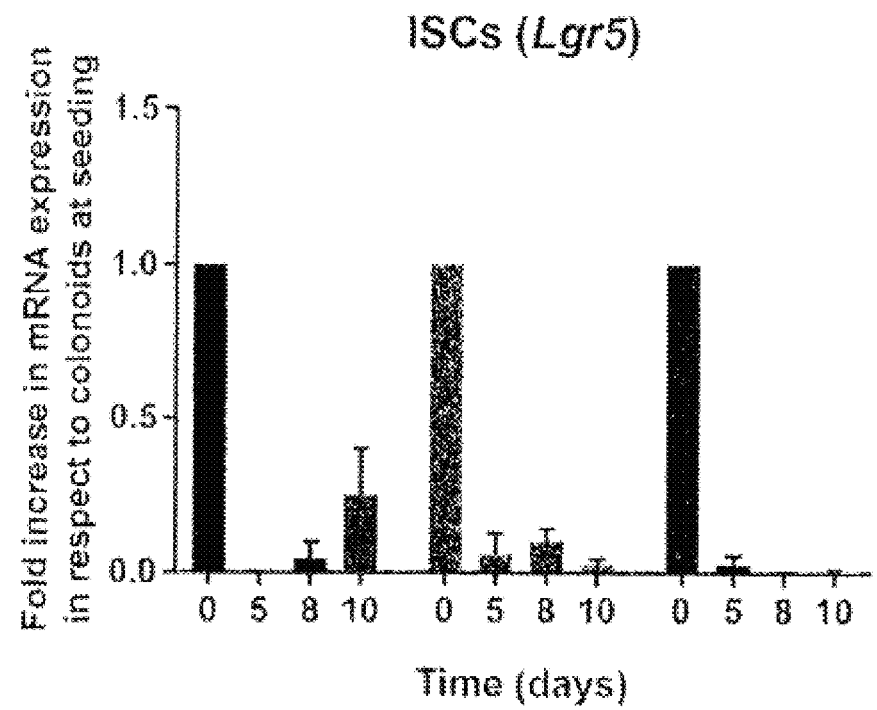
Figure 68E:
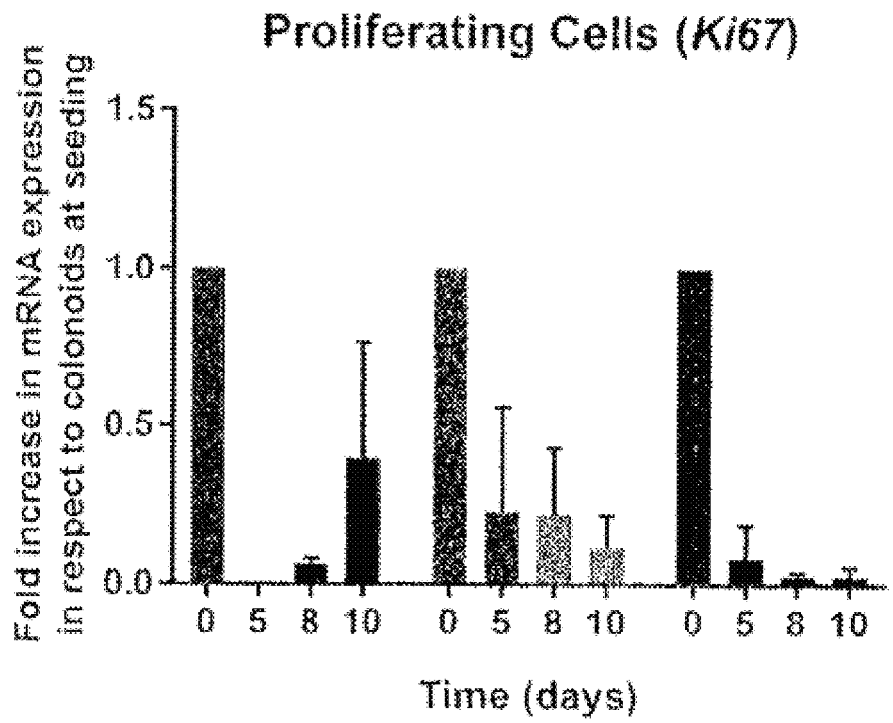
Figure 68H:
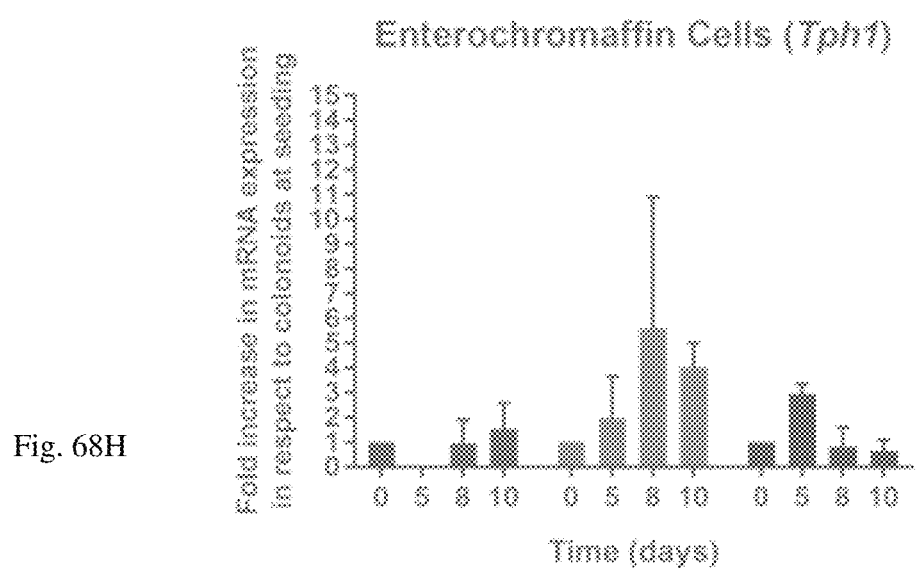

FIG. 67A-B shows quantification of the major intestinal cell types in one embodiment of Colon-Chip. Bar graphs show colon-chip values on the left, and in vivo colonic tissue values shown as grey bars on the right, of each box. FIG. 67A shows exemplary goblet cell numbers (MUC2+per DAPI stained nuclei—grey as a percentage, left, and ChgA+ EEC cells per DAPI stained nuclei (percentage), right. FIG. 67B shows exemplary ChgA+ EEC cells/GCG+ cells per DAPI stained nuclei—grey (percentage). Insets show representative confocal images used for providing data, showing representative cell types. In vivo values reference from Karam S M. Front Biosci 1999, 4:D286-298).; Lund ML, et al. Molecular Metabolism. 2018; 11:70-83; Petersen N, et al. The Journal of Clinical Investigation. 2015:125(1):379-385.

In some embodiments, colonoids-derived Colon Intestine-Chip demonstrated time-dependent epithelial maturation in Colon-Chips. Expression of mature intestinal cell-types specific markers in Colon-Chips confirms increased differentiation during the on-chip culture across 3 independent donors. Data is shown as fold increase in MRNA expression in respect to colonoids at seeding time (days), See, FIG. 68. Concomitant with epithelial differentiation, expression of sternness and proliferative cell-types decreases over time. Surprisingly, expression of enteroendocrine cells-specific markers reveals donor-dependent variability.

FIG. 68 shows tissue maturation by graphical comparison of development over time, left to right bars within each cell grouping, also across multiple different donors comparing development of cell types from 3 human donors. Colonoids derived from donor biopsies seeded onto chips showed physiologically relevant level of maturation in Colon Intestine-Chip. Graphs represent fold increases in mRNA expression levels of intestinal cell-type specific markers in respect to duplicate colonoids samples at the time of seeding. Intestinal cell-type specific markers were assessed at different days of Intestine-Chip growth (Day 0, 5, 8, and Day 10). * designates RNA samples from the day 5 time point used for RNA-seq analysis. Shows exemplary Absorptive Enterocytes (ALPI); Goblet cells identified by mucin 2 (MUC2); Paneth cells identified by lysozyme (LYZ); in addition to Stem cells (LGR5+); a proliferating cell biomarker, Ki67; and differentiation of enteroendocrine cell subtypes in colon-chips: EECs (ChgA); L-cells (Gcg) and Enterochromaffin Cells (Tph1).

B. Confirmation of Tuft Cell Differentiation in Colonoids-Derived Colon-Chips.

Expression of TRPM5 mRNA in colonoids-derived Colon-Chip showed donor-dependent fluctuations, over 0, 5, 8 and 10 days of incubation, confirming that Tuft cell differentiation is occurring on-chip. However expression of mRNA for Tuft cell biomarkers (ChAT and DCLK1) were undetectable, FIG. 69A. Quantification of Tuft Cell populations in Colon-Chips was done by confocal microscopy staining for TRPM5 and ChAT, FIG. 69B shows confirmation that Trpm5+/ChAT+ Tuft cells, a Takeda target cell type, are present in the Colon-Chip. FIG. 69C shows rpm5+/ChAT+ Tuft cells present at physiological levels.

Figure 69A:
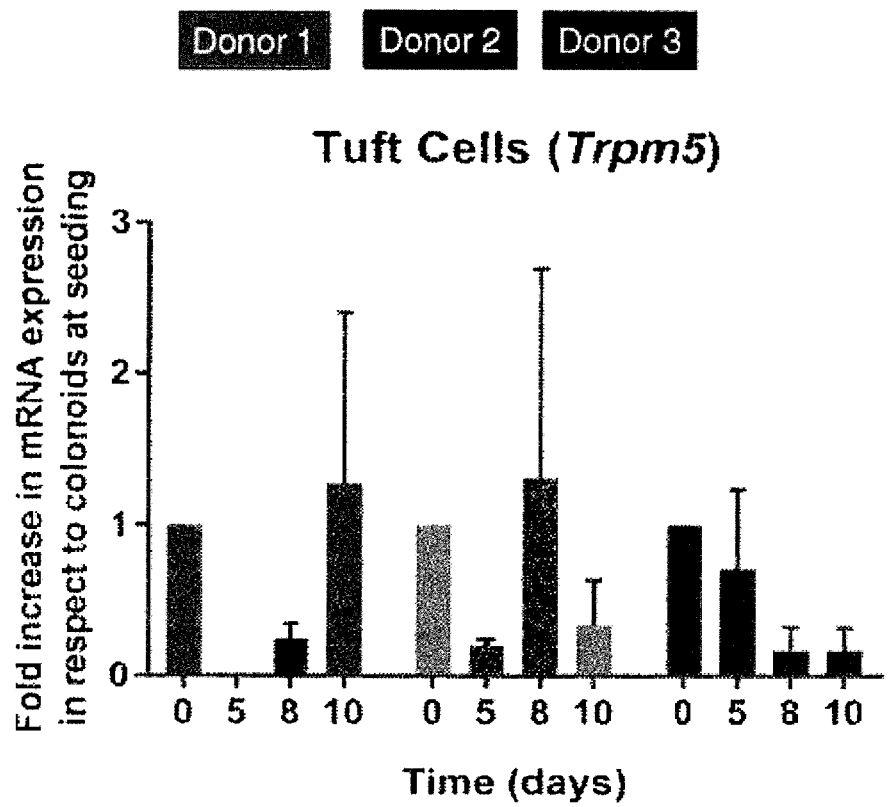
FIG. 69A-C shows exemplary markers detected for Tuft cells (TRPM5) for Colloids-derived Intestine chips.
Figure 69B:
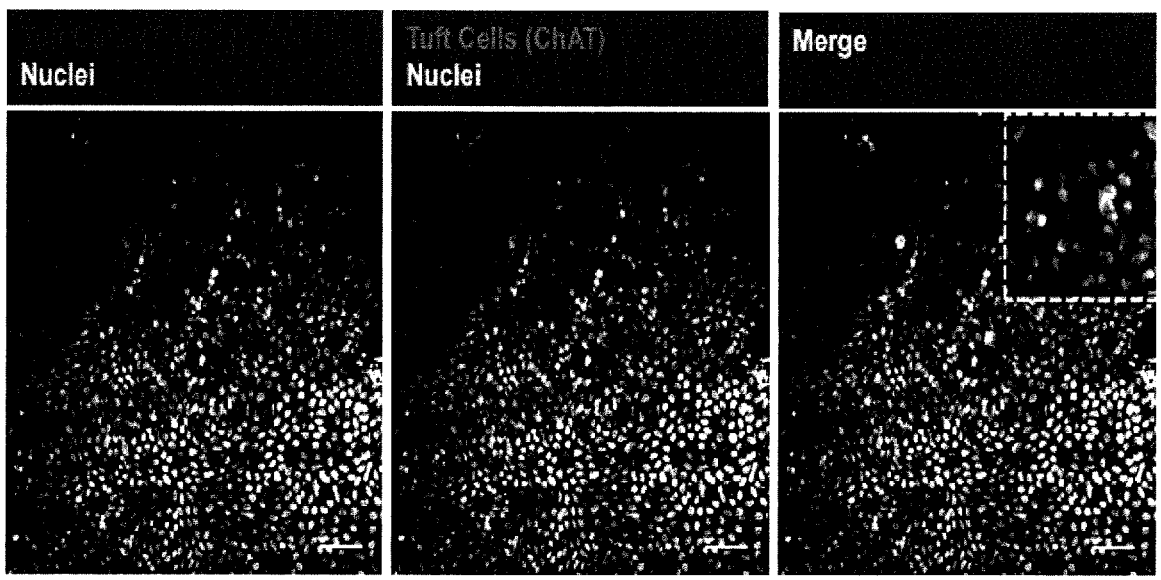
Figure 69C:
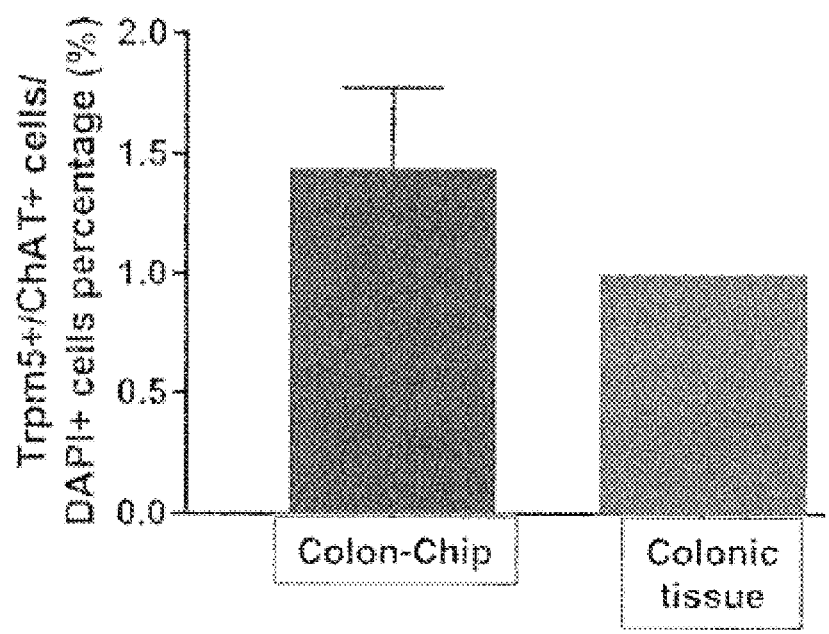

FIG. 69A-C shows exemplary markers detected for Tuft cells (TRPM5) for Colloids-derived Intestine chips. FIG. 69A shows levels of mRNA measured from colon epithelial layers on at least 3 chips, each one from one of the 3 donors confirming TRPM5 mRNA expression. FIG. 69B shows that two of the three combined biomarkers for Tuft Cells (TRPM5 and ChAT) were present after immunostaining in confocal microscope images. FIG. 69C shows that Trpm5+/ChAT+ Tuft cells, a Takeda target cell type, are present in the Colon-Chip at physiological levels.

Summary: Characterization of colonoids-derived Colon Intestine-Chip (in the presence of microvasculature) revealed the presence of cross-talk between the epithelium and endothelium that led to accelerated barrier formation; Confirmation of the differentiation of major intestinal cell types and quantification of cell populations; Increasing epithelial maturation is correlated with the decrease in sternness and proliferation; Differentiation was successful for providing enteroendocrine specific cell subtypes; and Confirmation of Tuft cell differentiation and quantification of Tuft cell population that is similar to human colonic tissue in vivo.

TABLE 5

Exemplary Cell Types Identified In Some Embodiment Of Duodenum, Ileum, And Colon Intestine-Chips.

| Chip/Cell | Present/ Absent | Test Results Based Upon | Evidence Immunofluorescence | qPCR | Est. Frequency |
|---|---|---|---|---|---|
| Duodenum-Chip | | | | | |
| Absorptive enterocytes | Present | IF; qPCR | Villin+ | Alpi+ | 89.0% ± 6.0[a] |
| Goblet cells | Present | IF; qPCR | Muc2+ | Muc2+ | 2.9% 0 ± 1.5[a] |
| Enteroendocrine cells | Present | IF; qPCR | ChrgA+ | ChrgA+ | 0.32% ± 0.1[a] |
| Paneth cells | Present | IF; qPCR | Lyz+ | Lyz+ | 2.1% ± 1.9[a] |
| Stem cells | Present | qPCR | nd (not determined) | Lgr5+ | nd |
| Ileum-Chip | | | | | |
| Absorptive enterocytes | Present | IF; qPCR | Viliin+ | Alpi+ | 91.2% ± 1.3[b] |
| Goblet cells | Present | IF; qPCR | Muc2+ | Muc2+; TFF3+ | 6.1% ± 1.4[b] |
| Enteroendocrine cells | Present | IF; qPCR | ChrgA+ | ChrgA+ | 1.2% ± 0.3[b] |
| Paneth cells | Present | IF; qPCR | Lyz+ | Lyz+ | 0.1% ± 0.2[b] |
| Stem cells | Present | qPCR | nd | Lgr5+ | nd |
| L cells | Present | IF; qPCR | GLP-1+ | Gcg+ | 0.7% ± 0.2[b] |
| Enterochromaffin cells | Present | IF; qPCR | 5-HT+ | Tph1+ | 0.5% ± 0.2[b] |
| Tuft cells | Inconclusive | IF; qPCR | Dclk1−; Trp5−; ChAT− | Dclk1−; Trp5+; ChAT− | nd |
| Colon-Chip | | | | | |
| Absorptive enterocytes | Present | IF; qPCR | Villin+ | Alpi-r | TBD |
| Goblet cells | Present | IIF; qPCRR | Muc2+ | Muc2+. TFF3+ | 4.0% ± 0.5[C] |
| Enteroendocrine cells | Present | IF; qPCR | ChrgA+ | ChrgA+ | 4.0% ± 0.7[C] |
| Paneth cells | Present | IF; qPCR | Lyz+ | Lyz+ | TBD |
| Stem cells | Present | qPCR | nd | Lgr5+ | nd |
| L cells | Present | IF; qPCR | GLP-1+ | Gcg+ | 1.9% ± 0.1[C] |
| Enterochromaffin cells | Present | IF; qPCR | 5-HT+ | Tph1+ | TBD |
| Tuft cells | Present | IF; qPCR | Trpm5+; ChAT+ | Trpm5+, Dclk1−, ChAT− | 1.4% ± 0.3[C] |

[a] quantification performed on day 8 of fluidic culture and based on 10 FOV/chip, 3 chips/donor, expressed as average across 3 different donors +/− SD.
[b] quantification performed on day 8 of fluidic culture based on 5 FOV/chip, 1 chips/donor, expressed as average across 3 different donors +/− SD.
[C] quantification performed on day 8 of fluidic culture based on 5 FOV/chip, 3 chips/donor, expressed as average across the chips from 1 donor +/− SD.

VII. Air/Liquid Interface (ALI).

In some embodiments, an Air-Liquid Interface (ALI) was developed and used in place of a Liquid-Liquid Interface (LLI) for fluidic devices. In one embodiment, Evaluation of the Effect of ALI on Mucosa-on-Chip-Timeline was determined. At Day 0-Seed HIF at 30,000 cells/chip. On Day 3—Seed Organoids, 2 wells/chip. On Day 7-media change and start ALI. IN some embodiments, Expansion Media (EM) was used. In some embodiments, Differentiation Media (DM) was used.

Figure 70A:
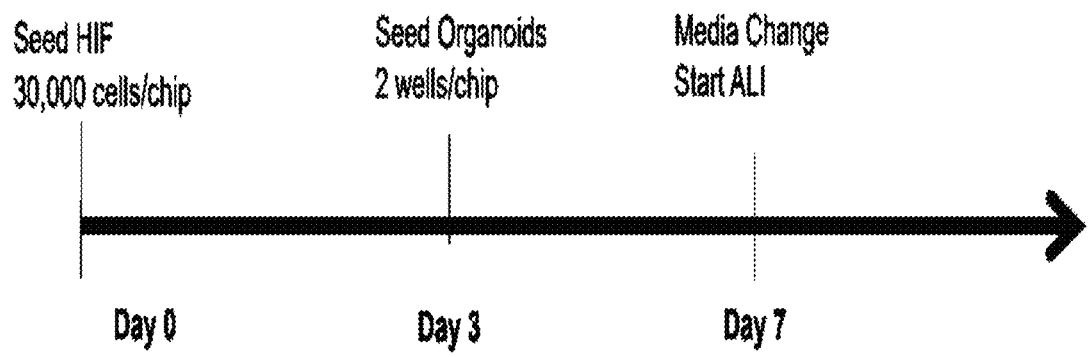
FIG. 70A-B demonstrates an exemplary timeline and shows bright field microscope images of cells used for seeding one embodiment of a colonoids (organoids)-derived colon-chip. In one embodiment of a colonoids (organoids)-derived colon-chip, the chip is used for evaluating the use of an ALI.
Figure 70B:
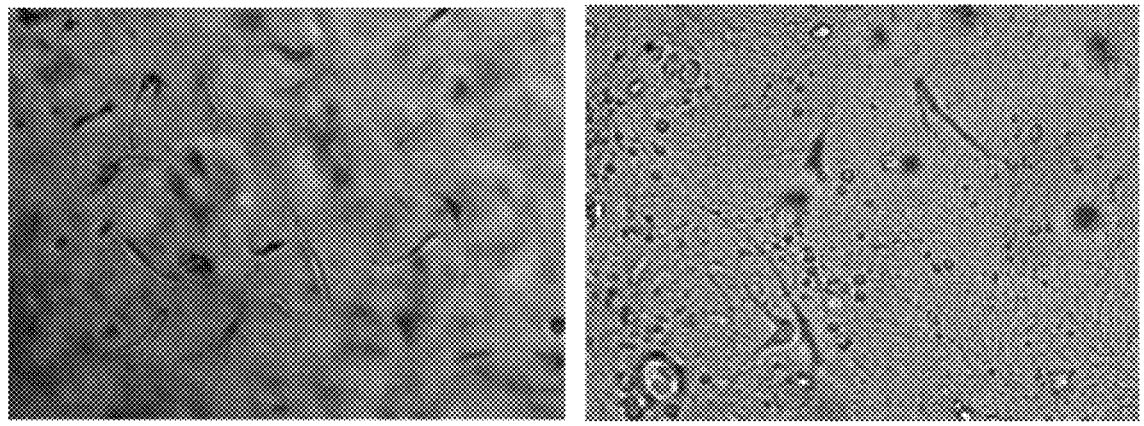

FIG. 70A-B demonstrates an exemplary timeline and shows bright field microscope images of cells used for seeding one embodiment of a colonoids (organoids)-derived colon-chip. In one embodiment of a colonoids (organoids)-derived colon-chip, the chip is used for evaluating the use of an ALI. FIG. 70A shows a schematic of an exemplary timeline for evaluating ALI. FIG. 70B shows Human Intestinal Fibroblasts at day 3 of culture, left, and Human Colonic Epithelium at day 4, right.

Figure 71:
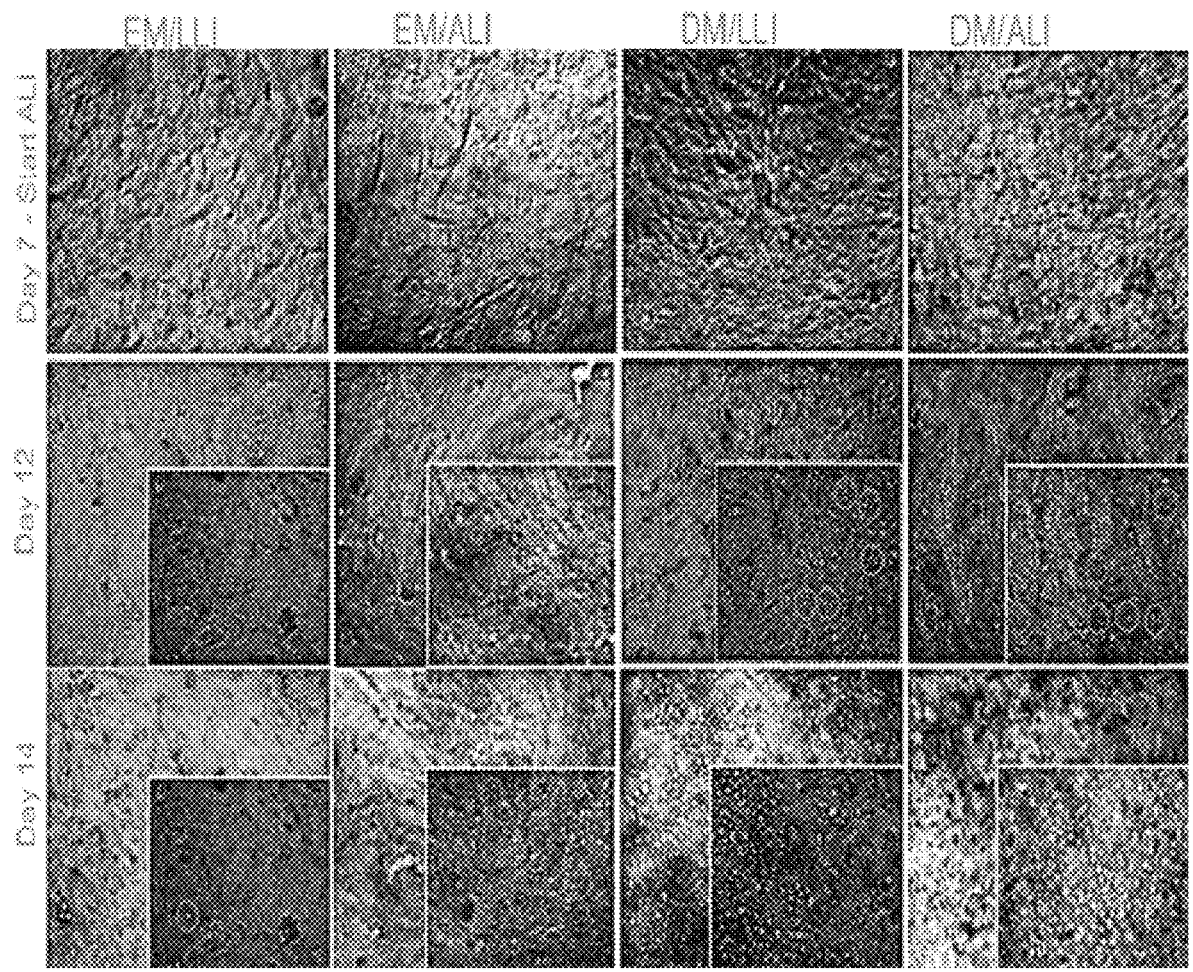
FIG. 71 shows exemplary bright field microscope images of cells on chip at day 7 (start of ALI), Day 12 and Day 14 in comparison to types of media (EM or DM) used with ALI or LLI. Inserts showing higher power micrographs of cells.

FIG. 71 shows exemplary bright field microscope images of cells on chip at day 7 (start of ALI), Day 12 and Day 14 in comparison to types of media (EM or DM) used with ALI or LLI. Inserts showing higher power micrographs of cells.

Surprisingly, Mucosa-on-Chip (i.e. Intestine-chip) can be maintained for 2 weeks at LLI and ALI in the presence of EM. Mucosa-on-Chip can be sustained for up to 12 days in DM media—after that time epithelium starts to shed off from the gel surface. Growth of Mucosa-on-chip supplied with EM media from the bottom and exposed to ALI from the top results in 2 weeks survival and some of the features of differentiated epithelium (presence of round cells—circled in blue are an indication of goblet cell differentiation). Conditions include, left to right panels: EM/LLI; EM/ALI; DM/LLI; DM/ALI. LLI=Liquid-Liquid Interface. ALI=Air-Liquid Interface. O=goblet cells.

DESCRIPTION OF PREFERRED EMBODIMENTS

In some embodiments, chips that may find use are described herein, with additional embodiments and descriptions in U.S. Pat. No. 8,647,861, "Organ mimic device with microchannels and methods of use and manufacturing thereof." filed Jul. 16, 2009, and in U.S. patent application Ser. No. 15/248,690, as examples, both of which are herein incorporated by reference in their entirety.

I. Open Top Microfluidic Chips.

The present disclosure relates to gut-on-chips, such as fluidic devices comprising one or more cells types for the simulation one or more of the function of gastrointestinal tract components. Accordingly, the present disclosure additionally describes open-top gut-on-chips, see, e.g. schematic in FIG. 32.

Figure 32:
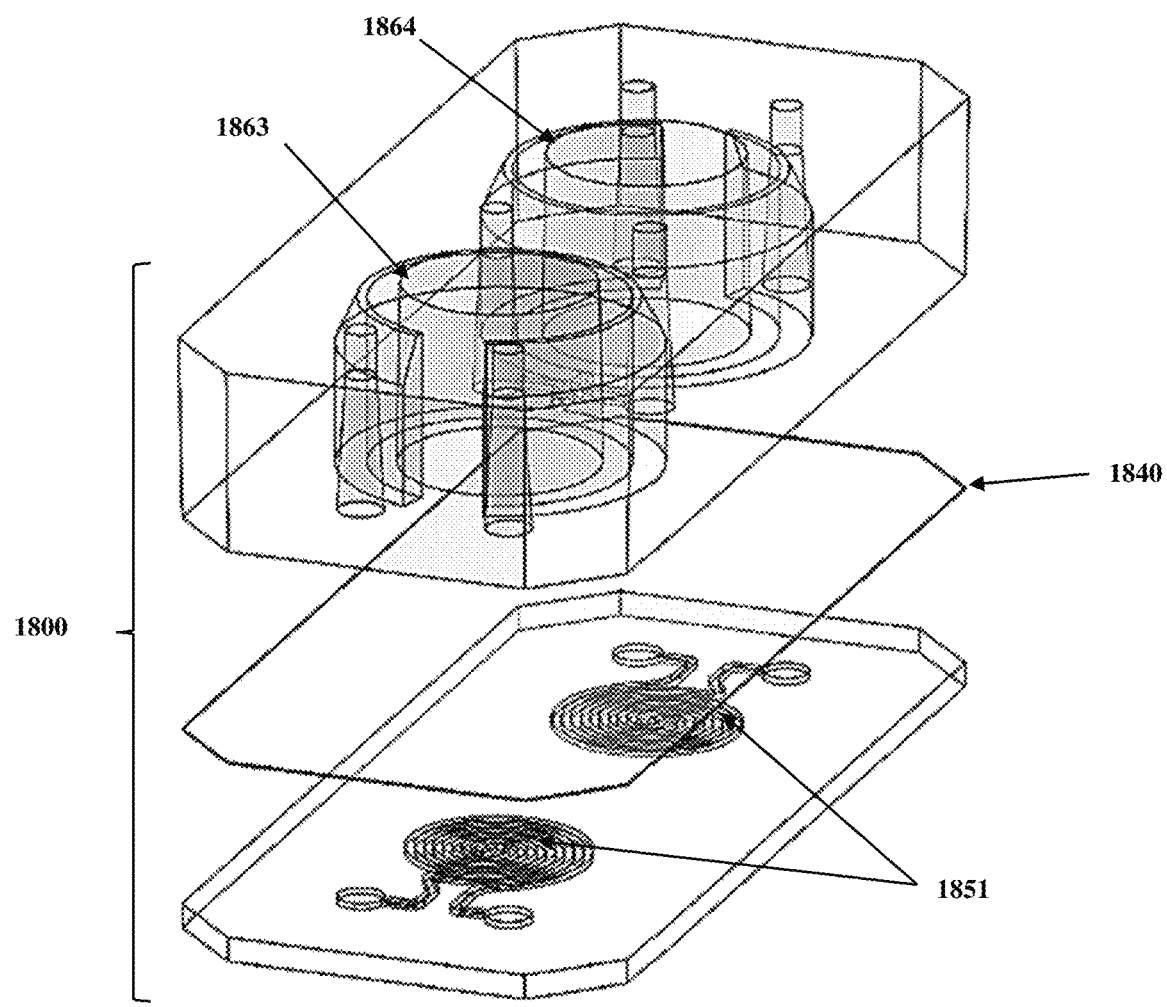
FIG. 32 shows an exemplary exploded view of one embodiment of an open-top chip device 1800, wherein a membrane 1840 resides between the bottom surface of the first chamber 1863 and the second chamber 1864 and the at least two spiral microchannels 1851.

FIG. 32 shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

II. Instrumentation.

Figure 1B:
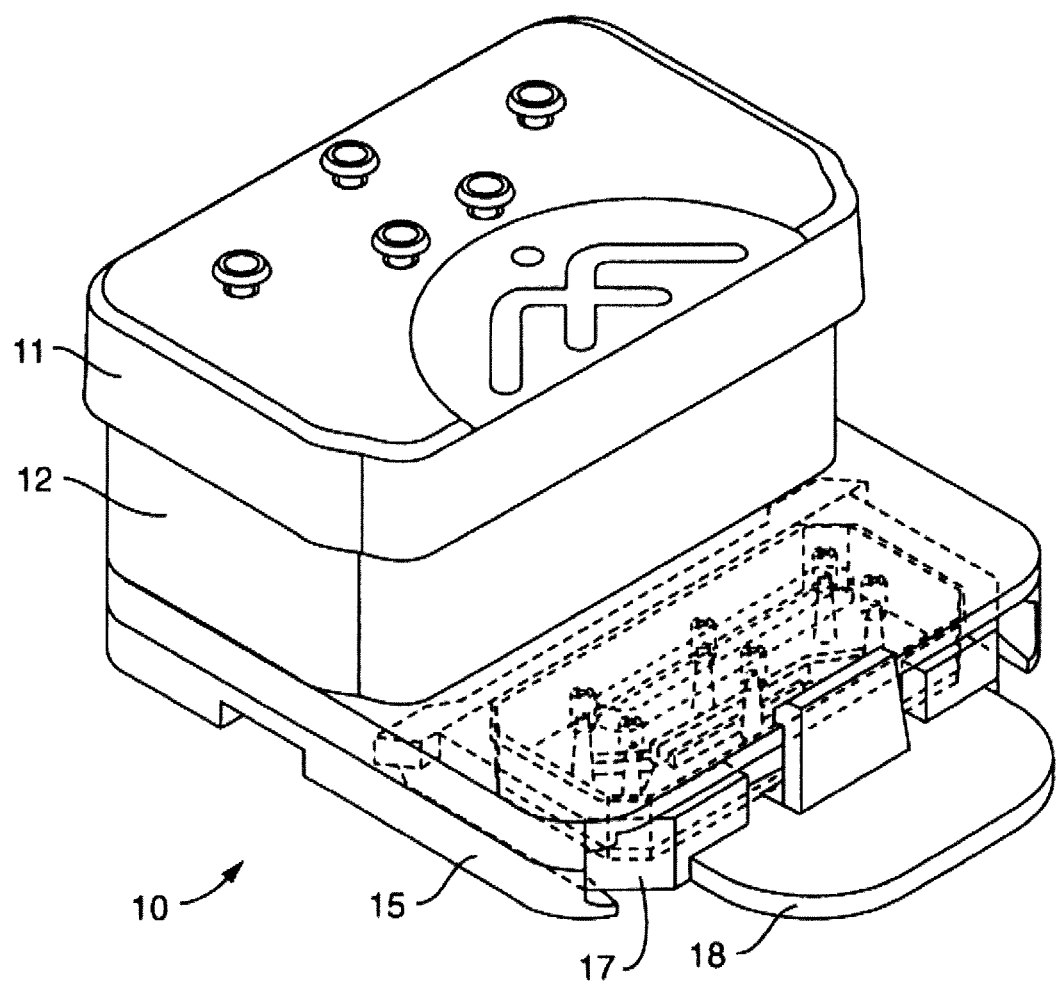
Figure 1C:
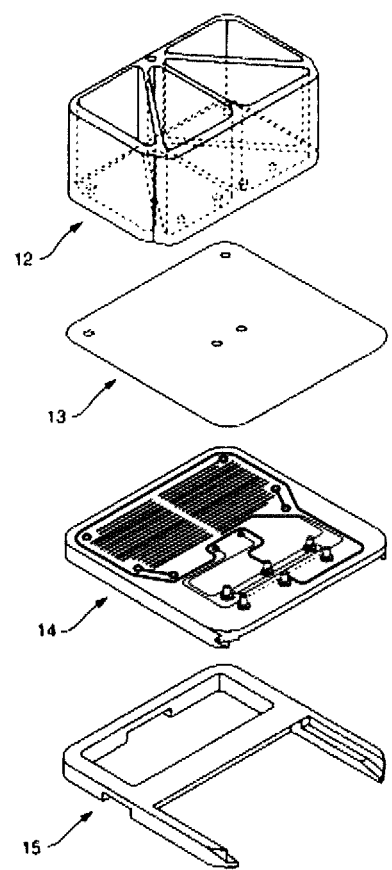

In one embodiment (as shown in FIGS. 1A, 1B and 1C), the perfusion manifold assembly (10) comprises i) a cover or lid (11) configured to serve as to top of ii) one or more fluid reservoirs (12), iii) a capping layer (13) under said fluid reservoir(s), iv) a fluidic backplane (14) under, and in fluidic communication with, said fluid reservoir(s), said fluidic backplane comprising a fluidic resistor, and v) a projecting member or skirt (15) for engaging the microfluidic device (16) or chip which is preferably positioned in a carrier (17), the chip having one or more microchannels (1) and in fluidic communication with one or more ports (2). The assembly can be used with or without the lid or cover. Other embodiments (discussed below) lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels.

Figure 2A:
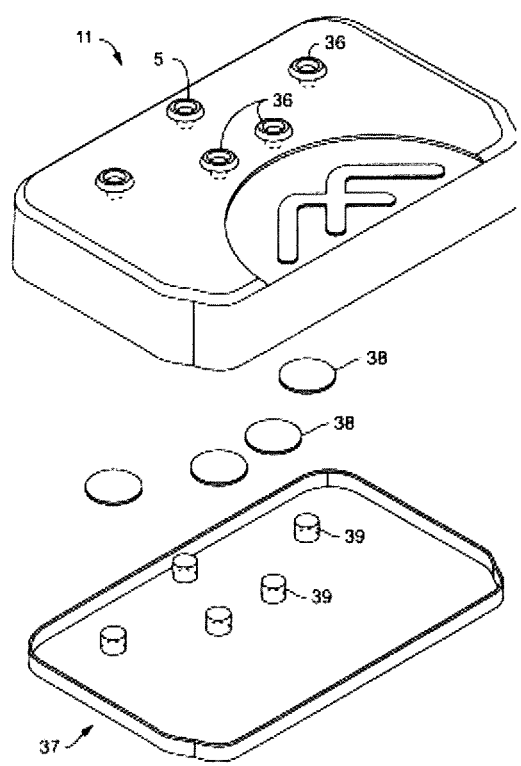
FIG. 2A is an exploded view of one embodiment of the cover assembly (11) comprising a pressure cover or pressure lid. In the illustrated embodiment, the pressure lid comprises a port (5) that allows pneumatic (e.g. vacuum) control of (optional) chip stretching to be communicated through the lid and a plurality of ports (36) (e.g. through-hole ports) (e.g. through-hole ports) associated with filters (38) (e.g. a 0.2 µm filter) and corresponding holes (39) in a gasket (37) positioned underneath the cover. In one embodiment, the cover or lid is made of polycarbonate. The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed.
Figure 2B:
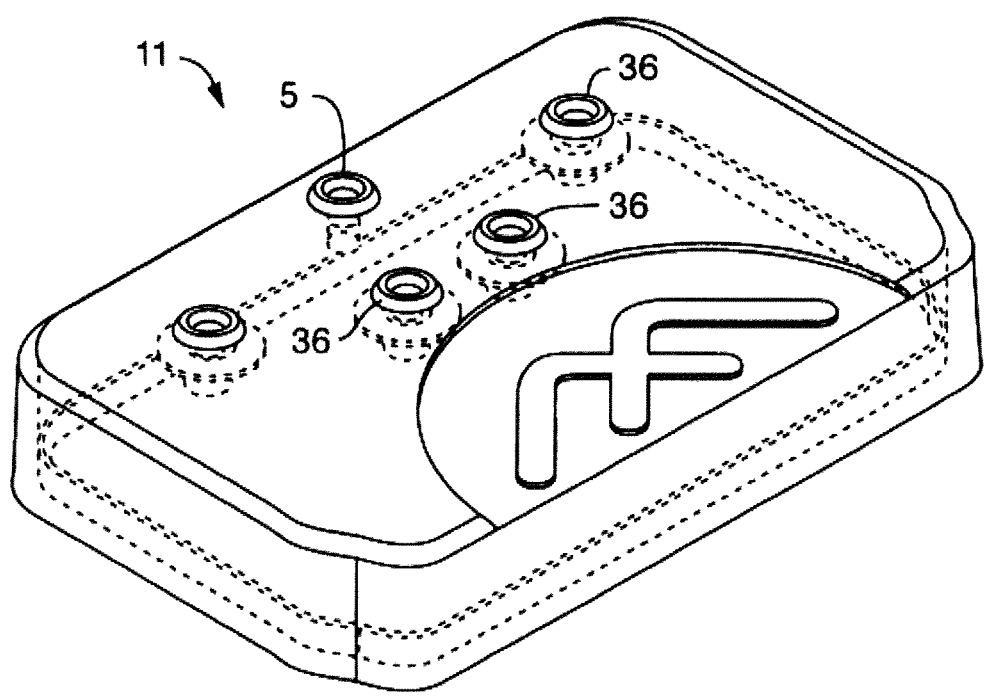
FIG. 2B shows the same embodiment of the cover assembly illustrated in FIG. 2A with the filters and gasket positioned within (and under) the cover.

FIG. 2A is an exploded view of one embodiment of the cover assembly (11) comprising a pressure cover or pressure lid. In the illustrated embodiment, the pressure lid comprises a port (5) that allows pneumatic (e.g. vacuum) control of (optional) chip stretching to be communicated through the lid and a plurality of ports (36) (e.g. through-hole ports) (e.g.

through-hole ports) associated with filters (38) (e.g. a 0.2 µm filter) and corresponding holes (39) in a gasket (37) positioned underneath the cover. In one embodiment, the cover or lid is made of polycarbonate. The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed. FIG. 2B shows the same embodiment of the cover assembly illustrated in FIG. 2A with the filters and gasket positioned within (and under) the cover.

Figure 3A:
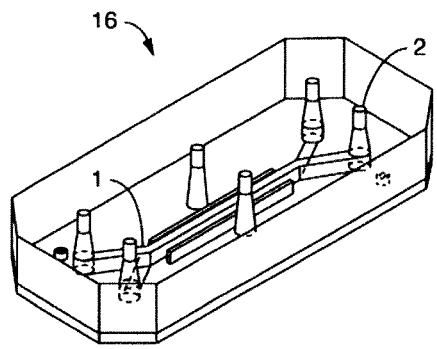
FIG. 3A shows one embodiment of the microfluidic device or chip (16), showing two channels (1), each with an inlet (2) and outlet port, as well as (optional) vacuum ports.
Figure 3B:
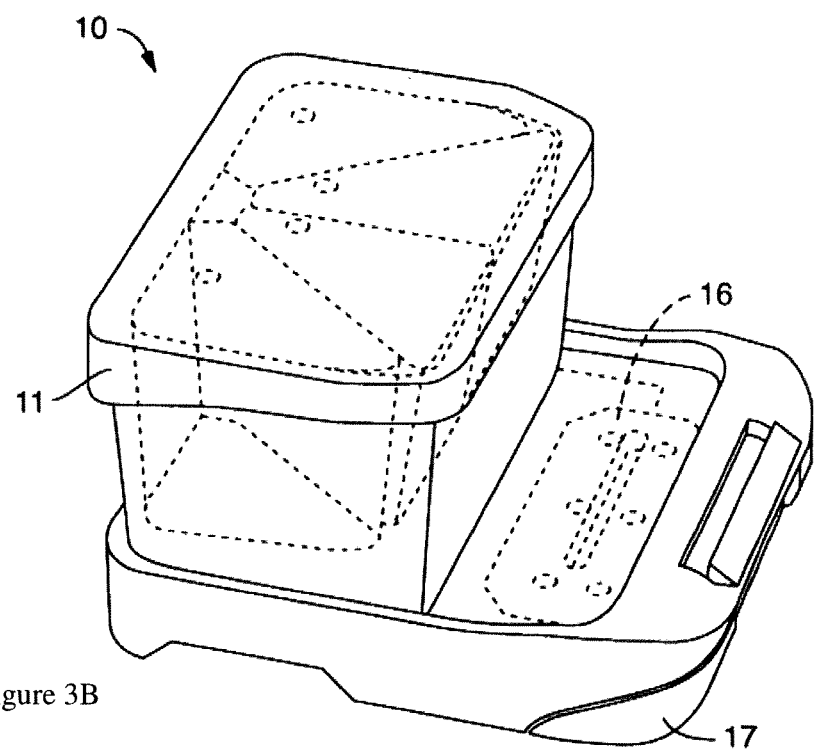
FIG. 3B is a topside schematic of an alternative embodiment of the perfusion disposable or "pod" (10) featuring the transparent (or translucent) cover (11) over the reservoirs, with the chip (16) inserted. The chip (16) can be seeded with cells and then placed in a carrier (17) for insertion into the perfusion disposable.

FIG. 3A shows one embodiment of the microfluidic device or chip (16), showing two channels (1), each with an inlet (2) and outlet port, as well as (optional) vacuum ports. FIG. 3B is a topside schematic of an alternative embodiment of the perfusion disposable or "pod" (10) featuring the transparent (or translucent) cover (11) over the reservoirs, with the chip (16) inserted. The chip (16) can be seeded with cells and then placed in a carrier (17) for insertion into the perfusion disposable.

Figure 4A:
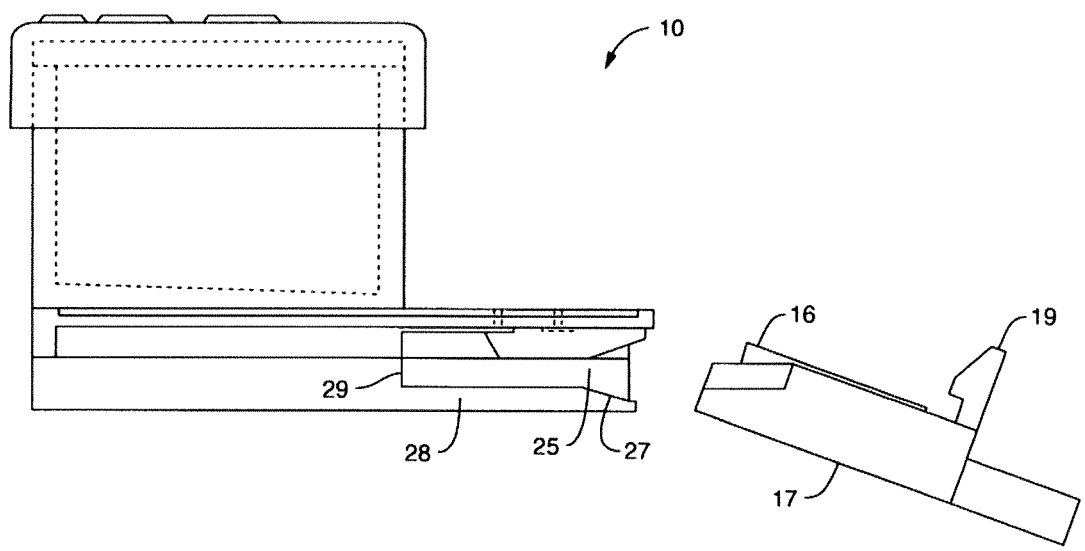
FIG. 4A shows a side view of one embodiment of a chip carrier (17) (with the chip inside) approaching (but not yet engaging) a side track (25) of a skirt of one embodiment of the perfusion manifold assembly (10), the carrier aligned at an angle matching an angled front end portion of the side track, angled slide (27) which provides a larger opening for easier initial positioning, followed by a linear or essentially linear portion (28), the carrier comprising a retention mechanism (19) configured as a upwardly protecting clip. Without being bound by theory, a suitably large angle permits chip engagement without smearing or premature engagement of liquid droplets present on the chip and/or the perfusion manifold assembly during the insertion and alignment processes.
Figure 4B:
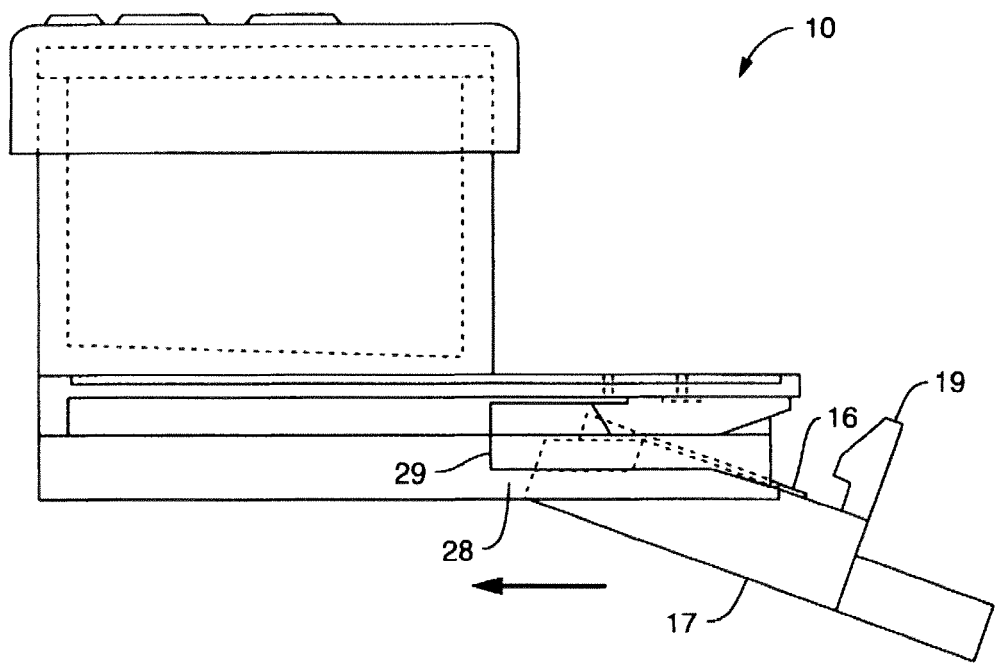
FIG. 4B shows a side view of one embodiment of a chip carrier (with the chip (16) inside) engaging a sidetrack of a skirt of one embodiment of (but not yet linked to) the perfusion manifold assembly.
Figure 4C:
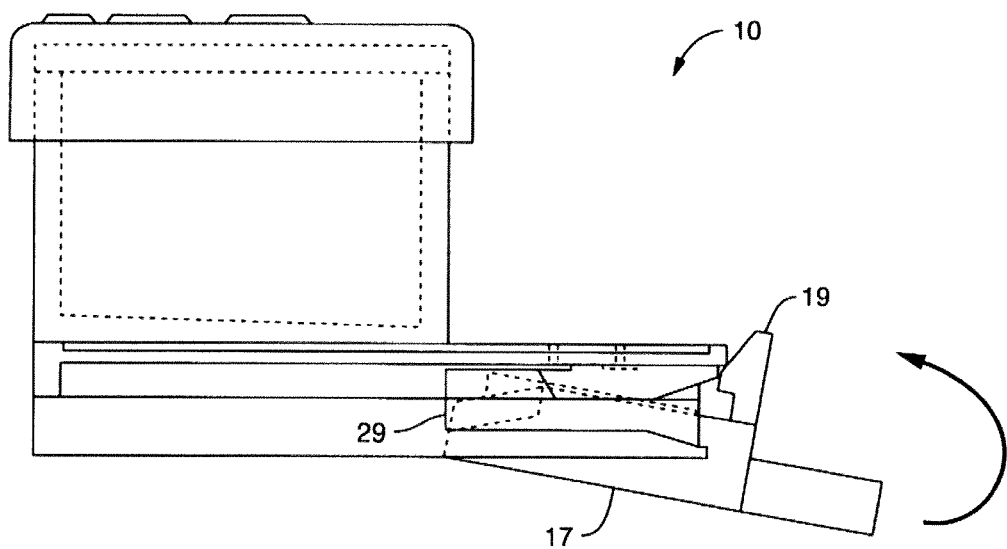
FIG. 4C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).
Figure 4D:
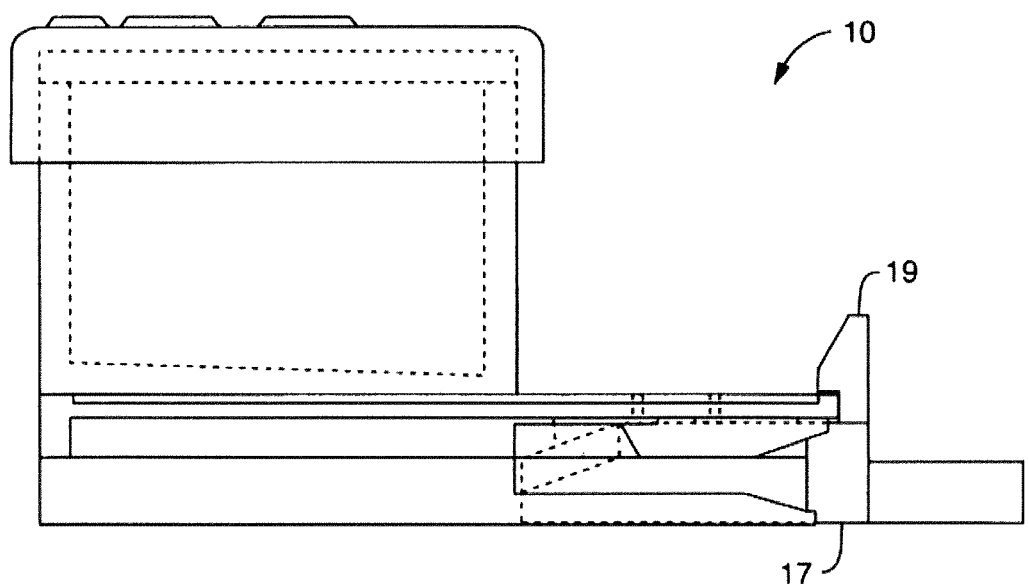
FIG. 4D shows a side view of one embodiment of a chip carrier (with the chip inside) detachably linked to the perfusion manifold assembly, where the retention mechanism is engaged to prevent movement.

FIG. 4A shows a side view of one embodiment of a chip carrier (17) (with the chip inside) approaching (but not yet engaging) a side track (25) of a skirt of one embodiment of the perfusion manifold assembly (10), the carrier aligned at an angle matching an angled front end portion of the side track, angled slide (27) which provides a larger opening for easier initial positioning, followed by a linear or essentially linear portion (28), the carrier comprising a retention mechanism (19) configured as an upwardly protecting clip. Without being bound by theory, a suitably large angle permits chip engagement without smearing or premature engagement of liquid droplets present on the chip and/or the perfusion manifold assembly during the insertion and alignment processes. FIG. 4B shows a side view of one embodiment of a chip carrier (with the chip (16) inside) engaging a side track of a skirt of one embodiment of (but not yet linked to) the perfusion manifold assembly. FIG. 4C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement). FIG. 4D shows a side view of one embodiment of a chip carrier (with the chip inside) detachably linked to the perfusion manifold assembly, where the retention mechanism is engaged to prevent movement.

Figure 5:
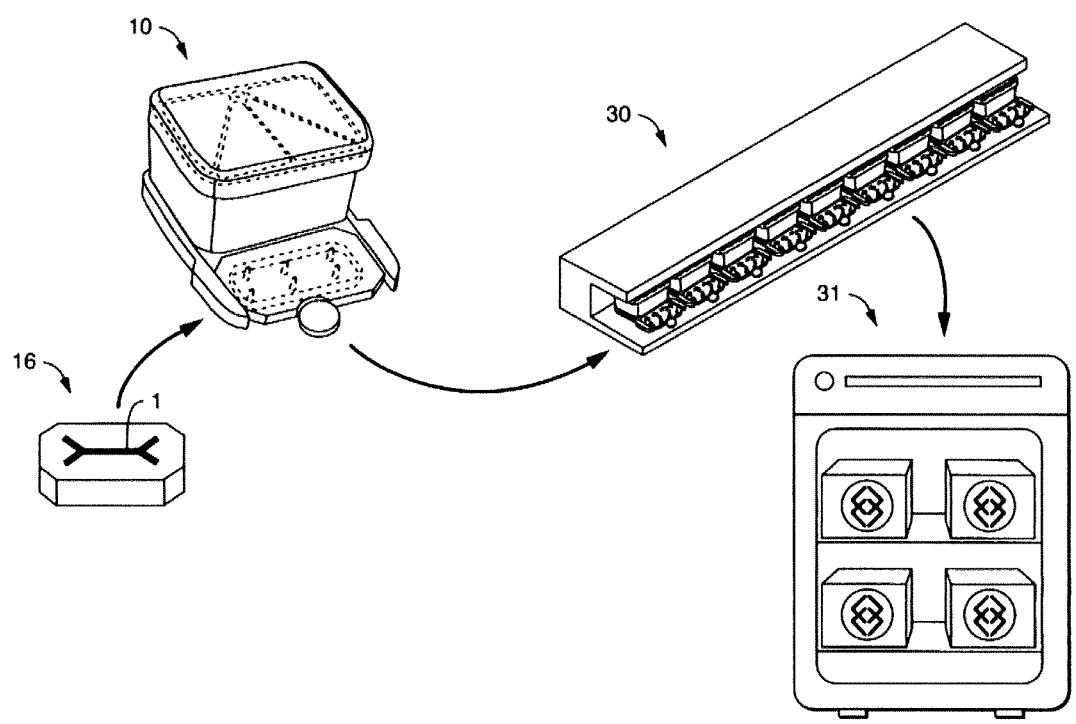
FIG. 5 is a schematic of one embodiment of a work flow (with arrows showing each progressive step), where the chip (16) is linked (e.g. snapped in) to a disposable perfusion manifold assembly ("perfusion disposable") (10), which in turn is positioned with other assemblies on a culture module (30), which is placed in an incubator (31).

FIG. 5 is a schematic of one embodiment of a work flow (with arrows showing each progressive step), where the chip (16) is linked (e.g. snapped in) to a disposable perfusion manifold assembly ("perfusion disposable") (10), which in turn is positioned with other assemblies on a culture module (30), which is placed in an incubator (31).

Figure 6:
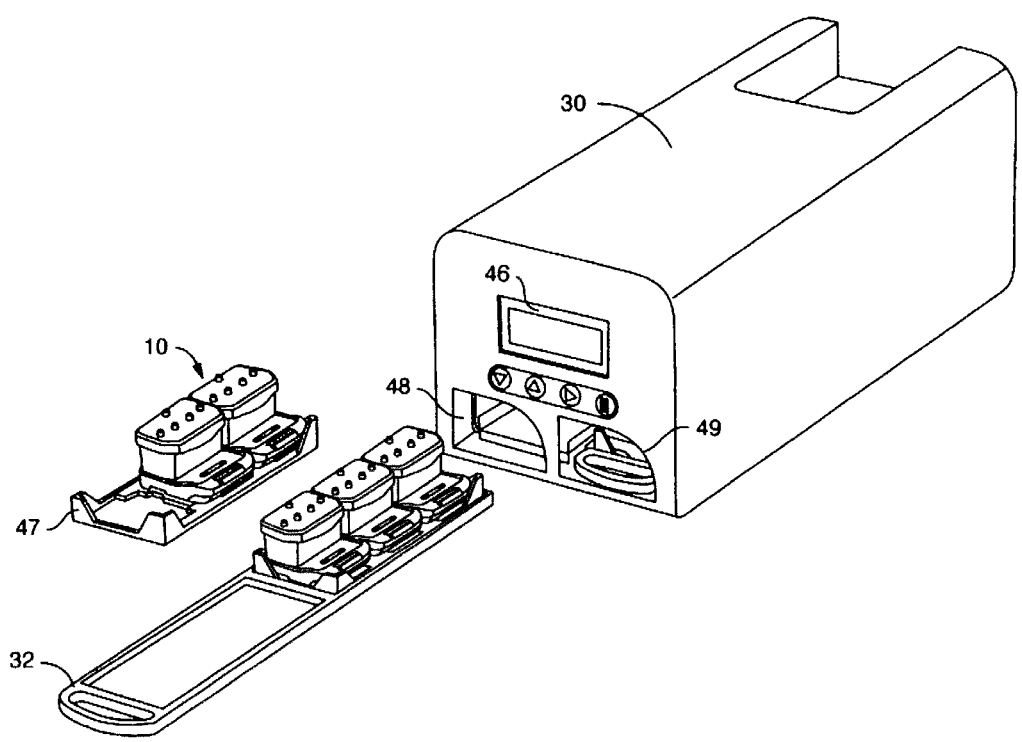
FIG. 6 is a schematic of another embodiment of the culture module (30) showing the tray (or rack) (32) and sub-tray (or nest) for transporting and inserting the perfusion disposables (10) into the culture module, which has two openings (48, 49) in the housing to receive the trays, and a user interface (46) to control the process of engaging the perfusion disposables and applying pressure. A typical incubator (not shown) can hold up to six modules (30).

FIG. 6 is a schematic of another embodiment of the culture module (30) showing the tray (or rack) (32) and sub-tray or nest (47) for transporting and inserting the perfusion disposables (10) into the culture module (30), which has two openings (48, 49) in the housing to receive the trays, and a user interface (46) to control the process of engaging the perfusion disposables and applying pressure. A typical incubator (not shown) can hold up to six modules (30).

Figure 7A:
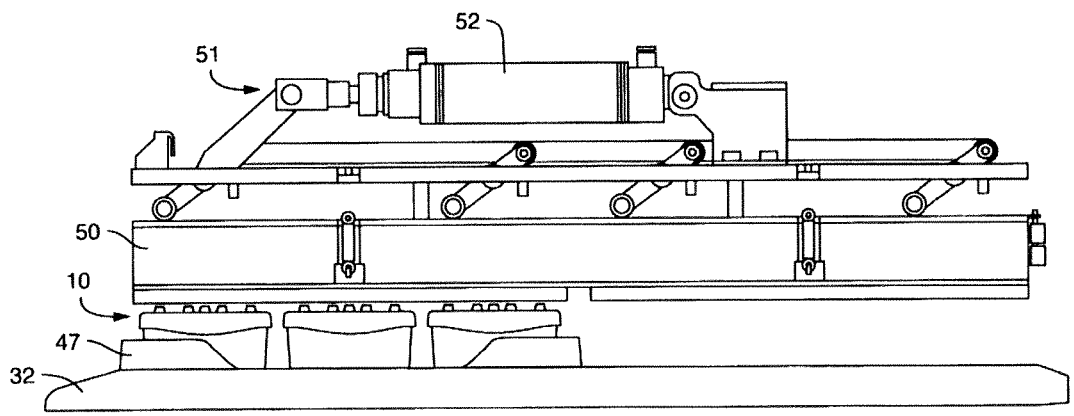
FIG. 7A is a schematic of the interior of one embodiment of the module (i.e. the housing has been removed), showing the pressure manifold (50) is in an open position, positioning of the tray (or rack) (32), sub-tray (or nest) (47), perfusion disposables (PDs) (10) under a pressure manifold (50) (but not engaging it, so the clearance is sufficient to remove them), with the actuation assembly (51) (including the pneumatic cylinder) (52) above. Three microfluidic devices or perfusion disposables are shown to illustrate, although more (e.g. 6, 9 or 12) are typically used at once.

FIG. 7A is a schematic of the interior of one embodiment of the module (i.e. the housing has been removed), showing the pressure manifold (50) is in an open position, positioning of the tray (or rack) (32), sub-tray (or nest) (47), perfusion disposables (PDs) (10) under a pressure manifold (50) (but not engaging it, so the clearance is sufficient to remove them), with the actuation assembly (51) (including the pneumatic cylinder) (52) above. Three microfluidic devices or perfusion disposables are shown to illustrate, although more (e.g. 6, 9 or 12) are typically used at once.

Figure 7B:
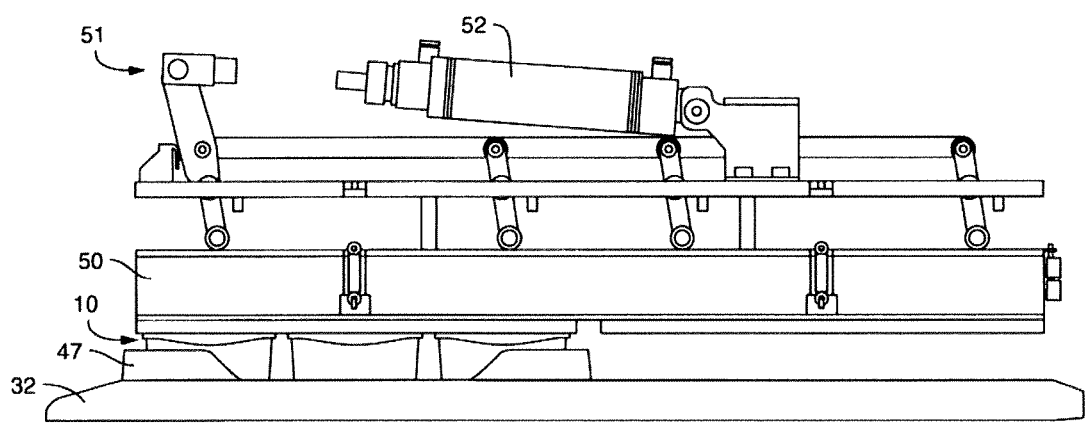
FIG. 7B is a schematic of the interior of one embodiment of the module (in an open position, i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages all of the perfusion disposables (10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes. In a preferred embodiment, integrated alignment features in the pressure manifold (50) provide guidance for each perfusion disposable (10). Again, three microfluidic devices or perfusion disposables are shown to illustrate, although more (e.g. 6, 9 or 12) are typically used at once.

FIG. 7B is a schematic of the interior of one embodiment of the module (i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages all of the perfusion disposables (10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes. In a preferred embodiment, integrated alignment features in the pressure manifold (50) provide guidance for each perfusion disposable (10). Again, three microfluidic devices or perfusion disposables are shown to illustrate, although more (e.g. 6, 9 or 12) are typically used at once.

Figure 8:
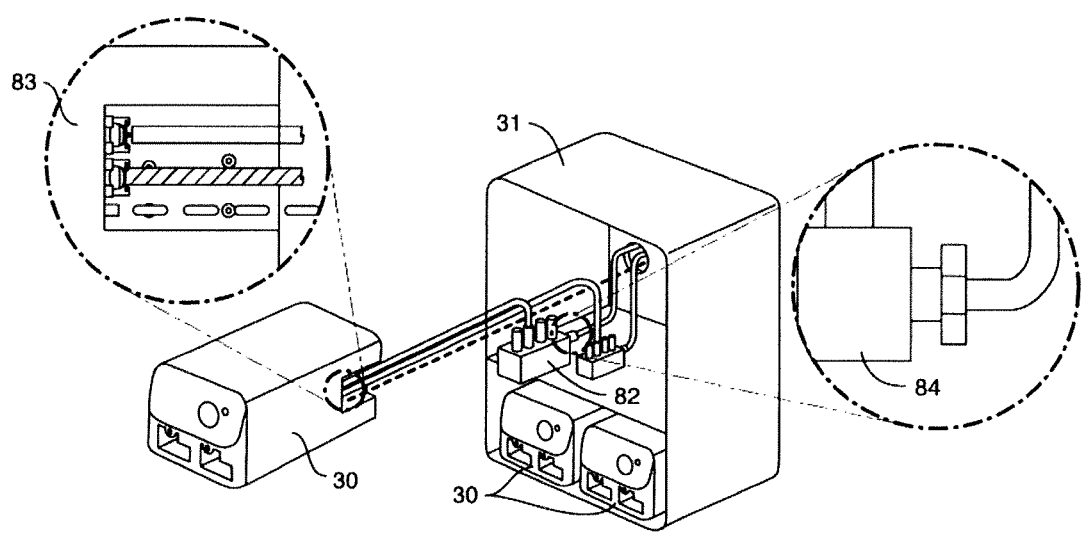
FIG. 8 is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections).

FIG. 8 is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections).

III. Chip Activation.

A. Chip Activation Compounds.

In one embodiment, bifunctional crosslinkers are used to attach one or more extracellular matrix (ECM) proteins. A variety of such crosslinkers are available commercially, including (but not limited to) the following compounds:

ANB-NOS (N-5-azido-2-nitrobenzoyloxysuccinimide)

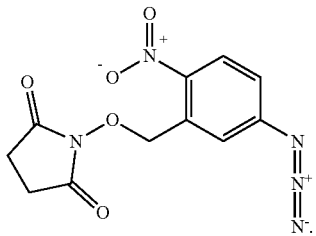

Sulfo-SAND (sulfosuccinimidyl 2-[m-azido-o-nitrobenzamido]ethyl-a, 3'-dithiopropionate):

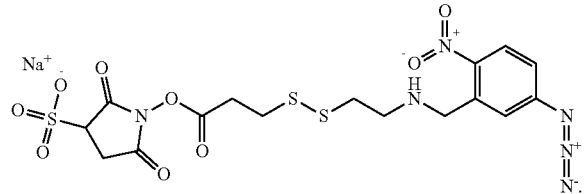

SANPAH (N-succinimidyl-6-[4'-azido-2'-nitrophenylamino]hexanoate)

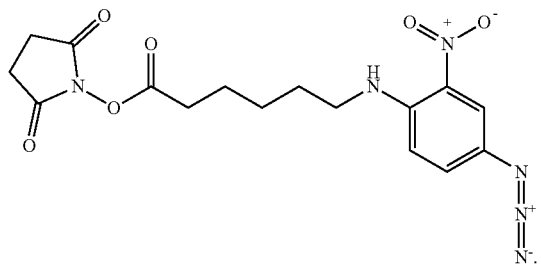

Sulfo-SANPAH (sulfosuccinimidyl-6-[4'-azido-2'-nitrophenylamino]hexanoate)

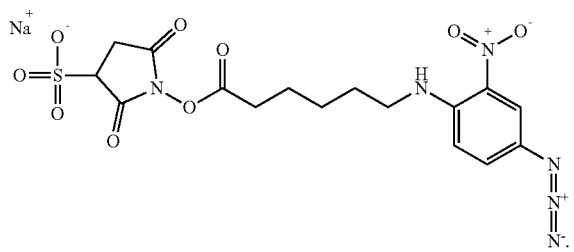

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups ($-NH_2$) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary Methods of Chip Activation.
Prepare and Sanitize Hood Working Space
1. S-1 Chip Handling—Use aseptic technique, hold Chip using Carrier
 b. Use 70% ethanol spray and wipe the exterior of Chip package prior to bringing into hood
 c. Open package inside hood
 d. Remove Chip and place in sterile petri dish (6 Chips/Dish)
 e. Label Chips and Dish with respective condition and Lot #
2. Surface Activation with Chip Activation Compound (light and time sensitive)
 a. Turn off light in biosafety hood
 b. Allow vial of Chip Activation Compound powder to fully equilibrate to ambient temperature (to prevent condensation inside the storage container, as reagent is moisture sensitive)
 c. Reconstitute the Chip Activation Compound powder with ER-2 solution
  i. Add 10 ml Buffer, such as HEPES, into a 15 ml conical covered with foil
  ii. Take 1 ml Buffer from above conical and add to chip Activation Compound (5 mg) bottle, pipette up and down to mix thoroughly and transfer to same conical
  iii. Repeat 3-5 times until chip Activation Compound is fully mixed
  iv. NOTE: Chip Activation Compound is single use only, discard immediately after finishing Chip activation, solution cannot be reused
 d. Wash channels
  i. Inject 200 ul of 70% ethanol into each channel and aspirate to remove all fluid from both channels
  ii. Inject 200 ul of Cell Culture Grade Water into each channel and aspirate to remove all fluid from both channels
  iii. Inject 200 ul of Buffer into each channel and aspirate to remove fluid from both channels
 e. Inject Chip Activation Compound Solution (in buffer) in both channels
  i. Use a P200 and pipette 200 ul to inject Chip Activation Compound/Buffer into each channel of each chip (200 ul should fill about 3 Chips (Both Channels))
  ii. Inspect channels by eye to be sure no bubbles are present. If bubbles are present, flush channel with Chip Activation Compound/Buffer until bubbles have been removed
 f. UV light activation of Chip Activation Compound Place Chips into UV light box
  i. UV light treat Chips for 20 min
   While the Chips are being treated, prepare ECM Solution.
  ii. After UV treatment, gently aspirate Chip Activation Compound/Buffer from channels via same ports until channels are free of solution
  iii. Carefully wash with 200 ul of Buffer solution through both channels and aspirate to remove all fluid from both channels
  iv. Carefully wash with 200 ul of sterile DPBS through both channels
  v. Carefully aspirate PBS from channels and move on to: ECM-to-Chip
VI. ECM-to-Chip
1. Calculate total volume of ECM solution needed to coat Chips
 a. Volume required per Chip=50 ul/Channel
 b. ECM diluent: PBS, prepared on ice
  i. Stock Concentrations for ECM coating:
   1. Collagen IV: 1 mg/ml (200 ul aliquots in −20 C)
   2. Fibronectin: 1 mg/ml (50 ul aliquots in 4 C)
   3. Matrigel: 10 mg/ml (200 ul aliquots in −20 C)
  ii. Working Concentrations for ECM coating:
   1. Collagen IV: 200 ug/ml
   2. Fibronectin: 30 ug/ml iii. Top Channel Coating: 50 ul Collagen IV (200 ug/ml) and Matrigel (100 ug/ml)
iv. Bottom Channel Coating: 50 ul Collagen IV (200 ug/ml) and Fibronectin (30 ug/ml)
2. Load Channels with ECM solution
   a. Place Chips in hood
   b. Pipette 50 ul of Top Channel Coating into Top Channel—keep the pipette plunger depressed until you see fluid come out opposite end of the channel, then take another pipette tip (200 ul tip) to close the outlet port. Once closed off, carefully remove the pipette tip, leaving the tip in the inlet port.
   c. Aspirate excess fluid from the surface of Chip (avoid direct contact with the port)
   d. Repeat 2b-2c, but with Bottom Channel Coating into Bottom Channel
3. Incubate at 37 C for a minimum of 2 hours up to overnight Exemplary Matrigel Coating Thaw Matrigel on ice and keep chilled to prevent solidification.
   a. Prepare Matrigel
      i. Matrigel Stock Concentration: 10 mg/ml
      ii. Matrigel Final Concentration: 250 ug/ml
      iii. Determine the volume of Matrigel needed to coat 50 ul of each Top Channel and resuspend accordingly in cell culture media
   b. Transfer the NUFFs-seeded Chips into the hood
   c. Wash both channels of each chip twice with 200 ul media
   a. Before inserting the tips, add a drop of media to prevent formation of bubbles
   b. Leave 50 ul media in bottom channel (Tips inserted)
   d. Add 50 ul 250 ug/ml matrigel to top channel (Tips inserted)
   e. Incubate at 37 C overnight V. Cells-to-Chip Chip Preparation
   a. Transfer the ECM coated Chips into the hood
   b. Gently wash Chips after ECM coating
      i. Pipette 200 ul of DPBS into bottom channel inlet port—keep the pipette plunger depressed until you see fluid come out opposite end of channel and aspirate outflow
      ii. Repeat the same procedure to wash top channel
      iii. Pipette 200 ul of DPBS into top channel inlet port—keep the pipette plunger depressed until you see fluid come out opposite end of the channel, then take another pipette tip (200 ul) to close the outlet port. Once closed off, carefully remove the pipette tip, leaving the tip in the inlet port
      iv. Repeat the same with the bottom channel
      v. Place back in incubator until cells are ready.

Experimental

EXAMPLES

The following examples illustrate some embodiments and Embodiments described herein. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1—Exemplary Methods and Readouts (Assays)

Complex Media Composition:
Conditioned media produced by adding one or more agents: L-Wnt3a (CRL-2647), Cultrex® R-spondin1 (RSPO1) and Noggin cells. In some embodiments, conditioned media from L-cells growing in culture is used. Recombinant growth factors may be used, including but not limited to: supplements and small molecules including: EGF, N-acetyl cysteine, Gastrin, etc.

Percoll/Medium.
In some embodiments, a Percoll liquid, e.g. media formulation of 50% is used in combination with assist immune recruitment assays On Chips, including but not limited to immune-cell types: PBMCs, white blood cells, lymphocytes, macrophages, neutrophils, B cells, T cells, killer cells, etc. Observe cells to assess morphology and viability: Capture representative images along the length of Chip, including but not limited to inlet junctions, outlet junctions, and center of Chip. Collect samples from the back side of the Reservoirs into pre-labeled tubes or 96 well plate Bright-Field Imaging:
As one example of a readout for comparative purposes, for use in drug testing, etc., Image Chips at Days 0, 2, 4, 6, 8, etc.

Example 2—Exemplary Seeding of Enteroids On-Chip

In one embodiment, microfluidic chips are seeded with Enteroids, obtained from biopsied tissues of different intestinal regions through collaboration with hospitals (Adult tissue), See, Table 1, and HIMEC, human small intestinal endothelial cells (commercially obtained from Cell Biologics).
1. Cell Preparation
   d. For the Intestine-Chip (Enteroids), Human Small Intestinal Microvascular Endothelial Cells (HIMECs) are seeded into the bottom channel and allowed to attach prior to seeding the primary enteroids
   e. Prepare cell suspension and count cell number
   f. Seeding density is specific to the cell type
      iii. HIMECs: 9 million cells/ml
After counting cells, adjust cell suspension to the appropriate density for seeding.
2. Bottom Channel Seeding (HIMECs)
Use ONE Chip First—Confirm Seeding Density Before Seeding Other Chips
   i. Prior to seeding, wash each channel with 200 ul of cell culture medium
   j. Pipette 30 cell culture media and insert in bottom inlet (Tips inserted)
   k. Agitate cell suspension gently before seeding each Chip to ensure a homogenous cell suspension
   l. Pipette 30 ul of the cell suspension and seed into the top channel inlet (Tips inserted)
   m. Place Chip on a Petri dish and transfer to the microscope to check the density
   n. After confirming the cell density, seed cells in the rest of the Chips
   o. Incubate inverted at 37 C for 30-45 min
   p. After confirming good cell attachment wash bottom channel with 200 ul of cell culture medium.

3. Enteroids Preparation
  b. Recover enteroids
    i. Transfer 24-well plate containing enteroids into hood
    ii. Carefully aspirate media from each well without disturbing enteroids
    iii. Pipette 500 ul Cell Recovery Solution (CRS) to each well
    iv. Use a mini cell scrapper and mix the matrigel with the CRS to collect the enteroids
    v. Use a 10 ml pipette and collect cells from 3 wells and transfer to a labeled 15 ml conical (Tube 1)—these cells will be used as your Cell at Seeding Control
    vi. Use the same pipette and collect cells from appropriate number of wells (we suggest use of two wells of enteroids for seeding one chip) and transfer to a different 15 ml conical (Tube 2)
    vii. Incubate on ice for 45 min with frequent tube inversion every 10 minutes to dissolve matrigel
  Chill the Centrifuge to 4 C Before Beginning
    viii. Centrifuge at 300 G, 5 min, 4 C
    ix. Aspirate supernatant from 15 ml conical without disturbing pellet
    x. Tap the conical to break the pellet and add the following to each tube:
      1. Tube 1: 300 ul Lysis Buffer and transfer to 1.5 ml Eppendorf tube (Store −80 C)
      2. Tube 2: 2 ml Digestion Solution and transfer to water bath for 3-6 minutes with frequent tapping every 1 minute to break up enteroids
    xi. After digestion, add 8 ml Advanced DMEM/F12 to Tube 2, invert, and centrifuge at same settings above
    xii. Aspirate supernatant and resuspend enteroids in Expansion Media containing Rock Inhibitor (1:1000) and CHIR (1:2000) (EM+): The volume is determined by 35 ul of media used per one chip×n, where n is the number of chips
4. Exemplary Chip, e.g. Top Channel Seeding (Enteroids)
  One Chip was Used First to Confirm Seeding Density Before Seeding Other Chips.
    h. Prior to seeding, wash each channel twice with 100 ul EM+
    i. Pipette 35 ul of EGM2-MV and insert in bottom inlet (Tips inserted)
    j. Agitate Enteroids suspension gently before seeding each Chip to ensure a homogenous cell suspension
    k. Pipette 35 ul of the Enteroids suspension and seed into the top channel inlet (Tips inserted)
    l. Place Chip on a Petri dish and transfer to the microscope to check the density
    m. After confirming the cell density, seed Enteroids in the rest of the Chips
    n. Incubate at 37 C overnight
Expansion Medium (with ROCK and CHIR) in both input Reservoirs of each Pod for 3 days, then only Expansion Medium for remaining days.
Recommend to change medium every 24-48 hours, depending on cell type once flow is started.
5. Enteroid Expansion after Seeding into Chip.
  Formulation for Expansion (EM; EM+) Table 2, and Differentiation media (DM) Table 3: Abbreviations: CM—Conditioned media, for use with enteroids, including colonoids.
6. Enteroids Differentiation.
  a. At day 4, aspirate media from both input Reservoirs and add 3 ml Differentiation Media.
  b. At day 6, replenish Differentiation Media in both input Reservoirs.
    Formulation for Expansion (EM; EM+) and Differentiation media (DM):
Abbreviations: CM—conditioned media.
  Differentiation Medium (100 ml total), Table 3: In order to differentiate cells the following media components are removed: Wnt3A, SB2001190 and the concentration of R-spondin and Noggin CM (conditioned media) needs to be reduced to 10% and 5%, respectively. Notch inhibitor (DAPT) can be added to further enhance differentiation.
  FIG. 13A-B shows an exemplary schematic representation of a timeline for seeding and growing cells (e.g. enteroids) in an intestine on-chip microfluidic device. FIG. 13A shows a morphology timeline after seeding cells. FIG. 13B shows an exemplary method starting by chip activation and ECM coating a day −1 (the day before day 0), cell seeding the chip with HMECs and enteroids in expansion media for 4 days. Day 3 starting flow at 60 ul per hour. Day 4 switching media to differentiation media (e.g. removing Wnt3A) for 4 days. Lower photograph of a chip orientates the Bright-field (Imaging) showing images of cells on chip at Day 0 (seeding) upper channel left and lower channel right. Chips are then imaged at Days 2, 4, 6, and 8 for monitoring cell growth and morphology.
  FIG. 14 shows bright-field micrographs over time, from the upper left panel at Day 0 to the lower right panel at Day 8, demonstrating development of a monolayer of cells in one embodiment of a microfluidic device. Initiation of flow is on Day 3 and observations of differentiation are on Day 4.
  FIG. 15A-D shows exemplary fluorescent micrographs of an intestinal cell layer in a microfluidic device comprising at least 4 types of intestinal cells present by Day 8 after 4 days in differentiation media. FIG. 15A shows exemplary absorptive enterocytes identified by villin (VIL). FIG. 15B shows exemplary enteroendocrine cells identified by chromogranin A (CHGA). FIG. 15C shows exemplary goblet cells identified by mucin 2 (MUC2) and FIG. 15D shows exemplary Paneth cells identified by lysozyme (LYZ). Stained DNA (Nuclei) and E-cadherin are shown.
  FIG. 16A-D shows Tissue Maturation by graphical comparison of development over time, left to right bars within each cell grouping, also across multiple different donors comparing development of cell types from 3 human donors. Enteroids derived from donor Biopsies were seeded onto chips showed physiologically relevant level of maturation in Intestine-Chip. Graphs represent mRNA expression levels of intestinal cell-type specific markers assessed at different days of Intestine-Chip growth (Day 4 and Day 8) in respect to the cells used for the Chip seeding. Commercially available RNA isolated from native human tissue (supplied by Amsbio) was used as a reference for In vivo Small Intestine. FIG. 16A shows exemplary Absorptive Enterocytes (ALPI). FIG. 16B shows exemplary Enteroendocrine cells identified by chromogranin A (CHGA). FIG. 16C shows exemplary Goblet cells identified by mucin 2 (MUC2) and FIG. 16D shows exemplary Paneth cells identified by lysozyme (LYZ). Absorptive Enteroendocrine cells do not develop as quickly as other intestinal cell types growing on-chip.
  FIG. 17 shows the Formation of Intestinal Barrier Function in a microfluidic device confirmed Across Different Donors showing a graph of permeability changes over time, day 3-day 8. Intestine-Chips derived from biopsy of 3 independent donors achieved comparable levels of intestinal barrier function to Lucifer Yellow (~450 Da). Thus, an intact barrier is formed by day 6 of culture. Step A—at Day 3, include a dye molecule, e.g. Dextran (Cascade Blue) or Lucifer Yellow (~450 Da) in media of top input Reservoirs. Step B—At days 4, 5, 6, 7, and 8, collect a 250 µl sample from each output reservoirs of each chip for barrier function of an intestine on-chip.

Example 3—Exemplary Methods of Immune Cell Recruitment

The following Sections (i.e. steps) were used for providing immune cell recruitment assays on-chip using intestine on-chip. In some embodiments, inflammation is induced in a microfluidic intestine on-chip by inducing inflammation with cytokines.

Section 1: Inflammatory Stimulation of Intestine-Chip: Cytokine Induced Inflammation.

Seed Intestine-Chip following general protocol; At day 5, divide all of the chips into at least two subgroups: 1) Controls—which will not be treated with the inflammatory stimuli, and 2) Inflamed by treatment for 4-24 hours with an inflammatory stimuli such as TNFalpha, IL-1beta or LPS. Then, aspirate the media in both output Reservoirs and input Reservoir of the Bottom Channel; Induce vascular inflammation in the Intestine-chip. In one embodiment, vascular inflammation is triggered by perfusing fresh EGM2-MV media, with an inflammatory stimuli added, through the Bottom Channel. Perfuse EGM2-MV media+/−inflammatory stimuli through the Bottom Channel of Intestine-Chip at 60 ul/h for 4-24 hours. In one preferred embodiment, stimulation is 24 hours. For the control, media without an inflammatory stimuli is used instead. In one embodiment to induce vascular inflammation in the Intestine-Chip a mix of cytokines at the clinically relevant concentrations (Cytomix: 50 pg/ml, IL-1B, 215 pg/ml, TNFalpha and 200 pg/ml IL-6) similar to the levels observed in the blood of chronically diseased patients is used. The choice of the inflammatory stimulus, composition of Cytomix and their concentrations can be adjusted dependently on the needs of the specific application.

FIG. 18A-B shows exemplary florescent microscope images and graphs demonstrating induction of adhesion molecule expression in intestinal endothelial cells on-chip 24 hours after induction of inflammation using clinically relevant levels of cytokines. FIG. 18A shows images of induced ICAM-1 and nuclei stained channels (left) and under higher magnification (right) for control (upper) and inflamed (lower) channels. FIG. 18B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1β 50 U/ml (approximately 50 pg/ml), IL-6 20 U/ml (approximately 200 pg/ml).

FIG. 18C-D shows exemplary increased PBMC recruitment after cytokines-induce inflammation of the endothelium of an inflamed intestine-Chip. FIG. 18C shows a larger arrow where PBMCs may be added to flow into the main vascular channel. Alternatively, small arrows point to ports where PBMCs may be added to the center area of the channel. Images on the right show white dots representing PBMCs attached to the endothelial layer for no PBMCs added to a chip that was not treated by cytokines, center control with PBMCs but no cytokine treatment and right panel where an inflamed endothelium has numerous attached PBMCs. Attached PBMCs are shown numerically as a total number/chip in an exemplary graph in FIG. 18D.

In other embodiments, Intestine On-Chip responds to low levels of cytokines present in the blood of chronically diseased patients by increased expression of adhesion molecules, See Table 4.

Section 2: Preparation of Immune Cells:

Thaw the frozen vial containing PBMC's ($3\times10^6$ cells for 24 chip experiment) in the water bath. Resuspend the cells in 10 ml of media, spin down at 400×g/5 min/RT Remove the supernatant and resuspend the cells in 5 uM Cell Tracker Red CMPTX (Cat #C34552) staining solution prepared by diluting 10 ul of 5 mM stock solution in 10 ml of RPMI media (with 5% FBS). Incubate the cells at 37 C (in a water bath) for 15-20 min protected from light. Add 40 ml of RPMI media to absorb any unload dye. Incubate for additional 5 min at 37 C (in a water bath) protected from light. Spin down the cells at 400×g/5 min/RT.

In some embodiments, an inflammatory intestine on-chip prepared in Section 1 and Section 2, combined with methods in Section 4, is used for modeling inflammation. However, in part due to challenges with controlling shear forces and rates, as described herein, in addition to the discovery that a 50% Percoll liquid lowered shear in a manner allowing maximal attachment of white blood cells, as opposed to 15% and 75% Percoll liquid solutions. Therefore, a 50% Percoll solution Section (step) was added Section 3: Addition of the Percoll Solution to Immune Cells (PBMC's):

Prepare 50% Percoll solution in RPMI media by mixing stock Percoll solution and RPMI media 1:1 (vol/vol) e.g. 10 ml of Percoll with 10 ml of RPMI media; in some embodiment, degass solutions using a steri-flip. Add 50% Percoll/RPMI solution to the cells to achieve final cell concentration of $2\times10^6$ cells/mi.

Section 4: Recruitment Assay:

Add PBMC's as a cell suspension in 50% Percoll/RPMI into the Input Reservoir of the Bottom Channel, while in the Input Reservoir of the Top Channel add appropriate epithelial cell media (see Protocol for Small Intestine-Chip). Perfuse the immune cell solution through the Bottom Channel at the Shear Stress of ~2dyn/cm2 (flow rate ~1200 ul/h) for 15 min. Aspirate media in both output Reservoirs. Add fresh RPMI media of Input Reservoirs of the Bottom Channel. Perfuse the Bottom Channel with RPMI media for additional 15 min at high flow rate of 1200 ul/h to remove cells that didn't adhere to the endothelial cell surface.

Section 5: Assessment of the Immune Cells Recruitment:

Image the cells that attached to endothelial cells using Immunofluorescent or Confocal Microscope (endothelial cells can be co-stained using Wheat Germ Agglutinin (WGA), if assessment needs to be performed in the life cells or VE-cadherin or other staining specific for endothelial cells, if post-fixation assessment is preferred) Immune Cells can be co-stained for CD14 or CD3 markers in order to differentiate them into different subpopulations of monocytes and lymphocytes, respectively Cells on-chips can be lysed in order to assess endothelial or immune cells gene expression Effluents can be collected from the Top and Bottom Output Reservoirs in order to assess cytokines and chemokines released by the cells.

After assessment of immune cell recruitment chips can be terminated by the fixation with 4% PFA or can be maintained in culture under the normal flow conditions of 60 ul/h for their further assessment, including studies of immune cell translocation into the epithelial channel, contribution of immune cells to Intestine-Chip response to luminally applied stimuli etc.

FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing labeled PBMC (peripheral mononuclear blood cells) (each dot or white dot represents one cell) attached to inflamed endothelium, under liquid flow where the liquid contained FIG. 19A 0% Percoll; FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell-endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

FIG. 20A-C shows embodiments of an intestine on chip emulating Immune Cell Recruitment on-Chip through providing physiological level of shear and fluid viscosity to emulate immune cell recruitment at epithelial-endothelial tissue interfaces. Embodiments of intestine on chip showing a florescent micrograph of stained cells FIG. 20A under Non physiological Shear in Vascular Channel and Non physiological Fluid Viscosity. FIG. 20B under Physiological Shear in Vascular Channel and Physiological Fluid Viscosity. PBMCs and inflamed HIMEC. FIG. 20C shows flow directions (arrows) on a chip schematic and the acquisition area and level where images were taken. Scale bar=100 micrometers. Physiological levels of shear and fluid viscosity emulate immune cell recruitment at the epithelial-endothelial (tissue-tissue) interface.

FIG. 20D-E shows one embodiment of an intestine on chip where flowing media without the addition of Percoll does not induce PBMC attachment at the same level of imaging as in FIG. 20C.

FIG. 21A-B shows that a change in the media viscosity does not affect the expression of adhesion molecules on endothelial cells (vascular compartment) on-chip. FIG. 21A is a chart showing relative mRNA expression between standard media (left, grey bars), viscous media (50% Percoll) (blue, middle bars) and inflammatory inducing media containing Cytomix cytokines (right, bars), after 24 hours of treatment. FIG. 21B shows micrographs of cells (left) corresponding to lower power micrographs of the channels (right). Stained ICAM-1 and nuclei. Upper is a control intestine on-chip, middle is an inflamed intestine on-chip and lower is a chip treated with viscous media, 50% Percoll, intestine on-chip.

FIG. 21C-D shows schematic images of intestinal tissue where FIG. 21C shows representative tissues as candidates for white blood cell interactions after diapedesis through the endothelial layer of a blood vessel and FIG. 21D illustrating exemplary cell surface adhesion molecules associated with stages of white blood cell, e.g. lymphocyte, interactions with endothelium. Starting with tethering, rolling, then when inflammatory adhesion molecules are present to trigger activation of the white blood cell, rolling becomes arrest of movement along the endothelial cell(s) followed by diapedesis through the endothelial layer.

Example 4—Exemplary Colon On-Chip

The following is an exemplary method of providing one embodiment of a Colon on-chip comprising irradiated fibroblast cells.

1. Cell Preparation
    a. For the Intestine-on-Chip (Colonoids), irradiated Newborn Human Foreskin Fibroblast (NUFFs) were seeded into the top channel and allowed to attach prior to seeding the primary enteroids
    b. Prepare cell suspension and count cell number
    c. Seeding density is specific to the cell type
        iv. NUFFs: 3 million cells/ml
    g. After counting cells, adjust cell suspension to the appropriate density for seeding 2. Top Channel Seeding (NUFFs)

Use ONE chip first to confirm seeding density before seeding other Chips.
    a. Prior to seeding, wash each channel with 200 ul of cell culture medium
    b. Pipette 30 cell culture media and insert in bottom inlet (Tips inserted)
    c. Agitate cell suspension gently before seeding each Chip to ensure a homogenous cell suspension
    d. Pipette 30 ul of the cell suspension and seed into the top channel inlet (Tips inserted)
    e. Place Chip on a Petri dish and transfer to the microscope to check the density
    f. After confirming the cell density, seed cells in the rest of the Chips
    g. Incubate at 37 C for 3-5 h.

3. Top Channel Seeding (Colonoids)

Reminder: Use ONE chip first—confirm seeding density before seeding other Chips
    a. Prior to seeding, wash each channel twice with 100 ul EM+
    b. Pipette 35 EM+ and insert in bottom inlet (Tips inserted)
    c. Agitate Enteroids suspension gently before seeding each Chip to ensure a homogenous cell suspension
    d. Pipette 35 ul of the Enteroids suspension and seed into the top channel inlet (Tips inserted)
    e. Place Chip on a Petri dish and transfer to the microscope to check the density
    f. After confirming the cell density, seed Enteroids in the rest of the Chips
    g. Incubate at 37 C overnight.

Incubate Expansion Medium (with ROCK and CHIR) in both input Reservoirs of each Pod for 3 days, then Expansion Medium (without ROCK and CHIR) for remaining days.

Expansion Medium (Top Channel) may contain 100 ug/ml Dextran, Cascade Blue, 3000 MW, Anionic, Lysine Fixable (ThermoFisher Scientific Catalog Number D7132) for barrier evaluation.

Section 1. Colon-Chip (Colonoids) Experimental Timeline (FIG. 22B) and Data Collection:
1. Bright-Field Imaging (FIG. 22C):
   a. Follow Steps for seeding chips.
   b. Capture representative images along the length of chip (e.g. Inlet Junction, Outlet Junction, and Center of Chip) at the following exemplary time points: Day −1, 0, 1, 4, 6, 8, 10, 14.

FIG. 22A-C shows differentiation of Enteroendocrine Cells Achieved in Colon-Chips. FIG. 22A schematic representation of one embodiment of a Colon on-chip, irradiated. Fibroblasts (e.g. mouse fibroblasts, human fibroblasts) underneath epithelial cells seeded from colonoids-enteroids. FIG. 22B schematic representation of an Experimental timeline of Colon On-Chip while FIG. 22C shows bright field micrograph images of cells over times shown on the timeline.

FIG. 23A-C shows exemplary florescent microscope images, focused on three different planes showing Epithelial-Fibroblast Tissue Interfaces. FIG. 23A upper area of epithelial cells, FIG. 23B lower plane of focus closer to fibroblasts, FIG. 23C fibroblasts located at the lower plane of focus. Vimentin staining identifies fibroblast cells. E-cadherin and nuclei.

Section 2. Barrier Function (FIG. 24A-B):
   a. Collect 250 ul effluent samples from both output Reservoirs of each Chip for Barrier Function:
   b. Collect at time points: Day 2, 4, 6, 8, 10, 12, 14
   c. Include in the plate set up: Standard Curve, Apical Blank, and Basal Blank Prior to collecting effluent samples, aspirate to remove media from the Outlet Reservoirs, without touching the port, at the following exemplary time points: Day 3, 5, 7, 9, 11, 13.

FIG. 24A-B demonstrates exemplary Barrier Function (Permeability) of one embodiment of a colon on-chip epithelial cells growing on top of irradiated fibroblasts. FIG. 24A Barrier Function (Permeability) as % of 3 kDa Dextran leakage). FIG. 24B shows exemplary florescent microscope images of the epithelial cell layer. E-cadherin and nuclei, left. ZO-1 and nuclei, right. Upper images show z-stacked side views of the epithelial layer.

Section 3. Differentiation.
   a. At day 10, aspirate media from both input Reservoirs and add 3 ml of Differentiation Media (See Media Formulation Table 3).
   Differentiation Medium (Top Channel) may contain 100 ug/ml Dextran, Cascade Blue, 3000 MW, Anionic, Lysine Fixable (ThermoFisher Scientific Catalog Number D7132).
   b. At day 12, replenish Differentiation Media in both input Reservoirs.

Example 5—Producing Enteroendocrine Cell Subsets in One Embodiment of a Microfluidic Intestine (Colon) On-Chip The presence of Enteroendocrine Cells (EEC) and several subsets were confirmed by gene expression analysis and immunofluorescence staining for EEC specific markers in colon on-chip.

FIG. 25A-G demonstrates exemplary florescent microscope images demonstrating subtypes of Enteroendocrine cells. FIG. 25A shows exemplary Enteroendocrine cells identified by chromogranin A (CHGA). FIG. 25B shows exemplary L-cells identified by glucogon. FIG. 25B shows exemplary Enterochromaffin cells identified by 5-HT. Stained DNA (Nuclei) and E-cadherin are shown. FIG. 25D shows an exemplary confocal microscope immunostained image over view of epithelial morphology in co-culture with fibroblasts showing goblet cells. Stained E-cadherin, Muc2, and nuclei are shown. FIG. 25E shows an exemplary phase contrast microscope image merged with data from a florescent image of tissue as in FIG. 25D, where goblet cells stained with MUC2. Goblet cells are forming in between villi-like structures. FIG. 25F shows an exemplary phase contrast microscope image over the entire main channel showing homogenous 3D villi-like structure formation where epithelium in direct contact with fibroblasts. FIG. 25G shows an exemplary phase contrast microscope image over the entire main channel showing 3D villi-like structures form in scattered areas of the chip where epithelium separated from fibroblasts with the PDMS membrane. Area outlined in blue is enlarged in the lower image.

Example-6. Exemplary Generation of L-Cells by Incorporation of Irradiated Fibroblasts with Enteroids as in the Previous Example 7

FIG. 26 shows relative mRNA expression for L-cells markers including GCG and PYY, that are increased in co-cultures of epithelium and irradiated fibroblasts (pink bar) compared to epithelium alone (grey bar), in addition to other subtype markers Enteroendocrine cells identified by chromogranin A (CHGA) and THP1.

FIG. 27A-B shows exemplary schematic diagrams of FIG. 27A an experimental timeline and FIG. 27B relative mRNA expression for L-cells markers including GCG and PYY, that are expressed in co-cultures of epithelium and irradiated fibroblasts (blue bar) compared to in vivo colon (biopsies).

Example 7—L-Cells Present in Colon-Chips are Biologically Active

In one embodiment of an intestine (colon) on chip, L-cells release GLP-1 in response to Forskolin/IBMX stimulation.

L-cells accounted for 1% (1.67+/−0.89) of intestinal epithelial cells types in Colon-Chip releasing GLP-1 in response to Forskolin/IBMX stimulation FIG. 28 shows an exemplary schematic of GLP-1, an L-cell produced and secreted hormone with multiple direct effects on human physiology. Adapted from: Baggio L L, Drucker D J (2007) Biology of incretins: GLP-1 and GIP. Gastroenterology 132(6):2131-57. In other words, L-cells have pleiotropic actions in peripheral tissues.

FIG. 29A-C demonstrates that L-cells present in Colon On-Chips are Biologically Active. FIG. 29A shows exemplary fluorescent micrographs of L cells within intestinal epithelial layers on chip. Upper micrograph shows nuclei staining within a microfluidic channel. Middle micrograph shows an epithelial layer within a microfluidic channel at higher magnification. Lower micrographs show an L cell (Glucagon) with Nuclei stained, left, a L-cell (Glucagon), middle, and Nuclei stained, right. FIG. 29B shows a chart of L-cell numbers. FIG. 29C shows comparative charts of L-cell function as exemplary GLP-1 secretion in response to stimulation with 10 μm Fsk/IBMX. L-cells account for 1% (1.67+/−0.89) of intestinal epithelial cells types in Colon-Chip release GLP-1 in response to Forskolin/IBMX stimulation.

Example 8—L-Cells Respond to Bile Acid Stimulation and Stretching

L-cells release GLP-1 into the vascular channel upon stimulation with bile acid (30 μM deoxycholic acid) and stretching.

FIG. 30 shows an exemplary demonstration that L-cells respond to bile acid stimulation and stretching as shown by a graphical corporation of increased GLP-1 secretion. L-cells release GLP-1 into the vascular channel upon stimulation with bile acid (30 μM deoxycholic acid) and stretching.

Example 9—Improved Timeline of Maturation

A faster establishment of intestinal impermeability as well as lower chip-to-chip variability was observed when using a culture module as described herein, in comparison to using a peristaltic pump for providing fluid flow. Permeability assays for small fluorescent dye and gene expression analysis revealed faster establishment of intestinal impermeability with lower chip-chip variability and correct tissue maturation in the culture module. Thus, incubating an Intestine-Chip in the culture module providing fluid flow shows faster establishment of a barrier, and tighter error bars in permeability experiments.

FIG. 31A-G shows an exemplary demonstration of faster establishment of intestinal permeability with lower chip to chip variability and faster development of cell types in maturing epithelial layers when using the culture module (described herein and shown in the figures), including but not limited to Epithelial cells identified by EpCAM, Paneth cells identified by lysozyme (LYZ), Absorptive Enterocytes identified by ALPI, Goblet cells identified by mucin 2 (MUC2), Enteroendocrine cells identified by chromogranin A (CHGA) and quiescent stem cells identified by (BMI1).

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in biochemistry, chemistry, microbiology, molecular biology, and medicine, or related fields are intended to be within the scope of the following claims.

What is claimed is:

1. A method of culturing intestinal cells in vitro, comprising:
  a. providing i) an intestinal enteroid or colonoid comprising human primary intestinal epithelial cells, ii) a plurality of endothelial cells and iii) a microfluidic culture device comprising a cell growth region comprising a membrane having a first surface and a second surface, wherein said surfaces are on opposing sides of said membrane;
  b. disrupting said intestinal enteroid or colonoid comprising human primary intestinal epithelial cells into enteroid or colonoid fragments;
  c. seeding said enteroid or colonoid fragments on said first surface of said cell growth region so as to create seeded primary intestinal epithelial cells;
  d. seeding endothelial cells on a second surface so as to create seeded endothelial cells, wherein said endothelial cells are seeded 1-6 days after seeding said primary intestinal epithelial cells;
  e. expanding said seeded primary intestinal epithelial cells so as to create a monolayer of epithelial cells; and
  f. differentiating said monolayer of epithelial cells so as to create two or more different differentiated intestinal cell types, wherein one of said two or more different differentiated intestinal cell types comprises L-cells.

2. The method of claim 1, wherein 2 days after seeding said endothelial cells, said membrane is subject to cyclic stretching.

3. The method of claim 1, one day after step c), starting flow.

4. The method of claim 1, wherein said endothelial cells are selected from the group consisting of adult derived human colonic microvascular endothelial cells (cHIMECs) and pediatric sources of Human Intestinal Microvascular Endothelial Cells (HIMECs).

5. The method of claim 1, wherein said human primary intestinal epithelial cells are from intestine tissue selected from the group consisting of a small intestinal duodenum, small intestinal jejunum, small intestinal ileum, and large intestinal colon.

* * * * *